US008241763B2

(12) United States Patent
Buesing et al.

(10) Patent No.: US 8,241,763 B2
(45) Date of Patent: Aug. 14, 2012

(54) MATERIALS FOR ORGANIC ELECTROLUMINESCENT DEVICES

(75) Inventors: Arne Buesing, Frankfurt am Main (DE); Philipp Stoessel, Frankfurt am Main (DE); Holger Heil, Darmstadt (DE)

(73) Assignee: Merck Patent GmbH (DE)

( * ) Notice: Subject to any disclaimer, the term of this patent is extended or adjusted under 35 U.S.C. 154(b) by 343 days.

(21) Appl. No.: 12/373,070

(22) PCT Filed: Jun. 20, 2007

(86) PCT No.: PCT/EP2007/005413

§ 371 (c)(1),
(2), (4) Date: Jan. 9, 2009

(87) PCT Pub. No.: WO2008/006449

PCT Pub. Date: Jan. 17, 2008

(65) Prior Publication Data

US 2009/0261717 A1 Oct. 22, 2009

(30) Foreign Application Priority Data

Jul. 11, 2006 (DE) ......................... 10 2006 031 990

(51) Int. Cl.
*H01L 51/54* (2006.01)

(52) U.S. Cl. ........ 428/690; 428/917; 313/540; 313/505; 313/506; 257/40; 257/E51.05; 546/79; 585/26

(58) Field of Classification Search .................. 428/690, 428/917; 313/504, 505, 506; 257/40, E51.05; 546/79; 585/526.26

See application file for complete search history.

(56) References Cited

U.S. PATENT DOCUMENTS

| | | | | |
|---|---|---|---|---|
| 5,942,340 A * | 8/1999 | Hu et al. | ....................... | 428/690 |
| 2008/0145708 A1 * | 6/2008 | Heil et al. | ..................... | 428/704 |

FOREIGN PATENT DOCUMENTS

| | | | |
|---|---|---|---|
| JP | 11-162642 A | 6/1999 |
| WO | WO-2004/020372 A1 | 3/2004 |
| WO | WO-2004/041901 A1 | 5/2004 |
| WO | WO-2007/061218 A1 | 5/2007 |

OTHER PUBLICATIONS

Buu-Hoi et. al., Further Studies in the Cyclodehydration . . . ,1960, Journal of the Chemical Society ,pp. 2690-2694.*
U.S. Appl. No. 12/373,004.
Hadizad, T., et al., “A general synthetic route to indenoflurene derivatives as new organic semiconductors,” Organic Letters, 2005, vol. 7, No. 5, pp. 795-797.
Py, C., et al., “Hole mobility and electroluminescence properties of a dithiophene indenofluorene,” J. Vac. Sci. Technol. A, May/Jun. 2006, vol. 24, No. 3, pp. 654-656.

* cited by examiner

*Primary Examiner* — Jennifer Chriss
*Assistant Examiner* — Gregory Clark
(74) *Attorney, Agent, or Firm* — Connolly Bove Lodge & Hutz LLP

(57) ABSTRACT

The present invention relates to the compounds of the formulae (1) to (6) and to organic electroluminescent devices, in particular blue-emitting devices, in which these compounds are used as host material or dopant in the emitting layer and/or as hole-transport material and/or as electron-transport material.

17 Claims, No Drawings

MATERIALS FOR ORGANIC ELECTROLUMINESCENT DEVICES

CROSS-REFERENCE TO RELATED APPLICATIONS

Related Applications

This application is a national stage application (under 35 U.S.C. §371) of PCT/EP2007/005413, filed Jun. 20, 2007, which claims benefit of German application 10 2006 031 990.7, filed Jul. 11, 2006.

BACKGROUND OF THE INVENTION

The present invention relates to organic semiconductors and to the use thereof in organic electronic devices.

Organic semiconductors are being developed for a number of different applications which can be ascribed to the electronics industry in the broadest sense. The structure of organic electroluminescent devices (OLEDs) in which these organic semiconductors are employed as functional materials is described, for example, in U.S. Pat. Nos. 4,539,507, 5,151,629, EP 0676461 and WO 98/27136. However, these devices still exhibit considerable problems which require urgent improvement:

1. The compounds usually used do not have a sufficiently low LUMO (lowest unoccupied molecular orbital). Compounds having a lower LUMO are required for easier electron injection and thus for a reduction in the operating voltage.
2. The colour coordinates of many blue emitters are still unsatisfactory.
3. The thermal stability, in particular of blue dopants, is inadequate.
4. The lifetime and efficiency of blue-emitting organic electroluminescent devices should be increased still further for high-quality applications.

For fluorescent OLEDs, condensed aromatic compounds, in particular anthracene or pyrene derivatives, for example 9,10-bis(2-naphthyl)anthracene (U.S. Pat. No. 5,935,721), are used, in particular, as host materials, especially for blue-emitting electroluminescent devices, in accordance with the prior art. WO 03/095445 and CN 1362464 disclose 9,10-bis(1-naphthyl)anthracene derivatives for use in OLEDs. Further anthracene derivatives are disclosed in WO 01/076323, WO 01/021729, WO 04/013073, WO 04/018588, WO 03/087023 and WO 04/018587. Host materials based on aryl-substituted pyrenes and chrysenes are disclosed in WO 04/016575. For high-quality applications, it is necessary to have improved host materials available.

Prior art which may be mentioned in the case of blue-emitting compounds is the use of arylvinylamines (for example WO 04/013073, WO 04/016575, WO 04/018587). However, these compounds are thermally unstable and cannot be evaporated without decomposition, which requires high technical complexity for OLED production and thus represents an industrial disadvantage. A further disadvantage is the emission colour of these compounds: while dark-blue emission (CIE y coordinates in the range 0.15-0.18) is described in the prior art with these compounds, it has not been possible to reproduce these colour coordinates in simple devices in accordance with the prior art. Green-blue emission is obtained here. It is not apparent how blue emission can be generated with these compounds. For high-quality applications, it is necessary to have improved emitters available, particularly in relation to device and sublimation stability.

The matrix material used in phosphorescent OLEDs is frequently 4,4'-bis(N-carbazolyl)biphenyl (CBP). The disadvantages are short lifetimes of the devices produced therewith and frequently high operating voltages, which result in low power efficiencies. In addition, CBP has an inadequately high glass transition temperature. Furthermore, it has been found that CBP is unsuitable for blue-emitting electroluminescent devices, which results in poor efficiency. In addition, the construction of the devices with CBP is complex since a hole-blocking layer and an electron-transport layer additionally have to be used, Improved triplet matrix materials, based on keto compounds, are described in WO 04/093207, but these likewise do not give satisfactory results with all triplet emitters.

The electron-transport compound used in organic electroluminescent devices is usually $AlQ_3$ (aluminium trishydroxyquinolinate) (U.S. Pat. No. 4,539,507). This cannot be vapour-deposited in a residue-free manner since it partially decomposes at the sublimation temperature, which represents a major problem, in particular for production plants. A further disadvantage is the strong hygroscopicity of $AlQ_3$, as is the low electron mobility, which results in higher voltages and thus in lower power efficiency. In order to prevent short circuits in the display, it would be desirable to increase the layer thickness; this is not possible with $AlQ_3$ owing to the low charge-carrier mobility and resultant increase in voltage. The inherent colour of $AlQ_3$ (yellow in the solid), which can result in colour shifts, especially in blue OLEDs, due to reabsorption and weak re-emission, furthermore proves unfavourable. Blue OLEDs can only be produced here with considerable efficiency and colour location deficiencies.

There thus continues to be a demand for improved materials, in particular emitting compounds, especially blue-emitting compounds, but also host materials for fluorescent and phosphorescent emitters, hole-transport materials and electron-transport materials, which are thermally stable, result in good efficiencies and at the same time in long lifetimes in organic electronic devices, give reproducible results during the production and operation of the device and are readily accessible synthetically.

BRIEF SUMMARY OF THE INVENTION

Surprisingly, it has been found that compounds in which a phenylene group is linked to a naphthyl, anthryl or phenanthrenyl group and to a phenyl group and in which, in addition, at least one bridge exists between the phenylene group and the phenyl group and at least one bridge exists between the phenylene group and the naphthyl or anthryl or phenanthrenyl group, and heterocyclic derivatives of these compounds are very suitable for use in organic electroluminescent devices. These compounds have high thermal stability. Furthermore, an increase in the efficiency and lifetime of the organic electronic device compared with materials in accordance with the prior art is possible using these materials. Furthermore, these materials are very suitable for use in organic electronic devices since they have a high glass transition temperature. The present invention therefore relates to these materials and to the use thereof in organic electronic devices.

DETAILED DESCRIPTION OF THE INVENTION

The invention relates to compounds of the formulae (1) to (6)

Formula (1)

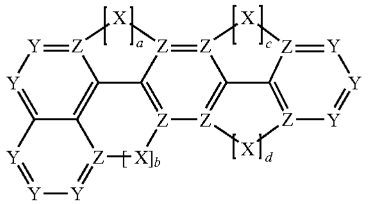

Formula (2)

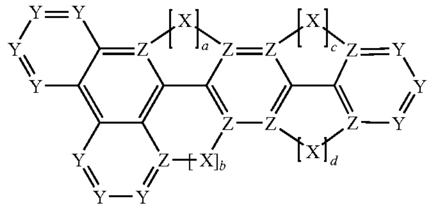

Formula (3)

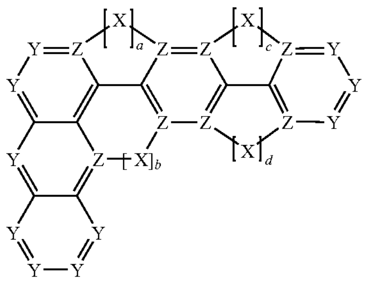

Formula (4)

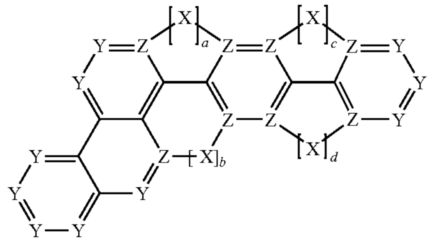

Formula (5)

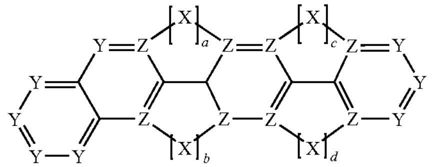

Formula (6)

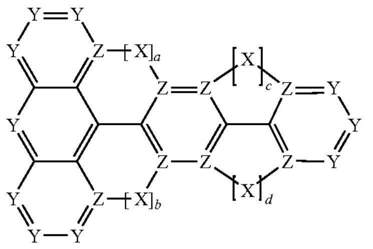

where the following applies to the symbols and indices:

Y is on each occurrence, identically or differently, $CR^1$ or N;

Z is equal to C if a bridge X is bonded to the group Z and is equal to Y if no bridge X is bonded to the group Z;

X is on each occurrence, identically or differently, a divalent bridge selected from $B(R^1)$, $C(R^1)_2$, $Si(R^1)_2$, C═O, $C═NR^1$, $C═C(R^1)_2$, O, S, S═O, $SO_2$, $N(R^1)$, $P(R^1)$ and $P(═O)R^1$;

$R^1$ is on each occurrence, identically or differently, H, F, Cl, Br, I, CHO, $N(Ar)_2$, C(═O)Ar, $P(═O)Ar_2$, S(═O)Ar, $S(═O)_2Ar$, $CR^2═CR^2Ar$, CN, $NO_2$, $Si(R^2)_3$, $B(OR^2)_2$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C═CR^2$, C≡C, $Si(R^2)_2$, $Ge(R^2)_2$, $Sn(R^2)_2$, C═O, C═S, C═Se, $C═NR^2$, $P(═O)(R^2)$, SO, $SO_2$, $NR^2$, O, S or $CONR^2$ and where one or more H atoms may be replaced by F, Cl, Br, I, CN or $NO_2$, or an aromatic or heteroaromatic ring system having 5 to 40 aromatic ring atoms, which may in each case be substituted by one or more radicals $R^2$, or an aryloxy or heteroaryloxy group having 5 to 40 aromatic ring atoms, which may be substituted by one or more radicals $R^2$, or a combination of these systems; two or more adjacent substituents $R^1$ here may also form a mono- or polycyclic ring system with one another;

Ar is on each occurrence, identically or differently, an aromatic or heteroaromatic ring system having 5 to 30 aromatic ring atoms, which may be substituted by one or more non-aromatic radicals $R^1$; two radicals Ar which are bonded to the same nitrogen or phosphorus atom may also be linked to one another by a single bond or a bridge selected from $B(R^2)$, $O(R^2)_2$, $Si(R^2)_2$, C═O, $C═NR^2$, $C═C(R^2)_2$, O, S, S═O, $SO_2$, $N(R^2)$, $P(R^2)$ and $P(═O)R^2$;

$R^2$ is on each occurrence, identically or differently, H or an aliphatic, aromatic and/or heteroaromatic hydrocarbon radical having 1 to 20 C atoms, in which, in addition, H atoms may be replaced by F; two or more adjacent substituents $R^2$ here may also form a mono- or polycyclic aliphatic or aromatic ring system with one another;

a, b, c, d is on each occurrence, identically or differently, 0 or 1, with the proviso that a+b=1 or 2 and c+d=1 or 2, where a=0 or b=0 or c=0 or d=0 in each case means that the corresponding bridge X is not present; the bridge X then does not stand for a single bond.

The compounds of the formulae (1) to (6) preferably have a glass transition temperature $T_G$ of greater than 70° C., particularly preferably greater than 100° C., very particularly preferably greater than 130° C.

For the purposes of this invention, adjacent radicals $R^1$ and $R^2$ are taken to mean radicals which are either bonded to the same carbon atom or to the same hetero atom or are bonded to adjacent carbon atoms.

For the purposes of this invention, an aryl group contains 6 to 40 C atoms; for the purposes of this invention, a heteroaryl group contains 2 to 40 C atoms and at least one heteroatom, with the proviso that the sum of C atoms and hetero atoms is at least 5. The heteroatoms are preferably selected from N, O and/or S. An aryl group or heteroaryl group here is taken to mean either a single aromatic ring, i.e. benzene, or a single heteroaromatic ring, for example pyridine, pyrimidine, thiophene, etc., or a condensed aryl or heteroaryl group, for example naphthalene, anthracene, pyrene, quinoline, isoquinoline, etc.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which a plurality of aryl or heteroaryl groups may also be interrupted by a short non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, benzophenone, etc., are also intended to be taken to mean aromatic ring systems for the purposes of this invention. An aromatic or heteroaromatic ring system is likewise taken to mean systems in which a plurality of aryl or heteroaryl groups are linked to one another by single bonds, for example biphenyl, terphenyl or bipyridine.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-40 aromatic ring atoms, which may also in each case be substituted by the above-mentioned radicals R and which can be linked to the aromatic or heteroaromatic ring system via any desired positions, is taken to mean, in particular, groups derived from benzene, naphthalene, anthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to structures of the formulae (1) to (6) in which a+b=1 and c+d=1.

Preferred embodiments of the structures of the formulae (1) to (6) are the structures of the formulae (7) to (28)

Formula (7)

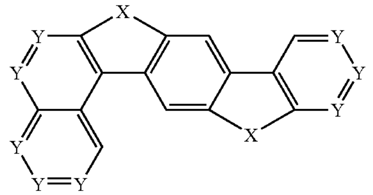

Formula (8)

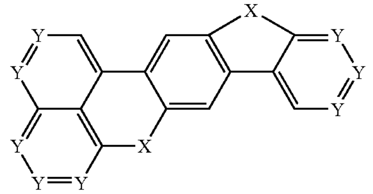

Formula (9)

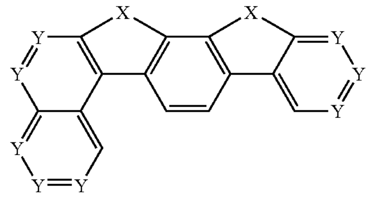

Formula (10)

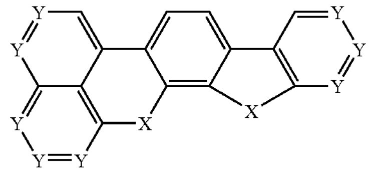

Formula (11)

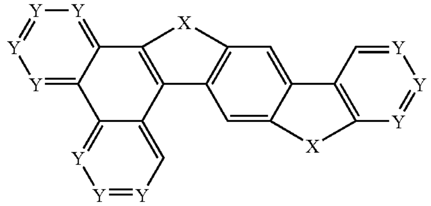

Formula (12)

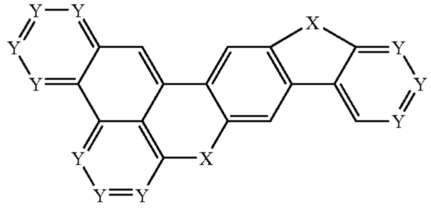

Formula (13)

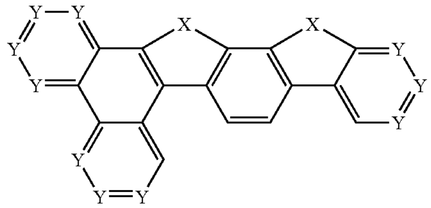

-continued
Formula (14)
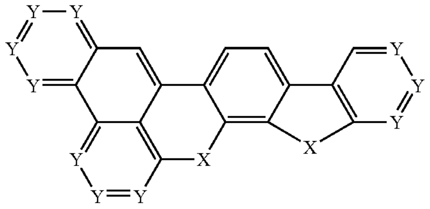
Formula (15)
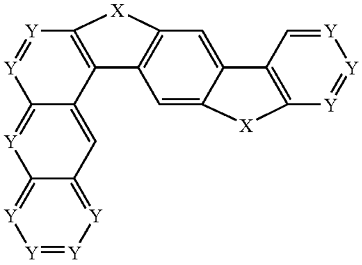
Formula (16)
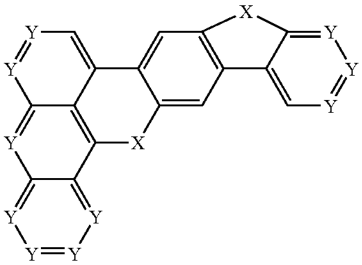
Formula (17)
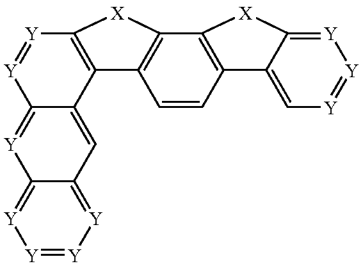
Formula (18)
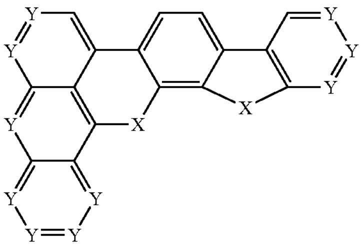
Formula (19)
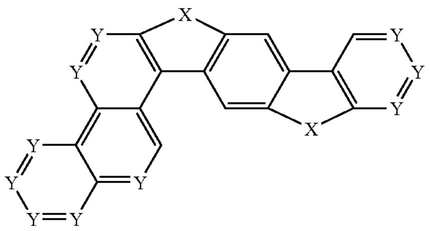
-continued
Formula (20)
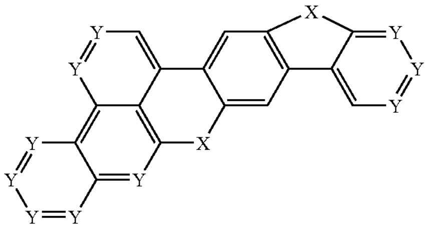
Formula (21)
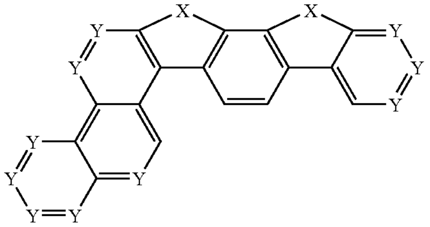
Formula (22)
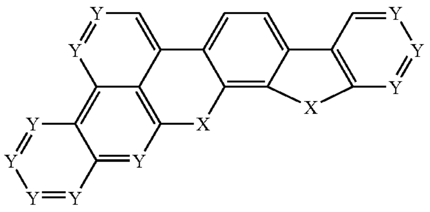
Formula (23)
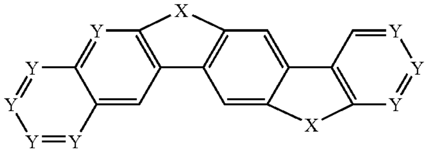
Formula (24)
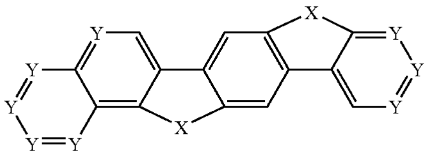
Formula (25)
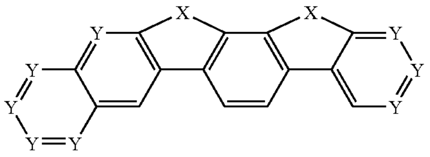
Formula (26)
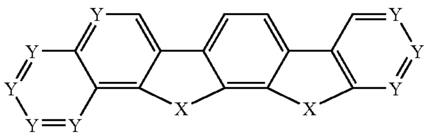
Formula (27)
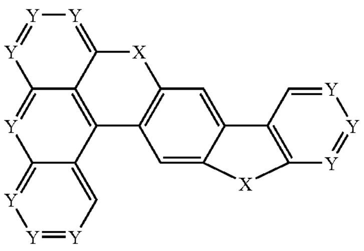

-continued

Formula (28)

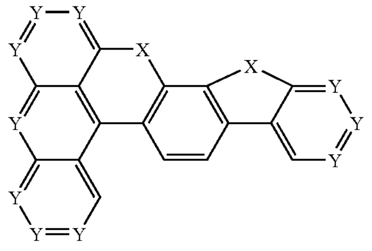

where the symbols X and Y have the same meaning as described above.

Preference is furthermore given to compounds of the formulae (1) to (28) in which the symbol Y stands for nitrogen a total of 0, 1, 2, 3 or 4 times, where the other symbols Y stand for $CR^1$. Particular preference is given to compounds of the formulae (1) to (28) in which the symbol Y stands for nitrogen a total of 0, 1 or 2 times. In a particularly preferred embodiment of the invention, the symbol Y stands for $CR^1$. In a particularly preferred embodiment, the structures of the formulae (1) to (6) are selected from the formulae (7a) to (28a)

Formula (7a)

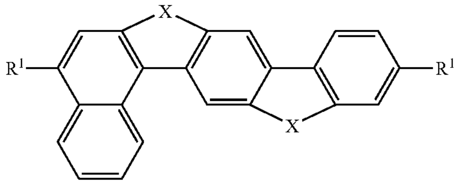

Formula (8a)

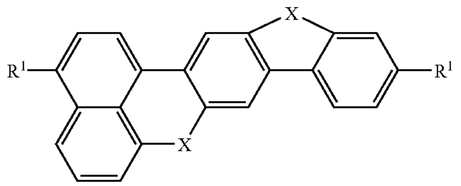

Formula (9a)

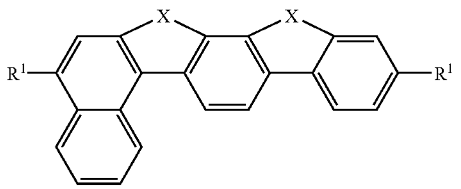

Formula (10a)

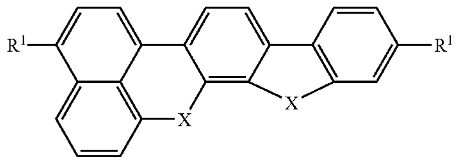

-continued

Formula (11a)

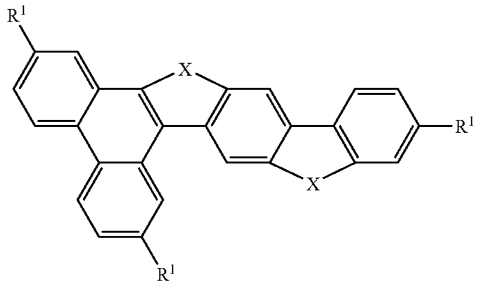

Formula (12a)

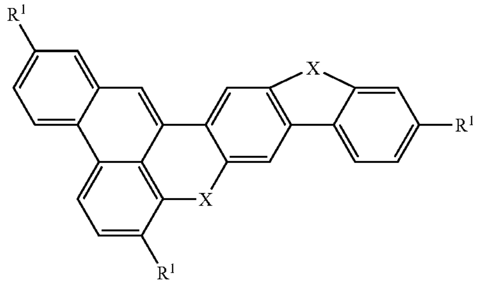

Formula (13a)

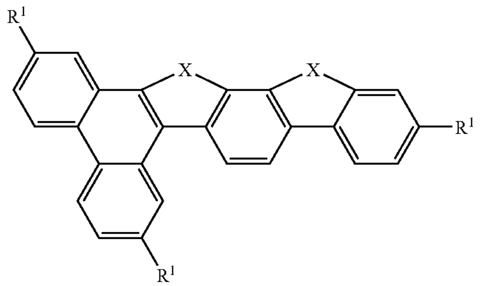

Formula (14a)

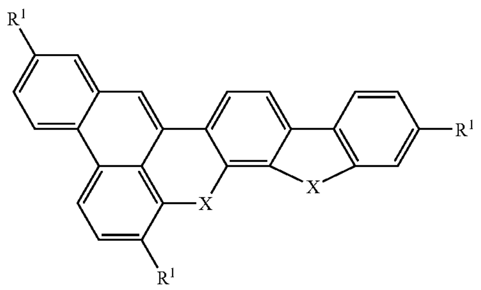

Formula (15a)

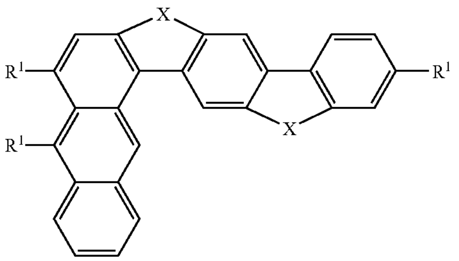

-continued
Formula (16a)
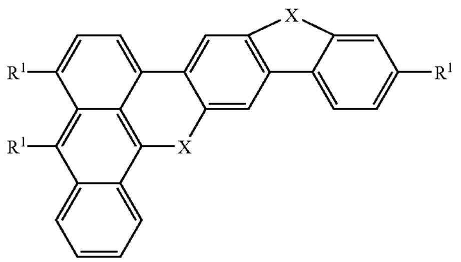
Formula (17a)
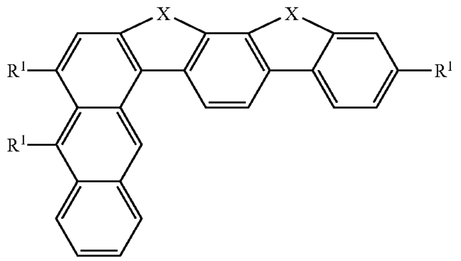
Formula (18a)
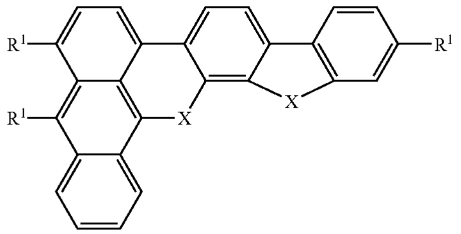
Formula (19a)
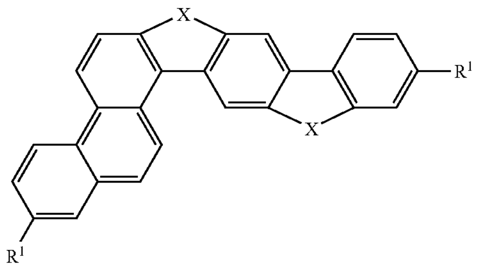
Formula (20a)
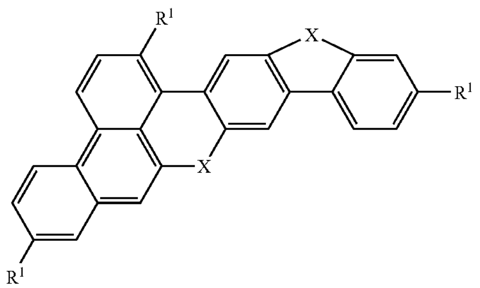
-continued
Formula (21a)
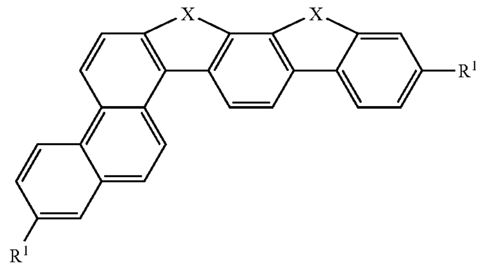
Formula (22a)
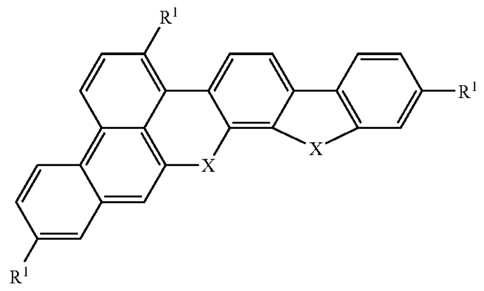
Formula (23a)
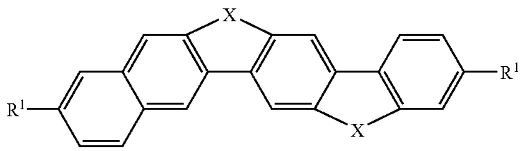
Formula (24a)
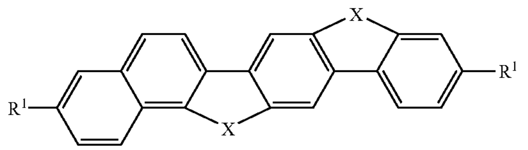
Formula (25a)
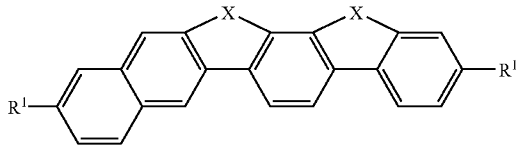
Formula (26a)
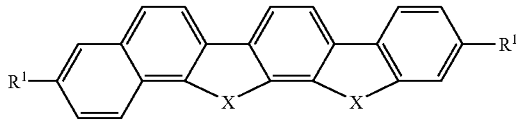
Formula (27a)
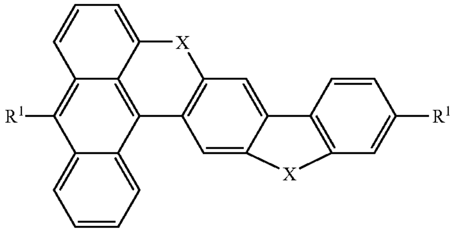

-continued

Formula (28a)

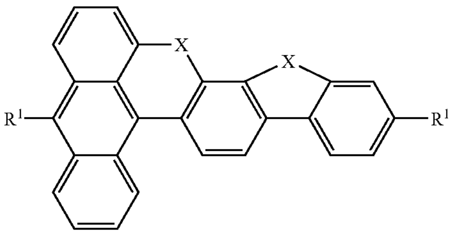

where the symbols X and $R^1$ have the same meaning as described above.

In the structures of the formulae (7a) to (28a), at least one radical $R^1$ is particularly preferably not equal to hydrogen; at least two radicals $R^1$ are particularly preferably not equal to hydrogen. It may also be preferred here for the radicals $R^1$ to be different. If only one radical $R^1$ is present, it is preferred for this to be bonded to the condensed aryl group of the system. However, it may also be bonded to the uncondensed phenyl ring.

Preference is furthermore given to compounds of the formulae (1) to (28) and (7a) to (28a) in which the symbol $R^1$, which is bonded to the aromatic parent structure of the formulae (1) to (6), stands, identically or differently on each occurrence, for a group $NAr_2$, as shown below, or for H, F, Br, C(═O)Ar, P(═O)$Ar_2$, $CR^2$═$CR^2$Ar, a straight-chain alkyl group having 1 to 5 C atoms or a branched alkyl group having 3 to 5 C atoms, where one or more non-adjacent $CH_2$ groups may be replaced by —$R^2$C═$CR^2$—, —C≡C— or —O— and where one or more H atoms may be replaced by F, or a triarylamine group having 18 to 30 C atoms, which may be substituted by one or more radicals $R^2$ or an aryl group having 6 to 16 C atoms or heteroaryl group having 2 to 16 C atoms or a spirobifluorene group, each of which may be substituted by one or more radicals $R^2$ or a combination of two or three of these systems. Particularly preferred radicals $R^1$ are, identically or differently on each occurrence, a group $NAr_2$, as shown below, or H, F, Br, C(═O)Ar, P(═O)$Ar_2$, methyl, ethyl, isopropyl, tert-butyl, where one or more H atoms may in each case be replaced by F, or a triphenylamine group, which may be substituted by one or more radicals $R^2$, or an aryl group having 6 to 14 C atoms or a spirobifluorene group, each of which may be substituted by one or more radicals $R^2$, or a combination of two of these systems. On incorporation into polymers, oligomers or dendrimers and in the case of compounds which are processed from solution, linear or branched alkyl chains having up to 10 C atoms are also preferred. Bromine as substituent is particularly preferred for the use of this compound as intermediate for the preparation of other compounds according to the invention or for the use as monomer for the preparation of polymers.

If the radical $R^1$ stands for a group $N(Ar)_2$, this group is preferably selected from the groups of the formula (29) or of the formula (30)

Formula (29)

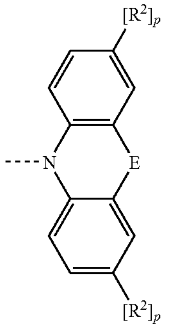

Formula (30)

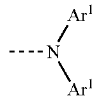

where $R^2$ has the meaning shown above and furthermore:

E stands for a single bond, O, S, $N(R^2)$ or $C(R^2)_2$;

$Ar^1$ is, identically or differently on each occurrence, an aryl or heteroaryl group having 5 to 20 aromatic ring atoms or a triarylamine group having 15 to 30 aromatic ring atoms, each of which may be substituted by one or more radicals $R^2$ or by Br, preferably an aryl or heteroaryl group having 6 to 14 aromatic ring atoms or a triarylamine group having 18 to 30 aromatic ring atoms, preferably having 18 to 22 aromatic ring atoms, each of which may be substituted by one or more radicals $R^2$ or by Br;

p is on each occurrence, identically or differently, 0 or 1.

$Ar^1$ particularly preferably stands, identically or differently, for phenyl, 1-naphthyl, 2-naphthyl, 2-, 3- or 4-triphenylamine, 1- or 2-naphthyldiphenylamine, each of which may be bonded via the naphthyl or phenyl group, or 1- or 2-dinaphthylphenylamine, each of which may be bonded via the naphthyl or phenyl group. These groups may each be substituted by one or more alkyl groups having 1 to 4 C atoms or by fluorine.

Preference is furthermore given to compounds of the formulae (1) to (28) and (5a) to (28a) in which the symbols X are on each occurrence, identically or differently, a divalent bridge selected from $C(R^1)_2$, C═O, C═$NR^1$, O, S, S═O, $SO_2$, $N(R^1)$, $P(R^1)$ and P(═O)$R^1$. Particular preference is given to compounds of the formulae (1) to (28) and (5a) to (28a) in which the symbols X are on each occurrence, identically or differently, selected from $C(R^1)_2$, $N(R^1)$, $P(R^1)$ and P(═O)($R^1$), very particularly preferably $C(R^1)_2$ or $N(R^1)$, in particular $C(R^1)_2$. It should explicitly be pointed out again here that a plurality of adjacent radicals $R^1$ or the group X may also form an aromatic or aliphatic ring system with one another here. If a plurality of radicals $R^1$ on a group $C(R^1)_2$ form a ring system with one another, this results in spiro structures. The formation of spiro structures of this type by the formation of ring systems between two groups $R^1$ on $C(R^1)_2$ is a further preferred embodiment of the invention. This applies in particular if $R^1$ stands for a substituted or unsubstituted phenyl group and the two phenyl groups together with the C atom of the bridge form a ring system.

Preferred radicals $R^1$ which are bonded to the bridges X are identical or different and are selected from H, straight-chain alkyl groups having 1 to 5 C atoms or branched alkyl groups having 3 to 5 C atoms, where one or more non-adjacent $CH_2$ groups may be replaced by —$R^2$C═$CR^2$—, —C≡C— or —O— and where one or more H atoms may be replaced by F, or aryl groups having 6 to 16 C atoms or heteroaryl groups having 2 to 16 C atoms, each of which may be substituted by one or more radicals $R^2$, or a combination of two or three of these systems; two of the radicals $R^1$ which are bonded to the same bridge atom may also form a ring system with one another here. Particularly preferred radicals $R^1$ which are bonded to the bridges X are identical or different and are selected from methyl, ethyl, isopropyl, tert-butyl, where in each case one or more H atoms may be replaced by F, or aryl groups having 6 to 14 C atoms, which may be substituted by one or more radicals $R^2$, or a combination of two of these systems; two of the radicals $R^1$ which are bonded to the same bridge atom may also form a ring system with one another. In the case of compounds which are processed from solution, linear or branched alkyl chains having up to 10 C atoms are also preferred.

Preference is furthermore given to symmetrically substituted compounds, i.e. compounds in which the substituents $R^1$ in the formulae (7a) to (28a) are selected identically.

Examples of preferred compounds of the formulae (1) to (6) are structures (1) to (338) depicted below.

(1)

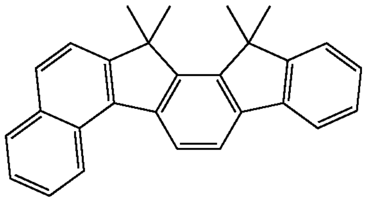

(2)

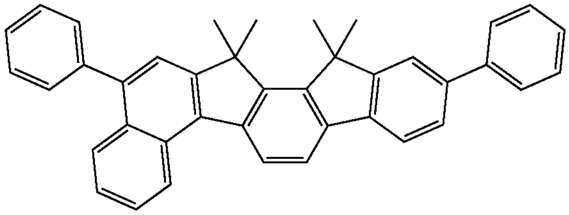

(3)

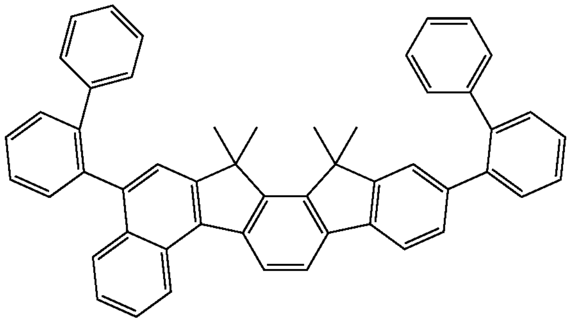

(4)

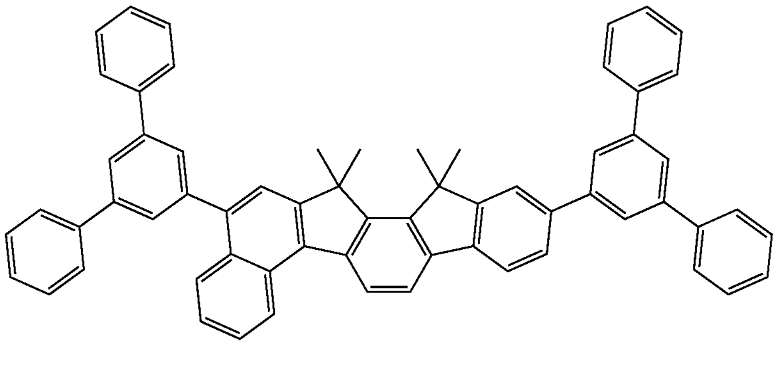

(5)

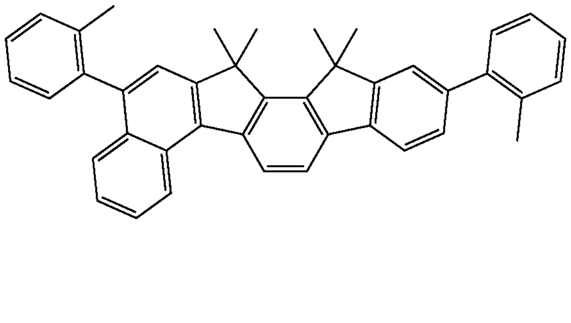

(6)

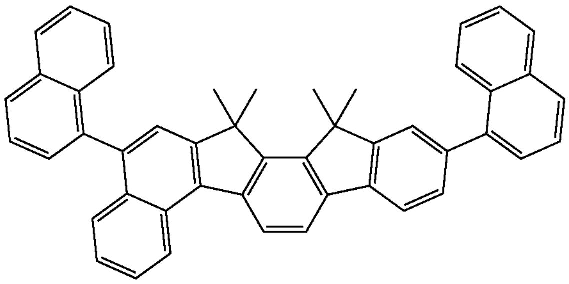

-continued
(7)
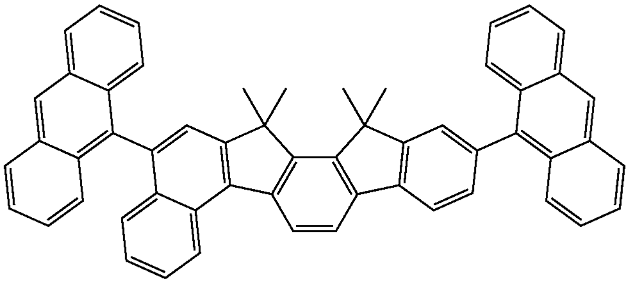
(8)
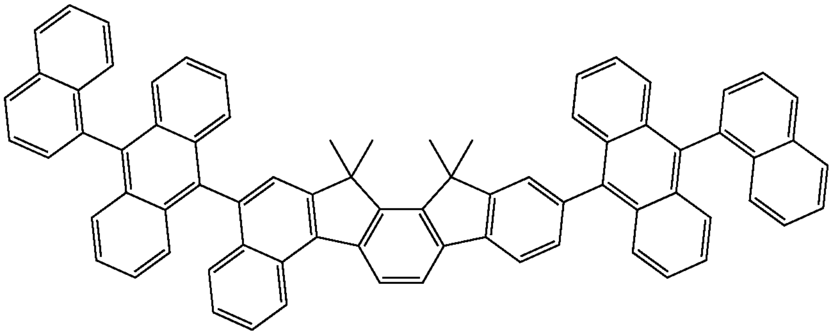
(9)
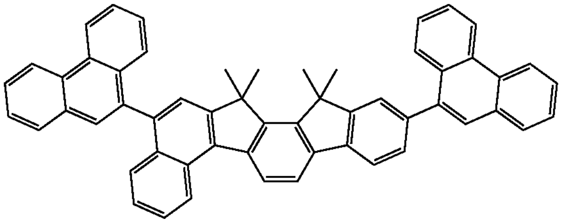
(10)
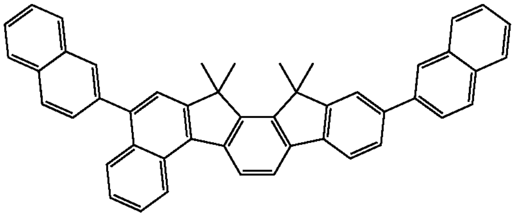
(11)
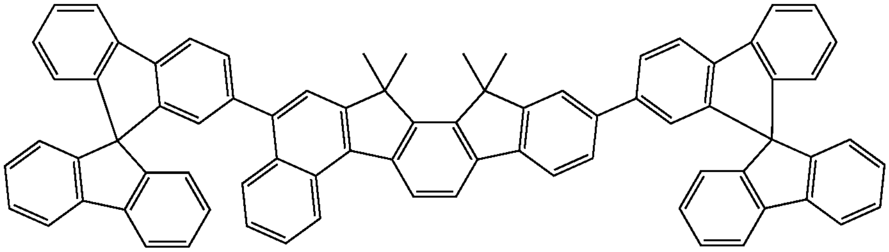
(12)
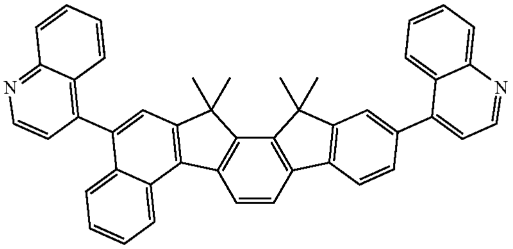
(13)
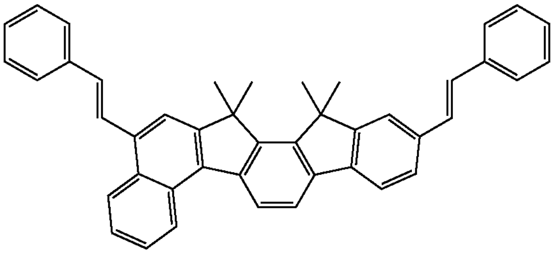

-continued
(14)
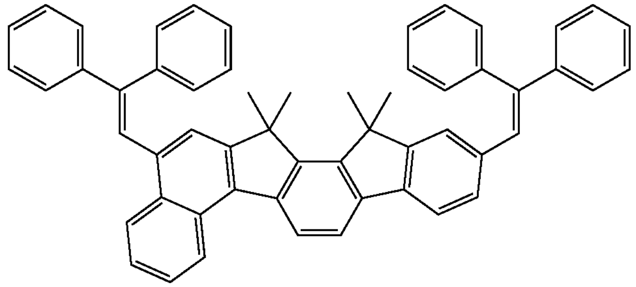
(15)
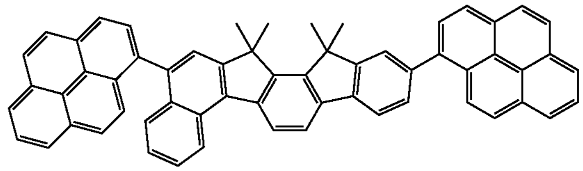
(16)
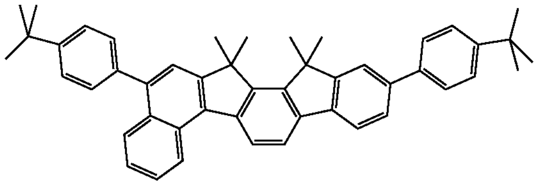
(17)
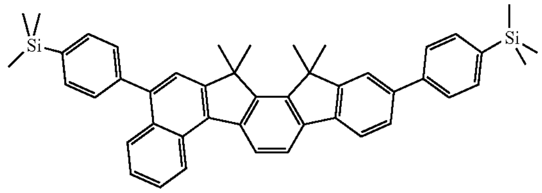
(18)
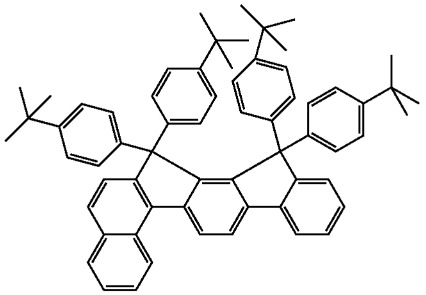
(19)
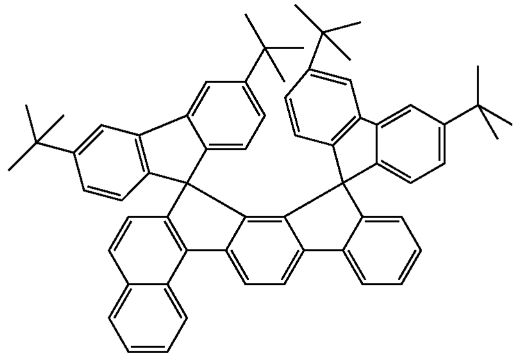
(20)
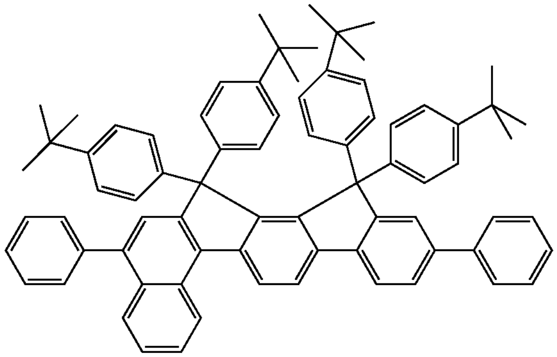
(21)
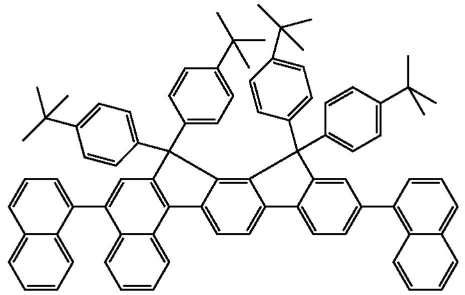
(22)
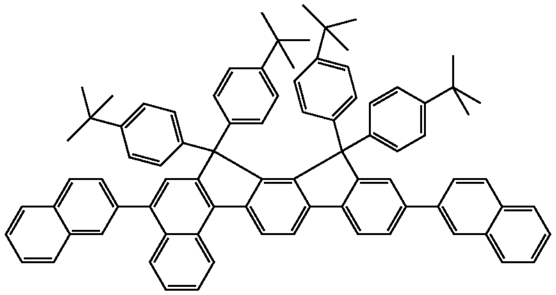

-continued
(23)
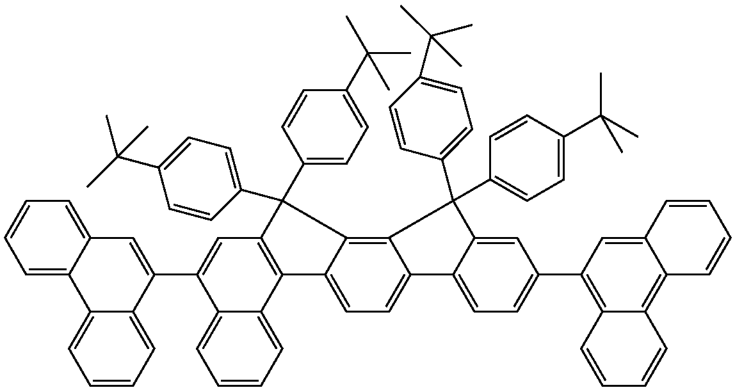
(24)
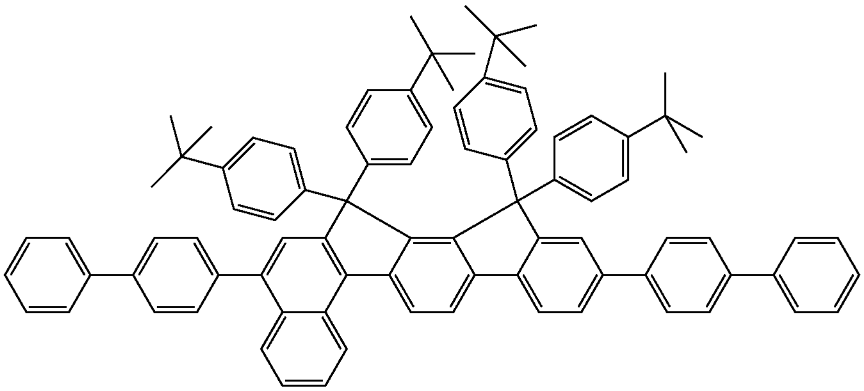
(25)
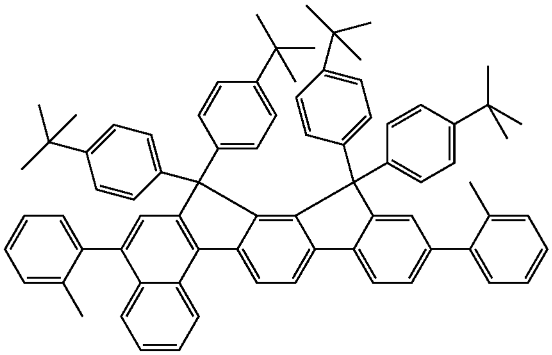
(26)
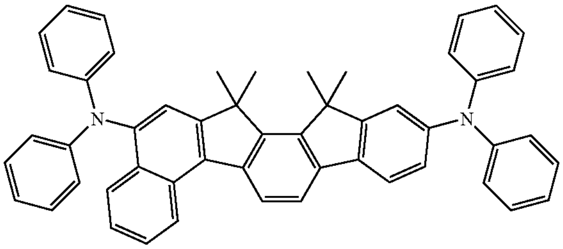
(27)
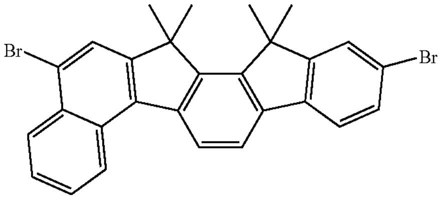
(28)
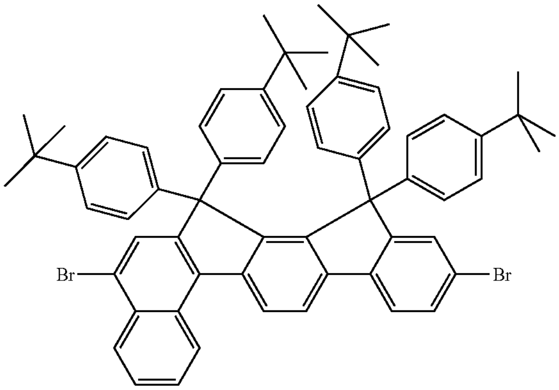

-continued
(29)
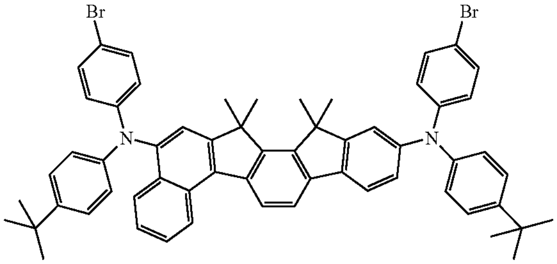
(30)
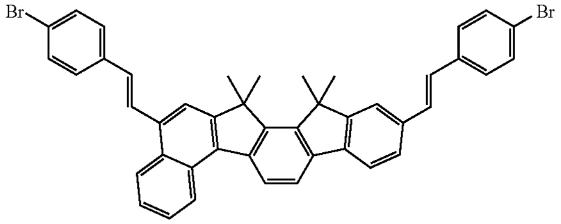
(31)
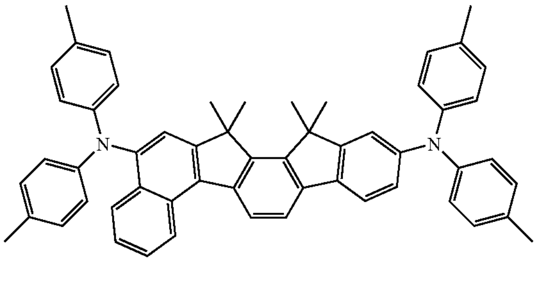
(32)
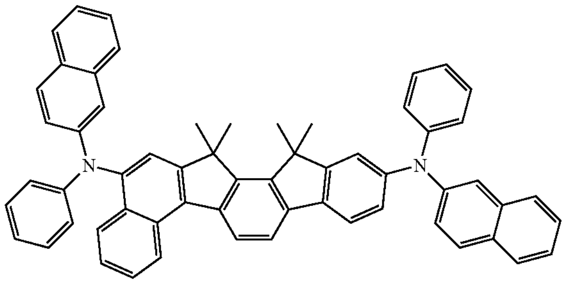
(33)
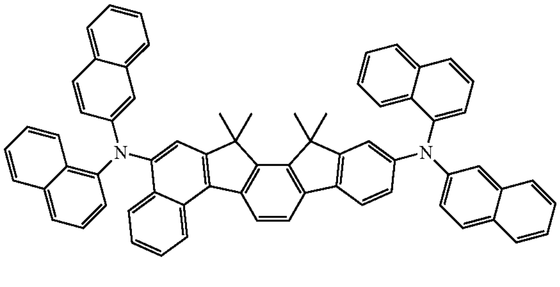
(34)
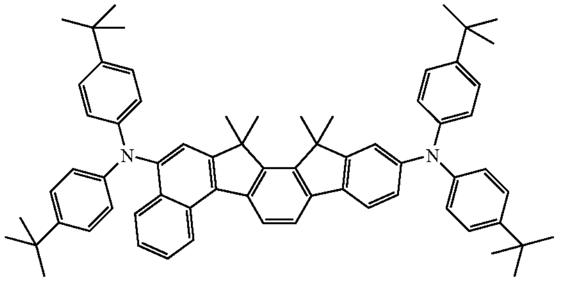
(35)
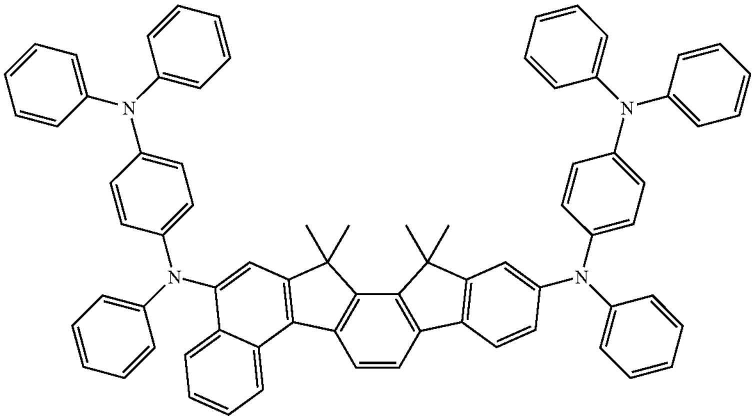

-continued
(36)
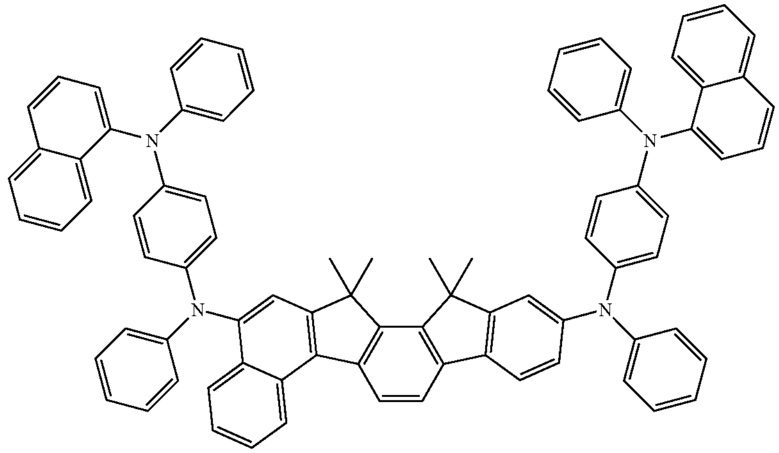
(37)
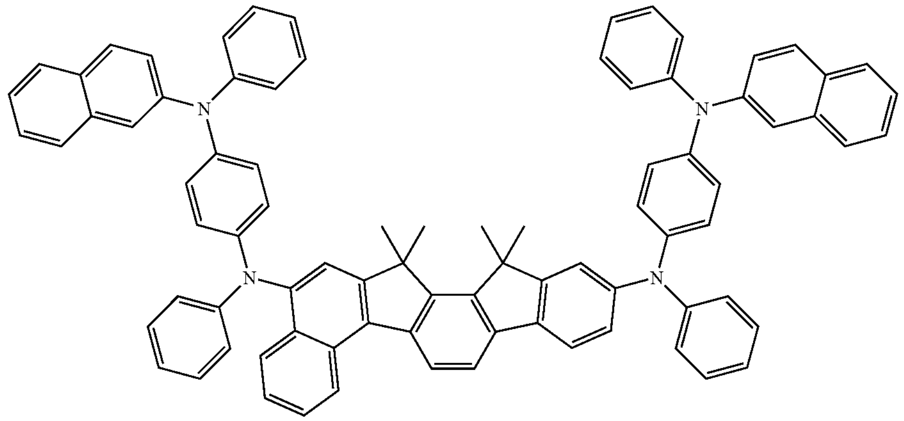
(38)
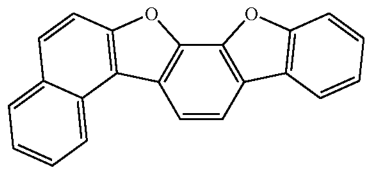
(39)
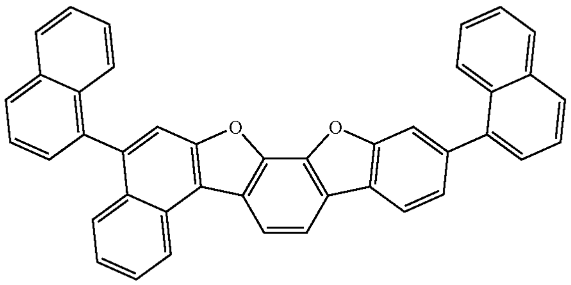
(40)
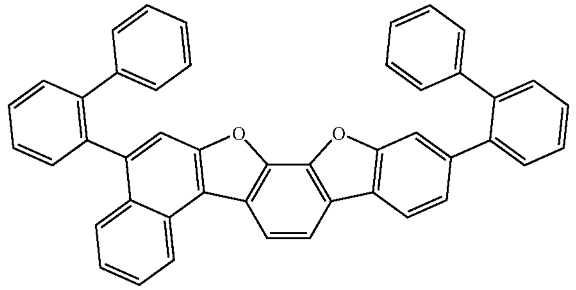
(41)
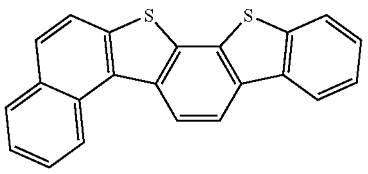

-continued
(42)
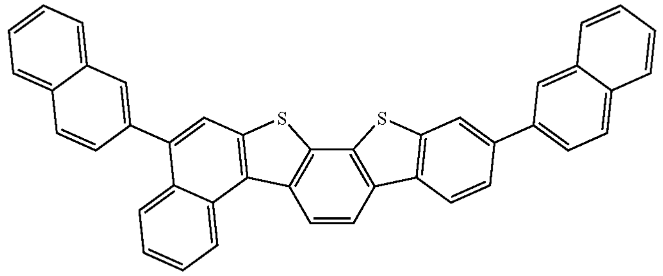
(43)
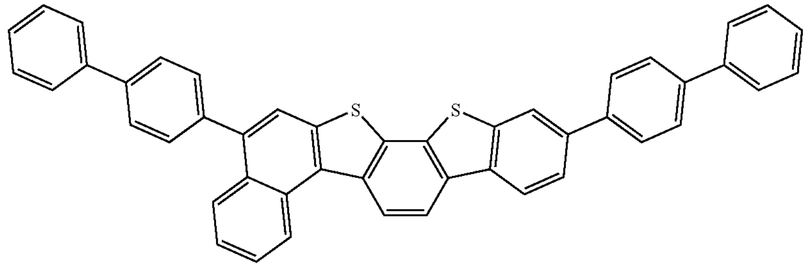
(44)
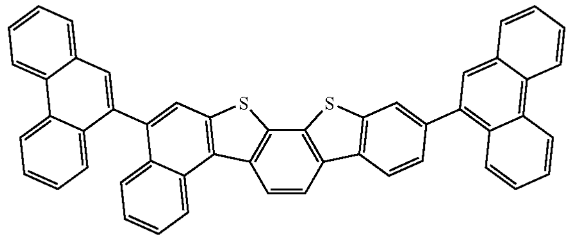
(45)
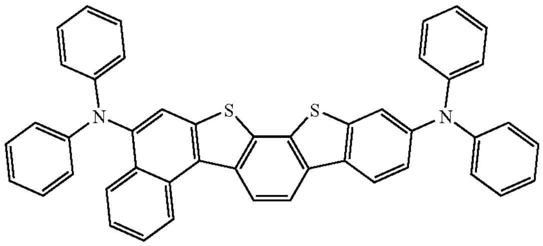
(46)
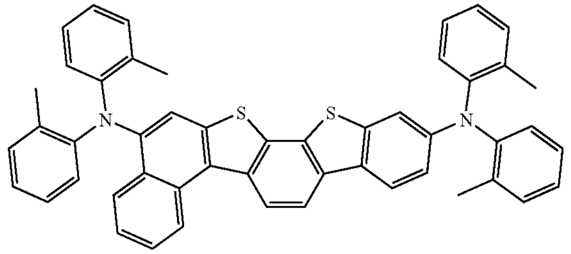
(47)
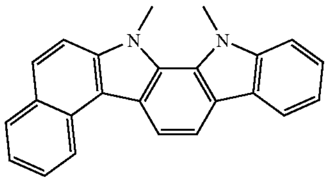
(48)
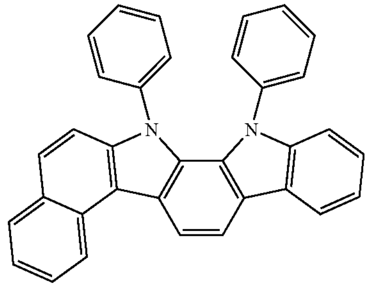
(49)
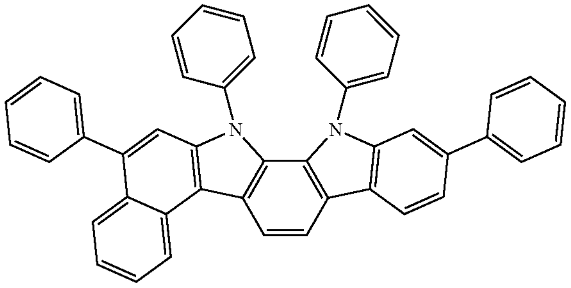

-continued
(50)
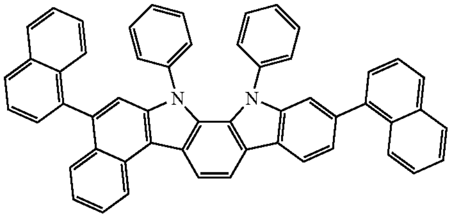
(51)
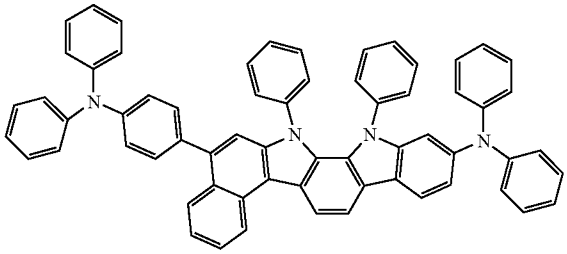
(52)
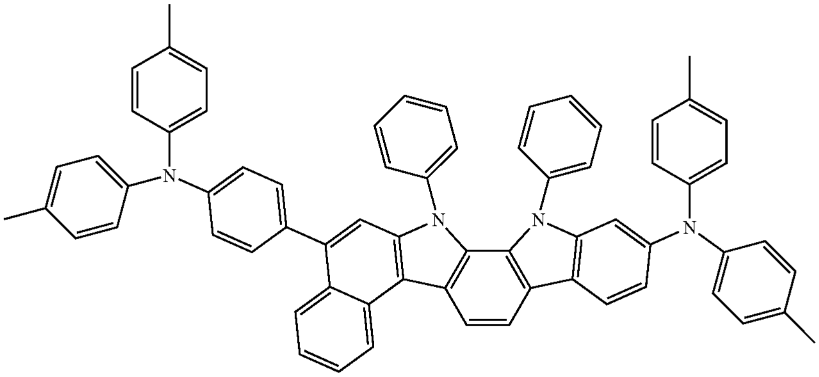
(53)
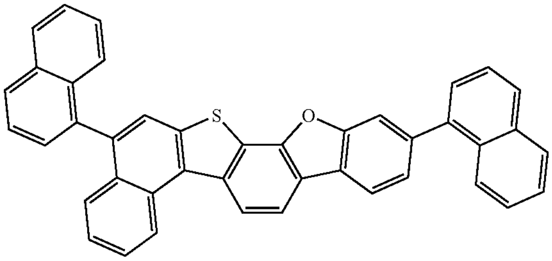
(54)
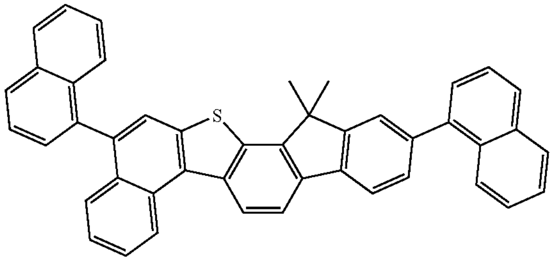
(55)
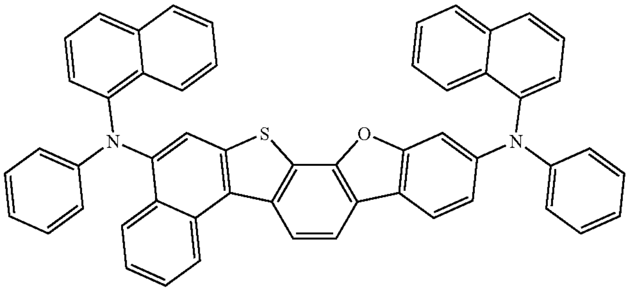
(56)
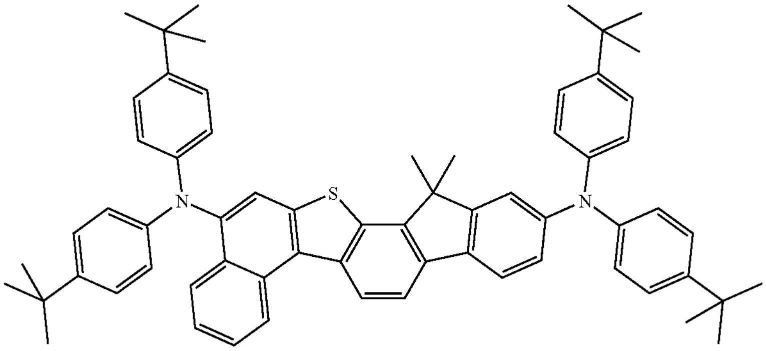

-continued
(57)
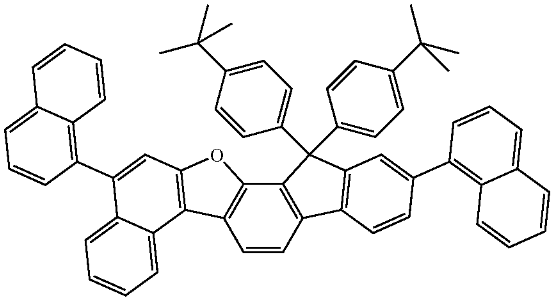
(58)
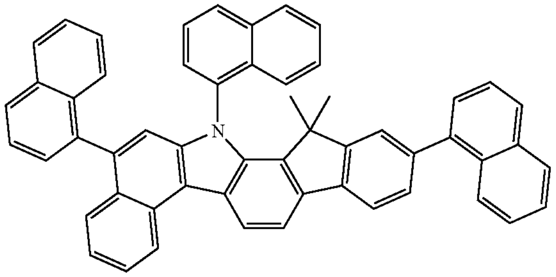
(59)
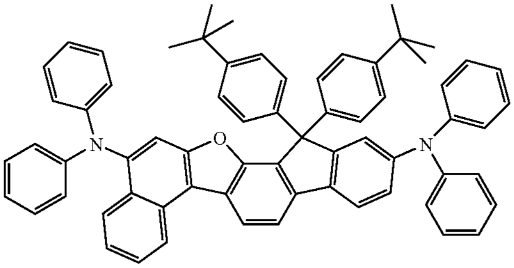
(60)
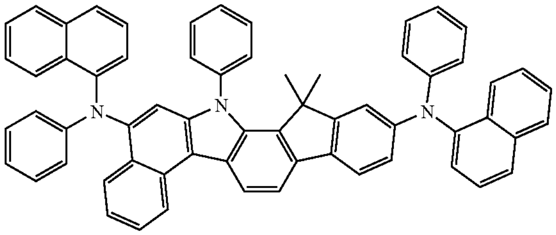
(61)
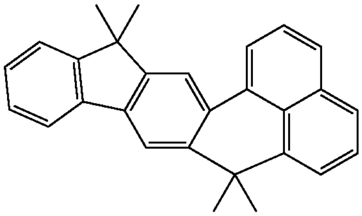
(62)
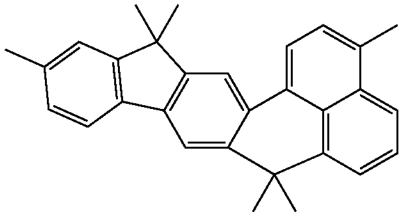
(63)
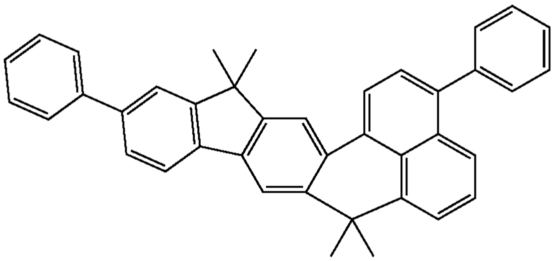
(64)
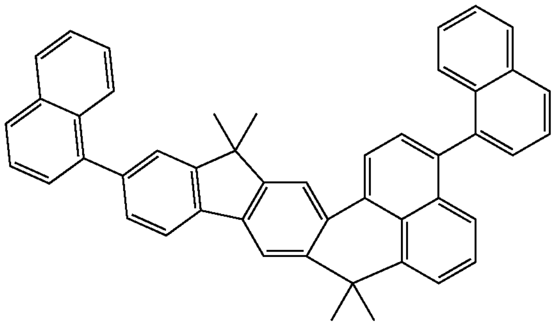
(65)
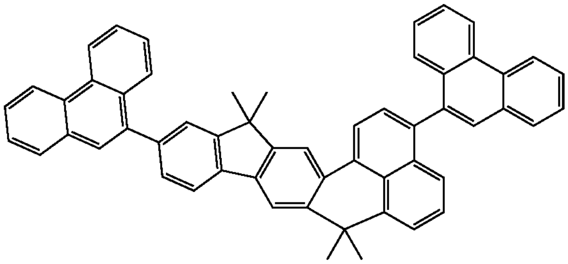
(66)
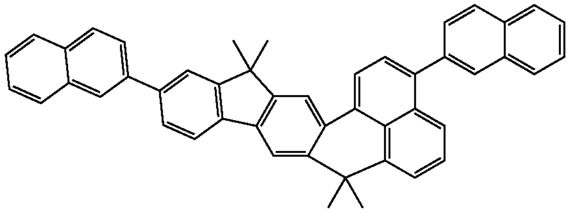

-continued
(67)
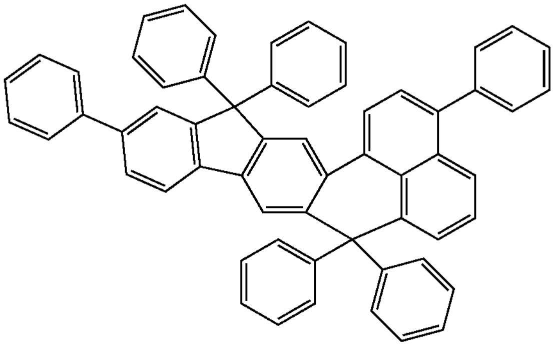
(68)
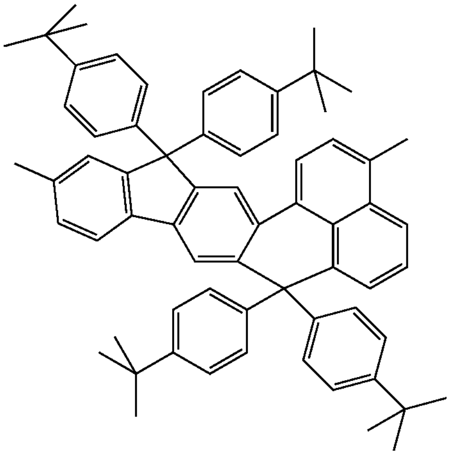
(69)
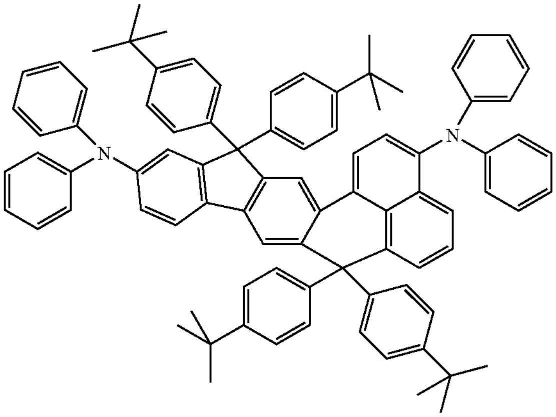
(70)
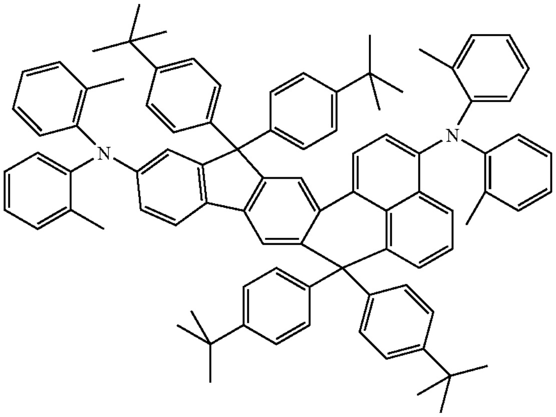
(71)
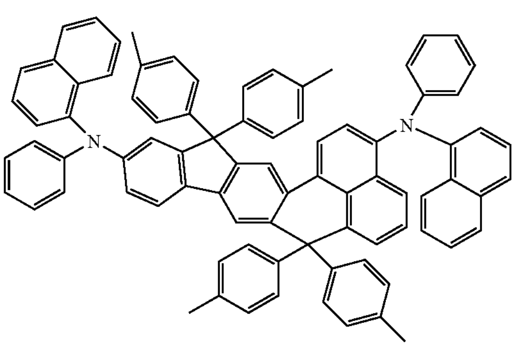
(72)
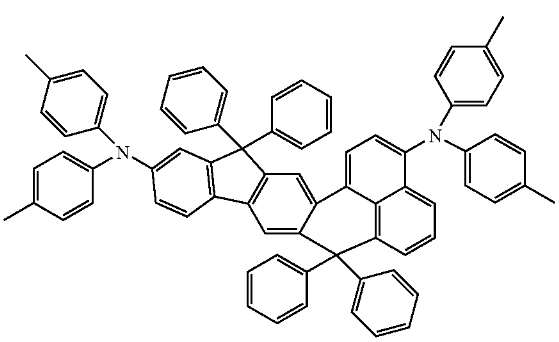

-continued
(73)
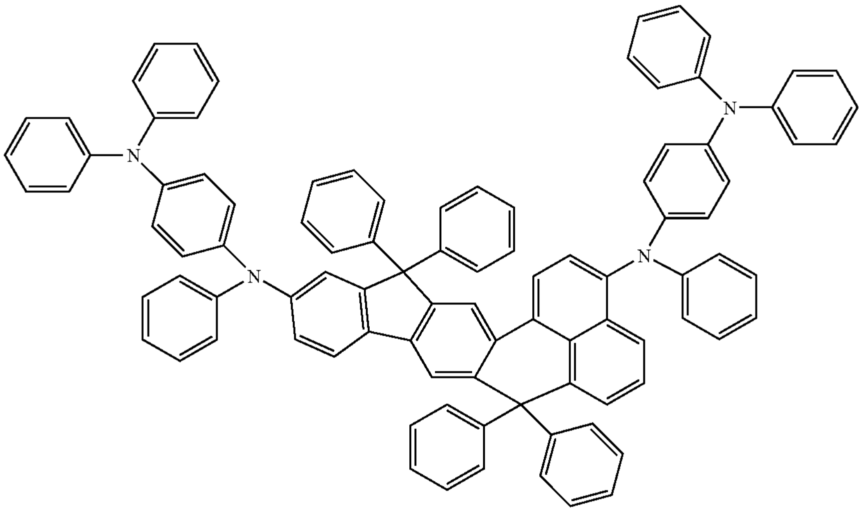
(74)
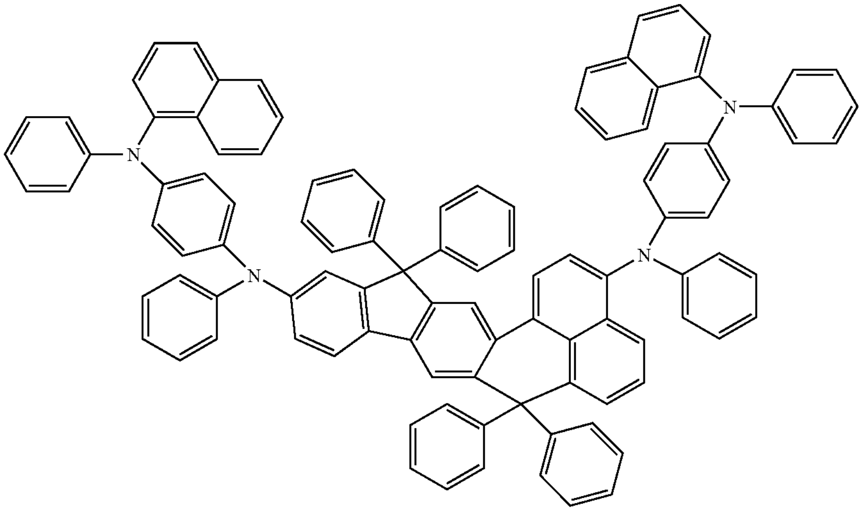
(75)
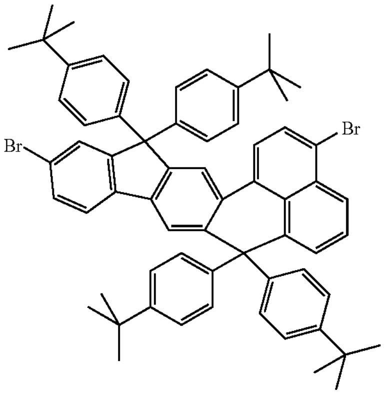
(76)
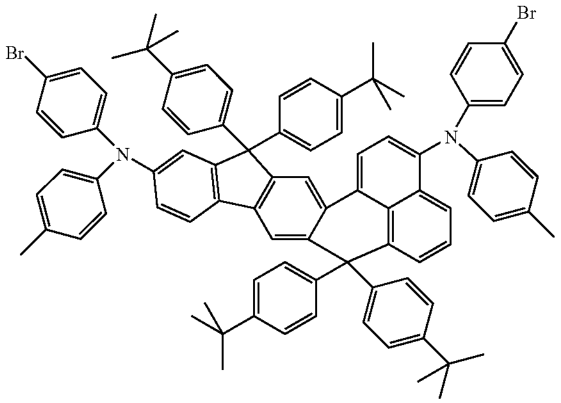

-continued
(77)
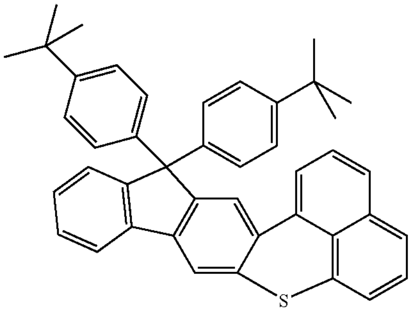
(78)
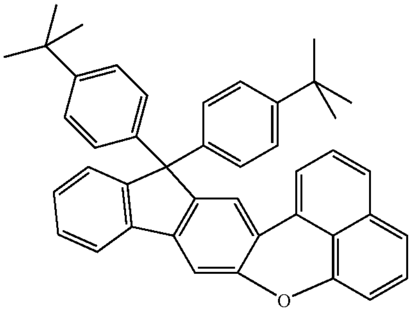
(79)
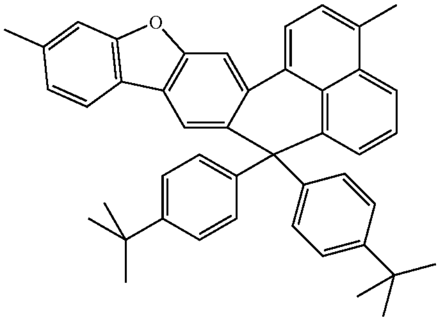
(80)
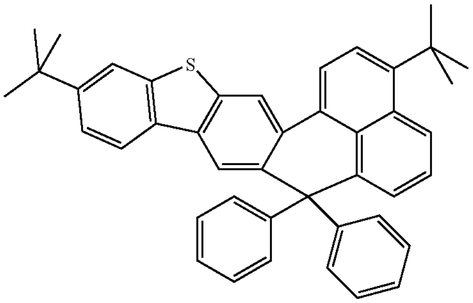
(81)
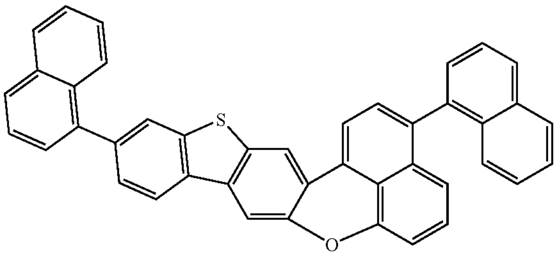
(82)
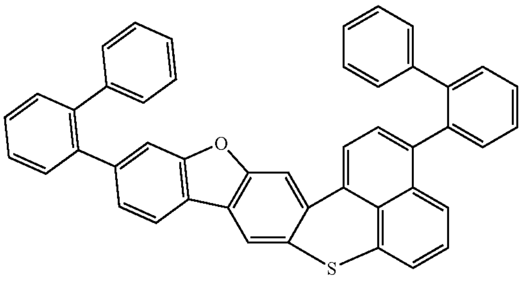
(83)
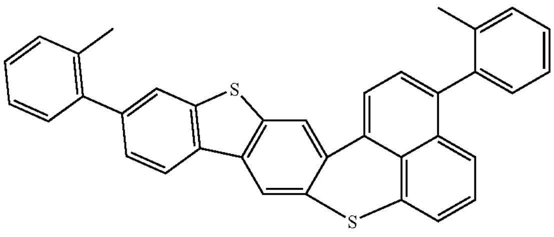
(84)
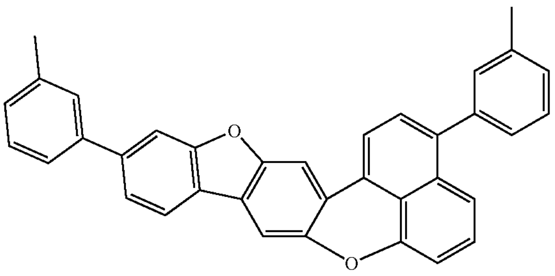
(85)
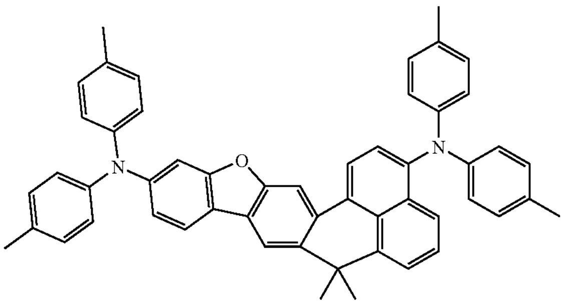
(86)
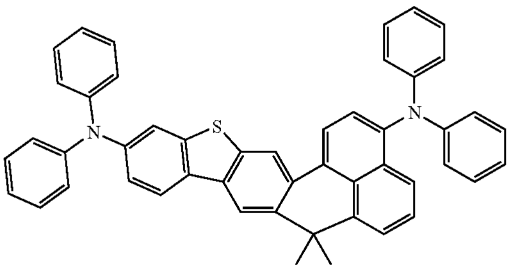

-continued
(87)
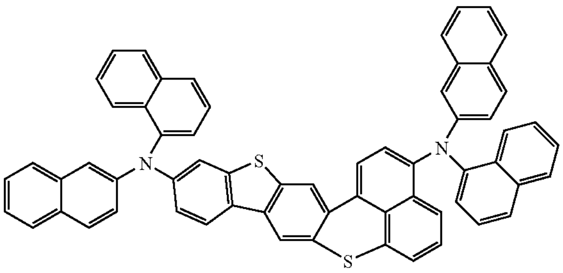
(88)
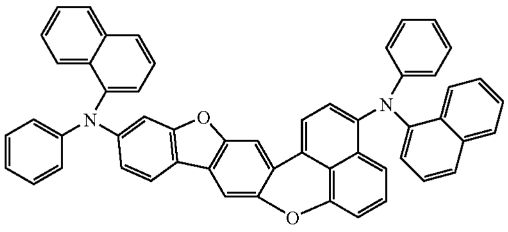
(89)
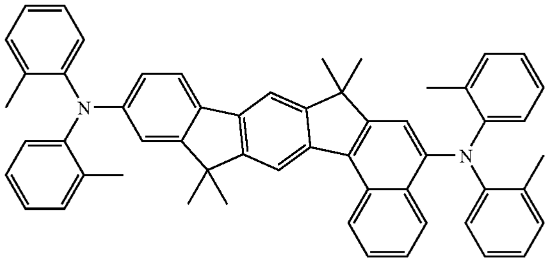
(90)
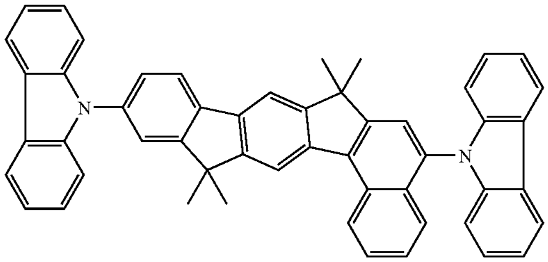
(91)
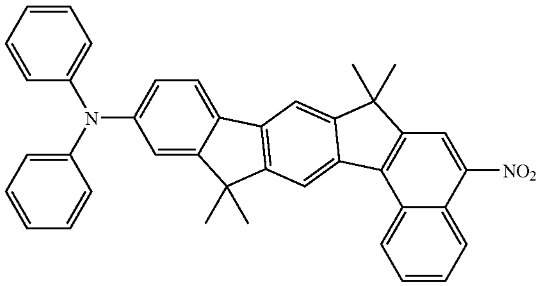
(92)
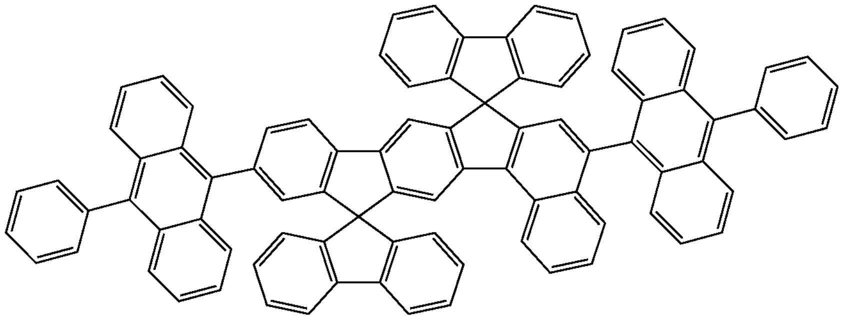
(93)
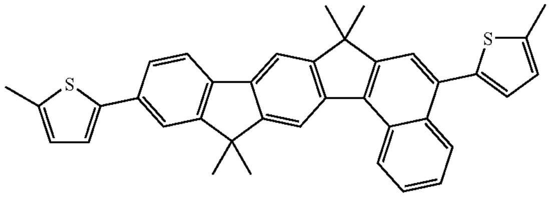
(94)
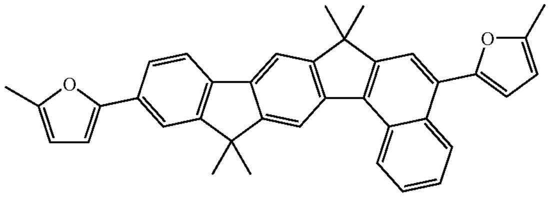

-continued
(95)
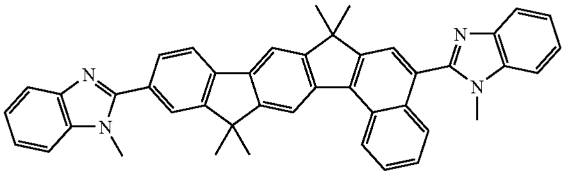
(96)
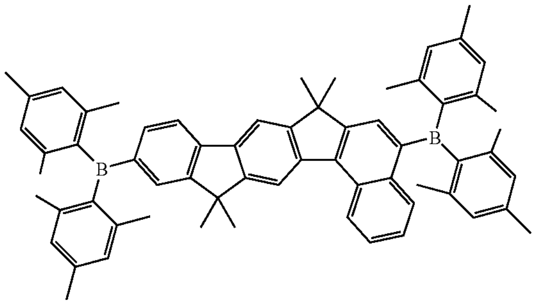
(97)
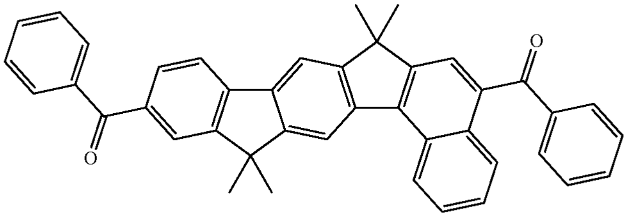
(98)
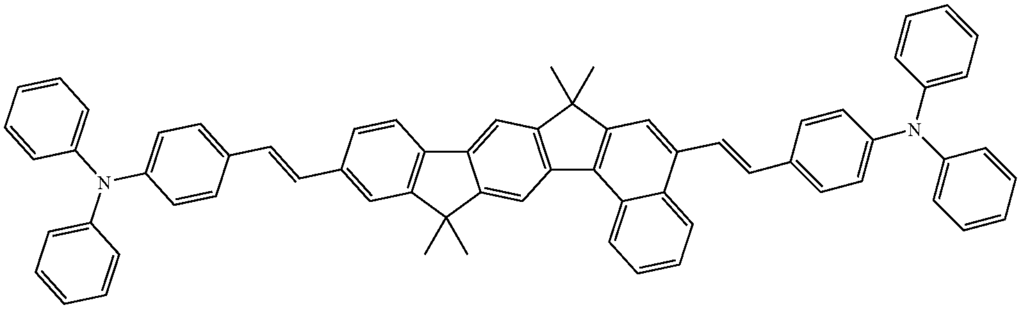
(99)
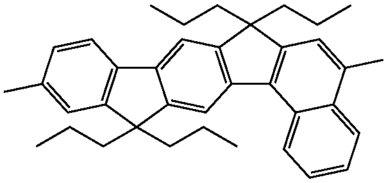
(100)
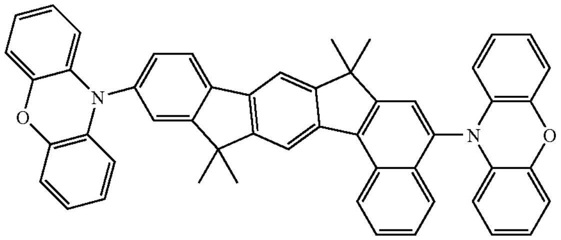
(101)
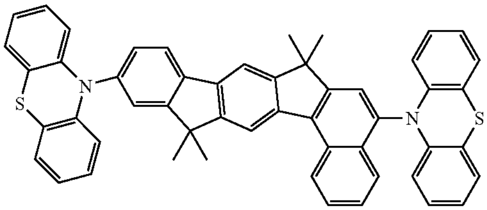
(102)
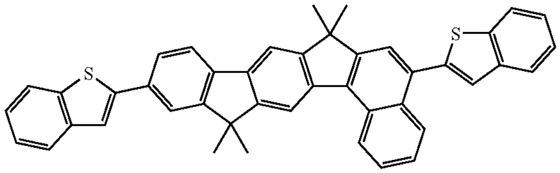
(103)
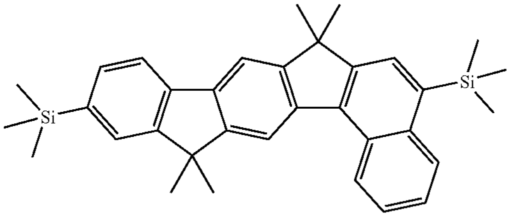

-continued
(104)
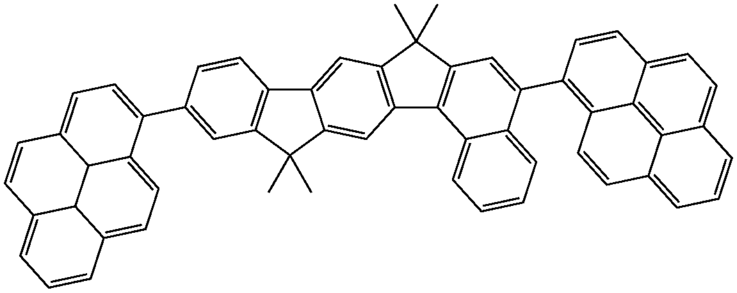
(105)
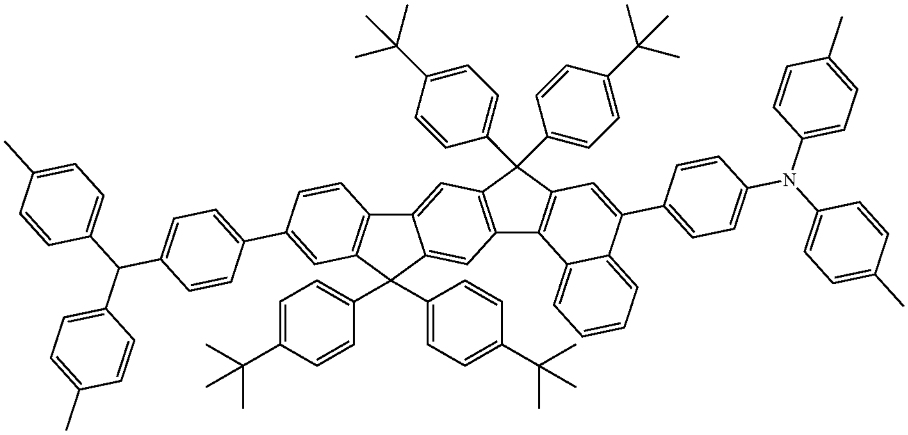
(106)
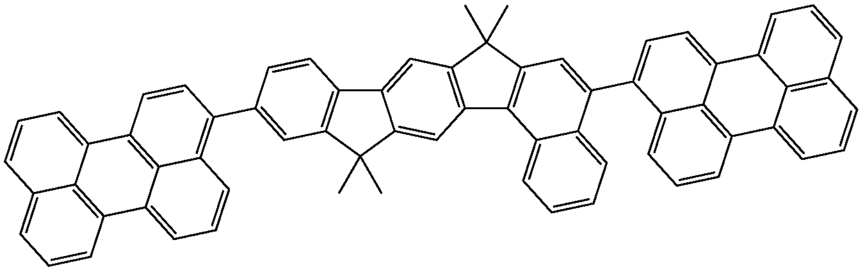
(107)
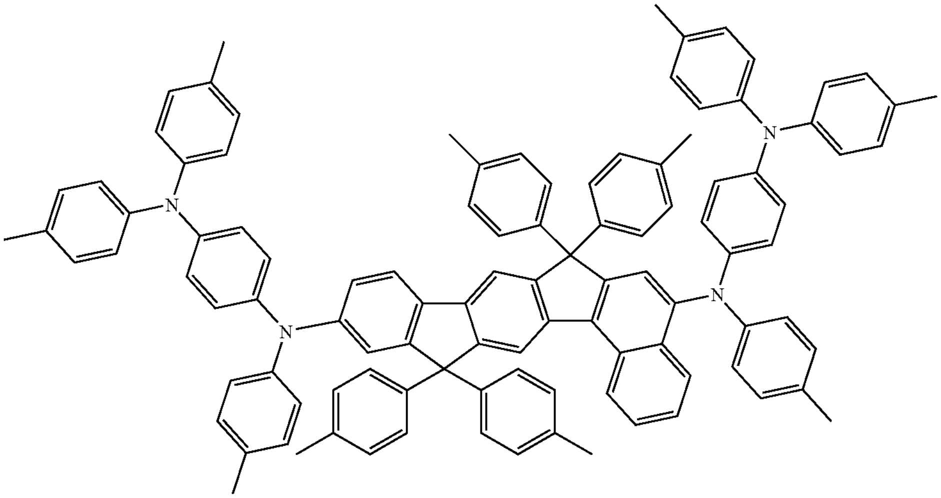

-continued
(108)
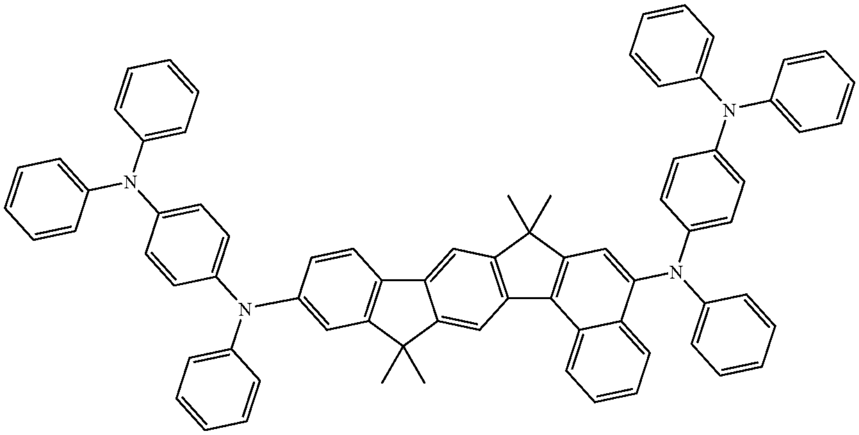
(109)
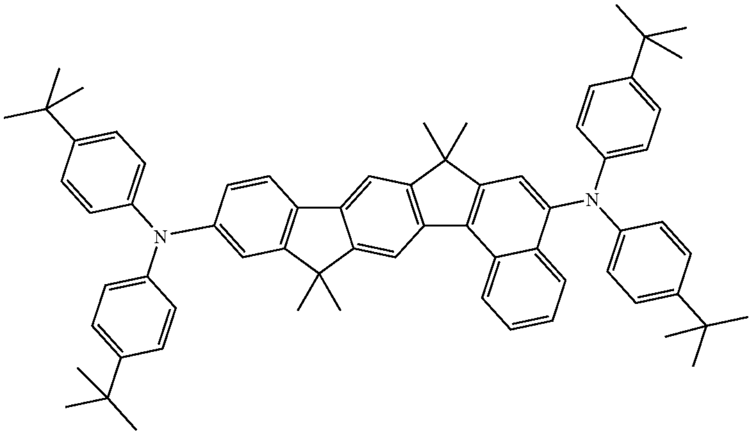
(110)
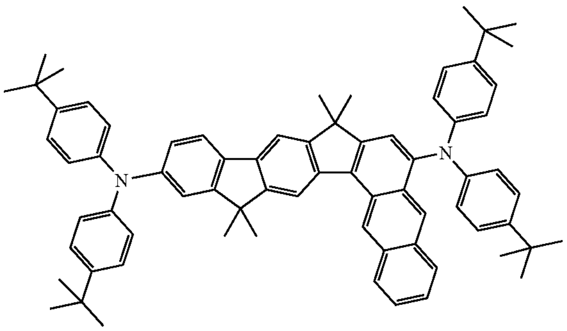
(111)
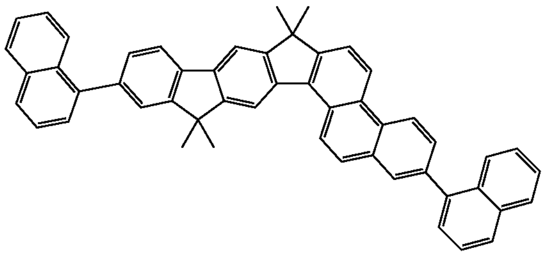
(112)
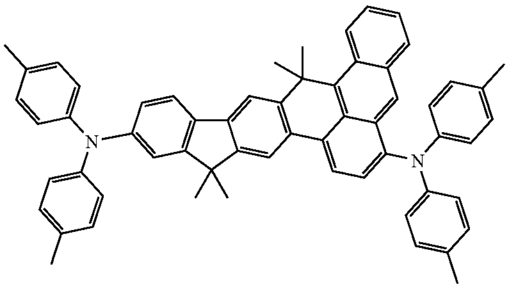
(113)
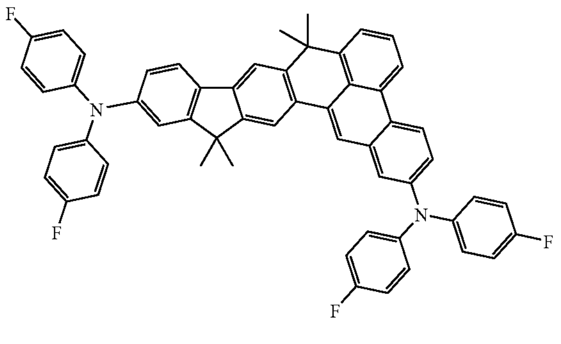

-continued
(114)
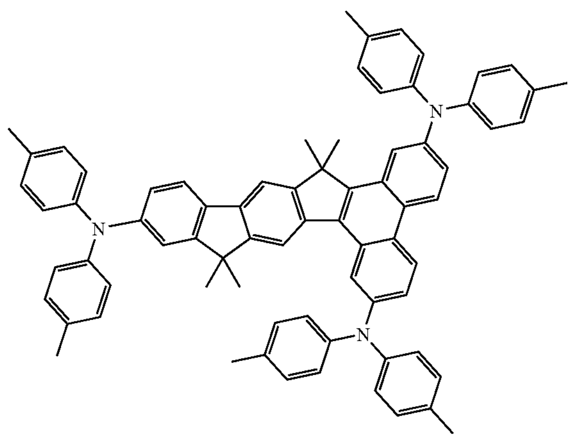
(115)
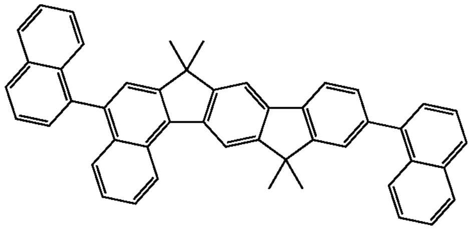
(116)
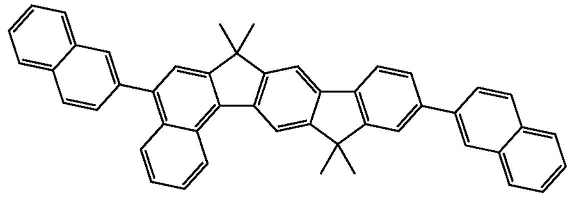
(117)
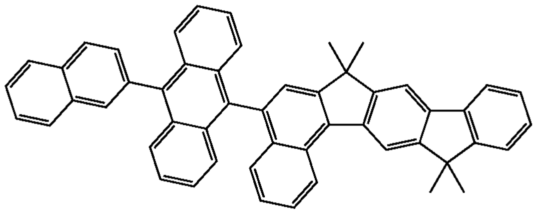
(118)
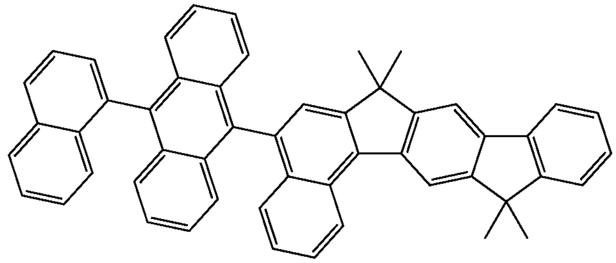
(119)
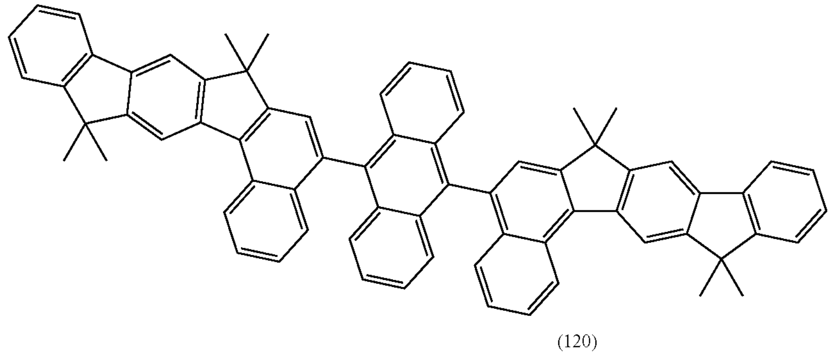
(120)
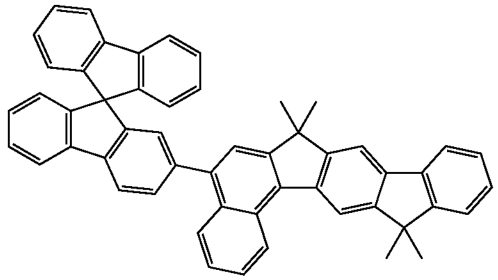
(121)
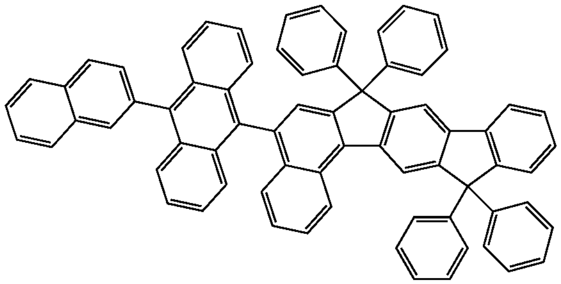

-continued
(122)
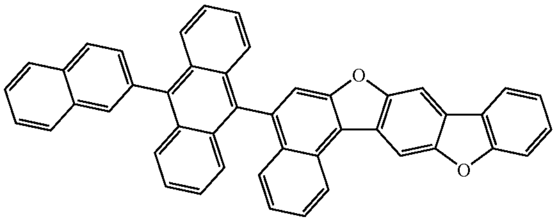
(123)
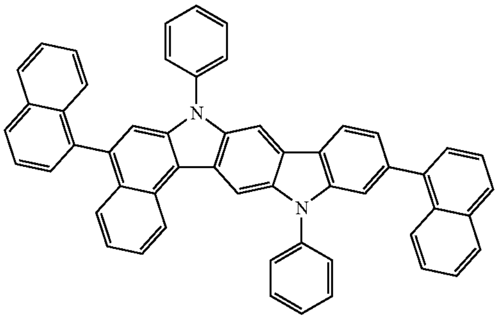
(124)
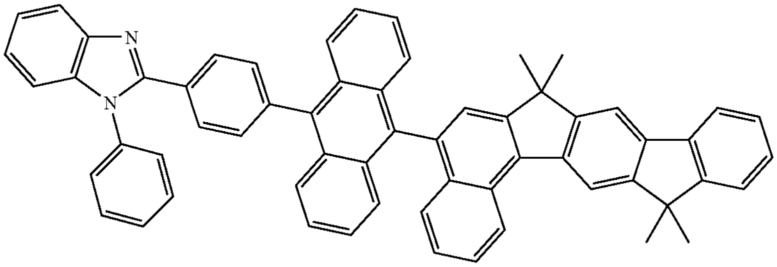
(125)
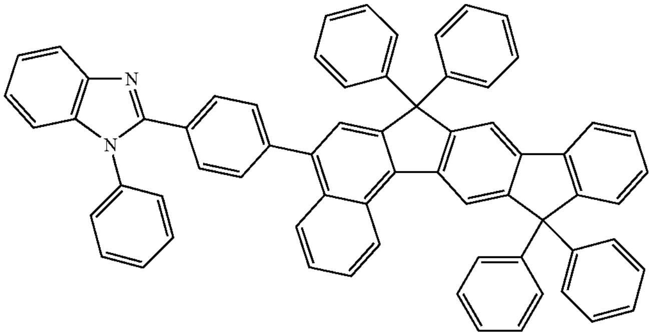
(126)
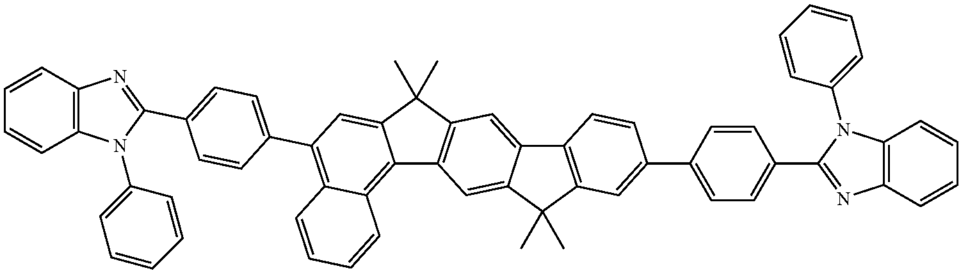

-continued
(127)
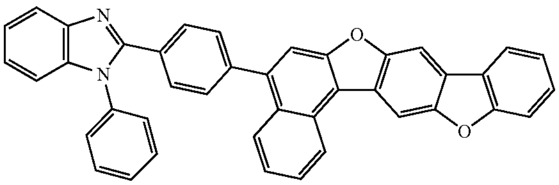
(128)
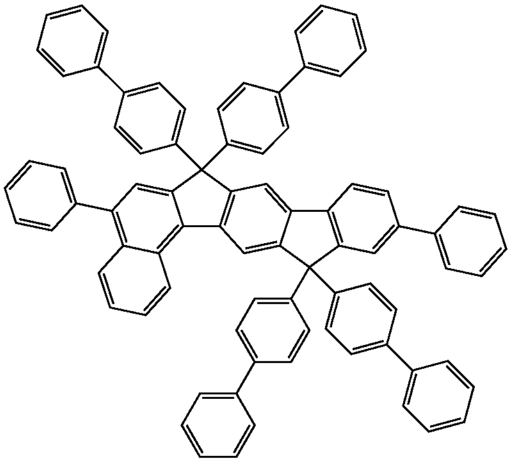
(129)
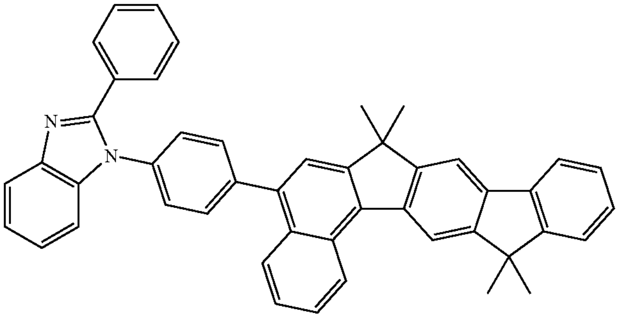
(130)
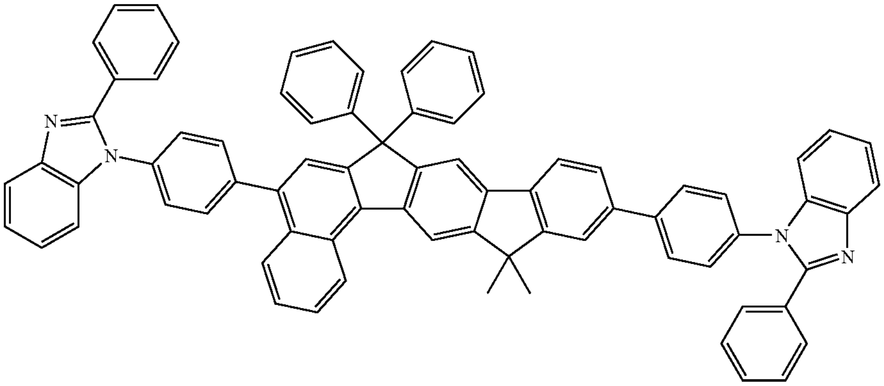
(131)
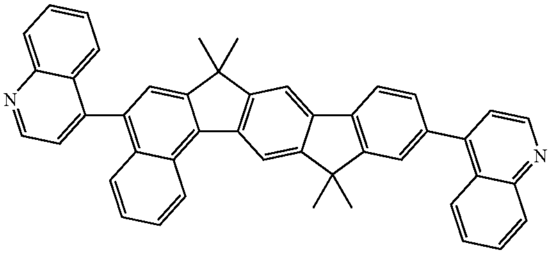
(132)
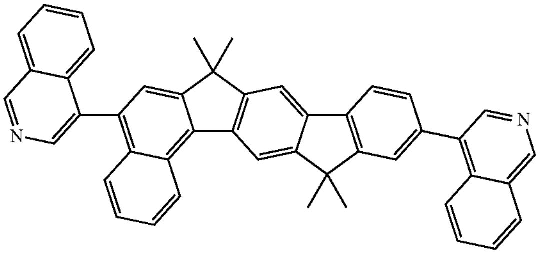

-continued
(133)
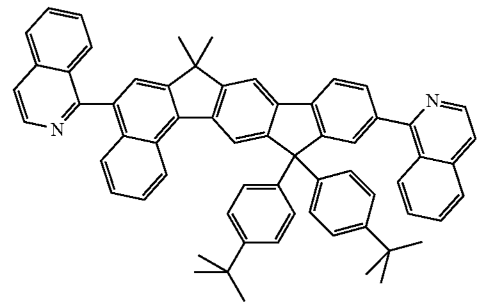
(134)
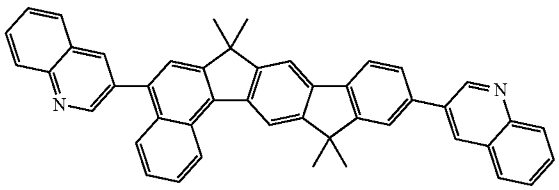
(135)
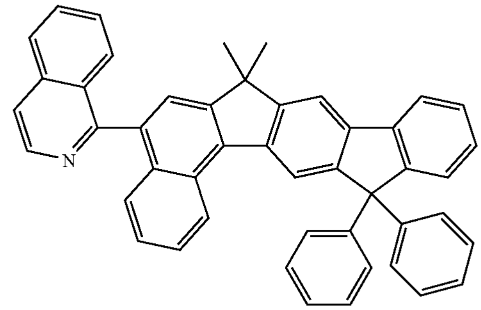
(136)
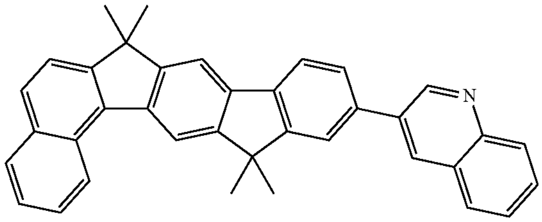
(137)
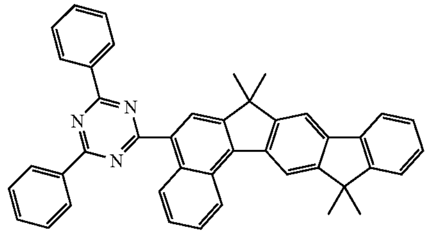
(138)
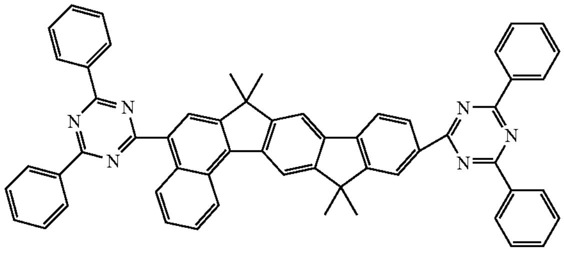
(139)
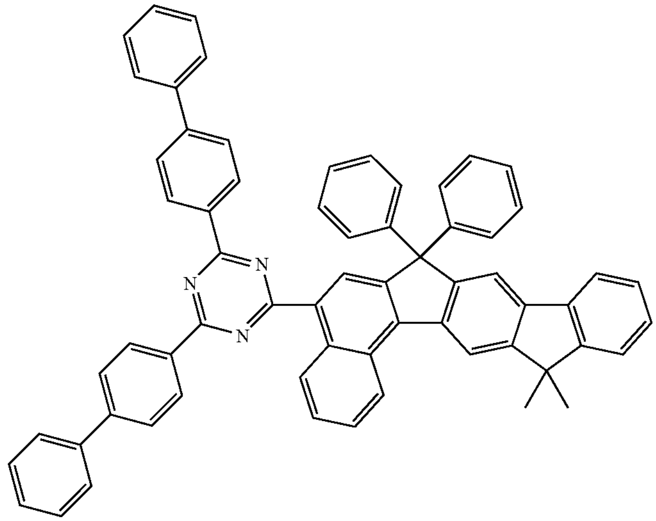

-continued
(140)
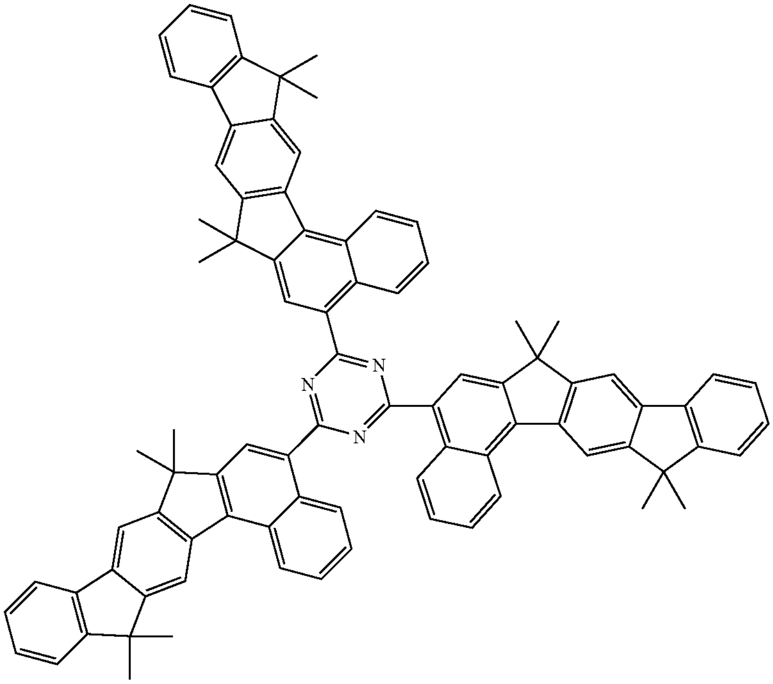
(141)
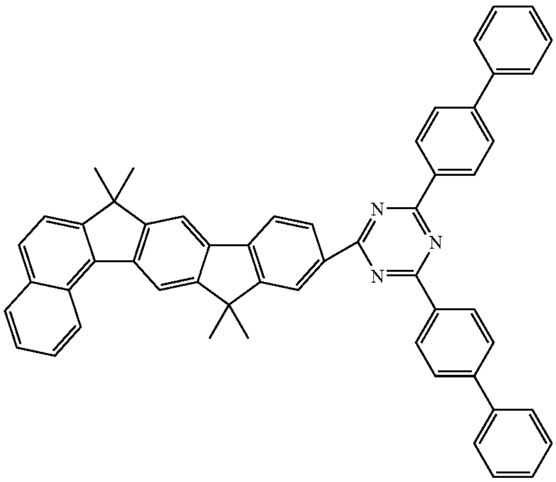
(142)
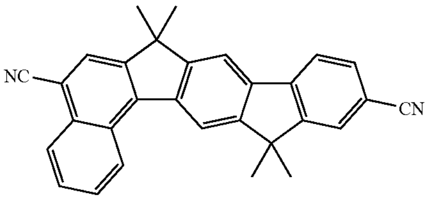
(143)
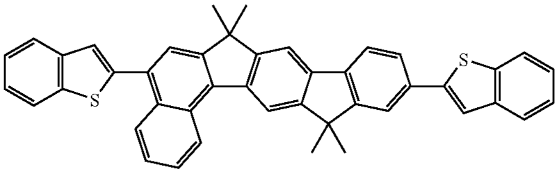
(144)
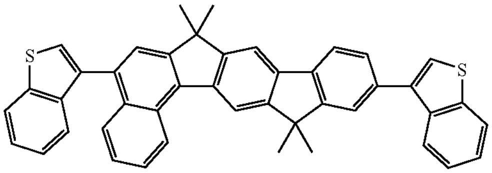

-continued
(145)
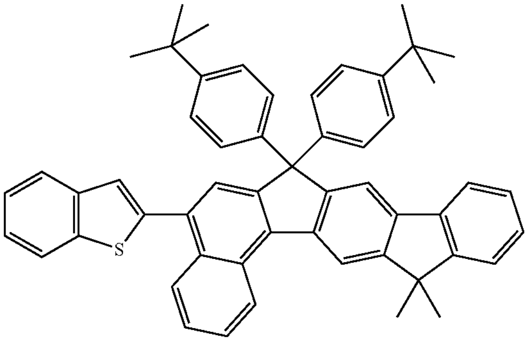
(146)
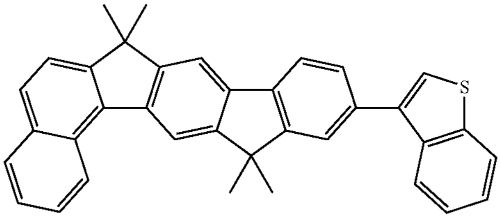
(147)
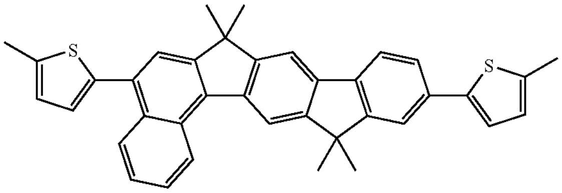
(148)
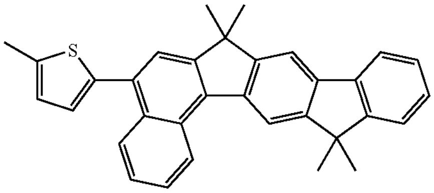
(149)
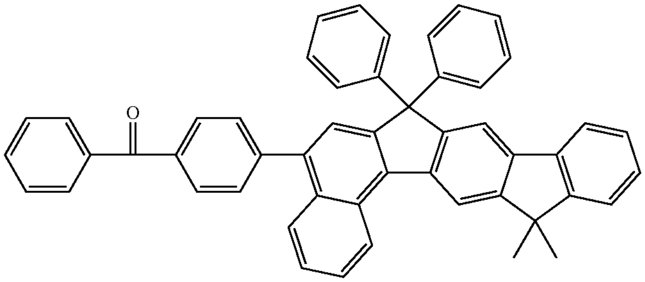
(150)
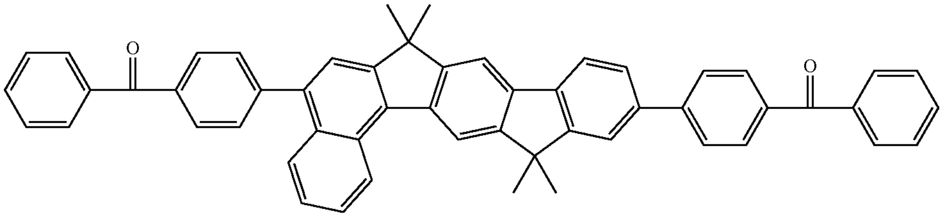
(151)
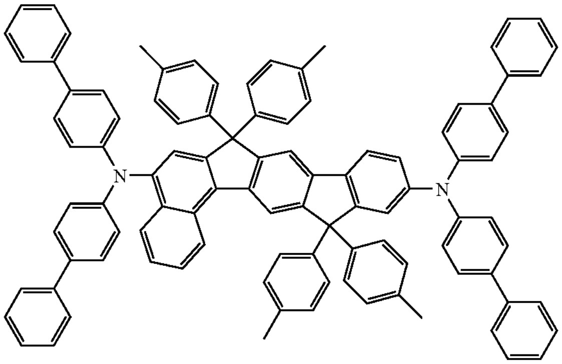
(152)
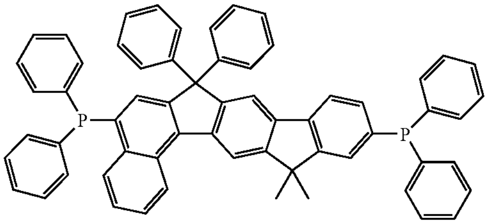

-continued
(153)
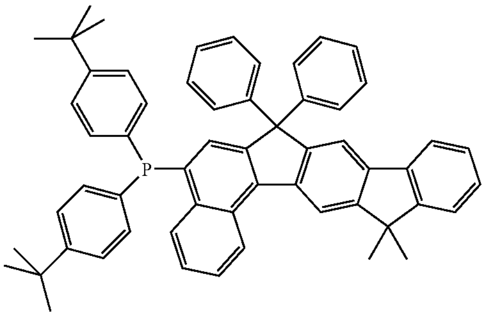
(154)
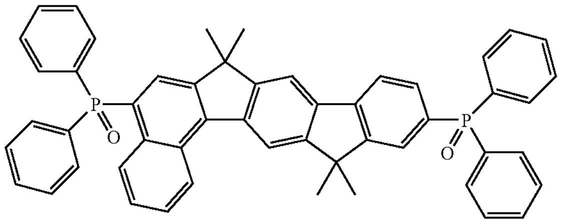
(155)
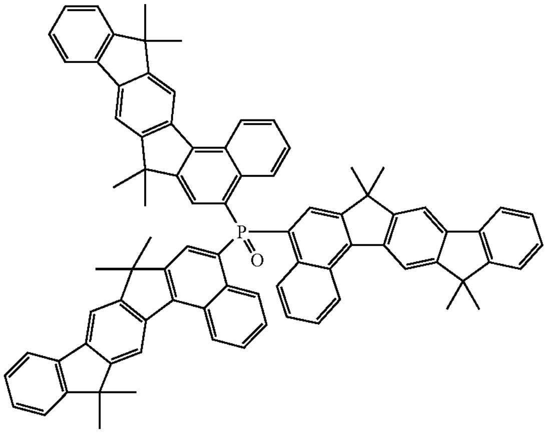
(156)
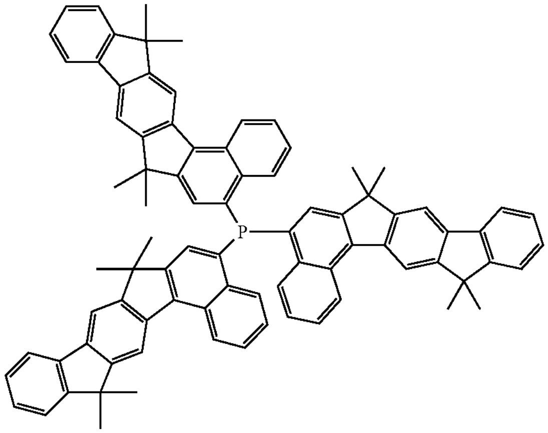
(157)
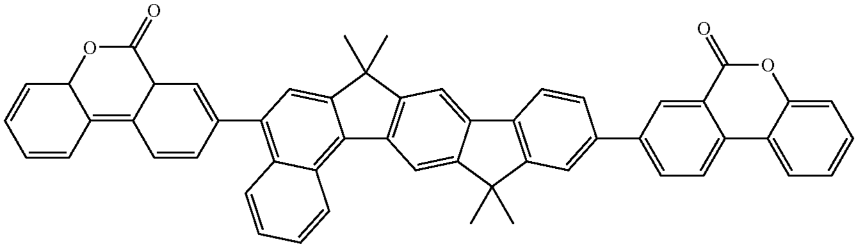
(158)
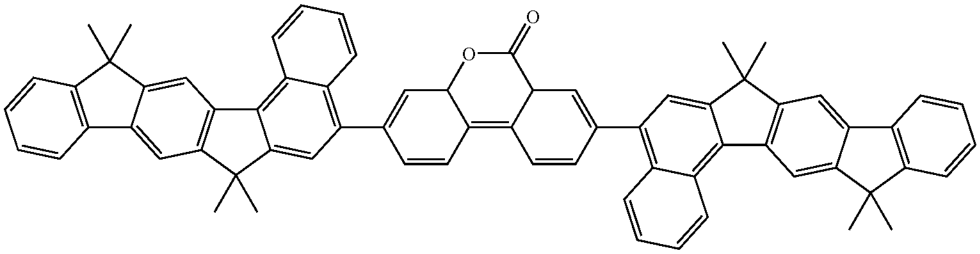
(159)
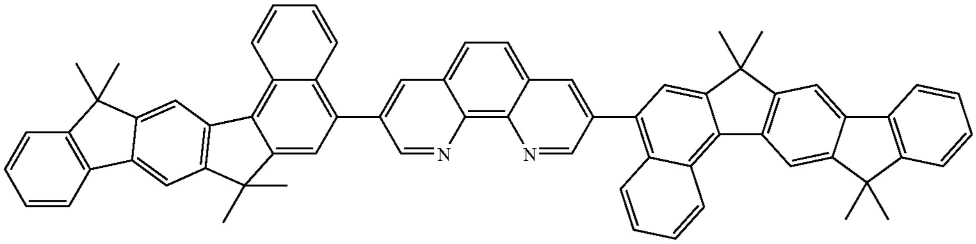

-continued
(160)
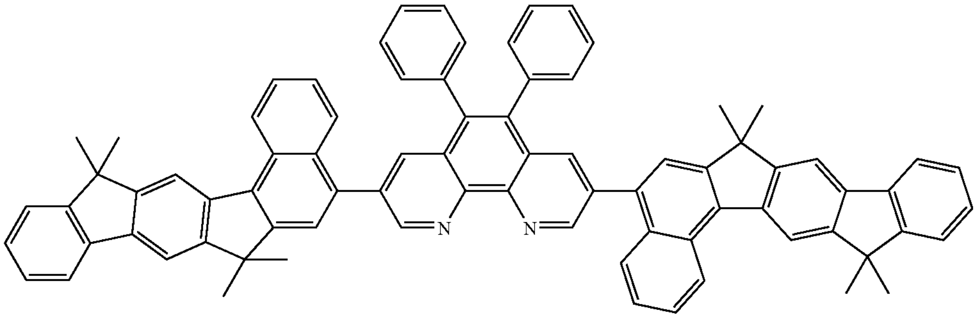
(161)
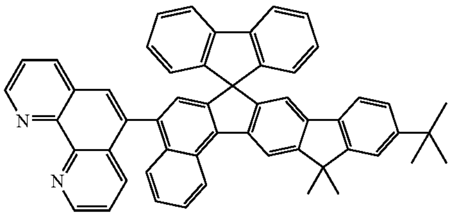
(162)
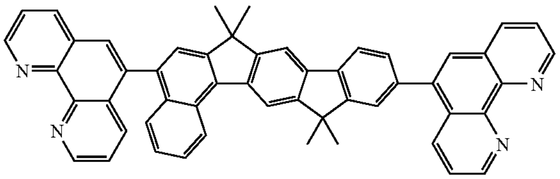
(163)
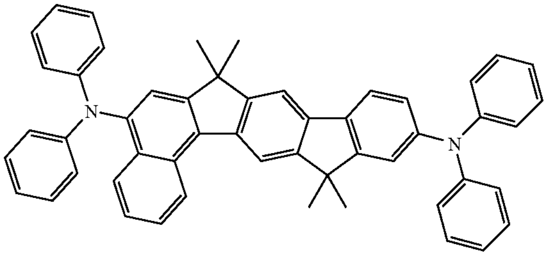
(164)
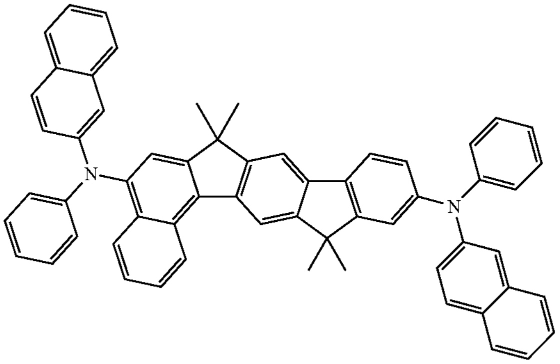
(165)
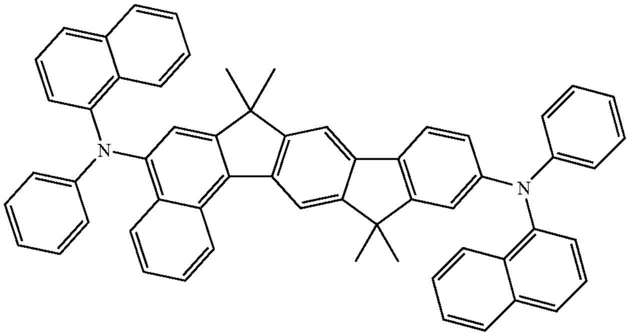
(166)
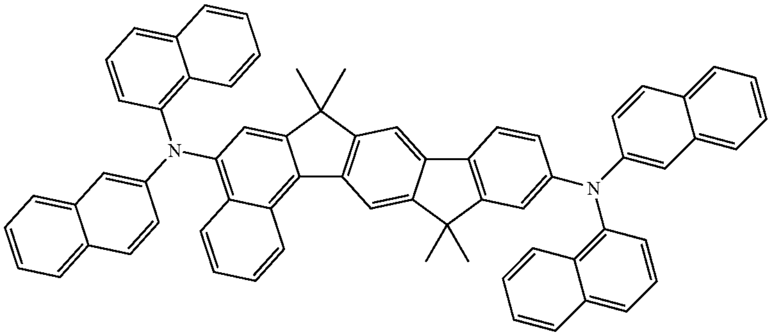

-continued
(167)
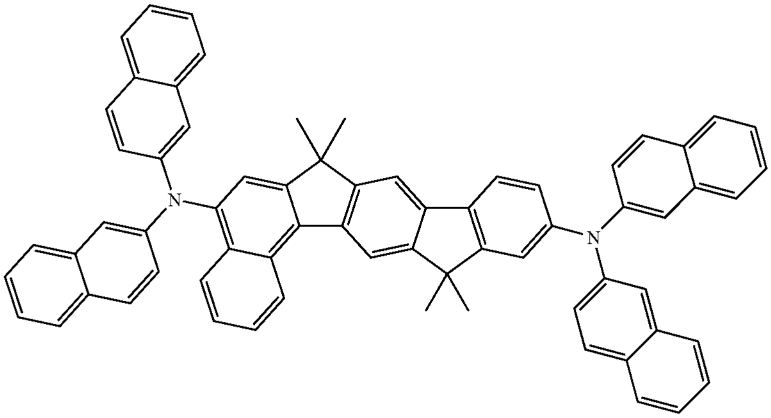
(168)
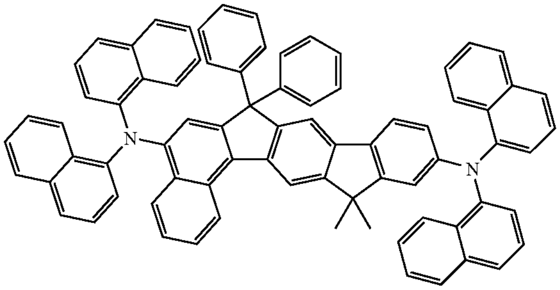
(169)
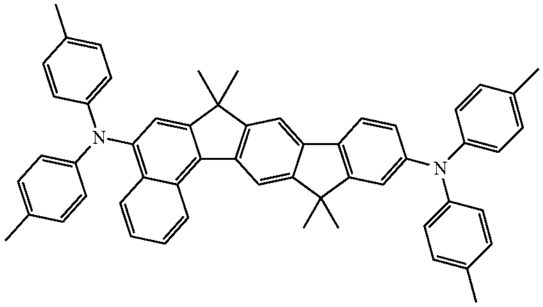
(170)
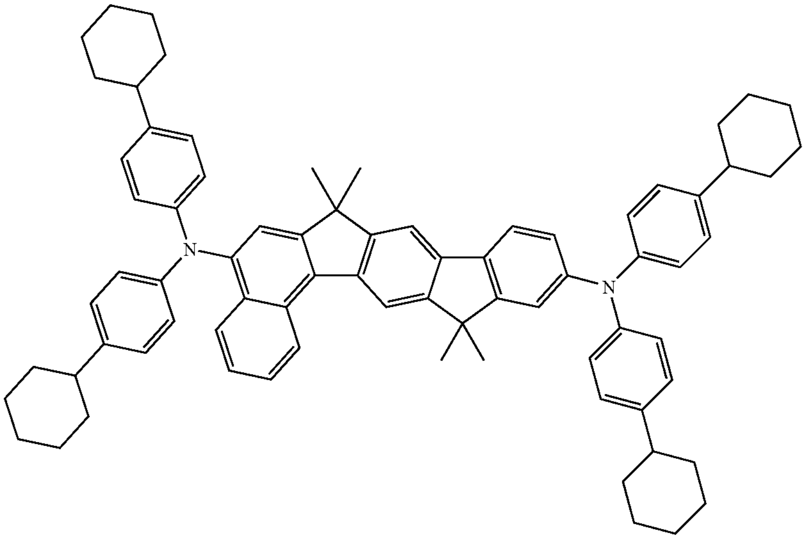
(171)
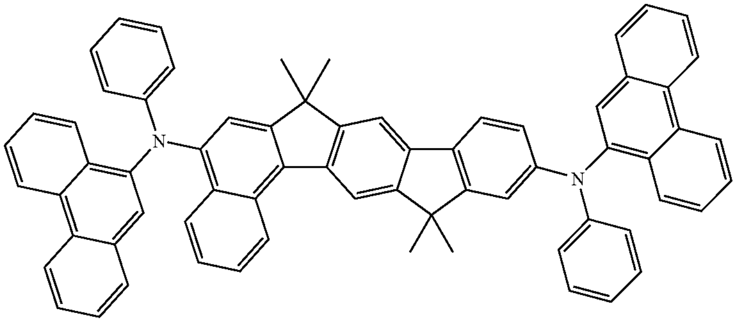

-continued
(172)
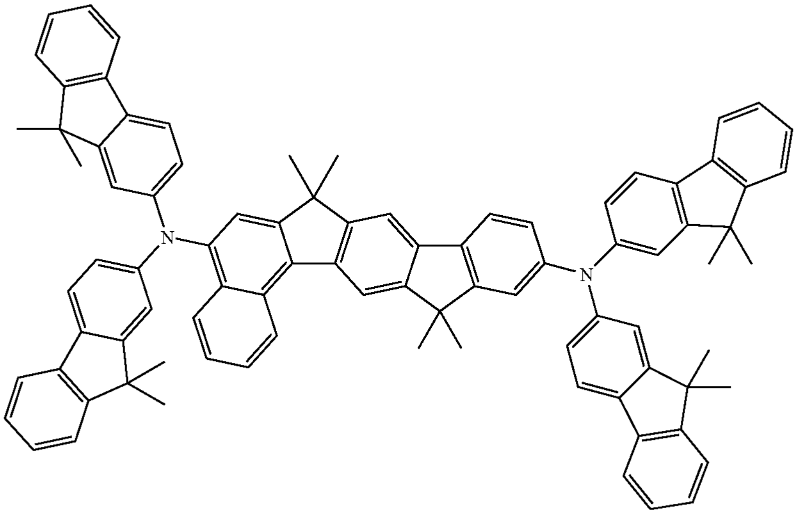
(173)
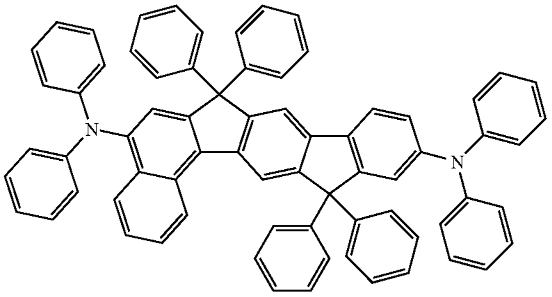
(174)
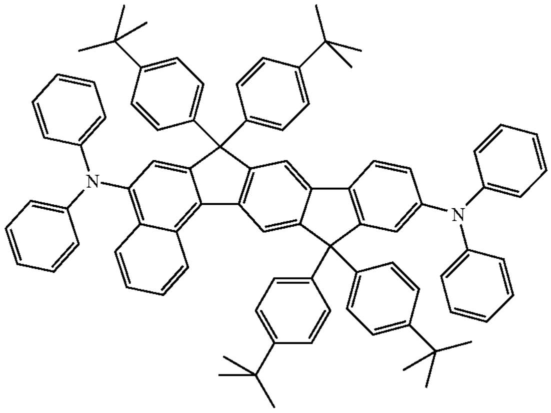
(175)
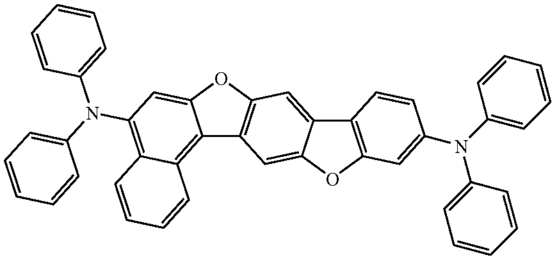
(176)
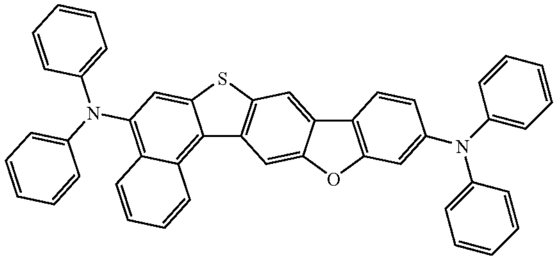
(177)
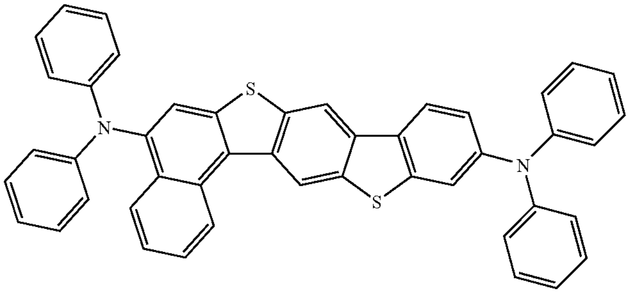

-continued
(178)
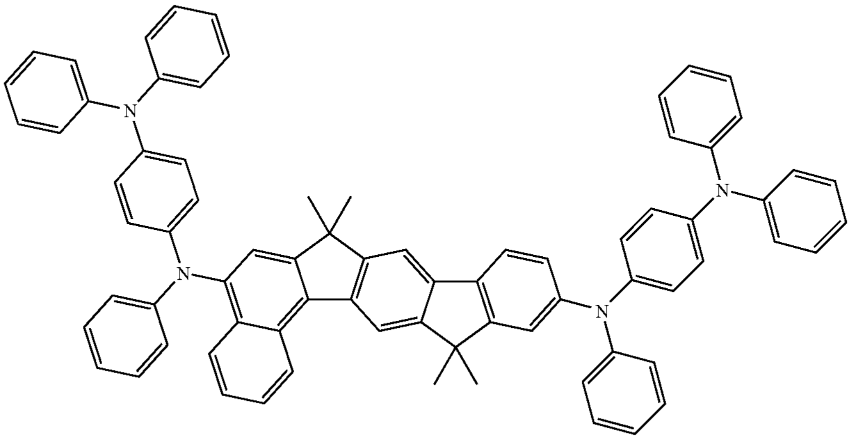
(179)
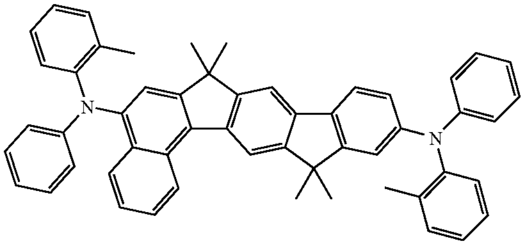
(180)
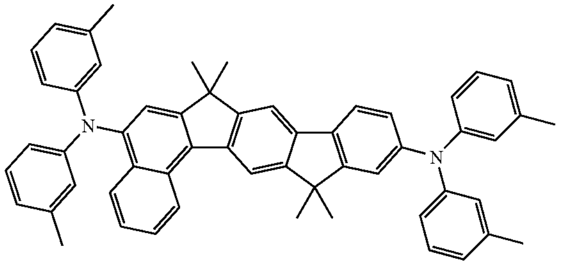
(181)
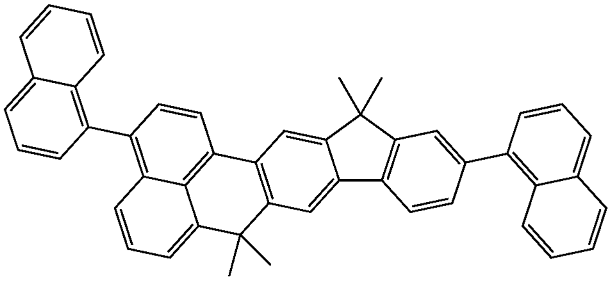
(182)
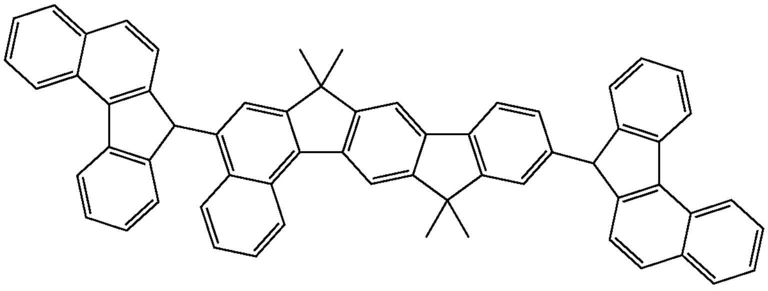

-continued
(183)
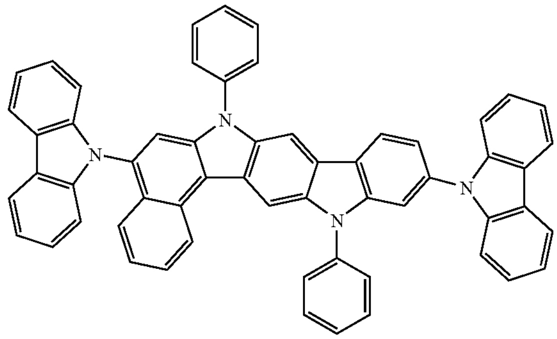
(184)
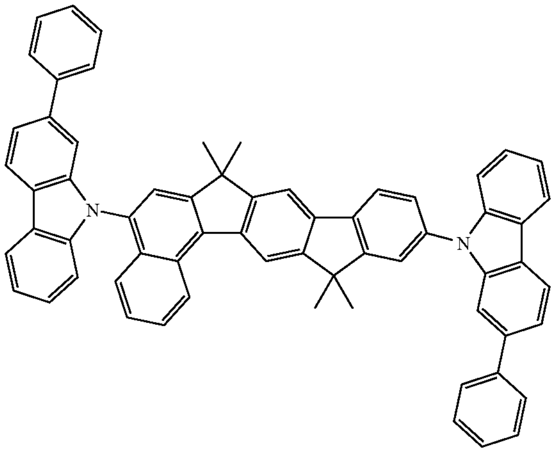
(185)
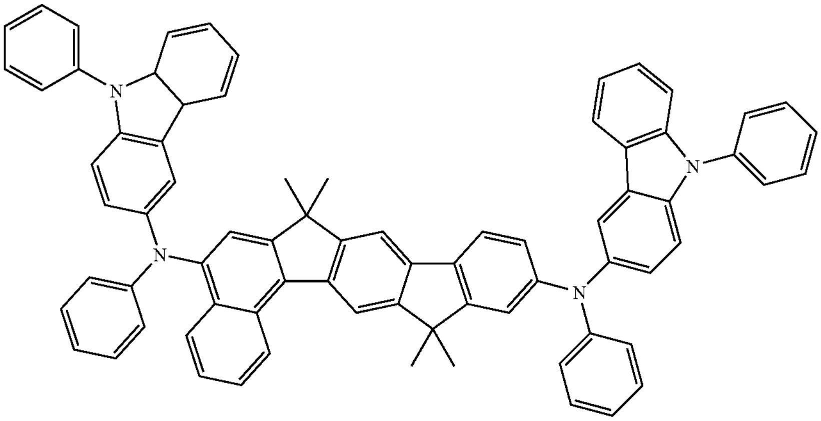
(186)
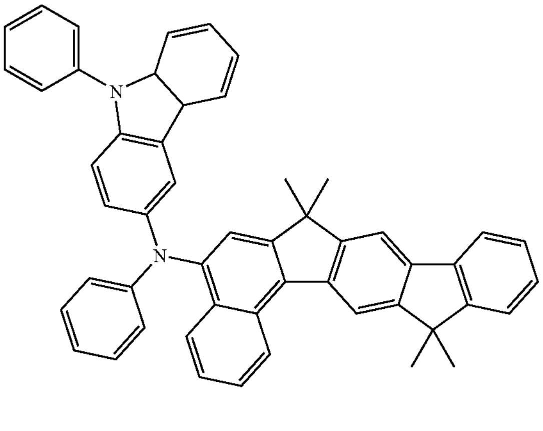
(187)
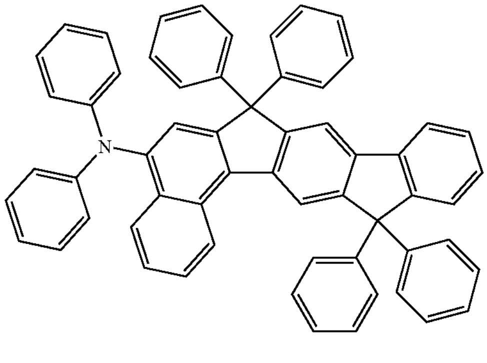

-continued
(188)
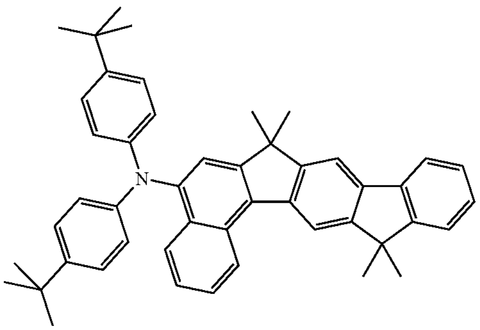
(189)
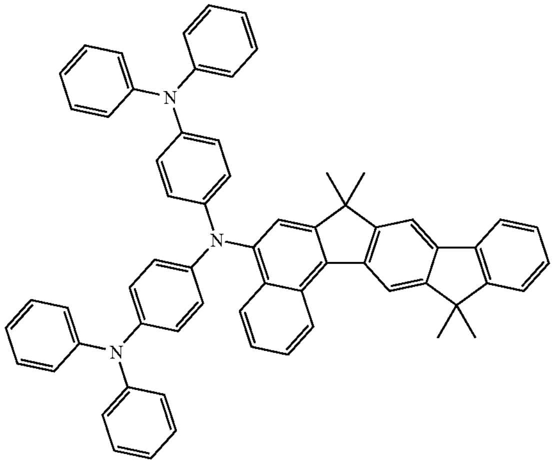
(190)
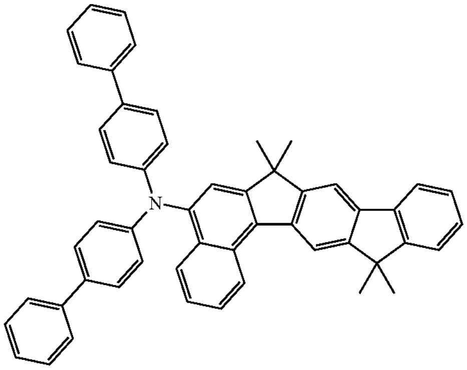
(191)
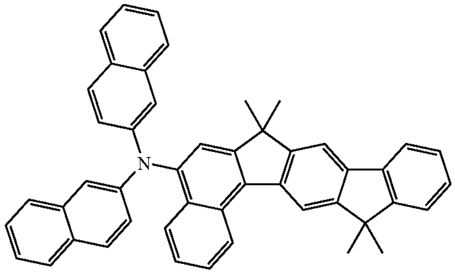
(192)
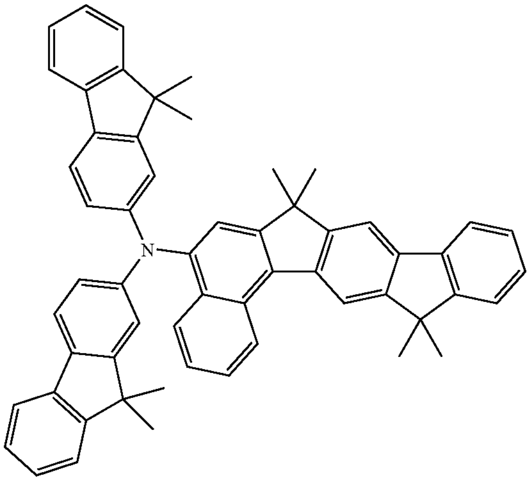
(193)
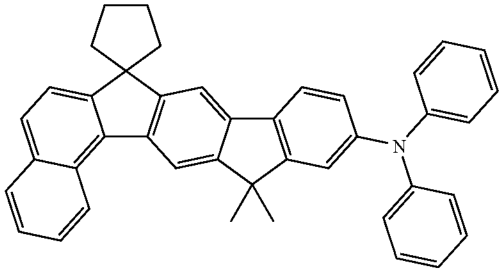

-continued
(194)
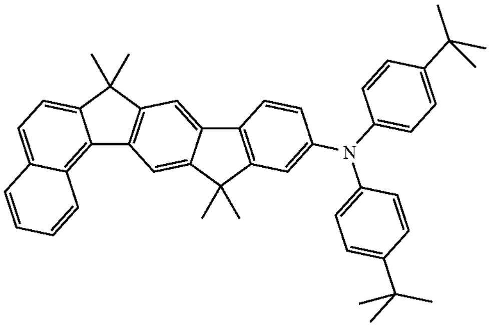
(195)
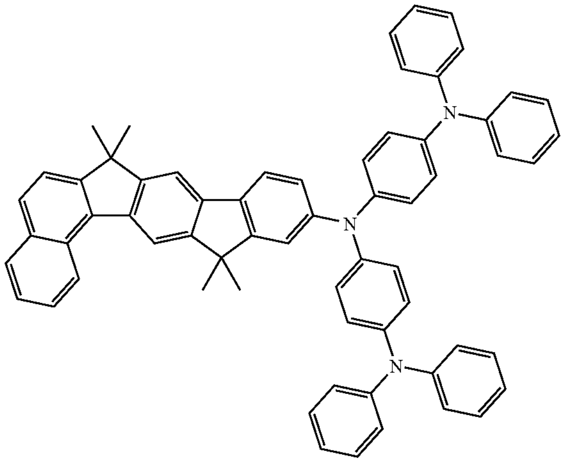
(196)
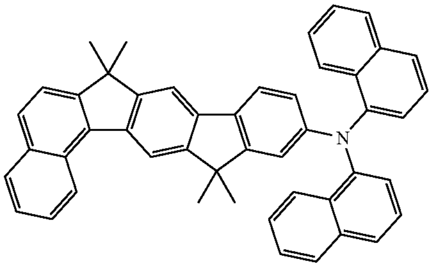
(197)
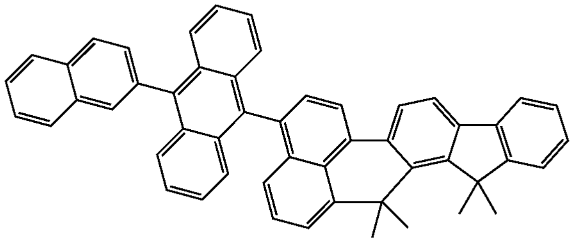
(198)
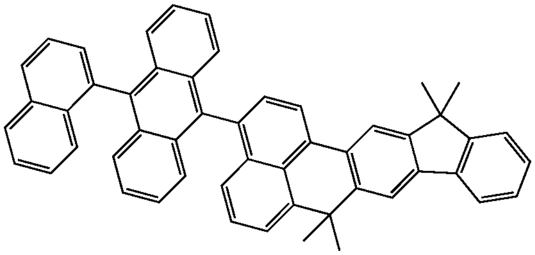
(199)
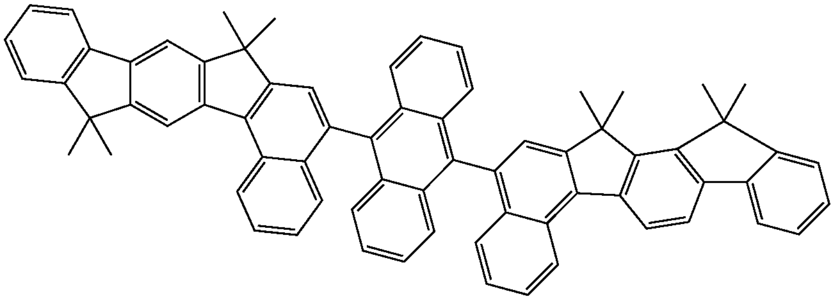

-continued
(200)
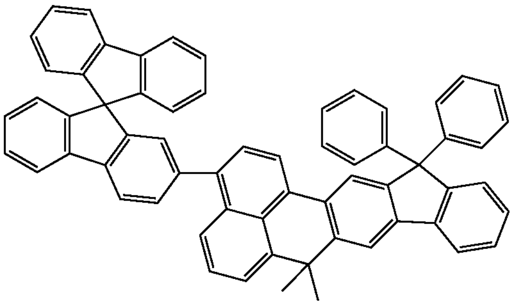
(201)
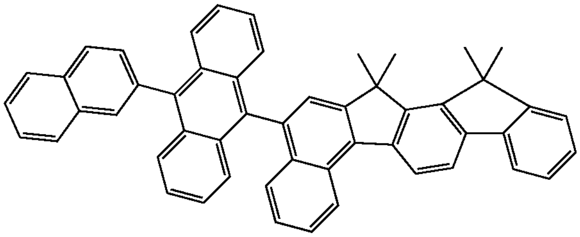
(202)
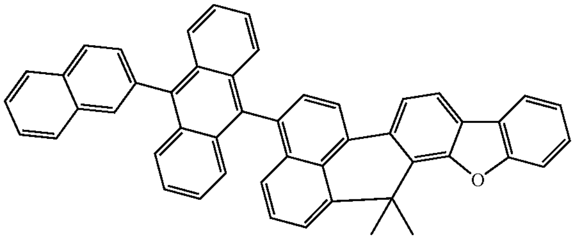
(203)
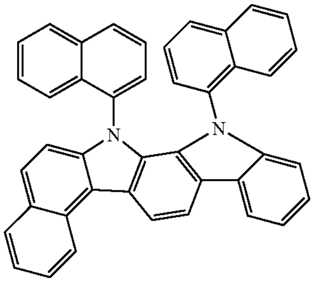
(204)
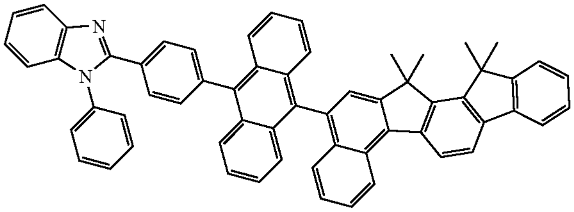
(205)
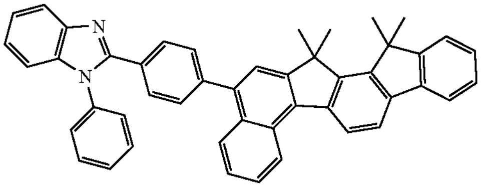
(206)
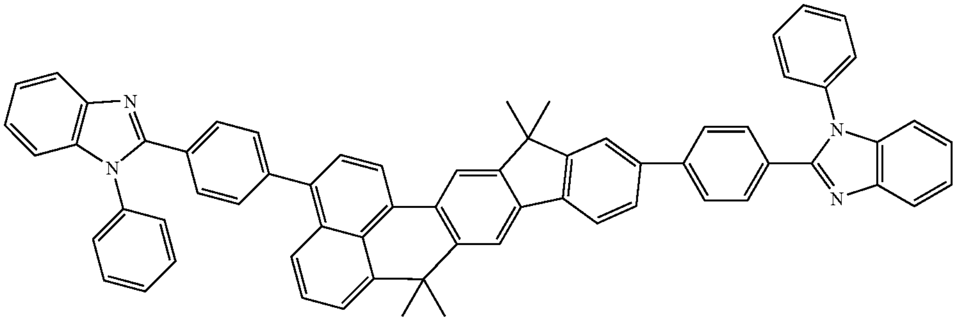
(207)
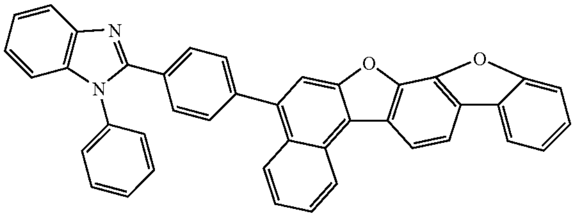
(208)
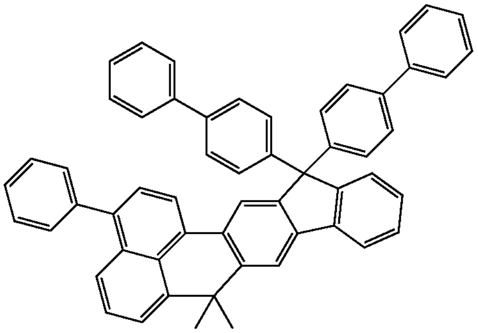

-continued
(209)
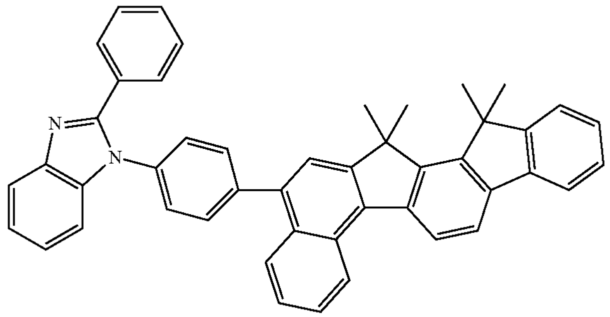
(210)
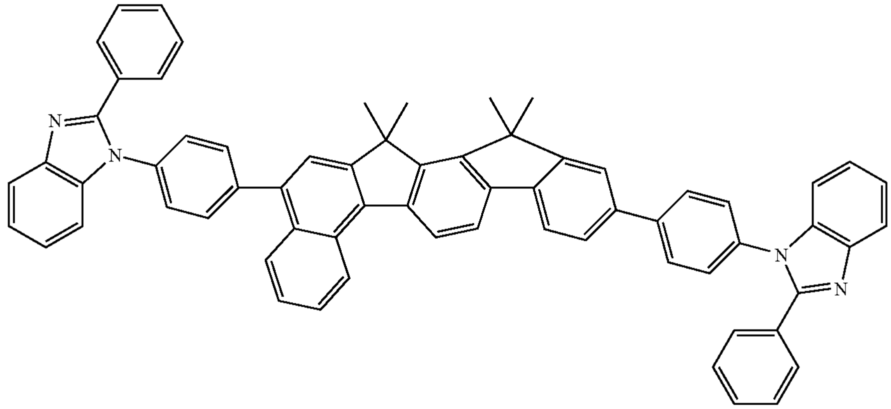
(211)
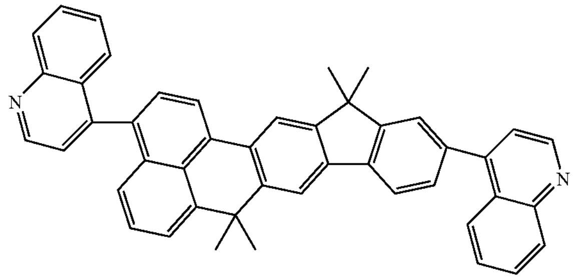
(212)
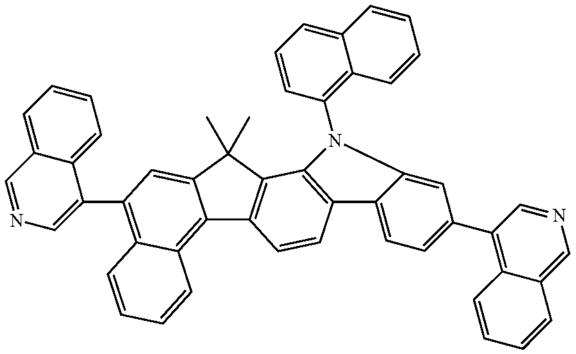
(213)
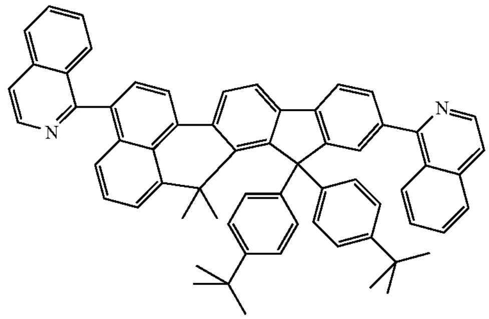
(214)
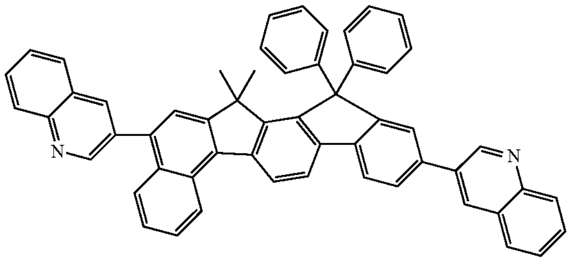

-continued
(215)
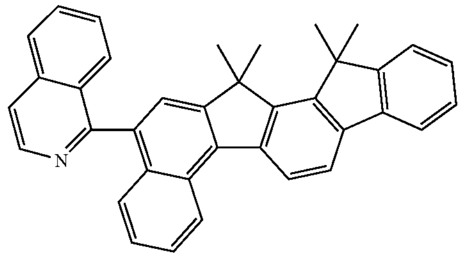
(216)
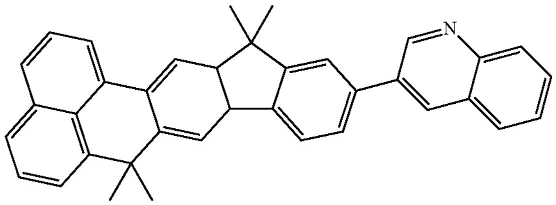
(217)
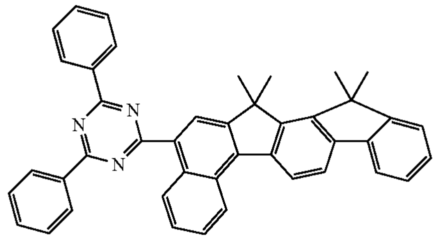
(218)
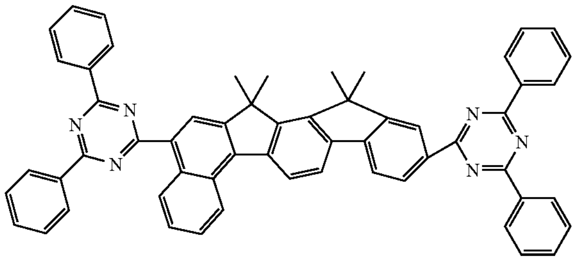
(219)
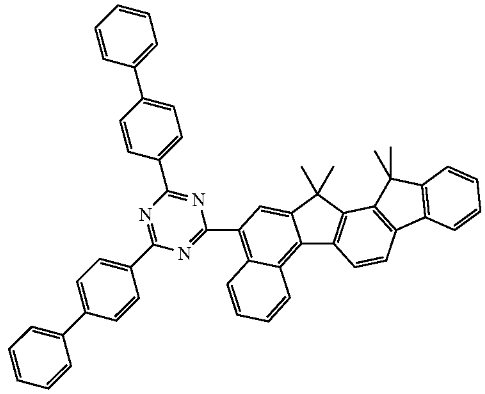
(220)
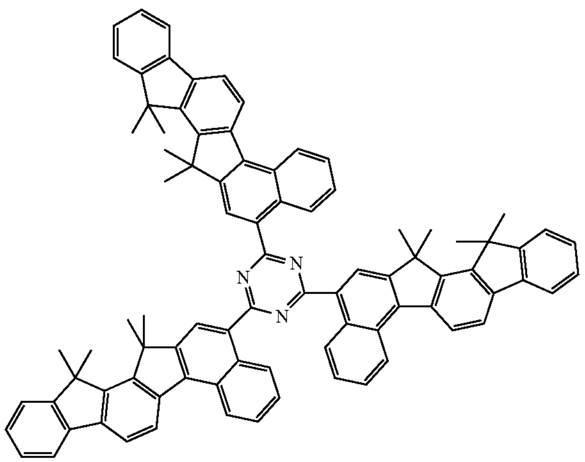
(221)
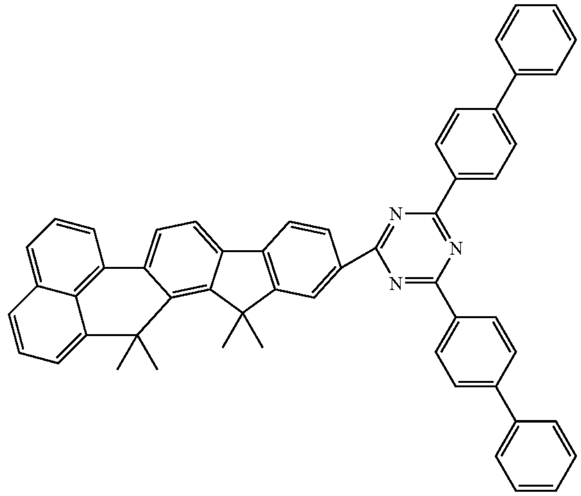
(222)
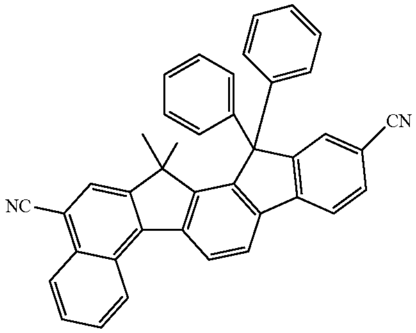

-continued
(223)
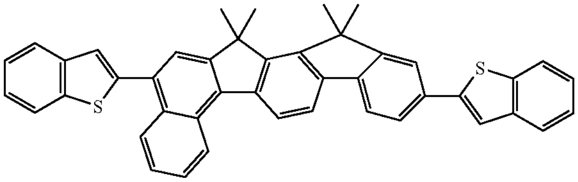
(224)
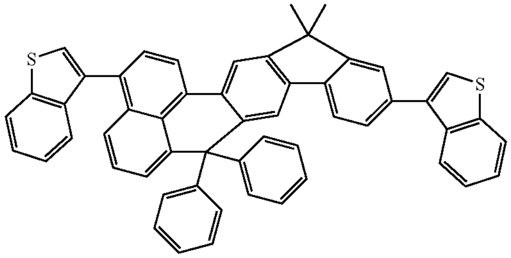
(225)
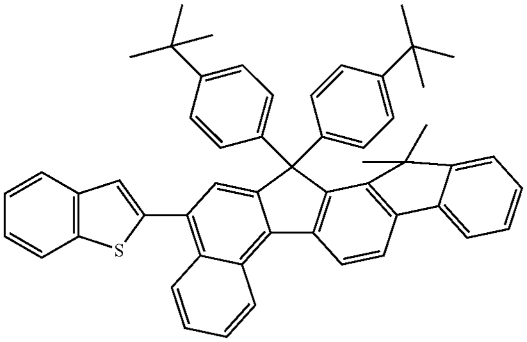
(226)
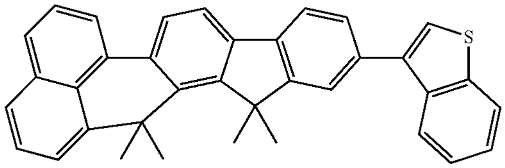
(227)
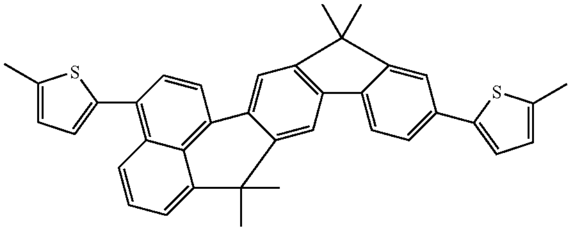
(228)
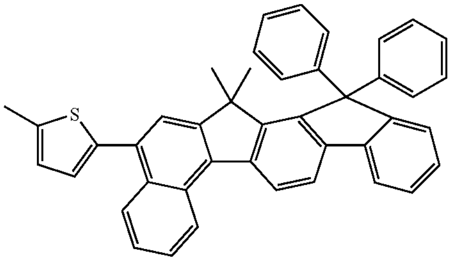
(229)
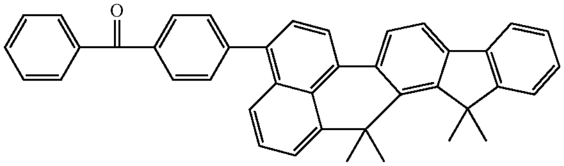
(230)
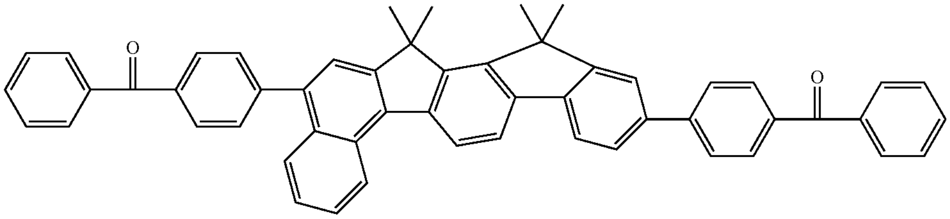
(231)
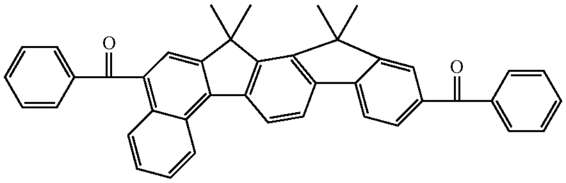
(232)
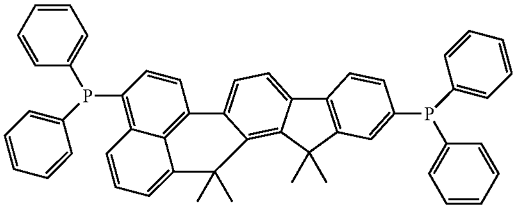

-continued
(233)
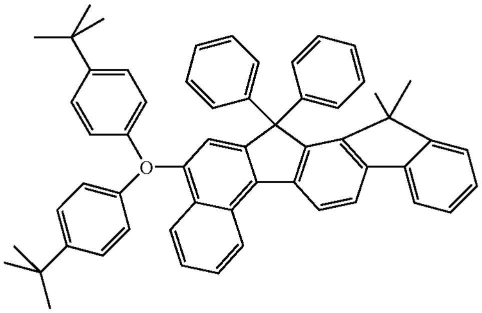
(234)
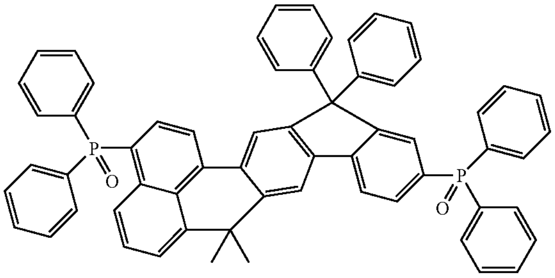
(235)
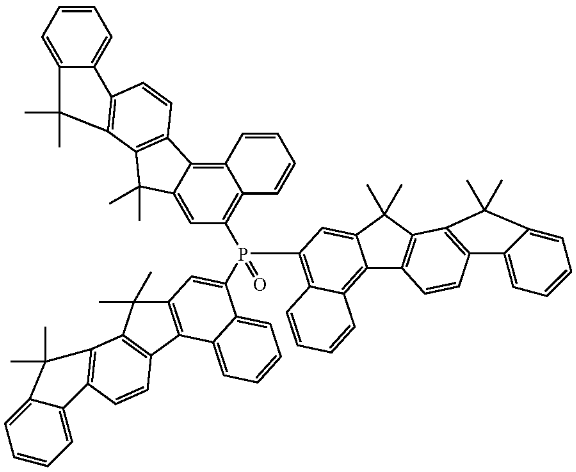
(236)
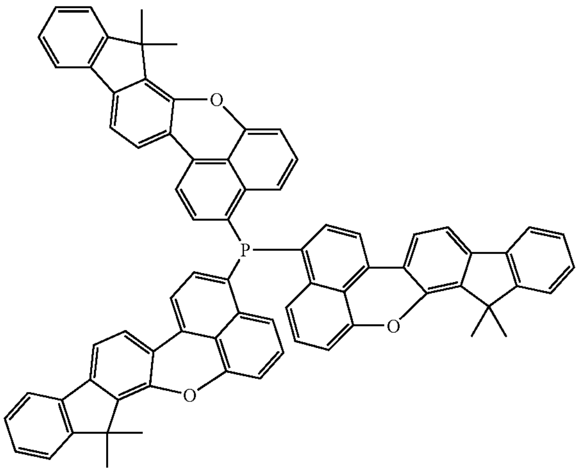
(237)
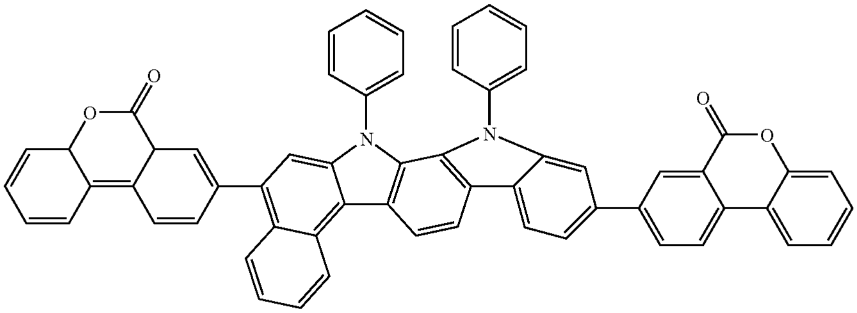
(238)
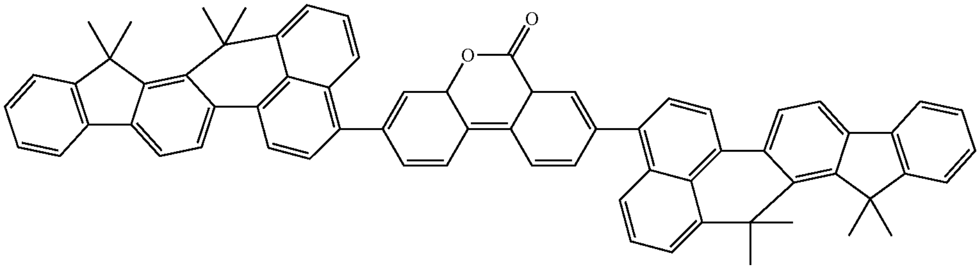

-continued
(239)
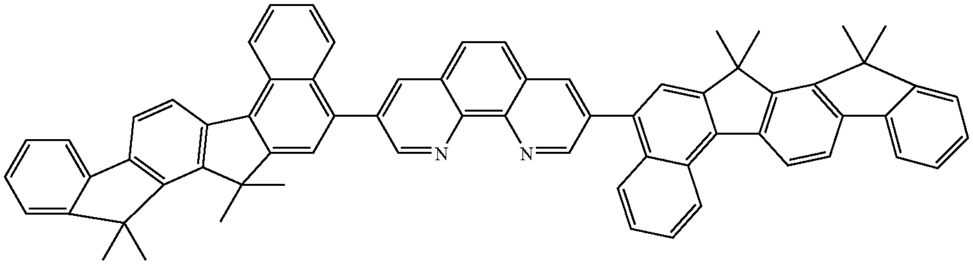
(240)
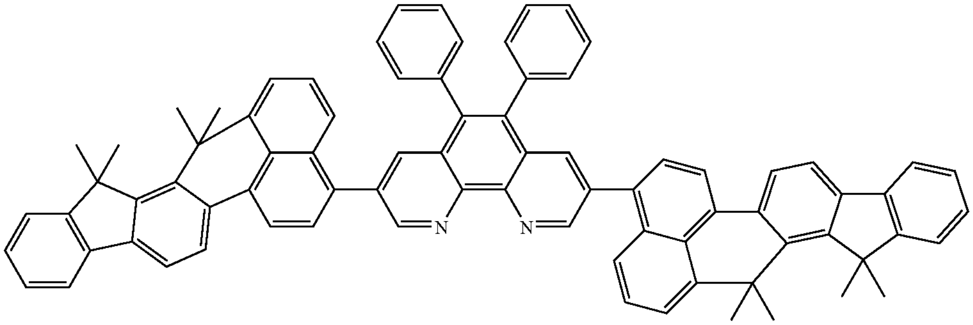
(241)
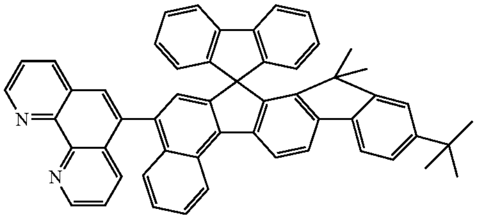
(242)
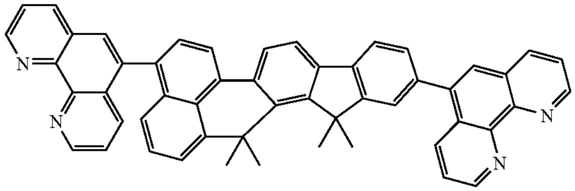
(243)
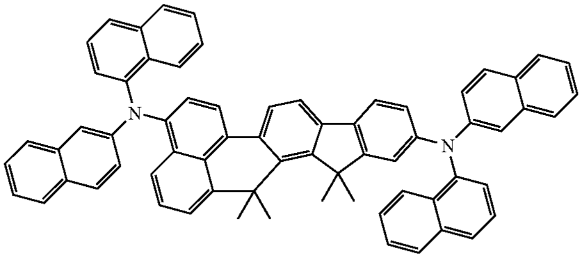
(244)
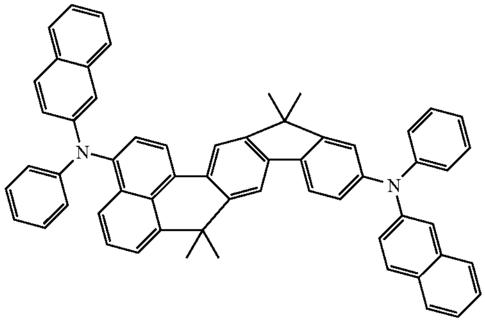
(245)
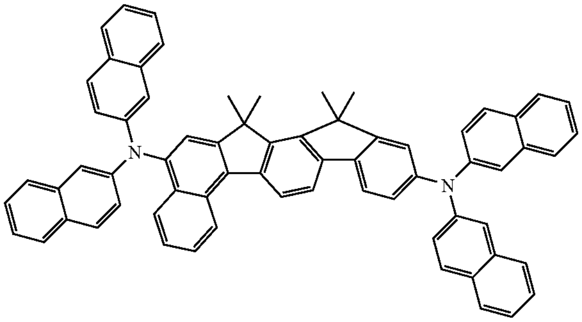
(246)
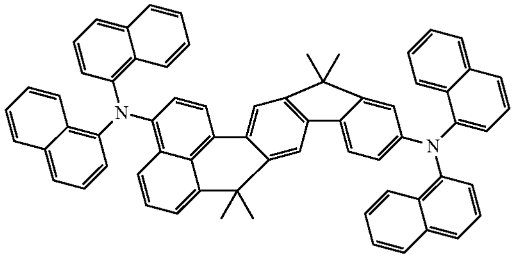

-continued
(247)
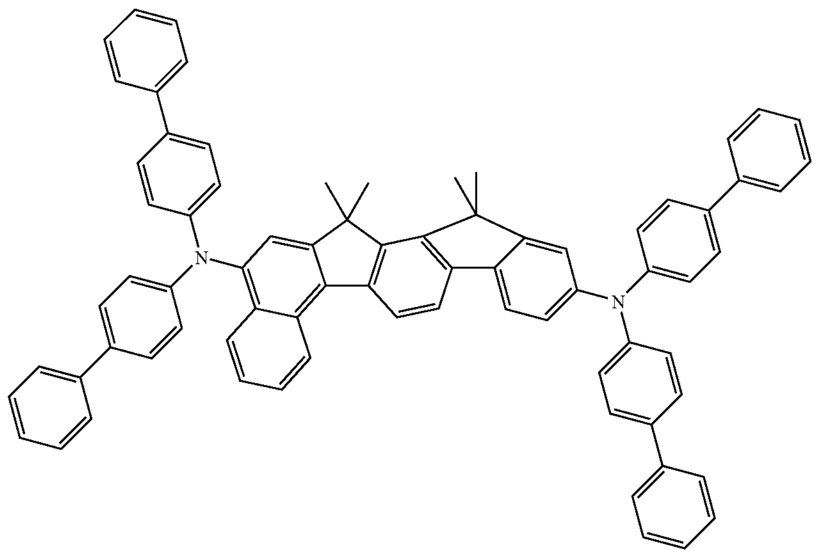
(248)
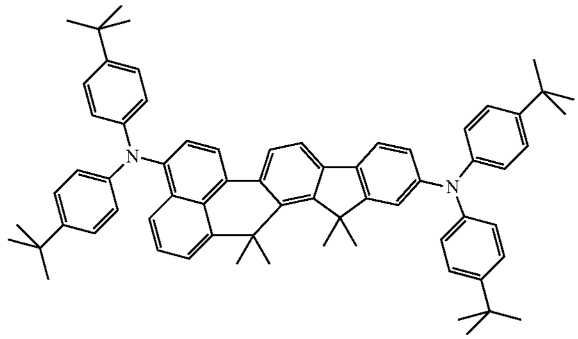
(249)
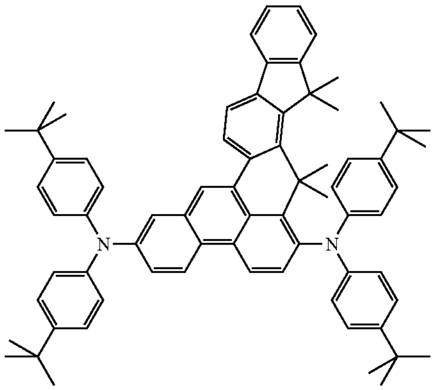
(250)
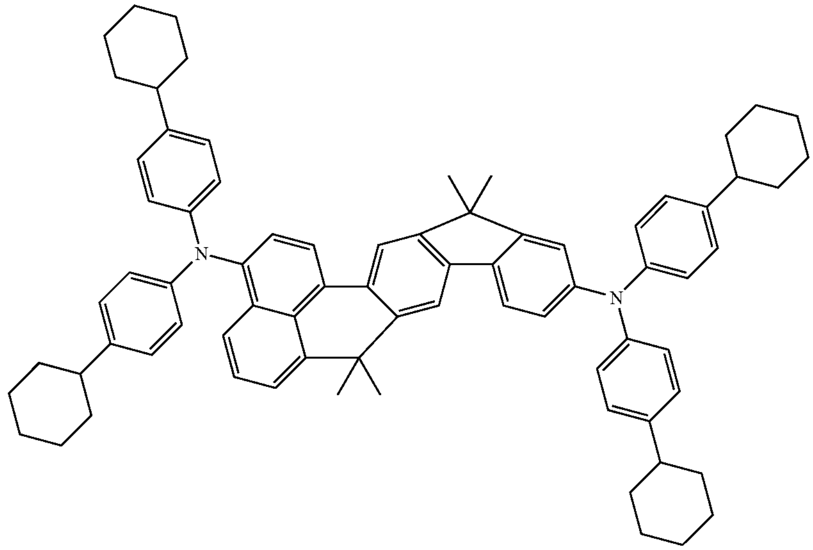

-continued
(251)
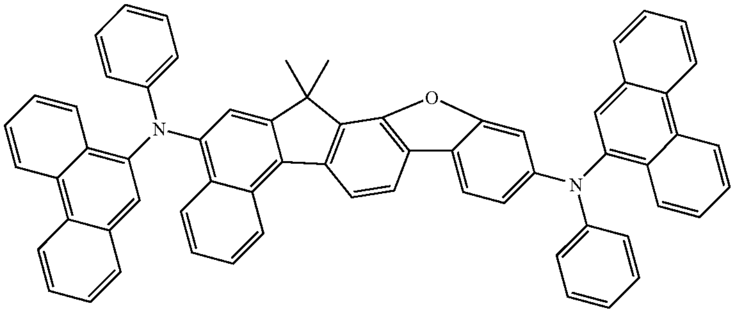
(252)
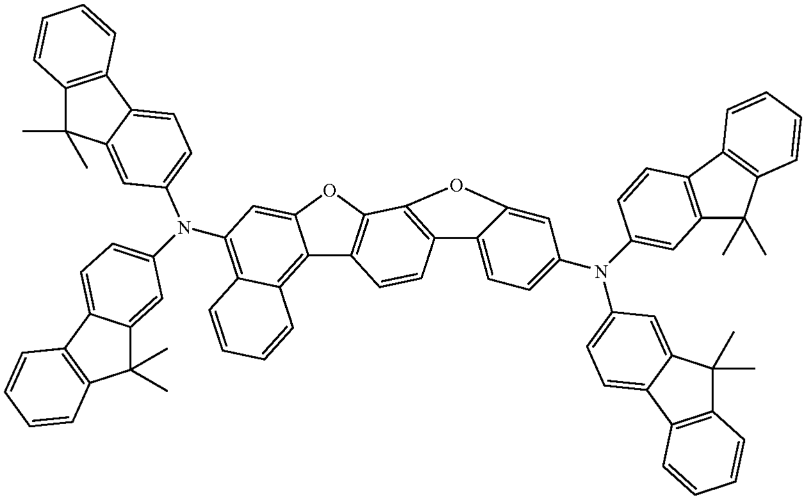
(253)
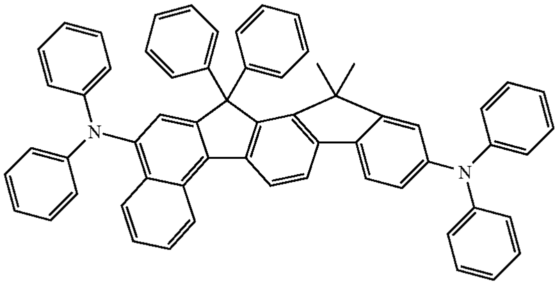
(254)
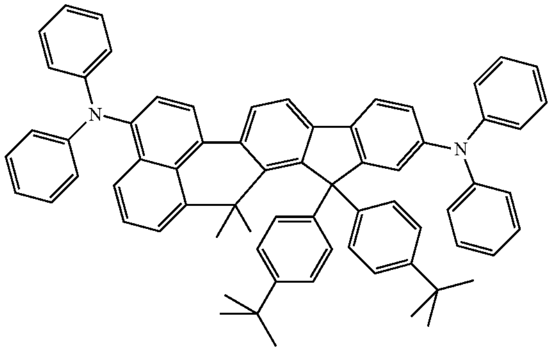
(255)
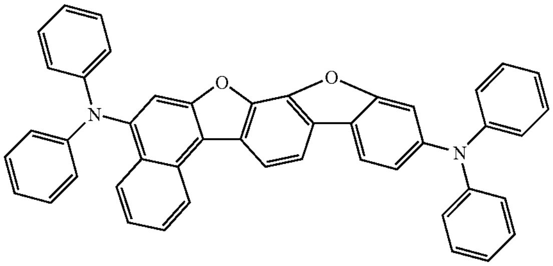
(256)
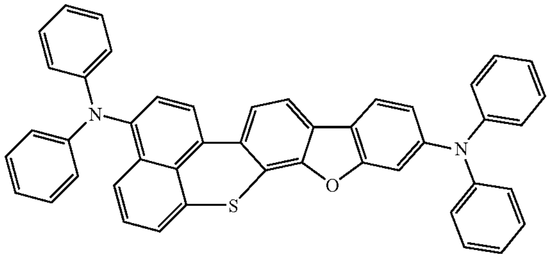

-continued
(257)
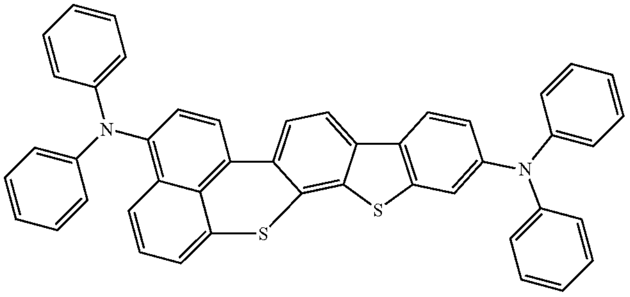
(258)
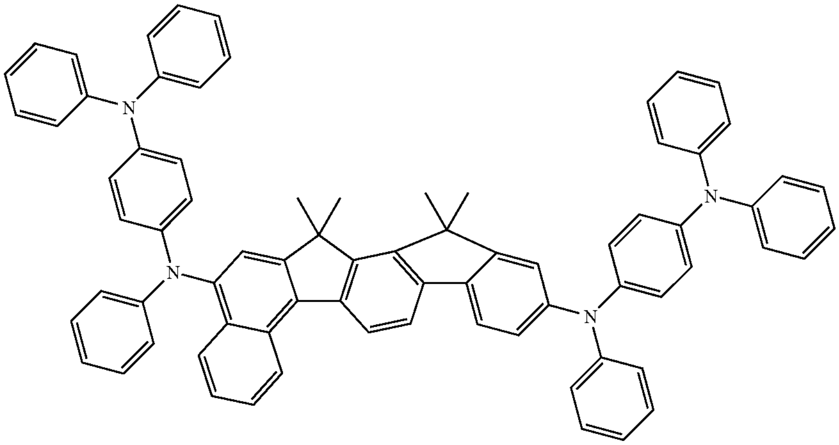
(259)
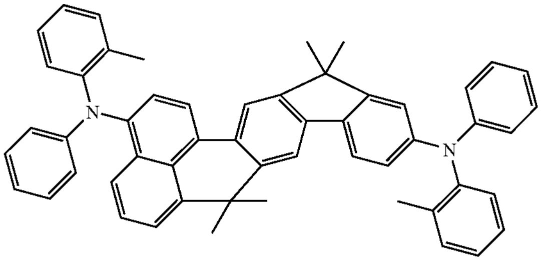
(260)
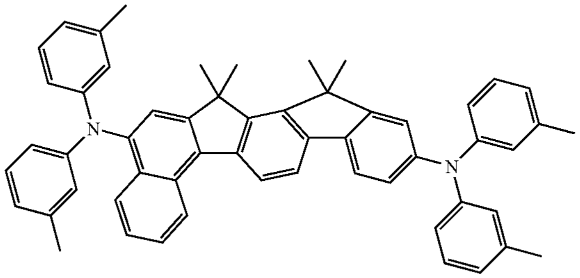
(261)
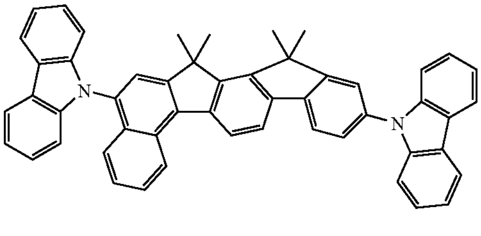
(262)
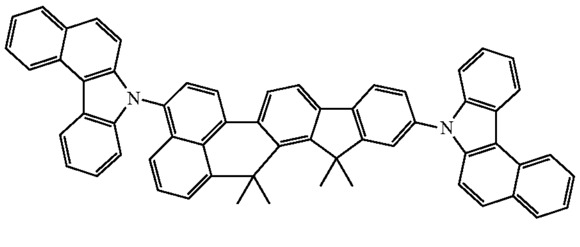

-continued
(263)
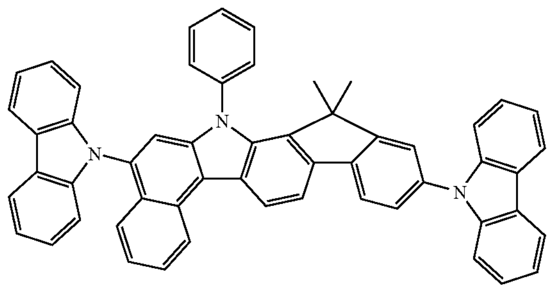
(264)
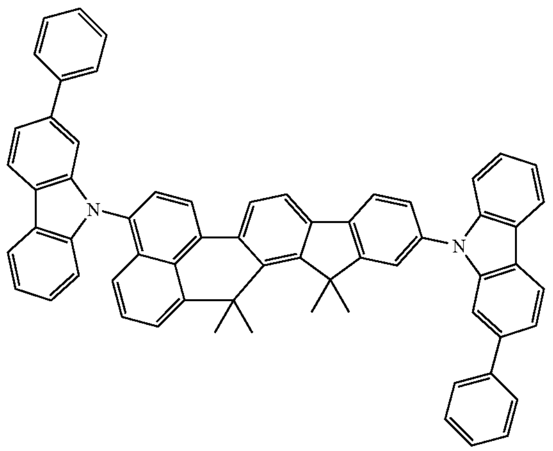
(265)
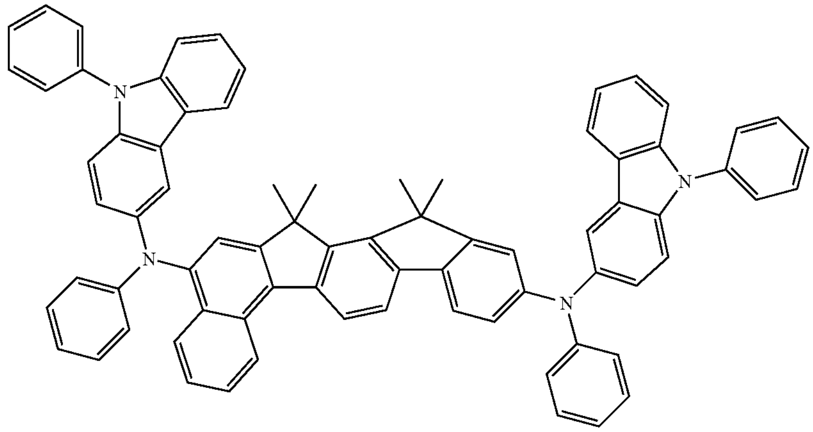
(266)
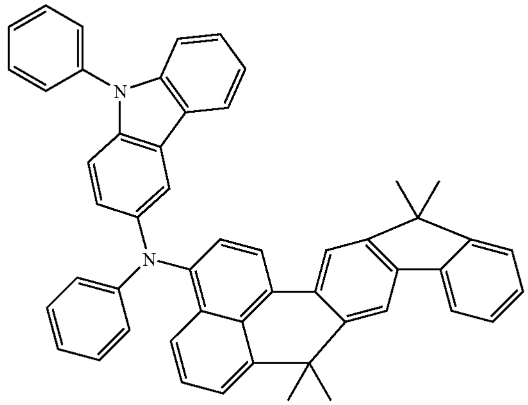
(267)
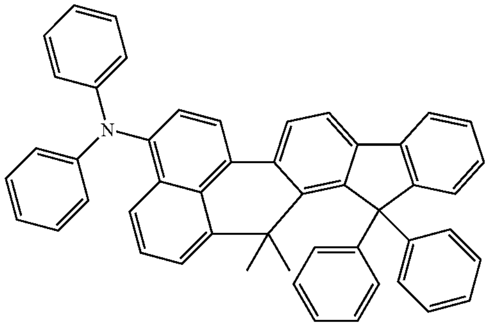

-continued
(268)
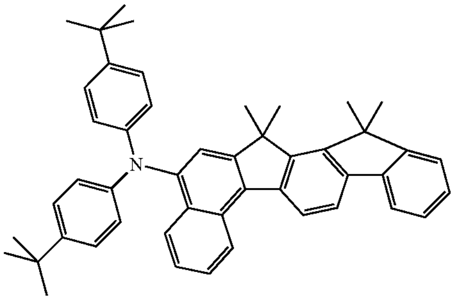
(269)
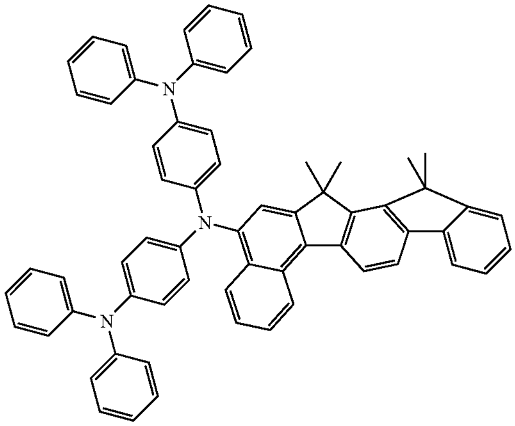
(270)
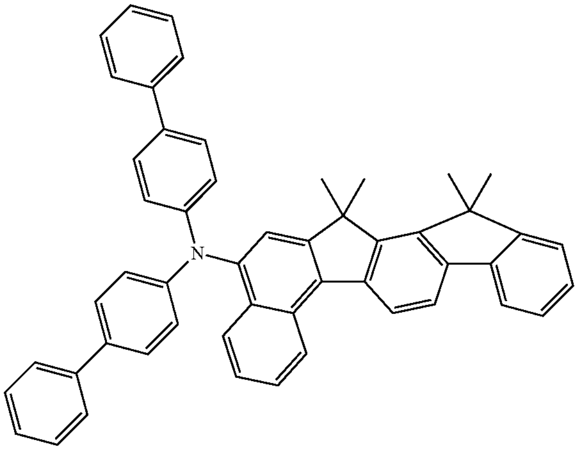
(271)
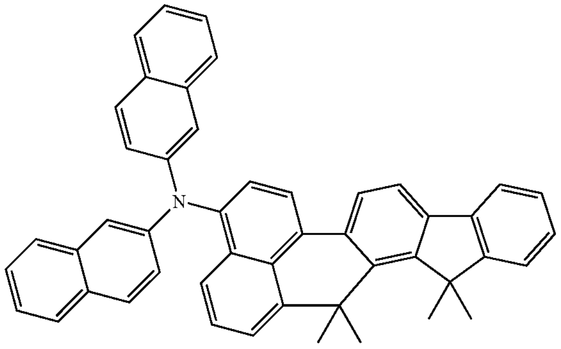
(272)
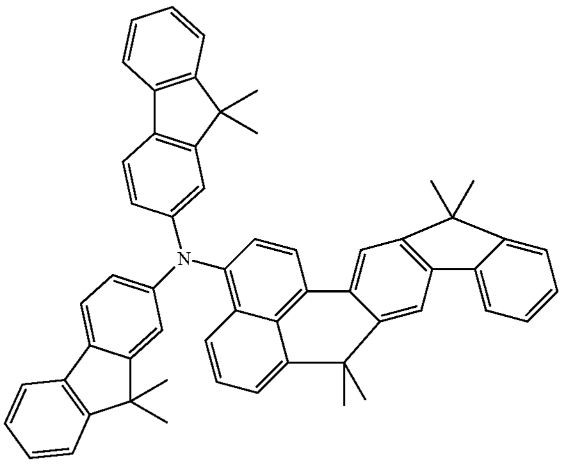
(273)
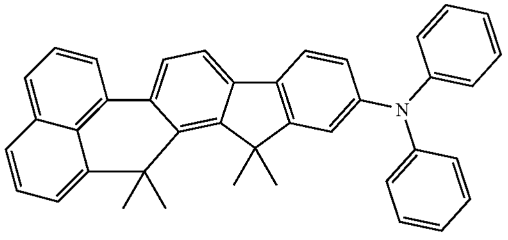

-continued
(274)
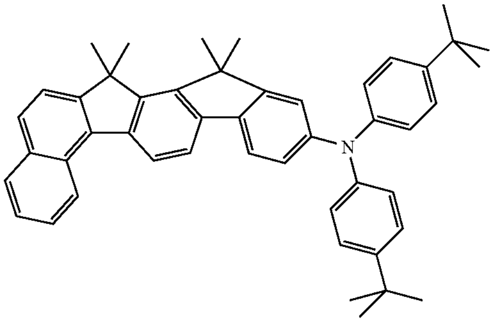
(275)
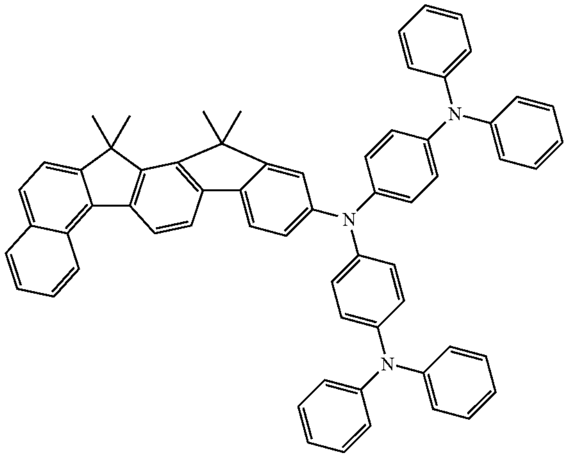
(276)
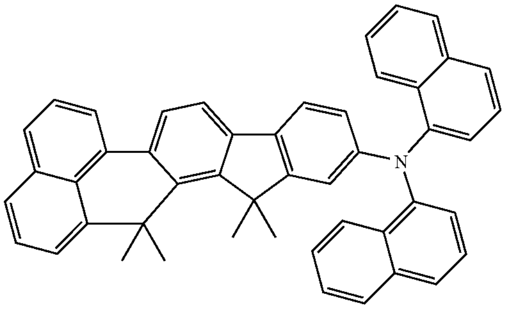
(277)
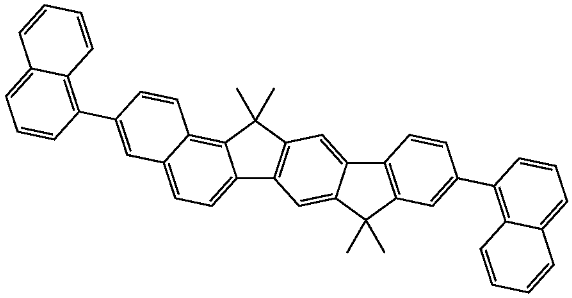
(278)
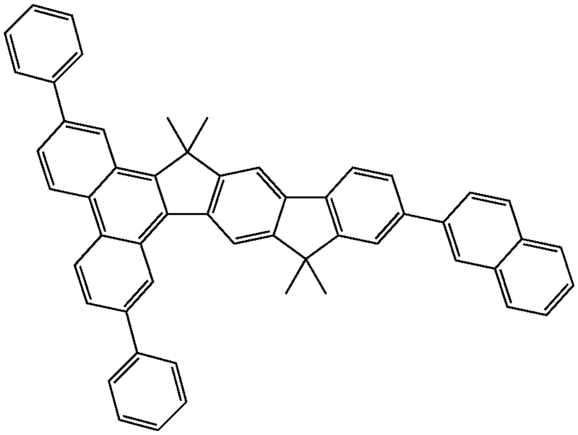
(279)
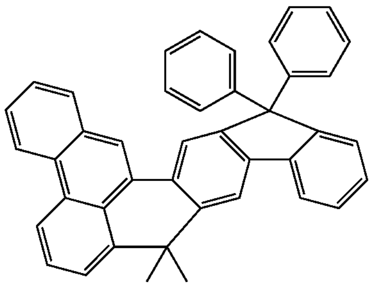
(280)
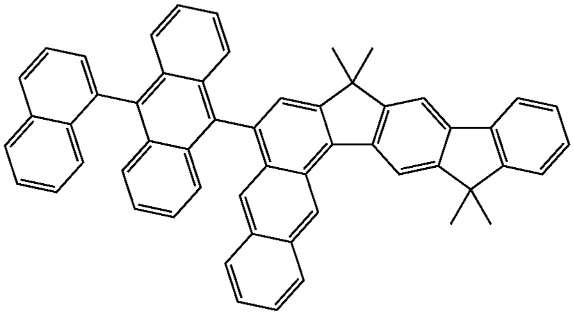
(281)
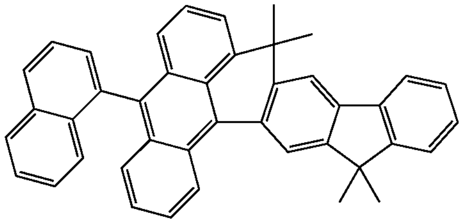

-continued
(282)
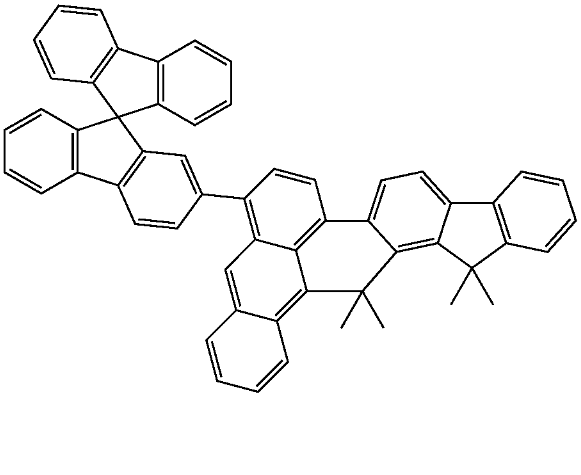
(283)
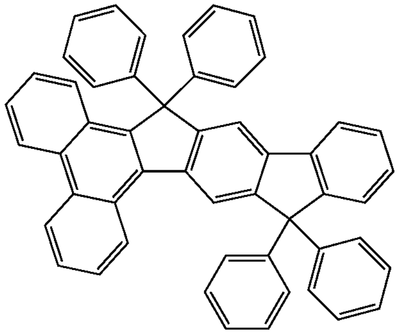
(284)
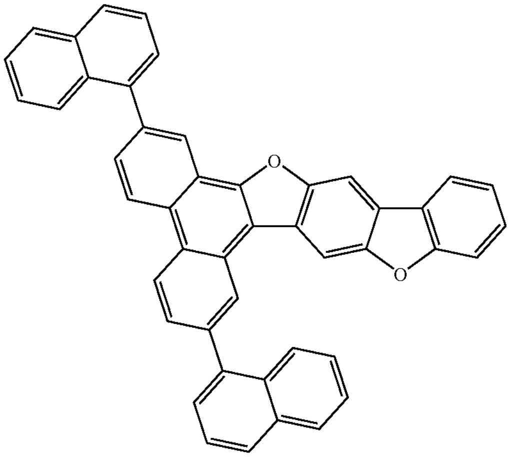
(285)
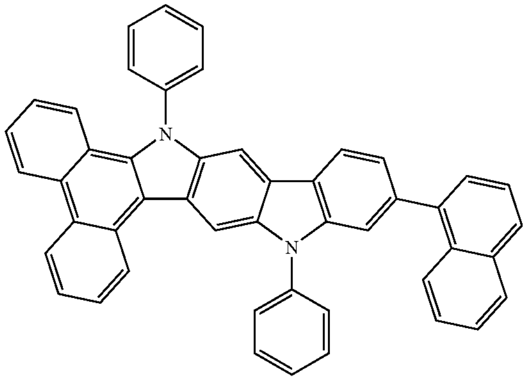
(286)
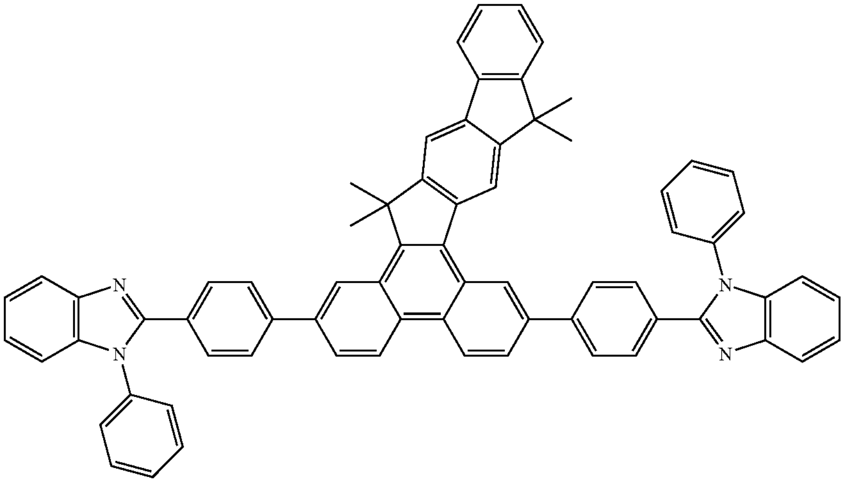

-continued
(287)
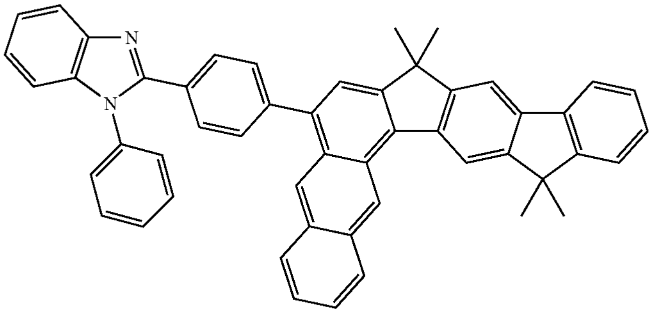
(288)
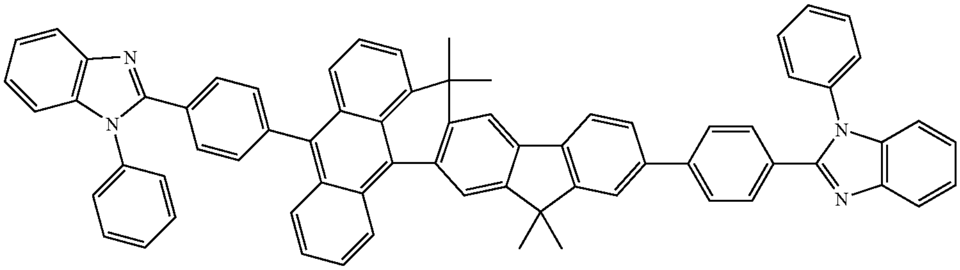
(289)
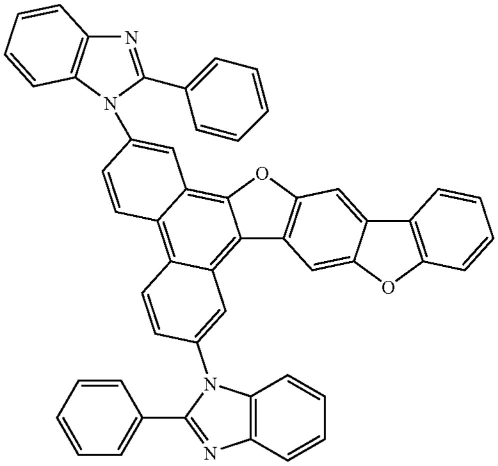
(290)
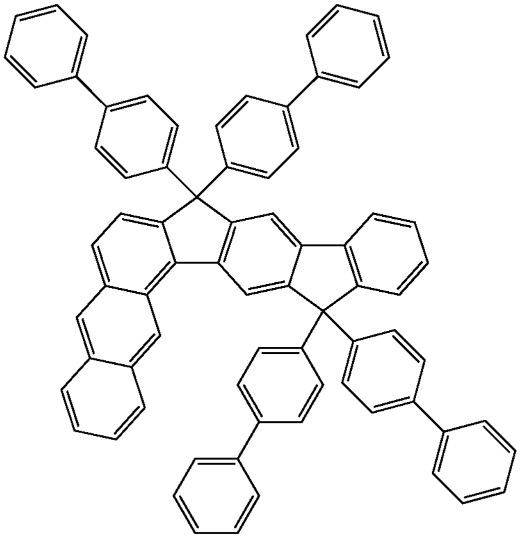
(291)
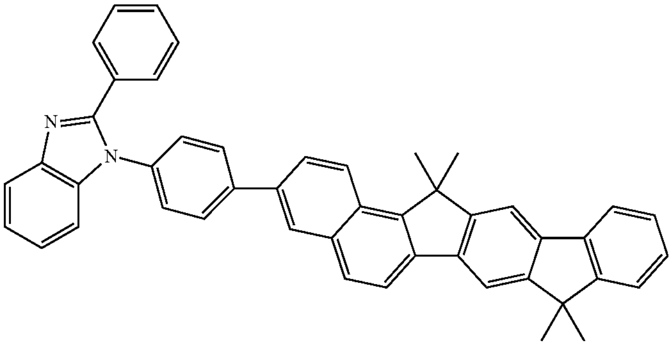

-continued
(292)
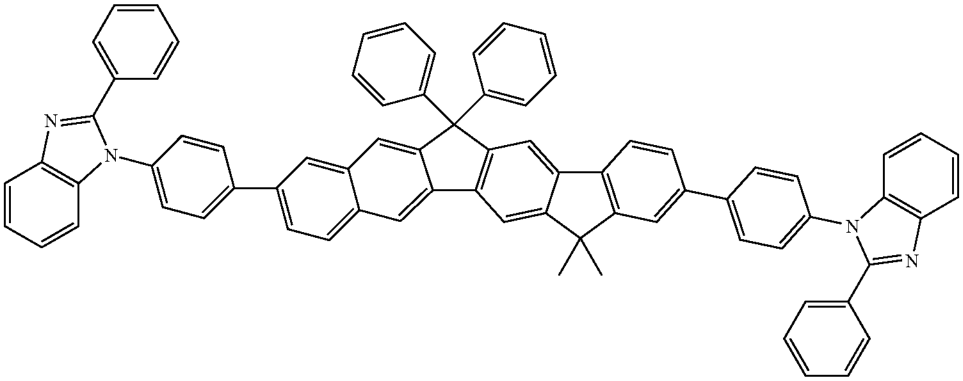
(293)
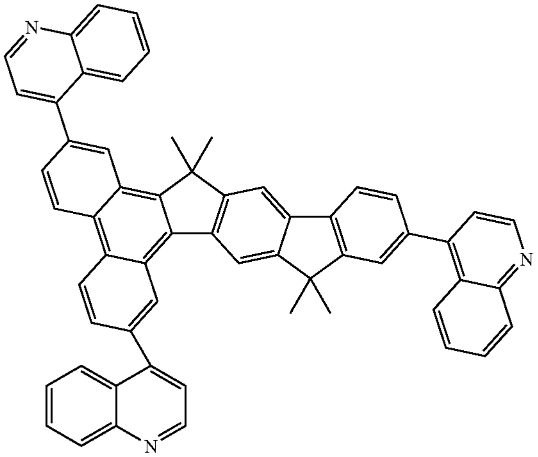
(294)
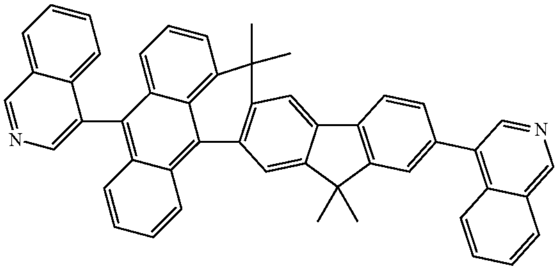
(295)
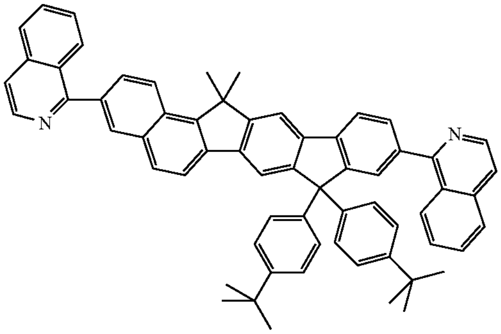
(296)
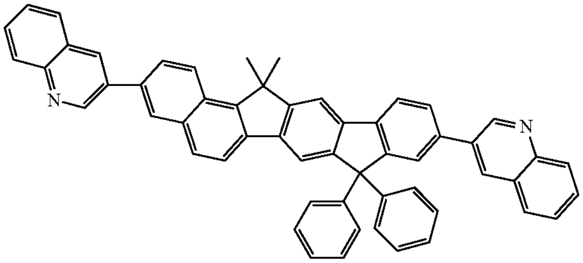
(297)
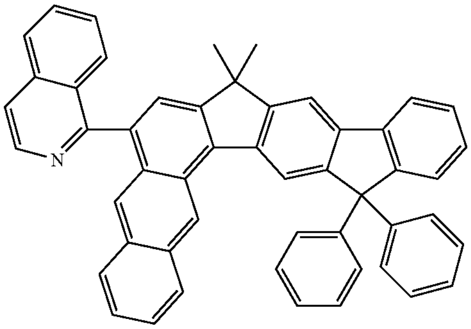
(298)
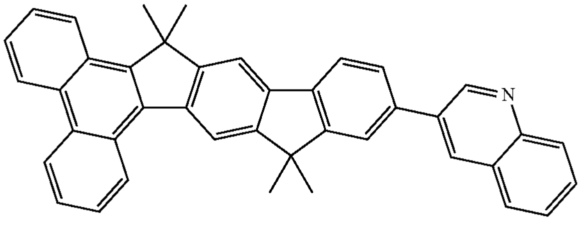

-continued
(299)
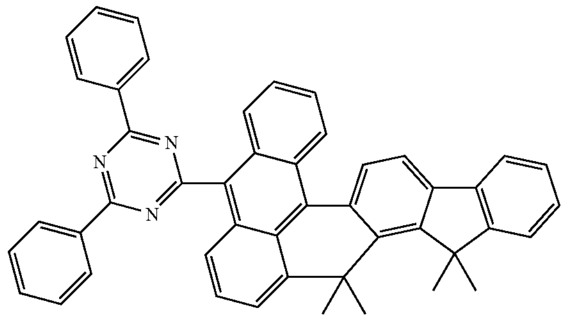
(300)
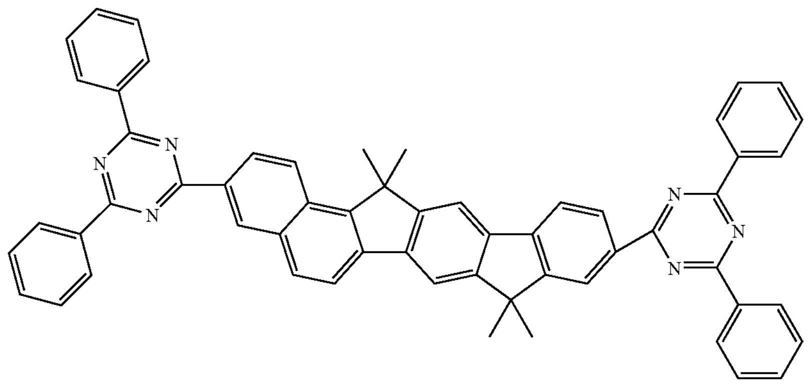
(301)
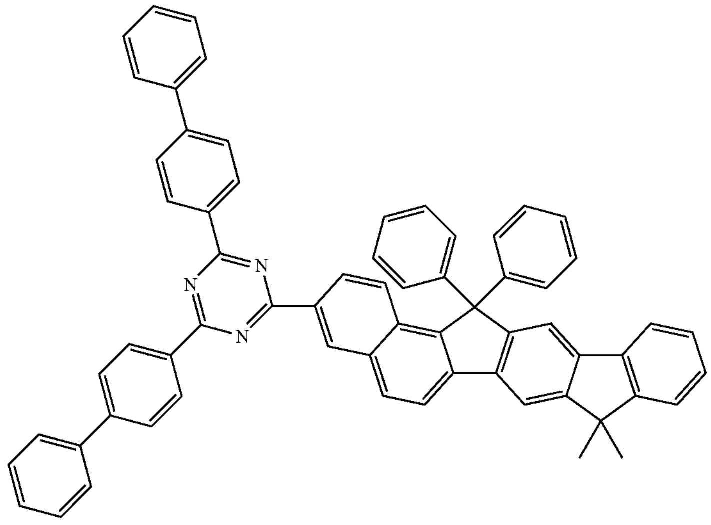

-continued
(302)
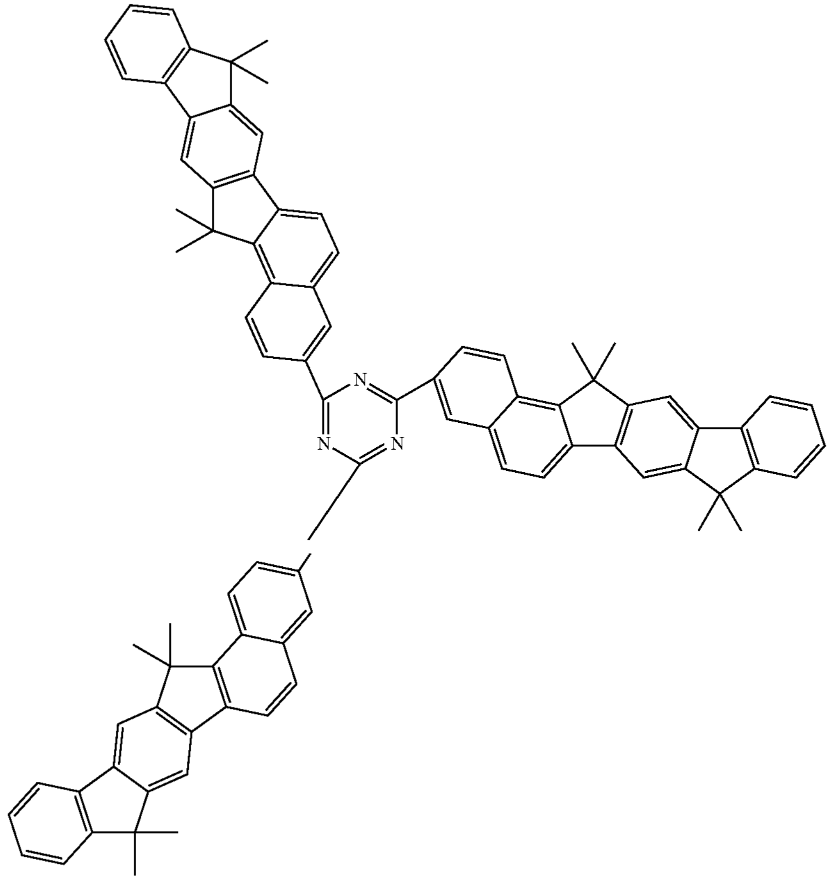
(303)
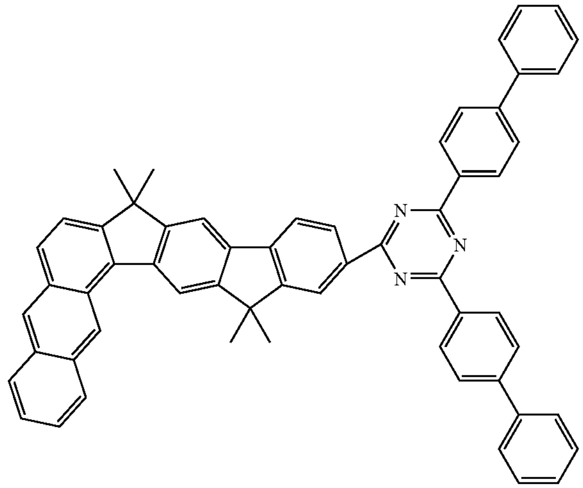
(304)
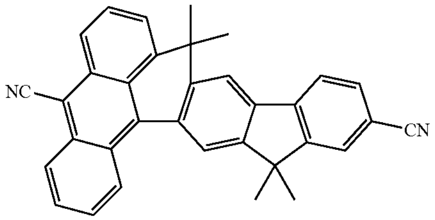
(305)
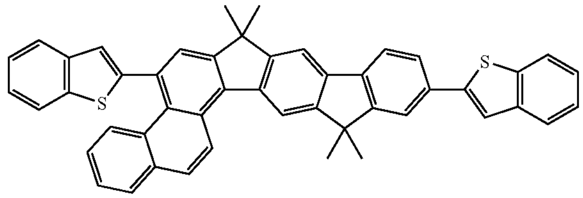
(306)
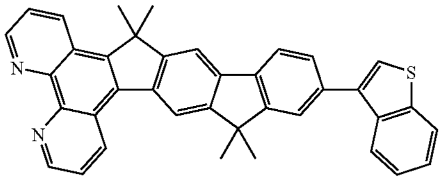

-continued
(307)
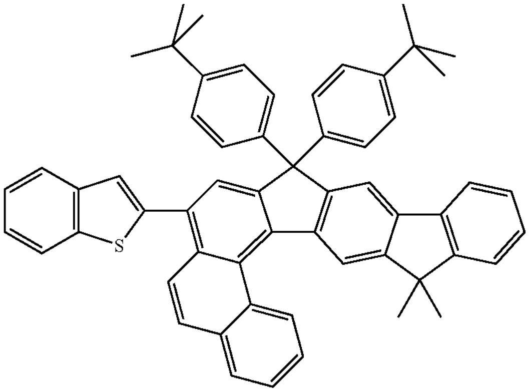
(308)
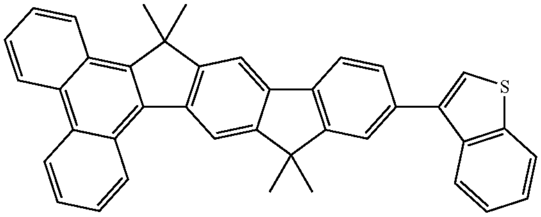
(309)
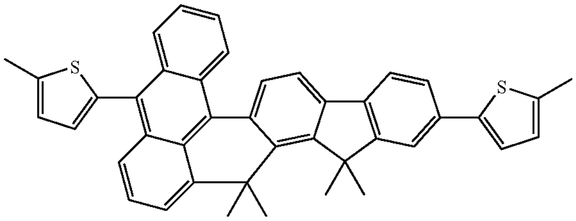
(310)
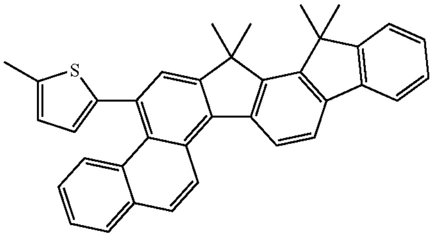
(311)
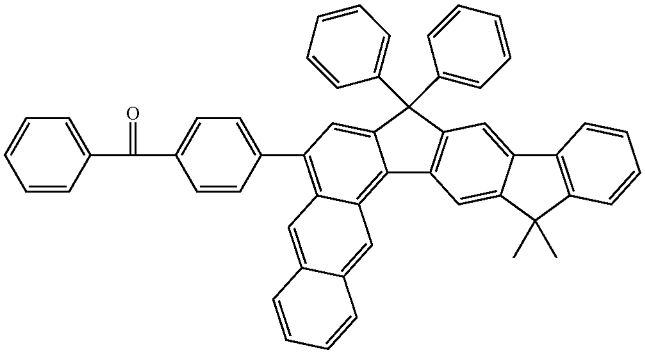
(312)
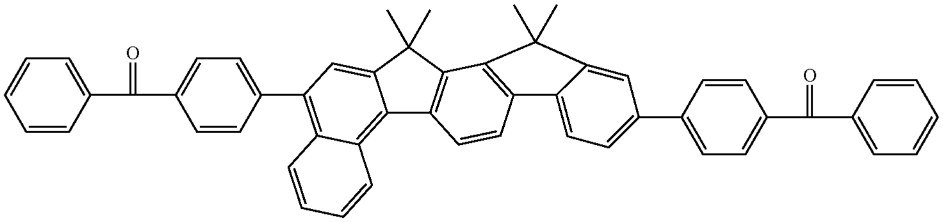

-continued
(313)
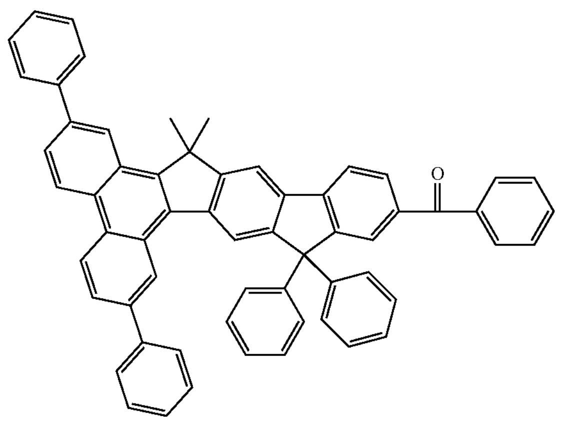
(314)
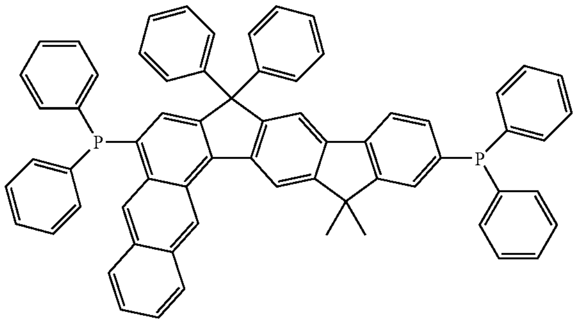
(315)
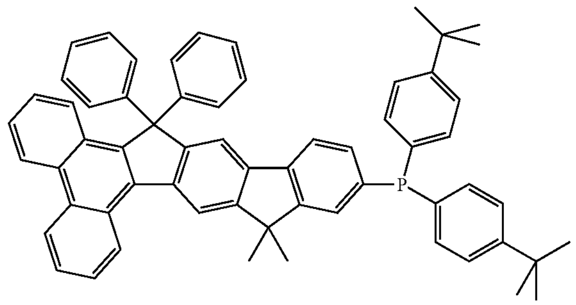
(316)
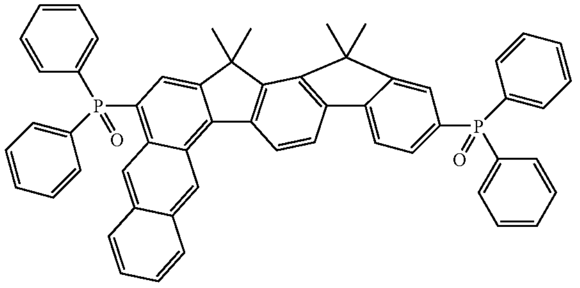
(317)
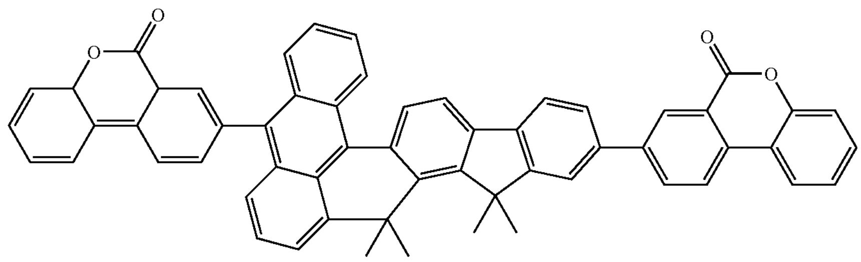
(318)
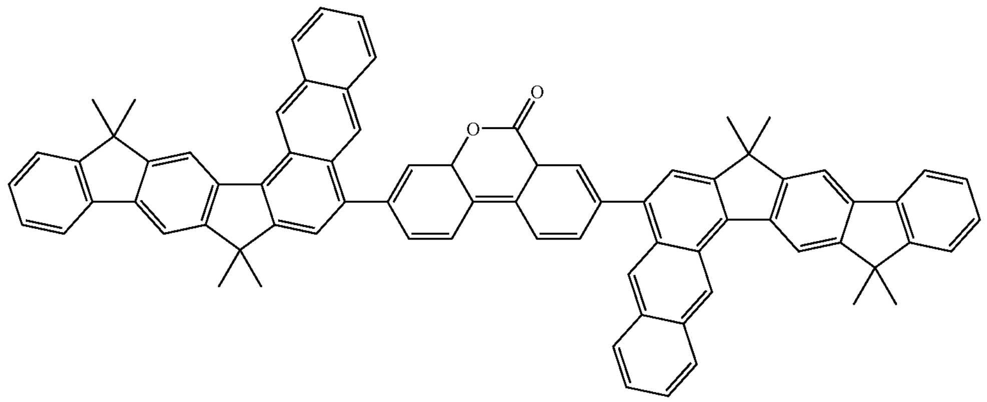

-continued
(319)
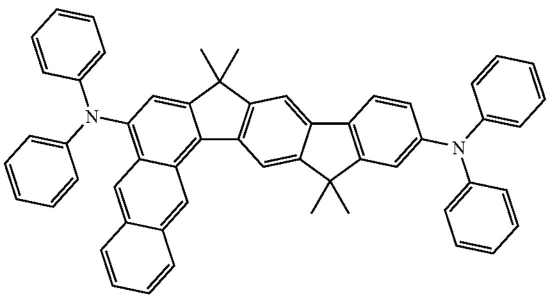
(320)
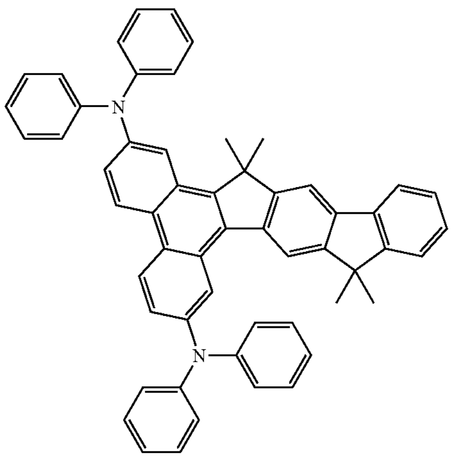
(321)
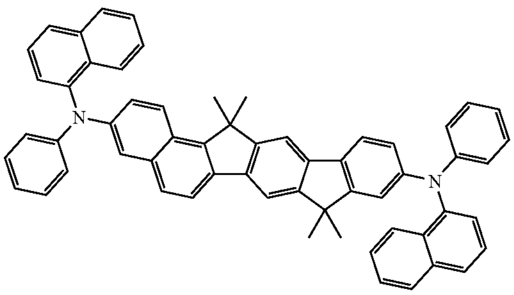
(322)
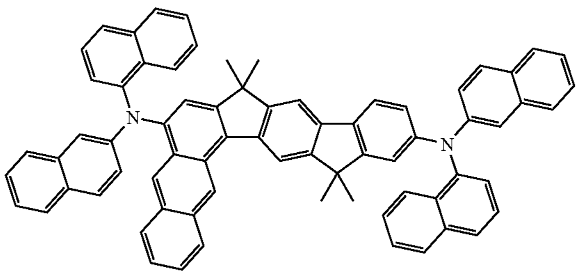
(323)
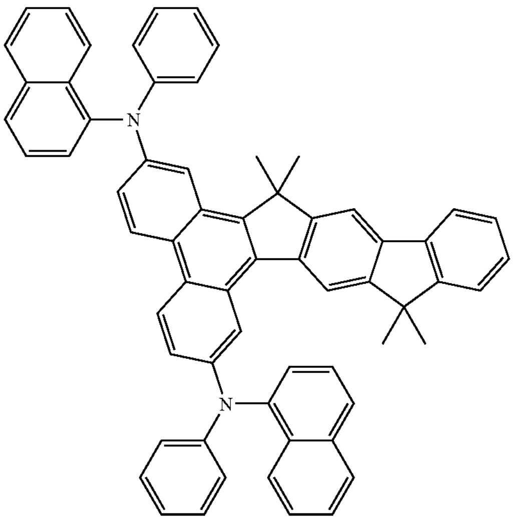
(324)
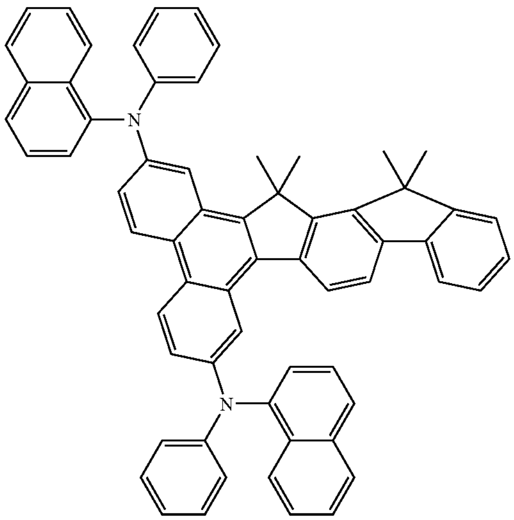

-continued
(325)
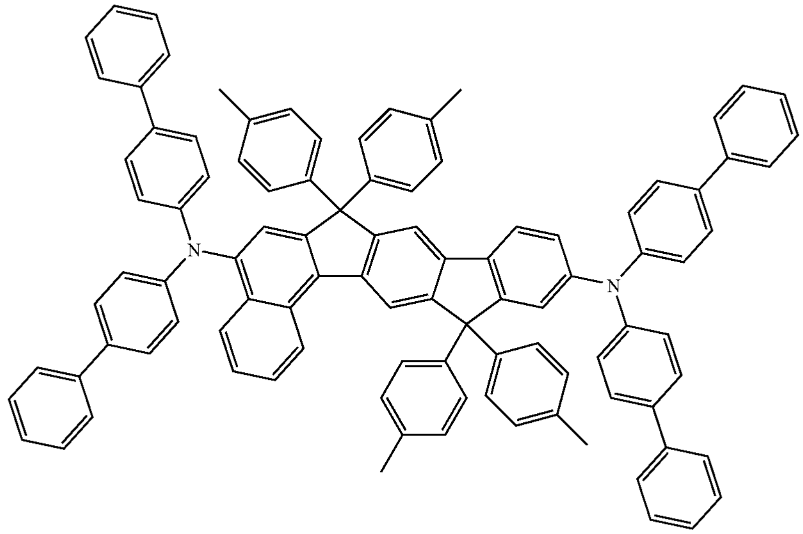
(326)
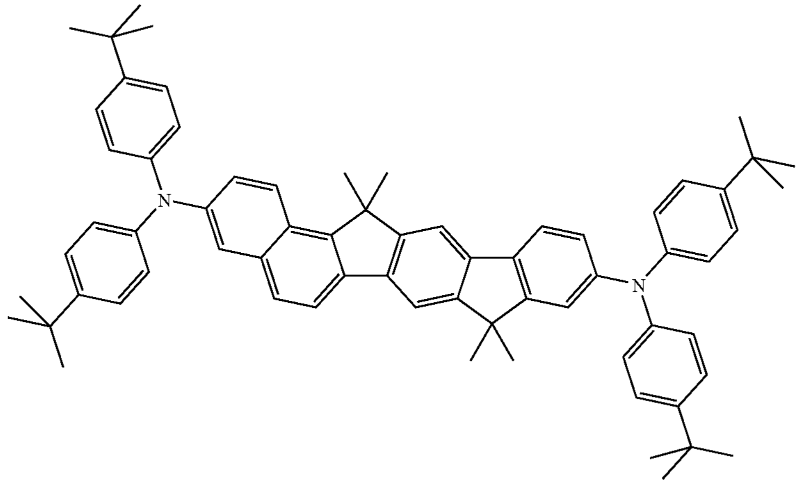
(327)
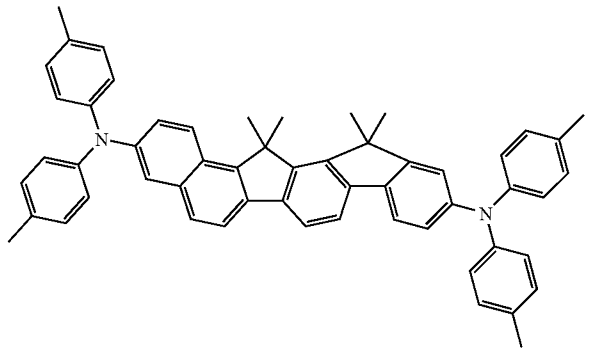
(328)
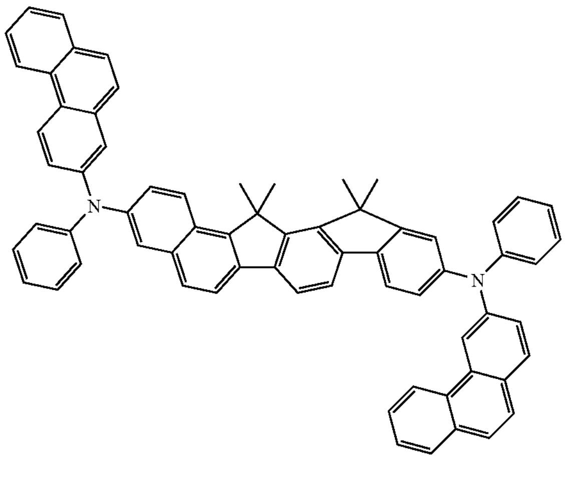

-continued
(329)
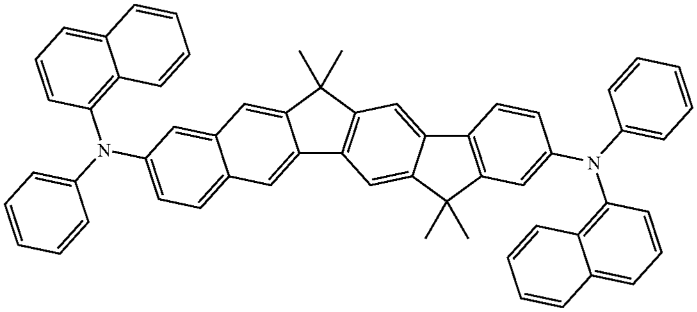
(330)
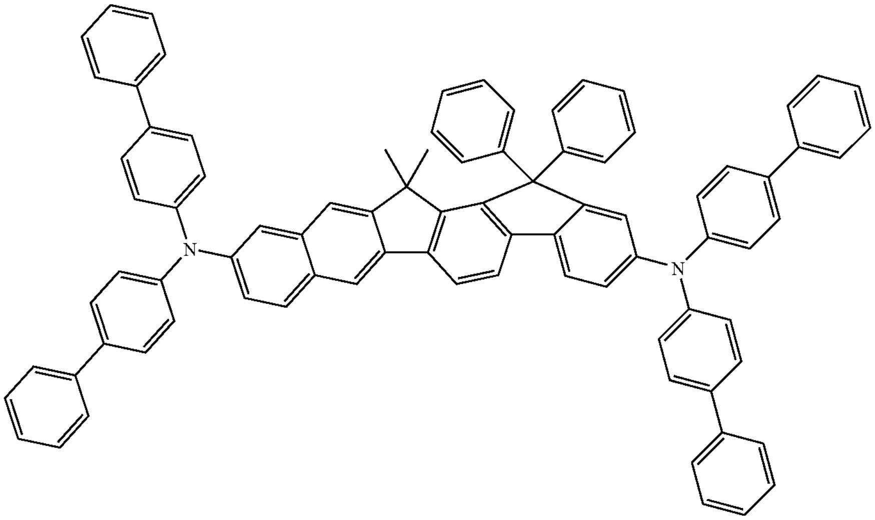
(331)
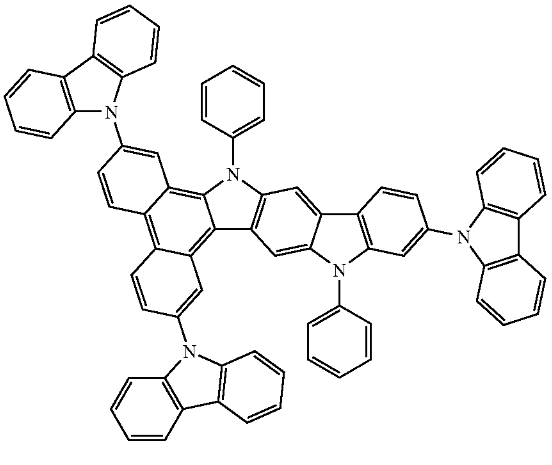
(332)
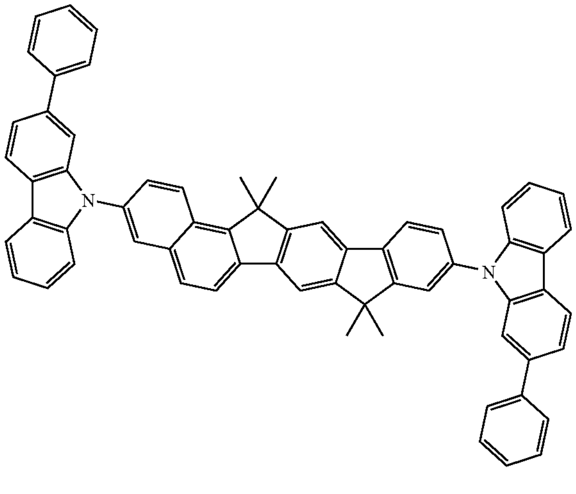

-continued
(333)
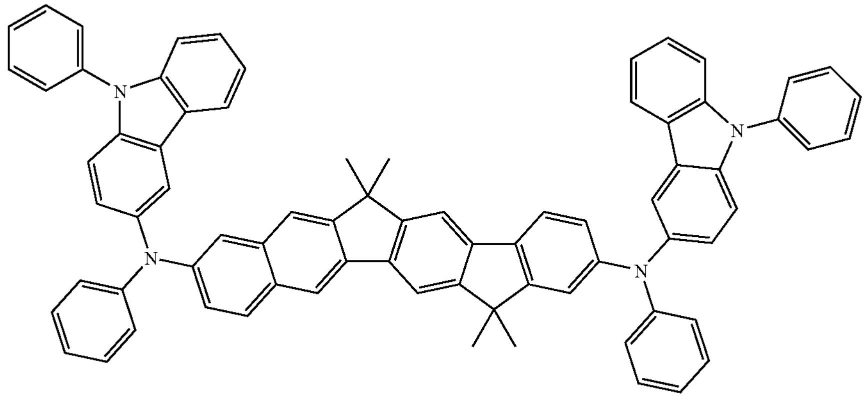
(334)
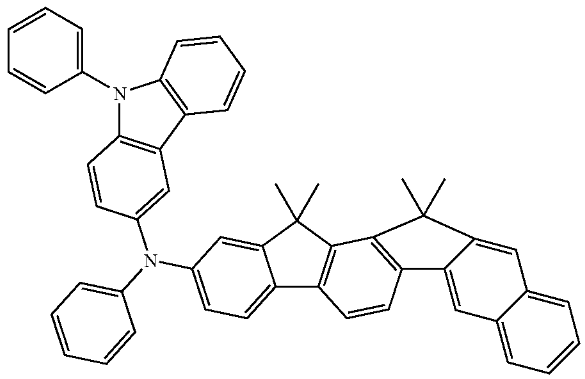
(335)
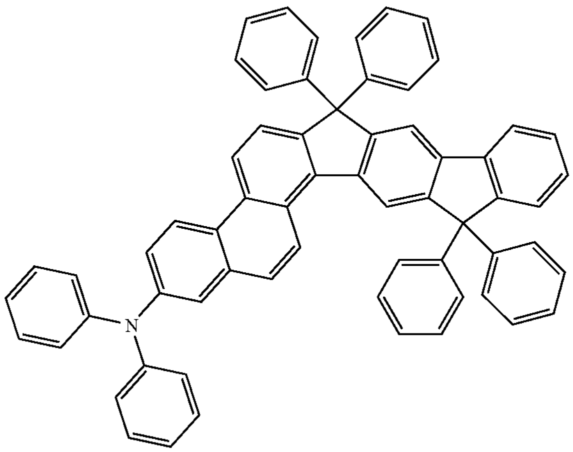
(336)
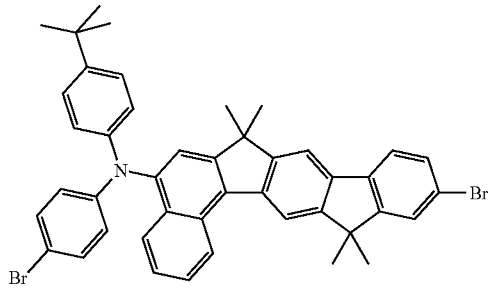
(337)
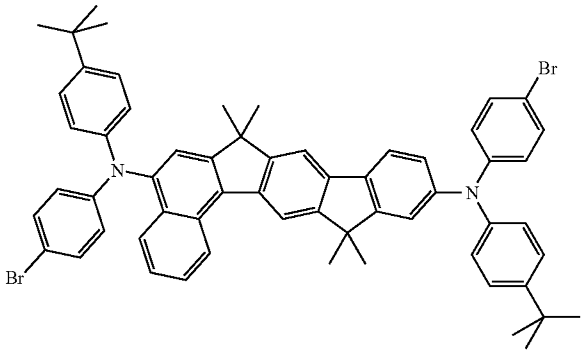
(338)
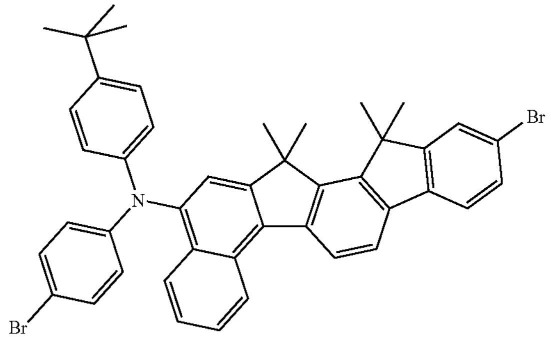

Further particularly preferred compounds are revealed by Table 1 below, where the radicals relate to the following structure:

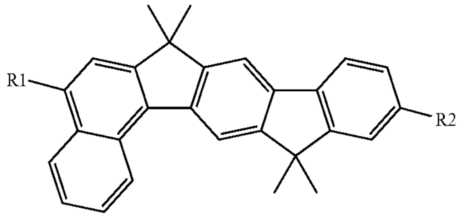

In Table 1, phenanthrenyl stands, in particular, for a 9-phenanthrenyl group. tBuPhenyl stands, in particular, for a para-tert-butylphenyl group. Just as preferred as the structures in Table 1 are the corresponding structures in which phenyl groups instead of methyl groups are bonded to the bridge X or in which para-tert-butylphenyl groups instead of methyl groups are bonded to the bridge X. Preference is likewise furthermore given to the structures in which ortho-tolyl groups or para-tolyl groups are bonded instead of meta-tolyl groups as groups Ar1, Ar2, Ar3 or Ar4.

TABLE 1

Preferred structures

| | | | R1 | | R2 | |
|---|---|---|---|---|---|---|
| No. | R1 | R2 | Ar1 | Ar2 | Ar3 | Ar4 |
| 1 | H | H | — | — | — | — |
| 2 | H | Phenyl | — | — | — | — |
| 3 | H | 1-Naphthyl | — | — | — | — |
| 4 | H | 2-Naphthyl | — | — | — | — |
| 5 | H | NAr3Ar4 | — | — | Phenyl | Phenyl |
| 6 | H | NAr3Ar4 | — | — | Phenyl | 1-Naphthyl |
| 7 | H | NAr3Ar4 | — | — | Phenyl | 2-Naphthyl |
| 8 | H | NAr3Ar4 | — | — | Phenyl | m-Tolyl |
| 9 | H | NAr3Ar4 | — | — | Phenyl | tBuPhenyl |
| 10 | H | NAr3Ar4 | — | — | Phenyl | Phenanthrenyl |
| 11 | H | NAr3Ar4 | — | — | 1-Naphthyl | 1-Naphthyl |
| 12 | H | NAr3Ar4 | — | — | 2-Naphthyl | 2-Naphthyl |
| 13 | H | NAr3Ar4 | — | — | m-Tolyl | m-Tolyl |
| 14 | H | NAr3Ar4 | — | — | tBuPhenyl | tBuPhenyl |
| 15 | H | Ph-NAr3Ar4 | — | — | Phenyl | Phenyl |
| 16 | H | Ph-NAr3Ar4 | — | — | Phenyl | 1-Naphthyl |
| 17 | H | Ph-NAr3Ar4 | — | — | Phenyl | 2-Naphthyl |
| 18 | H | Ph-NAr3Ar4 | — | — | Phenyl | m-Tolyl |
| 19 | H | Ph-NAr3Ar4 | — | — | Phenyl | tBuPhenyl |
| 20 | H | Ph-NAr3Ar4 | — | — | Phenyl | Phenanthrenyl |
| 21 | H | Ph-NAr3Ar4 | — | — | 1-Naphthyl | 1-Naphthyl |
| 22 | H | Ph-NAr3Ar4 | — | — | 2-Naphthyl | 2-Naphthyl |
| 23 | H | Ph-NAr3Ar4 | — | — | m-Tolyl | m-Tolyl |
| 24 | H | Ph-NAr3Ar4 | — | — | tBuPhenyl | tBuPhenyl |
| 25 | Phenyl | H | — | — | — | — |
| 26 | Phenyl | Phenyl | — | — | — | — |
| 27 | Phenyl | 1-Naphthyl | — | — | — | — |
| 28 | Phenyl | 2-Naphthyl | — | — | — | — |
| 29 | Phenyl | NAr3Ar4 | — | — | Phenyl | Phenyl |
| 30 | Phenyl | NAr3Ar4 | — | — | Phenyl | 1-Naphthyl |
| 31 | Phenyl | NAr3Ar4 | — | — | Phenyl | 2-Naphthyl |
| 32 | Phenyl | NAr3Ar4 | — | — | Phenyl | m-Tolyl |
| 33 | Phenyl | NAr3Ar4 | — | — | Phenyl | tBuPhenyl |
| 34 | Phenyl | NAr3Ar4 | — | — | Phenyl | Phenanthrenyl |
| 35 | Phenyl | NAr3Ar4 | — | — | 1-Naphthyl | 1-Naphthyl |
| 36 | Phenyl | NAr3Ar4 | — | — | 2-Naphthyl | 2-Naphthyl |
| 37 | Phenyl | NAr3Ar4 | — | — | m-Tolyl | m-Tolyl |
| 38 | Phenyl | NAr3Ar4 | — | — | tBuPhenyl | tBuPhenyl |
| 39 | Phenyl | Ph-NAr3Ar4 | — | — | Phenyl | Phenyl |
| 40 | Phenyl | Ph-NAr3Ar4 | — | — | Phenyl | 1-Naphthyl |
| 41 | Phenyl | Ph-NAr3Ar4 | — | — | Phenyl | 2-Naphthyl |
| 42 | Phenyl | Ph-NAr3Ar4 | — | — | Phenyl | m-Tolyl |
| 43 | Phenyl | Ph-NAr3Ar4 | — | — | Phenyl | tBuPhenyl |
| 44 | Phenyl | Ph-NAr3Ar4 | — | — | Phenyl | Phenanthrenyl |
| 45 | Phenyl | Ph-NAr3Ar4 | — | — | 1-Naphthyl | 1-Naphthyl |
| 46 | Phenyl | Ph-NAr3Ar4 | — | — | 2-Naphthyl | 2-Naphthyl |
| 47 | Phenyl | Ph-NAr3Ar4 | — | — | m-Tolyl | m-Tolyl |
| 48 | Phenyl | Ph-NAr3Ar4 | — | — | tBuPhenyl | tBuPhenyl |
| 49 | 1-Naphthyl | H | — | — | — | — |
| 50 | 1-Naphthyl | Phenyl | — | — | — | — |
| 51 | 1-Naphthyl | 1-Naphthyl | — | — | — | — |
| 52 | 1-Naphthyl | 2-Naphthyl | — | — | — | — |
| 53 | 1-Naphthyl | NAr3Ar4 | — | — | Phenyl | Phenyl |
| 54 | 1-Naphthyl | NAr3Ar4 | — | — | Phenyl | 1-Naphthyl |

TABLE 1-continued

| Preferred structures | | | | | | |
|---|---|---|---|---|---|---|
| | | | R1 | | R2 | |
| No. | R1 | R2 | Ar1 | Ar2 | Ar3 | Ar4 |
| 55 | 1-Naphthyl | NAr3Ar4 | — | — | Phenyl | 2-Naphthyl |
| 56 | 1-Naphthyl | NAr3Ar4 | — | — | Phenyl | m-Tolyl |
| 57 | 1-Naphthyl | NAr3Ar4 | — | — | Phenyl | tBuPhenyl |
| 58 | 1-Naphthyl | NAr3Ar4 | — | — | Phenyl | Phenanthrenyl |
| 59 | 1-Naphthyl | NAr3Ar4 | — | — | 1-Naphthyl | 1-Naphthyl |
| 60 | 1-Naphthyl | NAr3Ar4 | — | — | 2-Naphthyl | 2-Naphthyl |
| 61 | 1-Naphthyl | NAr3Ar4 | — | — | m-Tolyl | m-Tolyl |
| 62 | 1-Naphthyl | NAr3Ar4 | — | — | tBuPhenyl | tBuPhenyl |
| 63 | 1-Naphthyl | Ph-NAr3Ar4 | — | — | Phenyl | Phenyl |
| 64 | 1-Naphthyl | Ph-NAr3Ar4 | — | — | Phenyl | 1-Naphthyl |
| 65 | 1-Naphthyl | Ph-NAr3Ar4 | — | — | Phenyl | 2-Naphthyl |
| 66 | 1-Naphthyl | Ph-NAr3Ar4 | — | — | Phenyl | m-Tolyl |
| 67 | 1-Naphthyl | Ph-NAr3Ar4 | — | — | Phenyl | tBuPhenyl |
| 68 | 1-Naphthyl | Ph-NAr3Ar4 | — | — | Phenyl | Phenanthrenyl |
| 69 | 1-Naphthyl | Ph-NAr3Ar4 | — | — | 1-Naphthyl | 1-Naphthyl |
| 70 | 1-Naphthyl | Ph-NAr3Ar4 | — | — | 2-Naphthyl | 2-Naphthyl |
| 71 | 1-Naphthyl | Ph-NAr3Ar4 | — | — | m-Tolyl | m-Tolyl |
| 72 | 1-Naphthyl | Ph-NAr3Ar4 | — | — | tBuPhenyl | tBuPhenyl |
| 73 | 2-Naphthyl | H | — | — | — | — |
| 74 | 2-Naphthyl | Phenyl | — | — | — | — |
| 75 | 2-Naphthyl | 1-Naphthyl | — | — | — | — |
| 76 | 2-Naphthyl | 2-Naphthyl | — | — | — | — |
| 77 | 2-Naphthyl | NAr3Ar4 | — | — | Phenyl | Phenyl |
| 78 | 2-Naphthyl | NAr3Ar4 | — | — | Phenyl | 1-Naphthyl |
| 79 | 2-Naphthyl | NAr3Ar4 | — | — | Phenyl | 2-Naphthyl |
| 80 | 2-Naphthyl | NAr3Ar4 | — | — | Phenyl | m-Tolyl |
| 81 | 2-Naphthyl | NAr3Ar4 | — | — | Phenyl | tBuPhenyl |
| 82 | 2-Naphthyl | NAr3Ar4 | — | — | Phenyl | Phenanthrenyl |
| 83 | 2-Naphthyl | NAr3Ar4 | — | — | 1-Naphthyl | 1-Naphthyl |
| 84 | 2-Naphthyl | NAr3Ar4 | — | — | 2-Naphthyl | 2-Naphthyl |
| 85 | 2-Naphthyl | NAr3Ar4 | — | — | m-Tolyl | m-Tolyl |
| 86 | 2-Naphthyl | NAr3Ar4 | — | — | tBuPhenyl | tBuPhenyl |
| 87 | 2-Naphthyl | Ph-NAr3Ar4 | — | — | Phenyl | Phenyl |
| 88 | 2-Naphthyl | Ph-NAr3Ar4 | — | — | Phenyl | 1-Naphthyl |
| 89 | 2-Naphthyl | Ph-NAr3Ar4 | — | — | Phenyl | 2-Naphthyl |
| 90 | 2-Naphthyl | Ph-NAr3Ar4 | — | — | Phenyl | m-Tolyl |
| 91 | 2-Naphthyl | Ph-NAr3Ar4 | — | — | Phenyl | tBuPhenyl |
| 92 | 2-Naphthyl | Ph-NAr3Ar4 | — | — | Phenyl | Phenanthrenyl |
| 93 | 2-Naphthyl | Ph-NAr3Ar4 | — | — | 1-Naphthyl | 1-Naphthyl |
| 94 | 2-Naphthyl | Ph-NAr3Ar4 | — | — | 2-Naphthyl | 2-Naphthyl |
| 95 | 2-Naphthyl | Ph-NAr3Ar4 | — | — | m-Tolyl | m-Tolyl |
| 96 | 2-Naphthyl | Ph-NAr3Ar4 | — | — | tBuPhenyl | tBuPhenyl |
| 97 | NAr1Ar2 | H | Phenyl | Phenyl | — | — |
| 98 | NAr1Ar2 | Phenyl | Phenyl | Phenyl | — | — |
| 99 | NAr1Ar2 | 1-Naphthyl | Phenyl | Phenyl | — | — |
| 100 | NAr1Ar2 | 2-Naphthyl | Phenyl | Phenyl | — | — |
| 101 | NAr1Ar2 | NAr3Ar4 | Phenyl | Phenyl | Phenyl | Phenyl |
| 102 | NAr1Ar2 | NAr3Ar4 | Phenyl | Phenyl | Phenyl | 1-Naphthyl |
| 103 | NAr1Ar2 | NAr3Ar4 | Phenyl | Phenyl | Phenyl | 2-Naphthyl |
| 104 | NAr1Ar2 | NAr3Ar4 | Phenyl | Phenyl | Phenyl | m-Tolyl |
| 105 | NAr1Ar2 | NAr3Ar4 | Phenyl | Phenyl | Phenyl | tBuPhenyl |
| 106 | NAr1Ar2 | NAr3Ar4 | Phenyl | Phenyl | Phenyl | Phenanthrenyl |
| 107 | NAr1Ar2 | NAr3Ar4 | Phenyl | Phenyl | 1-Naphthyl | 1-Naphthyl |
| 108 | NAr1Ar2 | NAr3Ar4 | Phenyl | Phenyl | 2-Naphthyl | 2-Naphthyl |
| 109 | NAr1Ar2 | NAr3Ar4 | Phenyl | Phenyl | m-Tolyl | m-Tolyl |
| 110 | NAr1Ar2 | NAr3Ar4 | Phenyl | Phenyl | tBuPhenyl | tBuPhenyl |
| 111 | NAr1Ar2 | Ph-NAr3Ar4 | Phenyl | Phenyl | Phenyl | Phenyl |
| 112 | NAr1Ar2 | Ph-NAr3Ar4 | Phenyl | Phenyl | Phenyl | 1-Naphthyl |
| 113 | NAr1Ar2 | Ph-NAr3Ar4 | Phenyl | Phenyl | Phenyl | 2-Naphthyl |
| 114 | NAr1Ar2 | Ph-NAr3Ar4 | Phenyl | Phenyl | Phenyl | m-Tolyl |
| 115 | NAr1Ar2 | Ph-NAr3Ar4 | Phenyl | Phenyl | Phenyl | tBuPhenyl |
| 116 | NAr1Ar2 | Ph-NAr3Ar4 | Phenyl | Phenyl | Phenyl | Phenanthrenyl |
| 117 | NAr1Ar2 | Ph-NAr3Ar4 | Phenyl | Phenyl | 1-Naphthyl | 1-Naphthyl |
| 118 | NAr1Ar2 | Ph-NAr3Ar4 | Phenyl | Phenyl | 2-Naphthyl | 2-Naphthyl |
| 119 | NAr1Ar2 | Ph-NAr3Ar4 | Phenyl | Phenyl | m-Tolyl | m-Tolyl |
| 120 | NAr1Ar2 | Ph-NAr3Ar4 | Phenyl | Phenyl | tBuPhenyl | tBuPhenyl |
| 121 | NAr1Ar2 | H | Phenyl | 1-Naphthyl | — | — |
| 122 | NAr1Ar2 | Phenyl | Phenyl | 1-Naphthyl | — | — |
| 123 | NAr1Ar2 | 1-Naphthyl | Phenyl | 1-Naphthyl | — | — |
| 124 | NAr1Ar2 | 2-Naphthyl | Phenyl | 1-Naphthyl | — | — |
| 125 | NAr1Ar2 | NAr3Ar4 | Phenyl | 1-Naphthyl | Phenyl | Phenyl |
| 126 | NAr1Ar2 | NAr3Ar4 | Phenyl | 1-Naphthyl | Phenyl | 1-Naphthyl |
| 127 | NAr1Ar2 | NAr3Ar4 | Phenyl | 1-Naphthyl | Phenyl | 2-Naphthyl |
| 128 | NAr1Ar2 | NAr3Ar4 | Phenyl | 1-Naphthyl | Phenyl | m-Tolyl |

TABLE 1-continued

| Preferred structures | | | | | | |
|---|---|---|---|---|---|---|
| | | | R1 | | R2 | |
| No. R1 | | R2 | Ar1 | Ar2 | Ar3 | Ar4 |
| 129 | NAr1Ar2 | NAr3Ar4 | Phenyl | 1-Naphthyl | Phenyl | tBuPhenyl |
| 130 | NAr1Ar2 | NAr3Ar4 | Phenyl | 1-Naphthyl | Phenyl | Phenanthrenyl |
| 131 | NAr1Ar2 | NAr3Ar4 | Phenyl | 1-Naphthyl | 1-Naphthyl | 1-Naphthyl |
| 132 | NAr1Ar2 | NAr3Ar4 | Phenyl | 1-Naphthyl | 2-Naphthyl | 2-Naphthyl |
| 133 | NAr1Ar2 | NAr3Ar4 | Phenyl | 1-Naphthyl | m-Tolyl | m-Tolyl |
| 134 | NAr1Ar2 | NAr3Ar4 | Phenyl | 1-Naphthyl | tBuPhenyl | tBuPhenyl |
| 135 | NAr1Ar2 | Ph-NAr3Ar4 | Phenyl | 1-Naphthyl | Phenyl | Phenyl |
| 136 | NAr1Ar2 | Ph-NAr3Ar4 | Phenyl | 1-Naphthyl | Phenyl | 1-Naphthyl |
| 137 | NAr1Ar2 | Ph-NAr3Ar4 | Phenyl | 1-Naphthyl | Phenyl | 2-Naphthyl |
| 138 | NAr1Ar2 | Ph-NAr3Ar4 | Phenyl | 1-Naphthyl | Phenyl | m-Tolyl |
| 139 | NAr1Ar2 | Ph-NAr3Ar4 | Phenyl | 1-Naphthyl | Phenyl | tBuPhenyl |
| 140 | NAr1Ar2 | Ph-NAr3Ar4 | Phenyl | 1-Naphthyl | Phenyl | Phenanthrenyl |
| 141 | NAr1Ar2 | Ph-NAr3Ar4 | Phenyl | 1-Naphthyl | 1-Naphthyl | 1-Naphthyl |
| 142 | NAr1Ar2 | Ph-NAr3Ar4 | Phenyl | 1-Naphthyl | 2-Naphthyl | 2-Naphthyl |
| 143 | NAr1Ar2 | Ph-NAr3Ar4 | Phenyl | 1-Naphthyl | m-Tolyl | m-Tolyl |
| 144 | NAr1Ar2 | Ph-NAr3Ar4 | Phenyl | 1-Naphthyl | tBuPhenyl | tBuPhenyl |
| 145 | NAr1Ar2 | H | Phenyl | 2-Naphthyl | — | — |
| 146 | NAr1Ar2 | Phenyl | Phenyl | 2-Naphthyl | — | — |
| 147 | NAr1Ar2 | 1-Naphthyl | Phenyl | 2-Naphthyl | — | — |
| 148 | NAr1Ar2 | 2-Naphthyl | Phenyl | 2-Naphthyl | — | — |
| 149 | NAr1Ar2 | NAr3Ar4 | Phenyl | 2-Naphthyl | Phenyl | Phenyl |
| 150 | NAr1Ar2 | NAr3Ar4 | Phenyl | 2-Naphthyl | Phenyl | 1-Naphthyl |
| 151 | NAr1Ar2 | NAr3Ar4 | Phenyl | 2-Naphthyl | Phenyl | 2-Naphthyl |
| 152 | NAr1Ar2 | NAr3Ar4 | Phenyl | 2-Naphthyl | Phenyl | m-Tolyl |
| 153 | NAr1Ar2 | NAr3Ar4 | Phenyl | 2-Naphthyl | Phenyl | tBuPhenyl |
| 154 | NAr1Ar2 | NAr3Ar4 | Phenyl | 2-Naphthyl | Phenyl | Phenanthrenyl |
| 155 | NAr1Ar2 | NAr3Ar4 | Phenyl | 2-Naphthyl | 1-Naphthyl | 1-Naphthyl |
| 156 | NAr1Ar2 | NAr3Ar4 | Phenyl | 2-Naphthyl | 2-Naphthyl | 2-Naphthyl |
| 157 | NAr1Ar2 | NAr3Ar4 | Phenyl | 2-Naphthyl | m-Tolyl | m-Tolyl |
| 158 | NAr1Ar2 | NAr3Ar4 | Phenyl | 2-Naphthyl | tBuPhenyl | tBuPhenyl |
| 159 | NAr1Ar2 | Ph-NAr3Ar4 | Phenyl | 2-Naphthyl | Phenyl | Phenyl |
| 160 | NAr1Ar2 | Ph-NAr3Ar4 | Phenyl | 2-Naphthyl | Phenyl | 1-Naphthyl |
| 161 | NAr1Ar2 | Ph-NAr3Ar4 | Phenyl | 2-Naphthyl | Phenyl | 2-Naphthyl |
| 162 | NAr1Ar2 | Ph-NAr3Ar4 | Phenyl | 2-Naphthyl | Phenyl | m-Tolyl |
| 163 | NAr1Ar2 | Ph-NAr3Ar4 | Phenyl | 2-Naphthyl | Phenyl | tBuPhenyl |
| 164 | NAr1Ar2 | Ph-NAr3Ar4 | Phenyl | 2-Naphthyl | Phenyl | Phenanthrenyl |
| 165 | NAr1Ar2 | Ph-NAr3Ar4 | Phenyl | 2-Naphthyl | 1-Naphthyl | 1-Naphthyl |
| 166 | NAr1Ar2 | Ph-NAr3Ar4 | Phenyl | 2-Naphthyl | 2-Naphthyl | 2-Naphthyl |
| 167 | NAr1Ar2 | Ph-NAr3Ar4 | Phenyl | 2-Naphthyl | m-Tolyl | m-Tolyl |
| 168 | NAr1Ar2 | Ph-NAr3Ar4 | Phenyl | 2-Naphthyl | tBuPhenyl | tBuPhenyl |
| 169 | NAr1Ar2 | H | Phenyl | m-Tolyl | — | — |
| 170 | NAr1Ar2 | Phenyl | Phenyl | m-Tolyl | — | — |
| 171 | NAr1Ar2 | 1-Naphthyl | Phenyl | m-Tolyl | — | — |
| 172 | NAr1Ar2 | 2-Naphthyl | Phenyl | m-Tolyl | — | — |
| 173 | NAr1Ar2 | NAr3Ar4 | Phenyl | m-Tolyl | Phenyl | Phenyl |
| 174 | NAr1Ar2 | NAr3Ar4 | Phenyl | m-Tolyl | Phenyl | 1-Naphthyl |
| 175 | NAr1Ar2 | NAr3Ar4 | Phenyl | m-Tolyl | Phenyl | 2-Naphthyl |
| 176 | NAr1Ar2 | NAr3Ar4 | Phenyl | m-Tolyl | Phenyl | m-Tolyl |
| 177 | NAr1Ar2 | NAr3Ar4 | Phenyl | m-Tolyl | Phenyl | tBuPhenyl |
| 178 | NAr1Ar2 | NAr3Ar4 | Phenyl | m-Tolyl | Phenyl | Phenanthrenyl |
| 179 | NAr1Ar2 | NAr3Ar4 | Phenyl | m-Tolyl | 1-Naphthyl | 1-Naphthyl |
| 180 | NAr1Ar2 | NAr3Ar4 | Phenyl | m-Tolyl | 2-Naphthyl | 2-Naphthyl |
| 181 | NAr1Ar2 | NAr3Ar4 | Phenyl | m-Tolyl | m-Tolyl | m-Tolyl |
| 182 | NAr1Ar2 | NAr3Ar4 | Phenyl | m-Tolyl | tBuPhenyl | tBuPhenyl |
| 183 | NAr1Ar2 | Ph-NAr3Ar4 | Phenyl | m-Tolyl | Phenyl | Phenyl |
| 184 | NAr1Ar2 | Ph-NAr3Ar4 | Phenyl | m-Tolyl | Phenyl | 1-Naphthyl |
| 185 | NAr1Ar2 | Ph-NAr3Ar4 | Phenyl | m-Tolyl | Phenyl | 2-Naphthyl |
| 186 | NAr1Ar2 | Ph-NAr3Ar4 | Phenyl | m-Tolyl | Phenyl | m-Tolyl |
| 187 | NAr1Ar2 | Ph-NAr3Ar4 | Phenyl | m-Tolyl | Phenyl | tBuPhenyl |
| 188 | NAr1Ar2 | Ph-NAr3Ar4 | Phenyl | m-Tolyl | Phenyl | Phenanthrenyl |
| 189 | NAr1Ar2 | Ph-NAr3Ar4 | Phenyl | m-Tolyl | 1-Naphthyl | 1-Naphthyl |
| 190 | NAr1Ar2 | Ph-NAr3Ar4 | Phenyl | m-Tolyl | 2-Naphthyl | 2-Naphthyl |
| 191 | NAr1Ar2 | Ph-NAr3Ar4 | Phenyl | m-Tolyl | m-Tolyl | m-Tolyl |
| 192 | NAr1Ar2 | Ph-NAr3Ar4 | Phenyl | m-Tolyl | tBuPhenyl | tBuPhenyl |
| 193 | NAr1Ar2 | H | Phenyl | tBuPhenyl | — | — |
| 194 | NAr1Ar2 | Phenyl | Phenyl | tBuPhenyl | — | — |
| 195 | NAr1Ar2 | 1-Naphthyl | Phenyl | tBuPhenyl | — | — |
| 196 | NAr1Ar2 | 2-Naphthyl | Phenyl | tBuPhenyl | — | — |
| 197 | NAr1Ar2 | NAr3Ar4 | Phenyl | tBuPhenyl | Phenyl | Phenyl |
| 198 | NAr1Ar2 | NAr3Ar4 | Phenyl | tBuPhenyl | Phenyl | 1-Naphthyl |
| 199 | NAr1Ar2 | NAr3Ar4 | Phenyl | tBuPhenyl | Phenyl | 2-Naphthyl |
| 200 | NAr1Ar2 | NAr3Ar4 | Phenyl | tBuPhenyl | Phenyl | m-Tolyl |
| 201 | NAr1Ar2 | NAr3Ar4 | Phenyl | tBuPhenyl | Phenyl | tBuPhenyl |
| 202 | NAr1Ar2 | NAr3Ar4 | Phenyl | tBuPhenyl | Phenyl | Phenanthrenyl |

TABLE 1-continued

| Preferred structures | | | | | | |
|---|---|---|---|---|---|---|
| | | | R1 | | R2 | |
| No. | R1 | R2 | Ar1 | Ar2 | Ar3 | Ar4 |
| 203 | NAr1Ar2 | NAr3Ar4 | Phenyl | tBuPhenyl | 1-Naphthyl | 1-Naphthyl |
| 204 | NAr1Ar2 | NAr3Ar4 | Phenyl | tBuPhenyl | 2-Naphthyl | 2-Naphthyl |
| 205 | NAr1Ar2 | NAr3Ar4 | Phenyl | tBuPhenyl | m-Tolyl | m-Tolyl |
| 206 | NAr1Ar2 | NAr3Ar4 | Phenyl | tBuPhenyl | tBuPhenyl | tBuPhenyl |
| 207 | NAr1Ar2 | Ph-NAr3Ar4 | Phenyl | tBuPhenyl | Phenyl | Phenyl |
| 208 | NAr1Ar2 | Ph-NAr3Ar4 | Phenyl | tBuPhenyl | Phenyl | 1-Naphthyl |
| 209 | NAr1Ar2 | Ph-NAr3Ar4 | Phenyl | tBuPhenyl | Phenyl | 2-Naphthyl |
| 210 | NAr1Ar2 | Ph-NAr3Ar4 | Phenyl | tBuPhenyl | Phenyl | m-Tolyl |
| 211 | NAr1Ar2 | Ph-NAr3Ar4 | Phenyl | tBuPhenyl | Phenyl | tBuPhenyl |
| 212 | NAr1Ar2 | Ph-NAr3Ar4 | Phenyl | tBuPhenyl | Phenyl | Phenanthrenyl |
| 213 | NAr1Ar2 | Ph-NAr3Ar4 | Phenyl | tBuPhenyl | 1-Naphthyl | 1-Naphthyl |
| 214 | NAr1Ar2 | Ph-NAr3Ar4 | Phenyl | tBuPhenyl | 2-Naphthyl | 2-Naphthyl |
| 215 | NAr1Ar2 | Ph-NAr3Ar4 | Phenyl | tBuPhenyl | m-Tolyl | m-Tolyl |
| 216 | NAr1Ar2 | Ph-NAr3Ar4 | Phenyl | tBuPhenyl | tBuPhenyl | tBuPhenyl |
| 217 | NAr1Ar2 | H | Phenyl | Phenanthrenyl | — | — |
| 218 | NAr1Ar2 | Phenyl | Phenyl | Phenanthrenyl | — | — |
| 219 | NAr1Ar2 | 1-Naphthyl | Phenyl | Phenanthrenyl | — | — |
| 220 | NAr1Ar2 | 2-Naphthyl | Phenyl | Phenanthrenyl | — | — |
| 221 | NAr1Ar2 | NAr3Ar4 | Phenyl | Phenanthrenyl | Phenyl | Phenyl |
| 222 | NAr1Ar2 | NAr3Ar4 | Phenyl | Phenanthrenyl | Phenyl | 1-Naphthyl |
| 223 | NAr1Ar2 | NAr3Ar4 | Phenyl | Phenanthrenyl | Phenyl | 2-Naphthyl |
| 224 | NAr1Ar2 | NAr3Ar4 | Phenyl | Phenanthrenyl | Phenyl | m-Tolyl |
| 225 | NAr1Ar2 | NAr3Ar4 | Phenyl | Phenanthrenyl | Phenyl | tBuPhenyl |
| 226 | NAr1Ar2 | NAr3Ar4 | Phenyl | Phenanthrenyl | Phenyl | Phenanthrenyl |
| 227 | NAr1Ar2 | NAr3Ar4 | Phenyl | Phenanthrenyl | 1-Naphthyl | 1-Naphthyl |
| 228 | NAr1Ar2 | NAr3Ar4 | Phenyl | Phenanthrenyl | 2-Naphthyl | 2-Naphthyl |
| 229 | NAr1Ar2 | NAr3Ar4 | Phenyl | Phenanthrenyl | m-Tolyl | m-Tolyl |
| 230 | NAr1Ar2 | NAr3Ar4 | Phenyl | Phenanthrenyl | tBuPhenyl | tBuPhenyl |
| 231 | NAr1Ar2 | Ph-NAr3Ar4 | Phenyl | Phenanthrenyl | Phenyl | Phenyl |
| 232 | NAr1Ar2 | Ph-NAr3Ar4 | Phenyl | Phenanthrenyl | Phenyl | 1-Naphthyl |
| 233 | NAr1Ar2 | Ph-NAr3Ar4 | Phenyl | Phenanthrenyl | Phenyl | 2-Naphthyl |
| 234 | NAr1Ar2 | Ph-NAr3Ar4 | Phenyl | Phenanthrenyl | Phenyl | m-Tolyl |
| 235 | NAr1Ar2 | Ph-NAr3Ar4 | Phenyl | Phenanthrenyl | Phenyl | tBuPhenyl |
| 236 | NAr1Ar2 | Ph-NAr3Ar4 | Phenyl | Phenanthrenyl | Phenyl | Phenanthrenyl |
| 237 | NAr1Ar2 | Ph-NAr3Ar4 | Phenyl | Phenanthrenyl | 1-Naphthyl | 1-Naphthyl |
| 238 | NAr1Ar2 | Ph-NAr3Ar4 | Phenyl | Phenanthrenyl | 2-Naphthyl | 2-Naphthyl |
| 239 | NAr1Ar2 | Ph-NAr3Ar4 | Phenyl | Phenanthrenyl | m-Tolyl | m-Tolyl |
| 240 | NAr1Ar2 | Ph-NAr3Ar4 | Phenyl | Phenanthrenyl | tBuPhenyl | tBuPhenyl |
| 241 | NAr1Ar2 | H | 1-Naphthyl | 1-Naphthyl | — | — |
| 242 | NAr1Ar2 | Phenyl | 1-Naphthyl | 1-Naphthyl | — | — |
| 243 | NAr1Ar2 | 1-Naphthyl | 1-Naphthyl | 1-Naphthyl | — | — |
| 244 | NAr1Ar2 | 2-Naphthyl | 1-Naphthyl | 1-Naphthyl | — | — |
| 245 | NAr1Ar2 | NAr3Ar4 | 1-Naphthyl | 1-Naphthyl | Phenyl | Phenyl |
| 246 | NAr1Ar2 | NAr3Ar4 | 1-Naphthyl | 1-Naphthyl | Phenyl | 1-Naphthyl |
| 247 | NAr1Ar2 | NAr3Ar4 | 1-Naphthyl | 1-Naphthyl | Phenyl | 2-Naphthyl |
| 248 | NAr1Ar2 | NAr3Ar4 | 1-Naphthyl | 1-Naphthyl | Phenyl | m-Tolyl |
| 249 | NAr1Ar2 | NAr3Ar4 | 1-Naphthyl | 1-Naphthyl | Phenyl | tBuPhenyl |
| 250 | NAr1Ar2 | NAr3Ar4 | 1-Naphthyl | 1-Naphthyl | Phenyl | Phenanthrenyl |
| 251 | NAr1Ar2 | NAr3Ar4 | 1-Naphthyl | 1-Naphthyl | 1-Naphthyl | 1-Naphthyl |
| 252 | NAr1Ar2 | NAr3Ar4 | 1-Naphthyl | 1-Naphthyl | 2-Naphthyl | 2-Naphthyl |
| 253 | NAr1Ar2 | NAr3Ar4 | 1-Naphthyl | 1-Naphthyl | m-Tolyl | m-Tolyl |
| 254 | NAr1Ar2 | NAr3Ar4 | 1-Naphthyl | 1-Naphthyl | tBuPhenyl | tBuPhenyl |
| 255 | NAr1Ar2 | Ph-NAr3Ar4 | 1-Naphthyl | 1-Naphthyl | Phenyl | Phenyl |
| 256 | NAr1Ar2 | Ph-NAr3Ar4 | 1-Naphthyl | 1-Naphthyl | Phenyl | 1-Naphthyl |
| 257 | NAr1Ar2 | Ph-NAr3Ar4 | 1-Naphthyl | 1-Naphthyl | Phenyl | 2-Naphthyl |
| 258 | NAr1Ar2 | Ph-NAr3Ar4 | 1-Naphthyl | 1-Naphthyl | Phenyl | m-Tolyl |
| 259 | NAr1Ar2 | Ph-NAr3Ar4 | 1-Naphthyl | 1-Naphthyl | Phenyl | tBuPhenyl |
| 260 | NAr1Ar2 | Ph-NAr3Ar4 | 1-Naphthyl | 1-Naphthyl | Phenyl | Phenanthrenyl |
| 261 | NAr1Ar2 | Ph-NAr3Ar4 | 1-Naphthyl | 1-Naphthyl | 1-Naphthyl | 1-Naphthyl |
| 262 | NAr1Ar2 | Ph-NAr3Ar4 | 1-Naphthyl | 1-Naphthyl | 2-Naphthyl | 2-Naphthyl |
| 263 | NAr1Ar2 | Ph-NAr3Ar4 | 1-Naphthyl | 1-Naphthyl | m-Tolyl | m-Tolyl |
| 264 | NAr1Ar2 | Ph-NAr3Ar4 | 1-Naphthyl | 1-Naphthyl | tBuPhenyl | tBuPhenyl |
| 265 | NAr1Ar2 | H | 2-Naphthyl | 2-Naphthyl | — | — |
| 266 | NAr1Ar2 | Phenyl | 2-Naphthyl | 2-Naphthyl | — | — |
| 267 | NAr1Ar2 | 1-Naphthyl | 2-Naphthyl | 2-Naphthyl | — | — |
| 268 | NAr1Ar2 | 2-Naphthyl | 2-Naphthyl | 2-Naphthyl | — | — |
| 269 | NAr1Ar2 | NAr3Ar4 | 2-Naphthyl | 2-Naphthyl | Phenyl | Phenyl |
| 270 | NAr1Ar2 | NAr3Ar4 | 2-Naphthyl | 2-Naphthyl | Phenyl | 1-Naphthyl |
| 271 | NAr1Ar2 | NAr3Ar4 | 2-Naphthyl | 2-Naphthyl | Phenyl | 2-Naphthyl |
| 272 | NAr1Ar2 | NAr3Ar4 | 2-Naphthyl | 2-Naphthyl | Phenyl | m-Tolyl |
| 273 | NAr1Ar2 | NAr3Ar4 | 2-Naphthyl | 2-Naphthyl | Phenyl | tBuPhenyl |
| 274 | NAr1Ar2 | NAr3Ar4 | 2-Naphthyl | 2-Naphthyl | Phenyl | Phenanthrenyl |
| 275 | NAr1Ar2 | NAr3Ar4 | 2-Naphthyl | 2-Naphthyl | 1-Naphthyl | 1-Naphthyl |
| 276 | NAr1Ar2 | NAr3Ar4 | 2-Naphthyl | 2-Naphthyl | 2-Naphthyl | 2-Naphthyl |

TABLE 1-continued

| Preferred structures | | | | | | |
|---|---|---|---|---|---|---|
| | | | R1 | | R2 | |
| No. | R1 | R2 | Ar1 | Ar2 | Ar3 | Ar4 |
| 277 | NAr1Ar2 | NAr3Ar4 | 2-Naphthyl | 2-Naphthyl | m-Tolyl | m-Tolyl |
| 278 | NAr1Ar2 | NAr3Ar4 | 2-Naphthyl | 2-Naphthyl | tBuPhenyl | tBuPhenyl |
| 279 | NAr1Ar2 | Ph-NAr3Ar4 | 2-Naphthyl | 2-Naphthyl | Phenyl | Phenyl |
| 280 | NAr1Ar2 | Ph-NAr3Ar4 | 2-Naphthyl | 2-Naphthyl | Phenyl | 1-Naphthyl |
| 281 | NAr1Ar2 | Ph-NAr3Ar4 | 2-Naphthyl | 2-Naphthyl | Phenyl | 2-Naphthyl |
| 282 | NAr1Ar2 | Ph-NAr3Ar4 | 2-Naphthyl | 2-Naphthyl | Phenyl | m-Tolyl |
| 283 | NAr1Ar2 | Ph-NAr3Ar4 | 2-Naphthyl | 2-Naphthyl | Phenyl | tBuPhenyl |
| 284 | NAr1Ar2 | Ph-NAr3Ar4 | 2-Naphthyl | 2-Naphthyl | Phenyl | Phenanthrenyl |
| 285 | NAr1Ar2 | Ph-NAr3Ar4 | 2-Naphthyl | 2-Naphthyl | 1-Naphthyl | 1-Naphthyl |
| 286 | NAr1Ar2 | Ph-NAr3Ar4 | 2-Naphthyl | 2-Naphthyl | 2-Naphthyl | 2-Naphthyl |
| 287 | NAr1Ar2 | Ph-NAr3Ar4 | 2-Naphthyl | 2-Naphthyl | m-Tolyl | m-Tolyl |
| 288 | NAr1Ar2 | Ph-NAr3Ar4 | 2-Naphthyl | 2-Naphthyl | tBuPhenyl | tBuPhenyl |
| 289 | NAr1Ar2 | H | m-Tolyl | m-Tolyl | — | — |
| 290 | NAr1Ar2 | Phenyl | m-Tolyl | m-Tolyl | — | — |
| 291 | NAr1Ar2 | 1-Naphthyl | m-Tolyl | m-Tolyl | — | — |
| 292 | NAr1Ar2 | 2-Naphthyl | m-Tolyl | m-Tolyl | — | — |
| 293 | NAr1Ar2 | NAr3Ar4 | m-Tolyl | m-Tolyl | Phenyl | Phenyl |
| 294 | NAr1Ar2 | NAr3Ar4 | m-Tolyl | m-Tolyl | Phenyl | 1-Naphthyl |
| 295 | NAr1Ar2 | NAr3Ar4 | m-Tolyl | m-Tolyl | Phenyl | 2-Naphthyl |
| 296 | NAr1Ar2 | NAr3Ar4 | m-Tolyl | m-Tolyl | Phenyl | m-Tolyl |
| 297 | NAr1Ar2 | NAr3Ar4 | m-Tolyl | m-Tolyl | Phenyl | tBuPhenyl |
| 298 | NAr1Ar2 | NAr3Ar4 | m-Tolyl | m-Tolyl | Phenyl | Phenanthrenyl |
| 299 | NAr1Ar2 | NAr3Ar4 | m-Tolyl | m-Tolyl | 1-Naphthyl | 1-Naphthyl |
| 300 | NAr1Ar2 | NAr3Ar4 | m-Tolyl | m-Tolyl | 2-Naphthyl | 2-Naphthyl |
| 301 | NAr1Ar2 | NAr3Ar4 | m-Tolyl | m-Tolyl | m-Tolyl | m-Tolyl |
| 302 | NAr1Ar2 | NAr3Ar4 | m-Tolyl | m-Tolyl | tBuPhenyl | tBuPhenyl |
| 303 | NAr1Ar2 | Ph-NAr3Ar4 | m-Tolyl | m-Tolyl | Phenyl | Phenyl |
| 304 | NAr1Ar2 | Ph-NAr3Ar4 | m-Tolyl | m-Tolyl | Phenyl | 1-Naphthyl |
| 305 | NAr1Ar2 | Ph-NAr3Ar4 | m-Tolyl | m-Tolyl | Phenyl | 2-Naphthyl |
| 306 | NAr1Ar2 | Ph-NAr3Ar4 | m-Tolyl | m-Tolyl | Phenyl | m-Tolyl |
| 307 | NAr1Ar2 | Ph-NAr3Ar4 | m-Tolyl | m-Tolyl | Phenyl | tBuPhenyl |
| 308 | NAr1Ar2 | Ph-NAr3Ar4 | m-Tolyl | m-Tolyl | Phenyl | Phenanthrenyl |
| 309 | NAr1Ar2 | Ph-NAr3Ar4 | m-Tolyl | m-Tolyl | 1-Naphthyl | 1-Naphthyl |
| 310 | NAr1Ar2 | Ph-NAr3Ar4 | m-Tolyl | m-Tolyl | 2-Naphthyl | 2-Naphthyl |
| 311 | NAr1Ar2 | Ph-NAr3Ar4 | m-Tolyl | m-Tolyl | m-Tolyl | m-Tolyl |
| 312 | NAr1Ar2 | Ph-NAr3Ar4 | m-Tolyl | m-Tolyl | tBuPhenyl | tBuPhenyl |
| 313 | NAr1Ar2 | H | tBuPhenyl | tBuPhenyl | — | — |
| 314 | NAr1Ar2 | Phenyl | tBuPhenyl | tBuPhenyl | — | — |
| 315 | NAr1Ar2 | 1-Naphthyl | tBuPhenyl | tBuPhenyl | — | — |
| 316 | NAr1Ar2 | 2-Naphthyl | tBuPhenyl | tBuPhenyl | — | — |
| 317 | NAr1Ar2 | NAr3Ar4 | tBuPhenyl | tBuPhenyl | Phenyl | Phenyl |
| 318 | NAr1Ar2 | NAr3Ar4 | tBuPhenyl | tBuPhenyl | Phenyl | 1-Naphthyl |
| 319 | NAr1Ar2 | NAr3Ar4 | tBuPhenyl | tBuPhenyl | Phenyl | 2-Naphthyl |
| 320 | NAr1Ar2 | NAr3Ar4 | tBuPhenyl | tBuPhenyl | Phenyl | m-Tolyl |
| 321 | NAr1Ar2 | NAr3Ar4 | tBuPhenyl | tBuPhenyl | Phenyl | tBuPhenyl |
| 322 | NAr1Ar2 | NAr3Ar4 | tBuPhenyl | tBuPhenyl | Phenyl | Phenanthrenyl |
| 323 | NAr1Ar2 | NAr3Ar4 | tBuPhenyl | tBuPhenyl | 1-Naphthyl | 1-Naphthyl |
| 324 | NAr1Ar2 | NAr3Ar4 | tBuPhenyl | tBuPhenyl | 2-Naphthyl | 2-Naphthyl |
| 325 | NAr1Ar2 | NAr3Ar4 | tBuPhenyl | tBuPhenyl | m-Tolyl | m-Tolyl |
| 326 | NAr1Ar2 | NAr3Ar4 | tBuPhenyl | tBuPhenyl | tBuPhenyl | tBuPhenyl |
| 327 | NAr1Ar2 | Ph-NAr3Ar4 | tBuPhenyl | tBuPhenyl | Phenyl | Phenyl |
| 328 | NAr1Ar2 | Ph-NAr3Ar4 | tBuPhenyl | tBuPhenyl | Phenyl | 1-Naphthyl |
| 329 | NAr1Ar2 | Ph-NAr3Ar4 | tBuPhenyl | tBuPhenyl | Phenyl | 2-Naphthyl |
| 330 | NAr1Ar2 | Ph-NAr3Ar4 | tBuPhenyl | tBuPhenyl | Phenyl | m-Tolyl |
| 331 | NAr1Ar2 | Ph-NAr3Ar4 | tBuPhenyl | tBuPhenyl | Phenyl | tBuPhenyl |
| 332 | NAr1Ar2 | Ph-NAr3Ar4 | tBuPhenyl | tBuPhenyl | Phenyl | Phenanthrenyl |
| 333 | NAr1Ar2 | Ph-NAr3Ar4 | tBuPhenyl | tBuPhenyl | 1-Naphthyl | 1-Naphthyl |
| 334 | NAr1Ar2 | Ph-NAr3Ar4 | tBuPhenyl | tBuPhenyl | 2-Naphthyl | 2-Naphthyl |
| 335 | NAr1Ar2 | Ph-NAr3Ar4 | tBuPhenyl | tBuPhenyl | m-Tolyl | m-Tolyl |
| 336 | NAr1Ar2 | Ph-NAr3Ar4 | tBuPhenyl | tBuPhenyl | tBuPhenyl | tBuPhenyl |
| 337 | Ph-NAr1Ar2 | H | Phenyl | Phenyl | — | — |
| 338 | Ph-NAr1Ar2 | Phenyl | Phenyl | Phenyl | — | — |
| 339 | Ph-NAr1Ar2 | 1-Naphthyl | Phenyl | Phenyl | — | — |
| 340 | Ph-NAr1Ar2 | 2-Naphthyl | Phenyl | Phenyl | — | — |
| 341 | Ph-NAr1Ar2 | NAr3Ar4 | Phenyl | Phenyl | Phenyl | Phenyl |
| 342 | Ph-NAr1Ar2 | NAr3Ar4 | Phenyl | Phenyl | Phenyl | 1-Naphthyl |
| 343 | Ph-NAr1Ar2 | NAr3Ar4 | Phenyl | Phenyl | Phenyl | 2-Naphthyl |
| 344 | Ph-NAr1Ar2 | NAr3Ar4 | Phenyl | Phenyl | Phenyl | m-Tolyl |
| 345 | Ph-NAr1Ar2 | NAr3Ar4 | Phenyl | Phenyl | Phenyl | tBuPhenyl |
| 346 | Ph-NAr1Ar2 | NAr3Ar4 | Phenyl | Phenyl | Phenyl | Phenanthrenyl |
| 347 | Ph-NAr1Ar2 | NAr3Ar4 | Phenyl | Phenyl | 1-Naphthyl | 1-Naphthyl |
| 348 | Ph-NAr1Ar2 | NAr3Ar4 | Phenyl | Phenyl | 2-Naphthyl | 2-Naphthyl |
| 349 | Ph-NAr1Ar2 | NAr3Ar4 | Phenyl | Phenyl | m-Tolyl | m-Tolyl |
| 350 | Ph-NAr1Ar2 | NAr3Ar4 | Phenyl | Phenyl | tBuPhenyl | tBuPhenyl |

TABLE 1-continued

| Preferred structures | | | | | | |
|---|---|---|---|---|---|---|
| | | | R1 | | R2 | |
| No. | R1 | R2 | Ar1 | Ar2 | Ar3 | Ar4 |
| 351 | Ph-NAr1Ar2 | Ph-NAr3Ar4 | Phenyl | Phenyl | Phenyl | Phenyl |
| 352 | Ph-NAr1Ar2 | Ph-NAr3Ar4 | Phenyl | Phenyl | Phenyl | 1-Naphthyl |
| 353 | Ph-NAr1Ar2 | Ph-NAr3Ar4 | Phenyl | Phenyl | Phenyl | 2-Naphthyl |
| 354 | Ph-NAr1Ar2 | Ph-NAr3Ar4 | Phenyl | Phenyl | Phenyl | m-Tolyl |
| 355 | Ph-NAr1Ar2 | Ph-NAr3Ar4 | Phenyl | Phenyl | Phenyl | tBuPhenyl |
| 356 | Ph-NAr1Ar2 | Ph-NAr3Ar4 | Phenyl | Phenyl | Phenyl | Phenanthrenyl |
| 357 | Ph-NAr1Ar2 | Ph-NAr3Ar4 | Phenyl | Phenyl | 1-Naphthyl | 1-Naphthyl |
| 358 | Ph-NAr1Ar2 | Ph-NAr3Ar4 | Phenyl | Phenyl | 2-Naphthyl | 2-Naphthyl |
| 359 | Ph-NAr1Ar2 | Ph-NAr3Ar4 | Phenyl | Phenyl | m-Tolyl | m-Tolyl |
| 360 | Ph-NAr1Ar2 | Ph-NAr3Ar4 | Phenyl | Phenyl | tBuPhenyl | tBuPhenyl |
| 361 | Ph-NAr1Ar2 | H | Phenyl | 1-Naphthyl | — | — |
| 362 | Ph-NAr1Ar2 | Phenyl | Phenyl | 1-Naphthyl | — | — |
| 363 | Ph-NAr1Ar2 | 1-Naphthyl | Phenyl | 1-Naphthyl | — | — |
| 364 | Ph-NAr1Ar2 | 2-Naphthyl | Phenyl | 1-Naphthyl | — | — |
| 365 | Ph-NAr1Ar2 | NAr3Ar4 | Phenyl | 1-Naphthyl | Phenyl | Phenyl |
| 366 | Ph-NAr1Ar2 | NAr3Ar4 | Phenyl | 1-Naphthyl | Phenyl | 1-Naphthyl |
| 367 | Ph-NAr1Ar2 | NAr3Ar4 | Phenyl | 1-Naphthyl | Phenyl | 2-Naphthyl |
| 368 | Ph-NAr1Ar2 | NAr3Ar4 | Phenyl | 1-Naphthyl | Phenyl | m-Tolyl |
| 369 | Ph-NAr1Ar2 | NAr3Ar4 | Phenyl | 1-Naphthyl | Phenyl | tBuPhenyl |
| 370 | Ph-NAr1Ar2 | NAr3Ar4 | Phenyl | 1-Naphthyl | Phenyl | Phenanthrenyl |
| 371 | Ph-NAr1Ar2 | NAr3Ar4 | Phenyl | 1-Naphthyl | 1-Naphthyl | 1-Naphthyl |
| 372 | Ph-NAr1Ar2 | NAr3Ar4 | Phenyl | 1-Naphthyl | 2-Naphthyl | 2-Naphthyl |
| 373 | Ph-NAr1Ar2 | NAr3Ar4 | Phenyl | 1-Naphthyl | m-Tolyl | m-Tolyl |
| 374 | Ph-NAr1Ar2 | NAr3Ar4 | Phenyl | 1-Naphthyl | tBuPhenyl | tBuPhenyl |
| 375 | Ph-NAr1Ar2 | Ph-NAr3Ar4 | Phenyl | 1-Naphthyl | Phenyl | Phenyl |
| 376 | Ph-NAr1Ar2 | Ph-NAr3Ar4 | Phenyl | 1-Naphthyl | Phenyl | 1-Naphthyl |
| 377 | Ph-NAr1Ar2 | Ph-NAr3Ar4 | Phenyl | 1-Naphthyl | Phenyl | 2-Naphthyl |
| 378 | Ph-NAr1Ar2 | Ph-NAr3Ar4 | Phenyl | 1-Naphthyl | Phenyl | m-Tolyl |
| 379 | Ph-NAr1Ar2 | Ph-NAr3Ar4 | Phenyl | 1-Naphthyl | Phenyl | tBuPhenyl |
| 380 | Ph-NAr1Ar2 | Ph-NAr3Ar4 | Phenyl | 1-Naphthyl | Phenyl | Phenanthrenyl |
| 381 | Ph-NAr1Ar2 | Ph-NAr3Ar4 | Phenyl | 1-Naphthyl | 1-Naphthyl | 1-Naphthyl |
| 382 | Ph-NAr1Ar2 | Ph-NAr3Ar4 | Phenyl | 1-Naphthyl | 2-Naphthyl | 2-Naphthyl |
| 383 | Ph-NAr1Ar2 | Ph-NAr3Ar4 | Phenyl | 1-Naphthyl | m-Tolyl | m-Tolyl |
| 384 | Ph-NAr1Ar2 | Ph-NAr3Ar4 | Phenyl | 1-Naphthyl | tBuPhenyl | tBuPhenyl |
| 385 | Ph-NAr1Ar2 | H | Phenyl | 2-Naphthyl | — | — |
| 386 | Ph-NAr1Ar2 | Phenyl | Phenyl | 2-Naphthyl | — | — |
| 387 | Ph-NAr1Ar2 | 1-Naphthyl | Phenyl | 2-Naphthyl | — | — |
| 388 | Ph-NAr1Ar2 | 2-Naphthyl | Phenyl | 2-Naphthyl | — | — |
| 389 | Ph-NAr1Ar2 | NAr3Ar4 | Phenyl | 2-Naphthyl | Phenyl | Phenyl |
| 390 | Ph-NAr1Ar2 | NAr3Ar4 | Phenyl | 2-Naphthyl | Phenyl | 1-Naphthyl |
| 391 | Ph-NAr1Ar2 | NAr3Ar4 | Phenyl | 2-Naphthyl | Phenyl | 2-Naphthyl |
| 392 | Ph-NAr1Ar2 | NAr3Ar4 | Phenyl | 2-Naphthyl | Phenyl | m-Tolyl |
| 393 | Ph-NAr1Ar2 | NAr3Ar4 | Phenyl | 2-Naphthyl | Phenyl | tBuPhenyl |
| 394 | Ph-NAr1Ar2 | NAr3Ar4 | Phenyl | 2-Naphthyl | Phenyl | Phenanthrenyl |
| 395 | Ph-NAr1Ar2 | NAr3Ar4 | Phenyl | 2-Naphthyl | 1-Naphthyl | 1-Naphthyl |
| 396 | Ph-NAr1Ar2 | NAr3Ar4 | Phenyl | 2-Naphthyl | 2-Naphthyl | 2-Naphthyl |
| 397 | Ph-NAr1Ar2 | NAr3Ar4 | Phenyl | 2-Naphthyl | m-Tolyl | m-Tolyl |
| 398 | Ph-NAr1Ar2 | NAr3Ar4 | Phenyl | 2-Naphthyl | tBuPhenyl | tBuPhenyl |
| 399 | Ph-NAr1Ar2 | Ph-NAr3Ar4 | Phenyl | 2-Naphthyl | Phenyl | Phenyl |
| 400 | Ph-NAr1Ar2 | Ph-NAr3Ar4 | Phenyl | 2-Naphthyl | Phenyl | 1-Naphthyl |
| 401 | Ph-NAr1Ar2 | Ph-NAr3Ar4 | Phenyl | 2-Naphthyl | Phenyl | 2-Naphthyl |
| 402 | Ph-NAr1Ar2 | Ph-NAr3Ar4 | Phenyl | 2-Naphthyl | Phenyl | m-Tolyl |
| 403 | Ph-NAr1Ar2 | Ph-NAr3Ar4 | Phenyl | 2-Naphthyl | Phenyl | tBuPhenyl |
| 404 | Ph-NAr1Ar2 | Ph-NAr3Ar4 | Phenyl | 2-Naphthyl | Phenyl | Phenanthrenyl |
| 405 | Ph-NAr1Ar2 | Ph-NAr3Ar4 | Phenyl | 2-Naphthyl | 1-Naphthyl | 1-Naphthyl |
| 406 | Ph-NAr1Ar2 | Ph-NAr3Ar4 | Phenyl | 2-Naphthyl | 2-Naphthyl | 2-Naphthyl |
| 407 | Ph-NAr1Ar2 | Ph-NAr3Ar4 | Phenyl | 2-Naphthyl | m-Tolyl | m-Tolyl |
| 408 | Ph-NAr1Ar2 | Ph-NAr3Ar4 | Phenyl | 2-Naphthyl | tBuPhenyl | tBuPhenyl |
| 409 | Ph-NAr1Ar2 | H | Phenyl | m-Tolyl | — | — |
| 410 | Ph-NAr1Ar2 | Phenyl | Phenyl | m-Tolyl | — | — |
| 411 | Ph-NAr1Ar2 | 1-Naphthyl | Phenyl | m-Tolyl | — | — |
| 412 | Ph-NAr1Ar2 | 2-Naphthyl | Phenyl | m-Tolyl | — | — |
| 413 | Ph-NAr1Ar2 | NAr3Ar4 | Phenyl | m-Tolyl | Phenyl | Phenyl |
| 414 | Ph-NAr1Ar2 | NAr3Ar4 | Phenyl | m-Tolyl | Phenyl | 1-Naphthyl |
| 415 | Ph-NAr1Ar2 | NAr3Ar4 | Phenyl | m-Tolyl | Phenyl | 2-Naphthyl |
| 416 | Ph-NAr1Ar2 | NAr3Ar4 | Phenyl | m-Tolyl | Phenyl | m-Tolyl |
| 417 | Ph-NAr1Ar2 | NAr3Ar4 | Phenyl | m-Tolyl | Phenyl | tBuPhenyl |
| 418 | Ph-NAr1Ar2 | NAr3Ar4 | Phenyl | m-Tolyl | Phenyl | Phenanthrenyl |
| 419 | Ph-NAr1Ar2 | NAr3Ar4 | Phenyl | m-Tolyl | 1-Naphthyl | 1-Naphthyl |
| 420 | Ph-NAr1Ar2 | NAr3Ar4 | Phenyl | m-Tolyl | 2-Naphthyl | 2-Naphthyl |
| 421 | Ph-NAr1Ar2 | NAr3Ar4 | Phenyl | m-Tolyl | m-Tolyl | m-Tolyl |
| 422 | Ph-NAr1Ar2 | NAr3Ar4 | Phenyl | m-Tolyl | tBuPhenyl | tBuPhenyl |
| 423 | Ph-NAr1Ar2 | Ph-NAr3Ar4 | Phenyl | m-Tolyl | Phenyl | Phenyl |
| 424 | Ph-NAr1Ar2 | Ph-NAr3Ar4 | Phenyl | m-Tolyl | Phenyl | 1-Naphthyl |

TABLE 1-continued

| Preferred structures | | | | | | |
|---|---|---|---|---|---|---|
| | | | R1 | | R2 | |
| No. | R1 | R2 | Ar1 | Ar2 | Ar3 | Ar4 |
| 425 | Ph-NAr1Ar2 | Ph-NAr3Ar4 | Phenyl | m-Tolyl | Phenyl | 2-Naphthyl |
| 426 | Ph-NAr1Ar2 | Ph-NAr3Ar4 | Phenyl | m-Tolyl | Phenyl | m-Tolyl |
| 427 | Ph-NAr1Ar2 | Ph-NAr3Ar4 | Phenyl | m-Tolyl | Phenyl | tBuPhenyl |
| 428 | Ph-NAr1Ar2 | Ph-NAr3Ar4 | Phenyl | m-Tolyl | Phenyl | Phenanthrenyl |
| 429 | Ph-NAr1Ar2 | Ph-NAr3Ar4 | Phenyl | m-Tolyl | 1-Naphthyl | 1-Naphthyl |
| 430 | Ph-NAr1Ar2 | Ph-NAr3Ar4 | Phenyl | m-Tolyl | 2-Naphthyl | 2-Naphthyl |
| 431 | Ph-NAr1Ar2 | Ph-NAr3Ar4 | Phenyl | m-Tolyl | m-Tolyl | m-Tolyl |
| 432 | Ph-NAr1Ar2 | Ph-NAr3Ar4 | Phenyl | m-Tolyl | tBuPhenyl | tBuPhenyl |
| 433 | Ph-NAr1Ar2 | H | Phenyl | tBuPhenyl | — | — |
| 434 | Ph-NAr1Ar2 | Phenyl | Phenyl | tBuPhenyl | — | — |
| 435 | Ph-NAr1Ar2 | 1-Naphthyl | Phenyl | tBuPhenyl | — | — |
| 436 | Ph-NAr1Ar2 | 2-Naphthyl | Phenyl | tBuPhenyl | — | — |
| 437 | Ph-NAr1Ar2 | NAr3Ar4 | Phenyl | tBuPhenyl | Phenyl | Phenyl |
| 438 | Ph-NAr1Ar2 | NAr3Ar4 | Phenyl | tBuPhenyl | Phenyl | 1-Naphthyl |
| 439 | Ph-NAr1Ar2 | NAr3Ar4 | Phenyl | tBuPhenyl | Phenyl | 2-Naphthyl |
| 440 | Ph-NAr1Ar2 | NAr3Ar4 | Phenyl | tBuPhenyl | Phenyl | m-Tolyl |
| 441 | Ph-NAr1Ar2 | NAr3Ar4 | Phenyl | tBuPhenyl | Phenyl | tBuPhenyl |
| 442 | Ph-NAr1Ar2 | NAr3Ar4 | Phenyl | tBuPhenyl | Phenyl | Phenanthrenyl |
| 443 | Ph-NAr1Ar2 | NAr3Ar4 | Phenyl | tBuPhenyl | 1-Naphthyl | 1-Naphthyl |
| 444 | Ph-NAr1Ar2 | NAr3Ar4 | Phenyl | tBuPhenyl | 2-Naphthyl | 2-Naphthyl |
| 445 | Ph-NAr1Ar2 | NAr3Ar4 | Phenyl | tBuPhenyl | m-Tolyl | m-Tolyl |
| 446 | Ph-NAr1Ar2 | NAr3Ar4 | Phenyl | tBuPhenyl | tBuPhenyl | tBuPhenyl |
| 447 | Ph-NAr1Ar2 | Ph-NAr3Ar4 | Phenyl | tBuPhenyl | Phenyl | Phenyl |
| 448 | Ph-NAr1Ar2 | Ph-NAr3Ar4 | Phenyl | tBuPhenyl | Phenyl | 1-Naphthyl |
| 449 | Ph-NAr1Ar2 | Ph-NAr3Ar4 | Phenyl | tBuPhenyl | Phenyl | 2-Naphthyl |
| 450 | Ph-NAr1Ar2 | Ph-NAr3Ar4 | Phenyl | tBuPhenyl | Phenyl | m-Tolyl |
| 451 | Ph-NAr1Ar2 | Ph-NAr3Ar4 | Phenyl | tBuPhenyl | Phenyl | tBuPhenyl |
| 452 | Ph-NAr1Ar2 | Ph-NAr3Ar4 | Phenyl | tBuPhenyl | Phenyl | Phenanthrenyl |
| 453 | Ph-NAr1Ar2 | Ph-NAr3Ar4 | Phenyl | tBuPhenyl | 1-Naphthyl | 1-Naphthyl |
| 454 | Ph-NAr1Ar2 | Ph-NAr3Ar4 | Phenyl | tBuPhenyl | 2-Naphthyl | 2-Naphthyl |
| 455 | Ph-NAr1Ar2 | Ph-NAr3Ar4 | Phenyl | tBuPhenyl | m-Tolyl | m-Tolyl |
| 456 | Ph-NAr1Ar2 | Ph-NAr3Ar4 | Phenyl | tBuPhenyl | tBuPhenyl | tBuPhenyl |
| 457 | Ph-NAr1Ar2 | H | Phenyl | Phenanthrenyl | — | — |
| 458 | Ph-NAr1Ar2 | Phenyl | Phenyl | Phenanthrenyl | — | — |
| 459 | Ph-NAr1Ar2 | 1-Naphthyl | Phenyl | Phenanthrenyl | — | — |
| 460 | Ph-NAr1Ar2 | 2-Naphthyl | Phenyl | Phenanthrenyl | — | — |
| 461 | Ph-NAr1Ar2 | NAr3Ar4 | Phenyl | Phenanthrenyl | Phenyl | Phenyl |
| 462 | Ph-NAr1Ar2 | NAr3Ar4 | Phenyl | Phenanthrenyl | Phenyl | 1-Naphthyl |
| 463 | Ph-NAr1Ar2 | NAr3Ar4 | Phenyl | Phenanthrenyl | Phenyl | 2-Naphthyl |
| 464 | Ph-NAr1Ar2 | NAr3Ar4 | Phenyl | Phenanthrenyl | Phenyl | m-Tolyl |
| 465 | Ph-NAr1Ar2 | NAr3Ar4 | Phenyl | Phenanthrenyl | Phenyl | tBuPhenyl |
| 466 | Ph-NAr1Ar2 | NAr3Ar4 | Phenyl | Phenanthrenyl | Phenyl | Phenanthrenyl |
| 467 | Ph-NAr1Ar2 | NAr3Ar4 | Phenyl | Phenanthrenyl | 1-Naphthyl | 1-Naphthyl |
| 468 | Ph-NAr1Ar2 | NAr3Ar4 | Phenyl | Phenanthrenyl | 2-Naphthyl | 2-Naphthyl |
| 469 | Ph-NAr1Ar2 | NAr3Ar4 | Phenyl | Phenanthrenyl | m-Tolyl | m-Tolyl |
| 470 | Ph-NAr1Ar2 | NAr3Ar4 | Phenyl | Phenanthrenyl | tBuPhenyl | tBuPhenyl |
| 471 | Ph-NAr1Ar2 | Ph-NAr3Ar4 | Phenyl | Phenanthrenyl | Phenyl | Phenyl |
| 472 | Ph-NAr1Ar2 | Ph-NAr3Ar4 | Phenyl | Phenanthrenyl | Phenyl | 1-Naphthyl |
| 473 | Ph-NAr1Ar2 | Ph-NAr3Ar4 | Phenyl | Phenanthrenyl | Phenyl | 2-Naphthyl |
| 474 | Ph-NAr1Ar2 | Ph-NAr3Ar4 | Phenyl | Phenanthrenyl | Phenyl | m-Tolyl |
| 475 | Ph-NAr1Ar2 | Ph-NAr3Ar4 | Phenyl | Phenanthrenyl | Phenyl | tBuPhenyl |
| 476 | Ph-NAr1Ar2 | Ph-NAr3Ar4 | Phenyl | Phenanthrenyl | Phenyl | Phenanthrenyl |
| 477 | Ph-NAr1Ar2 | Ph-NAr3Ar4 | Phenyl | Phenanthrenyl | 1-Naphthyl | 1-Naphthyl |
| 478 | Ph-NAr1Ar2 | Ph-NAr3Ar4 | Phenyl | Phenanthrenyl | 2-Naphthyl | 2-Naphthyl |
| 479 | Ph-NAr1Ar2 | Ph-NAr3Ar4 | Phenyl | Phenanthrenyl | m-Tolyl | m-Tolyl |
| 480 | Ph-NAr1Ar2 | Ph-NAr3Ar4 | Phenyl | Phenanthrenyl | tBuPhenyl | tBuPhenyl |
| 481 | Ph-NAr1Ar2 | H | 1-Naphthyl | 1-Naphthyl | — | — |
| 482 | Ph-NAr1Ar2 | Phenyl | 1-Naphthyl | 1-Naphthyl | — | — |
| 483 | Ph-NAr1Ar2 | 1-Naphthyl | 1-Naphthyl | 1-Naphthyl | — | — |
| 484 | Ph-NAr1Ar2 | 2-Naphthyl | 1-Naphthyl | 1-Naphthyl | — | — |
| 485 | Ph-NAr1Ar2 | NAr3Ar4 | 1-Naphthyl | 1-Naphthyl | Phenyl | Phenyl |
| 486 | Ph-NAr1Ar2 | NAr3Ar4 | 1-Naphthyl | 1-Naphthyl | Phenyl | 1-Naphthyl |
| 487 | Ph-NAr1Ar2 | NAr3Ar4 | 1-Naphthyl | 1-Naphthyl | Phenyl | 2-Naphthyl |
| 488 | Ph-NAr1Ar2 | NAr3Ar4 | 1-Naphthyl | 1-Naphthyl | Phenyl | m-Tolyl |
| 489 | Ph-NAr1Ar2 | NAr3Ar4 | 1-Naphthyl | 1-Naphthyl | Phenyl | tBuPhenyl |
| 490 | Ph-NAr1Ar2 | NAr3Ar4 | 1-Naphthyl | 1-Naphthyl | Phenyl | Phenanthrenyl |
| 491 | Ph-NAr1Ar2 | NAr3Ar4 | 1-Naphthyl | 1-Naphthyl | 1-Naphthyl | 1-Naphthyl |
| 492 | Ph-NAr1Ar2 | NAr3Ar4 | 1-Naphthyl | 1-Naphthyl | 2-Naphthyl | 2-Naphthyl |
| 493 | Ph-NAr1Ar2 | NAr3Ar4 | 1-Naphthyl | 1-Naphthyl | m-Tolyl | m-Tolyl |
| 494 | Ph-NAr1Ar2 | NAr3Ar4 | 1-Naphthyl | 1-Naphthyl | tBuPhenyl | tBuPhenyl |
| 495 | Ph-NAr1Ar2 | Ph-NAr3Ar4 | 1-Naphthyl | 1-Naphthyl | Phenyl | Phenyl |
| 496 | Ph-NAr1Ar2 | Ph-NAr3Ar4 | 1-Naphthyl | 1-Naphthyl | Phenyl | 1-Naphthyl |
| 497 | Ph-NAr1Ar2 | Ph-NAr3Ar4 | 1-Naphthyl | 1-Naphthyl | Phenyl | 2-Naphthyl |
| 498 | Ph-NAr1Ar2 | Ph-NAr3Ar4 | 1-Naphthyl | 1-Naphthyl | Phenyl | m-Tolyl |

TABLE 1-continued

Preferred structures

| No. | R1 | R2 | R1 Ar1 | R1 Ar2 | R2 Ar3 | R2 Ar4 |
|---|---|---|---|---|---|---|
| 499 | Ph-NAr1Ar2 | Ph-NAr3Ar4 | 1-Naphthyl | 1-Naphthyl | Phenyl | tBuPhenyl |
| 500 | Ph-NAr1Ar2 | Ph-NAr3Ar4 | 1-Naphthyl | 1-Naphthyl | Phenyl | Phenanthrenyl |
| 501 | Ph-NAr1Ar2 | Ph-NAr3Ar4 | 1-Naphthyl | 1-Naphthyl | 1-Naphthyl | 1-Naphthyl |
| 502 | Ph-NAr1Ar2 | Ph-NAr3Ar4 | 1-Naphthyl | 1-Naphthyl | 2-Naphthyl | 2-Naphthyl |
| 503 | Ph-NAr1Ar2 | Ph-NAr3Ar4 | 1-Naphthyl | 1-Naphthyl | m-Tolyl | m-Tolyl |
| 504 | Ph-NAr1Ar2 | Ph-NAr3Ar4 | 1-Naphthyl | 1-Naphthyl | tBuPhenyl | tBuPhenyl |
| 505 | Ph-NAr1Ar2 | H | 2-Naphthyl | 2-Naphthyl | — | — |
| 506 | Ph-NAr1Ar2 | Phenyl | 2-Naphthyl | 2-Naphthyl | — | — |
| 507 | Ph-NAr1Ar2 | 1-Naphthyl | 2-Naphthyl | 2-Naphthyl | — | — |
| 508 | Ph-NAr1Ar2 | 2-Naphthyl | 2-Naphthyl | 2-Naphthyl | — | — |
| 509 | Ph-NAr1Ar2 | NAr3Ar4 | 2-Naphthyl | 2-Naphthyl | Phenyl | Phenyl |
| 510 | Ph-NAr1Ar2 | NAr3Ar4 | 2-Naphthyl | 2-Naphthyl | Phenyl | 1-Naphthyl |
| 511 | Ph-NAr1Ar2 | NAr3Ar4 | 2-Naphthyl | 2-Naphthyl | Phenyl | 2-Naphthyl |
| 512 | Ph-NAr1Ar2 | NAr3Ar4 | 2-Naphthyl | 2-Naphthyl | Phenyl | m-Tolyl |
| 513 | Ph-NAr1Ar2 | NAr3Ar4 | 2-Naphthyl | 2-Naphthyl | Phenyl | tBuPhenyl |
| 514 | Ph-NAr1Ar2 | NAr3Ar4 | 2-Naphthyl | 2-Naphthyl | Phenyl | Phenanthrenyl |
| 515 | Ph-NAr1Ar2 | NAr3Ar4 | 2-Naphthyl | 2-Naphthyl | 1-Naphthyl | 1-Naphthyl |
| 516 | Ph-NAr1Ar2 | NAr3Ar4 | 2-Naphthyl | 2-Naphthyl | 2-Naphthyl | 2-Naphthyl |
| 517 | Ph-NAr1Ar2 | NAr3Ar4 | 2-Naphthyl | 2-Naphthyl | m-Tolyl | m-Tolyl |
| 518 | Ph-NAr1Ar2 | NAr3Ar4 | 2-Naphthyl | 2-Naphthyl | tBuPhenyl | tBuPhenyl |
| 519 | Ph-NAr1Ar2 | Ph-NAr3Ar4 | 2-Naphthyl | 2-Naphthyl | Phenyl | Phenyl |
| 520 | Ph-NAr1Ar2 | Ph-NAr3Ar4 | 2-Naphthyl | 2-Naphthyl | Phenyl | 1-Naphthyl |
| 521 | Ph-NAr1Ar2 | Ph-NAr3Ar4 | 2-Naphthyl | 2-Naphthyl | Phenyl | 2-Naphthyl |
| 522 | Ph-NAr1Ar2 | Ph-NAr3Ar4 | 2-Naphthyl | 2-Naphthyl | Phenyl | m-Tolyl |
| 523 | Ph-NAr1Ar2 | Ph-NAr3Ar4 | 2-Naphthyl | 2-Naphthyl | Phenyl | tBuPhenyl |
| 524 | Ph-NAr1Ar2 | Ph-NAr3Ar4 | 2-Naphthyl | 2-Naphthyl | Phenyl | Phenanthrenyl |
| 525 | Ph-NAr1Ar2 | Ph-NAr3Ar4 | 2-Naphthyl | 2-Naphthyl | 1-Naphthyl | 1-Naphthyl |
| 526 | Ph-NAr1Ar2 | Ph-NAr3Ar4 | 2-Naphthyl | 2-Naphthyl | 2-Naphthyl | 2-Naphthyl |
| 527 | Ph-NAr1Ar2 | Ph-NAr3Ar4 | 2-Naphthyl | 2-Naphthyl | m-Tolyl | m-Tolyl |
| 528 | Ph-NAr1Ar2 | Ph-NAr3Ar4 | 2-Naphthyl | 2-Naphthyl | tBuPhenyl | tBuPhenyl |
| 529 | Ph-NAr1Ar2 | H | m-Tolyl | m-Tolyl | — | — |
| 530 | Ph-NAr1Ar2 | Phenyl | m-Tolyl | m-Tolyl | — | — |
| 531 | Ph-NAr1Ar2 | 1-Naphthyl | m-Tolyl | m-Tolyl | — | — |
| 532 | Ph-NAr1Ar2 | 2-Naphthyl | m-Tolyl | m-Tolyl | — | — |
| 533 | Ph-NAr1Ar2 | NAr3Ar4 | m-Tolyl | m-Tolyl | Phenyl | Phenyl |
| 534 | Ph-NAr1Ar2 | NAr3Ar4 | m-Tolyl | m-Tolyl | Phenyl | 1-Naphthyl |
| 535 | Ph-NAr1Ar2 | NAr3Ar4 | m-Tolyl | m-Tolyl | Phenyl | 2-Naphthyl |
| 536 | Ph-NAr1Ar2 | NAr3Ar4 | m-Tolyl | m-Tolyl | Phenyl | m-Tolyl |
| 537 | Ph-NAr1Ar2 | NAr3Ar4 | m-Tolyl | m-Tolyl | Phenyl | tBuPhenyl |
| 538 | Ph-NAr1Ar2 | NAr3Ar4 | m-Tolyl | m-Tolyl | Phenyl | Phenanthrenyl |
| 539 | Ph-NAr1Ar2 | NAr3Ar4 | m-Tolyl | m-Tolyl | 1-Naphthyl | 1-Naphthyl |
| 540 | Ph-NAr1Ar2 | NAr3Ar4 | m-Tolyl | m-Tolyl | 2-Naphthyl | 2-Naphthyl |
| 541 | Ph-NAr1Ar2 | NAr3Ar4 | m-Tolyl | m-Tolyl | m-Tolyl | m-Tolyl |
| 542 | Ph-NAr1Ar2 | NAr3Ar4 | m-Tolyl | m-Tolyl | tBuPhenyl | tBuPhenyl |
| 543 | Ph-NAr1Ar2 | Ph-NAr3Ar4 | m-Tolyl | m-Tolyl | Phenyl | Phenyl |
| 544 | Ph-NAr1Ar2 | Ph-NAr3Ar4 | m-Tolyl | m-Tolyl | Phenyl | 1-Naphthyl |
| 545 | Ph-NAr1Ar2 | Ph-NAr3Ar4 | m-Tolyl | m-Tolyl | Phenyl | 2-Naphthyl |
| 546 | Ph-NAr1Ar2 | Ph-NAr3Ar4 | m-Tolyl | m-Tolyl | Phenyl | m-Tolyl |
| 547 | Ph-NAr1Ar2 | Ph-NAr3Ar4 | m-Tolyl | m-Tolyl | Phenyl | tBuPhenyl |
| 548 | Ph-NAr1Ar2 | Ph-NAr3Ar4 | m-Tolyl | m-Tolyl | Phenyl | Phenanthrenyl |
| 549 | Ph-NAr1Ar2 | Ph-NAr3Ar4 | m-Tolyl | m-Tolyl | 1-Naphthyl | 1-Naphthyl |
| 550 | Ph-NAr1Ar2 | Ph-NAr3Ar4 | m-Tolyl | m-Tolyl | 2-Naphthyl | 2-Naphthyl |
| 551 | Ph-NAr1Ar2 | Ph-NAr3Ar4 | m-Tolyl | m-Tolyl | m-Tolyl | m-Tolyl |
| 552 | Ph-NAr1Ar2 | Ph-NAr3Ar4 | m-Tolyl | m-Tolyl | tBuPhenyl | tBuPhenyl |
| 553 | Ph-NAr1Ar2 | H | tBuPhenyl | tBuPhenyl | — | — |
| 554 | Ph-NAr1Ar2 | Phenyl | tBuPhenyl | tBuPhenyl | — | — |
| 555 | Ph-NAr1Ar2 | 1-Naphthyl | tBuPhenyl | tBuPhenyl | — | — |
| 556 | Ph-NAr1Ar2 | 2-Naphthyl | tBuPhenyl | tBuPhenyl | — | — |
| 557 | Ph-NAr1Ar2 | NAr3Ar4 | tBuPhenyl | tBuPhenyl | Phenyl | Phenyl |
| 558 | Ph-NAr1Ar2 | NAr3Ar4 | tBuPhenyl | tBuPhenyl | Phenyl | 1-Naphthyl |
| 559 | Ph-NAr1Ar2 | NAr3Ar4 | tBuPhenyl | tBuPhenyl | Phenyl | 2-Naphthyl |
| 560 | Ph-NAr1Ar2 | NAr3Ar4 | tBuPhenyl | tBuPhenyl | Phenyl | m-Tolyl |
| 561 | Ph-NAr1Ar2 | NAr3Ar4 | tBuPhenyl | tBuPhenyl | Phenyl | tBuPhenyl |
| 562 | Ph-NAr1Ar2 | NAr3Ar4 | tBuPhenyl | tBuPhenyl | Phenyl | Phenanthrenyl |
| 563 | Ph-NAr1Ar2 | NAr3Ar4 | tBuPhenyl | tBuPhenyl | 1-Naphthyl | 1-Naphthyl |
| 564 | Ph-NAr1Ar2 | NAr3Ar4 | tBuPhenyl | tBuPhenyl | 2-Naphthyl | 2-Naphthyl |
| 565 | Ph-NAr1Ar2 | NAr3Ar4 | tBuPhenyl | tBuPhenyl | m-Tolyl | m-Tolyl |
| 566 | Ph-NAr1Ar2 | NAr3Ar4 | tBuPhenyl | tBuPhenyl | tBuPhenyl | tBuPhenyl |
| 567 | Ph-NAr1Ar2 | Ph-NAr3Ar4 | tBuPhenyl | tBuPhenyl | Phenyl | Phenyl |
| 568 | Ph-NAr1Ar2 | Ph-NAr3Ar4 | tBuPhenyl | tBuPhenyl | Phenyl | 1-Naphthyl |
| 569 | Ph-NAr1Ar2 | Ph-NAr3Ar4 | tBuPhenyl | tBuPhenyl | Phenyl | 2-Naphthyl |
| 570 | Ph-NAr1Ar2 | Ph-NAr3Ar4 | tBuPhenyl | tBuPhenyl | Phenyl | m-Tolyl |
| 571 | Ph-NAr1Ar2 | Ph-NAr3Ar4 | tBuPhenyl | tBuPhenyl | Phenyl | tBuPhenyl |
| 572 | Ph-NAr1Ar2 | Ph-NAr3Ar4 | tBuPhenyl | tBuPhenyl | Phenyl | Phenanthrenyl |

TABLE 1-continued

| Preferred structures | | | | | | |
|---|---|---|---|---|---|---|
| | | | R1 | | R2 | |
| No. | R1 | R2 | Ar1 | Ar2 | Ar3 | Ar4 |
| 573 | Ph-NAr1Ar2 | Ph-NAr3Ar4 | tBuPhenyl | tBuPhenyl | 1-Naphthyl | 1-Naphthyl |
| 574 | Ph-NAr1Ar2 | Ph-NAr3Ar4 | tBuPhenyl | tBuPhenyl | 2-Naphthyl | 2-Naphthyl |
| 575 | Ph-NAr1Ar2 | Ph-NAr3Ar4 | tBuPhenyl | tBuPhenyl | m-Tolyl | m-Tolyl |
| 576 | Ph-NAr1Ar2 | Ph-NAr3Ar4 | tBuPhenyl | tBuPhenyl | tBuPhenyl | tBuPhenyl |

The compounds of the formulae (1) to (6) according to the invention can be prepared by synthetic steps known to the person skilled in the art. Thus, the various parent structures can be prepared, for example, by coupling a fluorene to a carbonyl-substituted naphthalene, anthracene or phenanthrene, adduction of an alkyl- or arylmetal derivative and acid-catalysed cyclisation of the corresponding tertiary alcohol, as shown in scheme 1 using the example of naphthalene. Hetero analogues can be synthesised correspondingly through the use of the corresponding heterocyclic compound, for example carbazole, dibenzofuran, dibenzothiophene, etc. If correspondingly functionalised heterocycles are employed instead of naphthalene, anthracene or phenanthrene, the heterocyclic parent structures are accessible. These parent structures can be functionalised by standard methods, for example by Friedel-Crafts alkylation or acylation. Furthermore, the parent structures can be halogenated by standard methods of organic chemistry. Depending on the halogenation conditions selected, the mono- or dihalogenated compound is obtained selectively. Thus, the corresponding rnonobrominated compound is obtained selectively with one equivalent of NBS, while the corresponding dibrominated compound is obtained selectively with two equivalents of bromine. The brominated or iodinated compounds represent the basis for further functionalisations. Thus, they can be reacted with arylboronic acids or arylboronic acid derivatives by Suzuki coupling or with organotin compounds by the Stille method to give extended aromatic compounds. Coupling to aromatic or aliphatic amines by the Hartwig-Buchwald method gives the corresponding amines, as shown in scheme 1. They can furthermore be converted into ketones via lithiation and reaction with electrophiles, such as benzonitrile, and subsequent acidic hydrolysis or into phosphine oxides with chlorodiarylphosphines and subsequent oxidation.

Scheme 1 a)

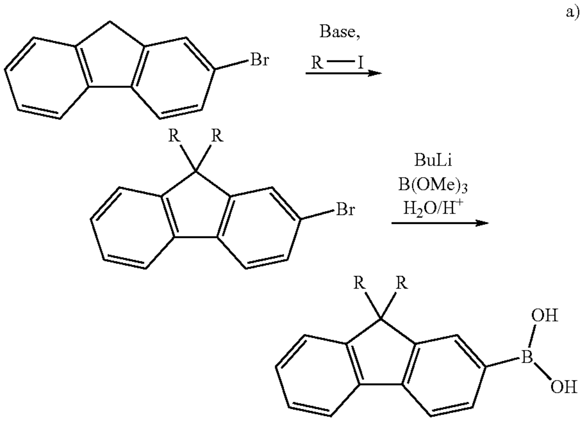

-continued b)

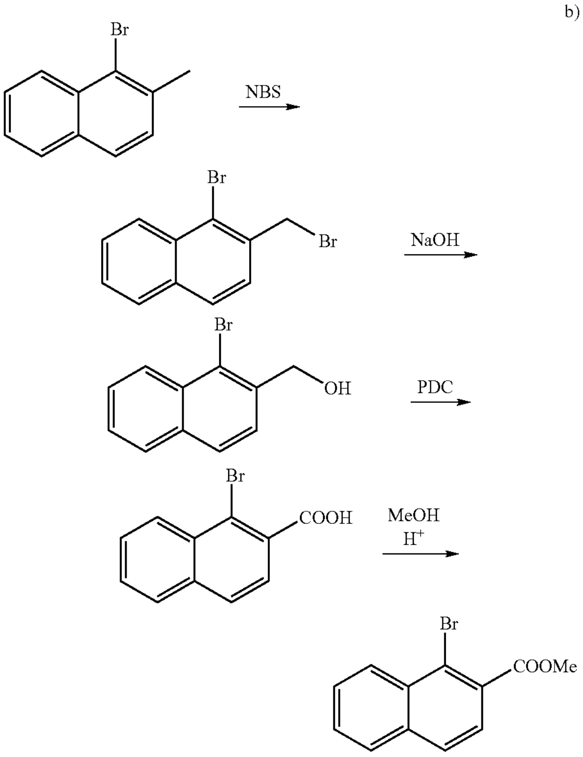

c)

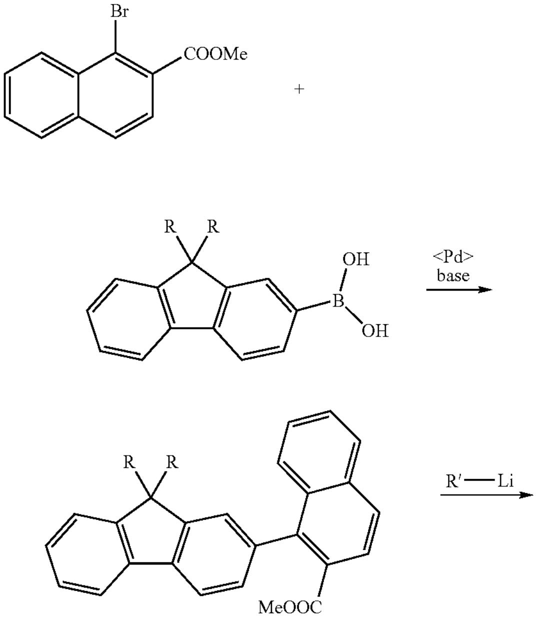

-continued

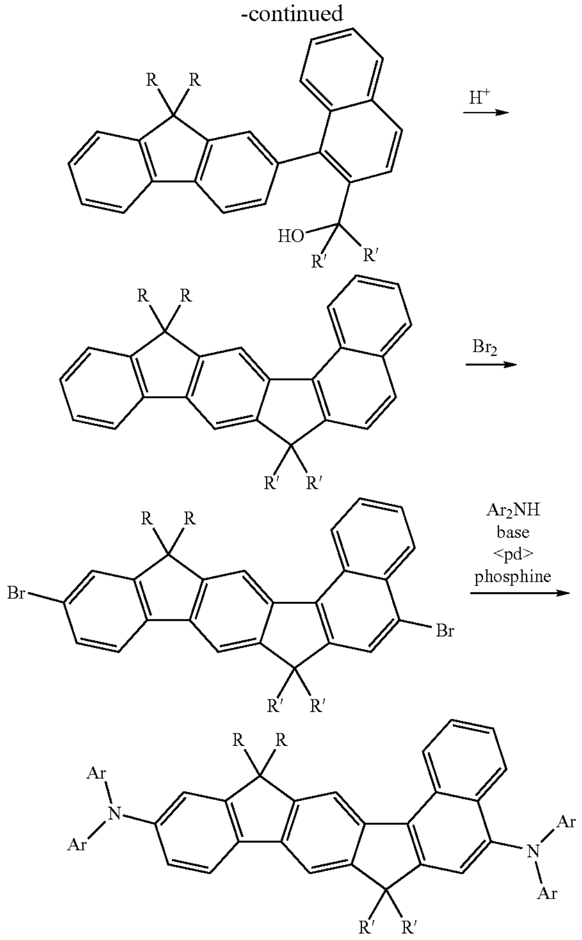

The invention furthermore relates to a process for the preparation of the parent structures of the compounds of the formulae (1) to (6) by coupling a fluorene carrying a reactive group to a carbonyl-functionalised naphthalene, phenanthrene or anthracene, each carrying a reactive group, followed by the adduction of an alkyl- or arylmetal reagent and an acid-catalysed cyclisation reaction. Suitable coupling reactions between the fluorene and the naphthalene or anthracene or phenanthrene are, in particular, transition-metal-catalysed coupling reactions, in particular Suzuki coupling, so that, in particular, the coupling of a boronic acid derivative, for example a fluoreneboronic acid derivative, to a halogen derivative, for example a halonaphthalene, -anthracene or -phenanthrene derivative, is possible here. The reactive groups are thus preferably halogen, in particular bromine, and boronic acid derivatives. Particularly suitable for the adduction of the alkyl- or arylmetal reagent are alkyl- or aryllithium compounds and Grignard compounds.

The invention furthermore relates to a process for the preparation of functionalised compounds of the formulae (1) to (6) by alkylation or acylation of the corresponding unfunctionalised compound or by halogenation of the unfunctionalised compound, followed by coupling to a functionalised aromatic compound or to a mono- or disubstituted amine or followed by metallation and reaction with electrophiles. The halogenation is preferably a bromination. Suitable coupling reactions between the parent structure of the formulae (1) to (6) and the aryl substituent are, in particular, transition-metal-catalysed coupling reactions, in particular Suzuki coupling, so that, in particular, the coupling of a boronic acid derivative to a halogen derivative is possible here. A suitable coupling reaction to a mono- or disubstituted amine is, in particular, palladium-catalysed Hartwig-Buchwald coupling.

In the synthesis, both the 5-membered ring/5-membered ring derivatives and also the 5-membered ring/6-membered ring derivatives or mixtures of these compounds may be formed. Which isomers are formed and in what ratio they are formed depends on the precise synthetic conditions. If mixtures are formed, these can either be separated and processed further as pure compounds or they can be employed as a mixture.

The compounds according to the invention described above, in particular compounds which are substituted by reactive leaving groups, such as bromine, iodine, boronic acid or boronic acid ester, can be used as monomers for the preparation of corresponding dimers, trimers, tetramers, pentamers, oligomers, polymers or as the core of dendrimers. The oligomerisation or polymerisation here is preferably carried out via the halogen functionality or the boronic acid functionality.

The invention therefore furthermore relates to dimers, trimers, tetramers, pentamers, oligomers, polymers or dendrimers comprising one or more compounds of the formulae (1) to (6), where one or more radicals $R^1$ represent bonds between the compounds of the formulae (1) to (6) in the dimer, trimer, tetramer or pentamer or bonds from the compound of the formulae (1) to (6) to the polymer, oligomer or dendrimer. For the purposes of this invention, an oligomer is taken to mean a compound which has at least six units of the formulae (1) to (6). The polymers, oligomers or dendrimers may be conjugated, partially conjugated or non-conjugated. The trimers, tetramers, pentamers, oligomers or polymers may be linear or branched. In the structures linked in a linear manner, the units of the formulae (1) to (6) can either be linked directly to one another or they can be linked to one another via a divalent group, for example via a substituted or unsubstituted alkylene group, via a heteroatom or via a divalent aromatic or heteroaromatic group. In branched structures, three or more units of the formulae (1) to (6) may, for example, be linked via a trivalent or polyvalent group, for example via a trivalent or potyvalent aromatic or heteroaromatic group, to form a branched trimer, tetramer, pentamer, oligomer or polymer.

The same preferences as described above apply to the recurring units of the formulae (1) to (6) in dimers, trimers, tetramers, pentamers, oligomers and polymers.

For the preparation of the oligomers or polymers, the monomers according to the invention are homopolymerised or copolymerised with further monomers. Suitable and preferred comonomers are selected from fluorenes (for example as described in EP 842208 or WO 00/22026), spirobifluorenes (for example as described in EP 707020, EP 894107 or WO 06/061181), paraphenylenes (for example as described in WO 92/18552), carbazoles (for example as described in WO 04/070772 or WO 04/113468), thiophenes (for example as described in EP 1028136), dihydrophenanthrenes (for example as described in WO 05/014689), cis- and trans-indenofluorenes (for example as described in WO 04/041901 or WO 04/113412), ketones (for example as described in WO 05/040302), phenanthrenes (for example as described in WO 05/104264 or WO 07/017066) or also a plurality of these units. The polymers, oligomers and dendrimers usually also contain further units, for example emitting (fluorescent or phosphorescent) units, such as, for example, vinyltriarylamines (for example as described in the unpublished application DE 102005060473.0) or phosphorescent metal complexes (for example as described in WO 06/003000), and/or charge-transport units, in particular those based on triarylamines.

Since either one or two halogen functionalities, preferably bromine, can be introduced selectively into the compounds according to the invention, as described in greater detail above, it is possible to synthesise the dimers, trimers, tetramers, pentamers, etc., specifically. Thus, for example, two monofunctionalised compounds can be coupled in a Suzuki coupling or a Yamamoto coupling to give the corresponding dimers. The corresponding tetramers are accessible selectively by halogenation and further coupling to monofunctionalised compounds. Furthermore, two monofunctionalised compounds can be coupled to a difunctionalised compound to give the corresponding trimer. The coupling reaction here is preferably a Suzuki coupling. The corresponding pentamers are accessible selectively by halogenation, preferably bromination, and further coupling to monofunctionalised compounds. The selective synthesis of these compounds is depicted in scheme 2 in general terms for the preparation of the trimers. Correspondingly, as described above, the dimers, tetramers, pentamers, etc., can be synthesised. These syntheses can be carried out entirely analogously with other substituents on the structures and also with other bridges X. It is likewise possible to functionalise the dimers, trimers, tetramers, pentamers, etc., further by, for example, halogenating them, followed by reaction with a diarylamine in a Hartwig-Buchwaid coupling to give the corresponding aromatic amines.

Apart from the cathode, anode and the emitting layer, the organic electroluminescent device may also comprise further layers. These are selected, for example, from in each case one or more hole-injection layers, hole-transport layers, electron-transport layers, electron-injection layers and/or charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*). However, it should be pointed out that each of these layers does not necessarily have to be present.

In a further preferred embodiment of the invention, the organic electroluminescent device comprises a plurality of emitting layers, where at least one organic layer comprises at least one compound of the formulae (1) to (6). These emission layers particularly preferably have in total a plurality of emission maxima between 380 nm and 750 nm, resulting overall in white emission, i.e. different emitting compounds which are able to fluoresce or phosphoresce and emit blue and yellow, orange or red light are used in the emitting layers. Particular preference is given to three-layer systems, i.e. systems having three emitting layers, where at least one of these layers comprises at least one compound of the formulae (1) to (6) and where the three layers exhibit blue, green and orange or red emission (for the basic structure see, for example, WO 05/011013). Likewise suitable for white emission are emitters which have broad-band emission bands and thus exhibit white emission.

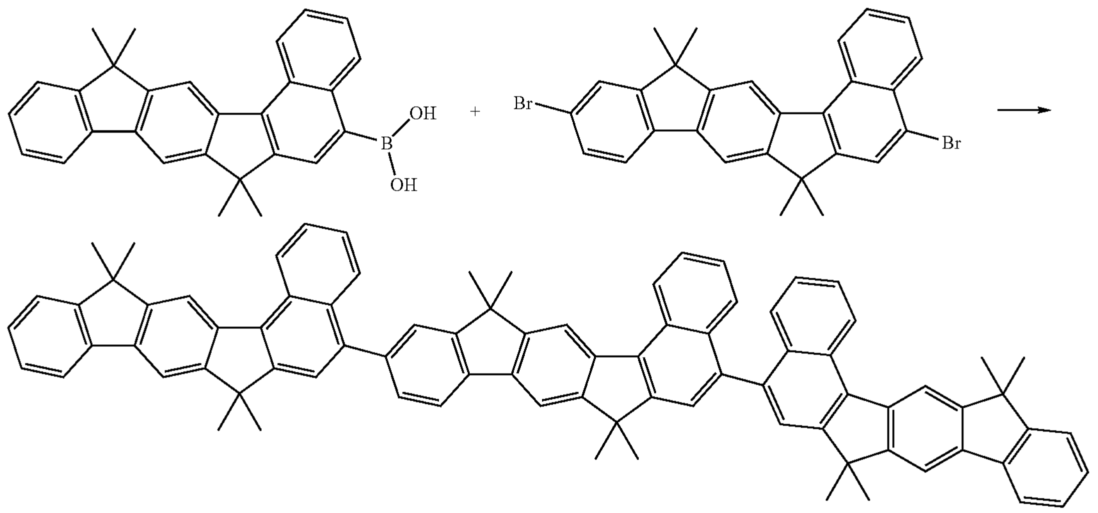

The compounds of the formulae (1) to (6) are suitable for use in electronic devices, in particular in organic electroluminescent devices (OLEDs, PLEDs). Depending on the substitution, the compounds are employed in different functions and layers.

The invention therefore furthermore relates to the use of compounds of the formulae (1) to (6) in electronic devices, in particular in organic electroluminescent devices.

The invention furthermore relates to organic electronic devices comprising at least one compound of the formulae (1) to (6), in particular organic electroluminescent devices, comprising anode, cathode and at least one emitting layer, characterised in that at least one organic layer, which may be an emitting layer or another layer, comprises at least one compound of the formulae (1) to (6).

In an embodiment of the invention, the compounds of the formulae (1) to (6) are employed as host material for a fluorescent dopant. In this case, one or more substituents $R^1$ are preferably selected from simple or condensed aryl or heteroaryl groups, in particular phenyl, o-, m- or p-biphenyl, 1- or 2-naphthyl, anthryl, in particular phenylanthryl or 1- or 2-naphthylanthryl, 2-fluorenyl and 2-spirobifluorenyl, each of which may be substituted by one or more radicals $R^2$. This applies, in particular, to the radicals $R^1$ on the structures of the formulae (7a) to (28a).

A host material in a system comprising host and dopant is taken to mean the component which is present in the higher proportion in the system. In a system comprising one host and a plurality of dopants, the host is taken to mean the component whose proportion in the mixture is the highest.

The proportion of the host material of the formulae (1) to (6) in the emitting layer is between 50.0 and 99.9% by weight, preferably between 80.0 and 99.5% by weight, particularly preferably between 90.0 and 99.0% by weight. The proportion of the dopant is correspondingly between 0.1 and 50.0% by weight, preferably between 0.5 and 20.0% by weight, particularly preferably between 1.0 and 10.0% by weight.

Preferred dopants in fluorescent devices are selected from the class of the monostyrylamines, distyrylamines, tristyrylamines, tetrastyrylamines and arylamines. A monostyrylamine is taken to mean a compound which contains one styryl group and at least one amine, which is preferably aromatic. A distyrylamine is taken to mean a compound which contains two styryl groups and at least one amine, which is preferably aromatic. A tristyrylamine is taken to mean a compound which contains three styryl groups and at least one amine, which is preferably aromatic. A tetrastyrylamine is taken to mean a compound which contains four styryl groups and at least one amine, which is preferably aromatic. For the purposes of this invention, an arylamine or an aromatic amine is taken to mean a compound which contains three aromatic or heteroaromatic ring systems bonded directly to the nitrogen, at least one of which is preferably a condensed ring system having at least 14 aromatic ring atoms. The styryl groups are particularly preferably stilbenes, which may also be further substituted on the double bond or on the aromatic rings. Examples of dopants of this type are substituted or unsubstituted tristilbenamines or further dopants which are described, for example, in WO 06/000388, WO 06/058737, WO 06/000389 and in the unpublished patent applications DE 102005058543.4 and DE 102006015183.6. Compounds as described in WO 06/122630 and as described in the unpublished patent application DE 102006025846.0 are furthermore preferred as dopants.

In a further embodiment of the invention, the compounds of the formulae (1) to (6) are employed as matrix for phosphorescent dopants. In this case, one or more substituents $R^1$ and/or bridges X preferably contain at least one group C═O, P(═O) and/or $SO_2$. These groups are particularly preferably bonded directly to the central unit according to the invention and furthermore particularly preferably also contain one or in the case of the phosphine oxide two further aromatic substituents. This applies, in particular, to the radicals $R^1$ on the structures of the formulae (7a) to (28a).

In phosphorescent devices, the dopant is preferably selected from the class of the metal complexes containing at least one element having an atomic number of greater than 20, preferably greater than 38 and less than 84, particularly preferably greater than 56 and less than 80. Preference is given to the use of metal complexes which contain copper, molybdenum, tungsten, rhenium, ruthenium, osmium, rhodium, iridium, palladium, platinum, silver, gold or europium, in particular iridium. Phosphorescent materials as used in accordance with the prior art are generally suitable for this purpose.

In yet another embodiment of the invention, the compounds of the formulae (1) to (6) are employed as emitting materials. The compounds are suitable, in particular, as emitting compounds If at least one substituent $R^1$ contains at least one vinylaryl unit, at least one vinylarylamine unit and/or at least one arylamino unit. Preferred arylamino units are the groups of the formulae (29) and (30) depicted above. This applies, in particular, to the radicals $R^1$ on the structures of the formulae (7a) to (28a). Particularly preferred dopants are those in which two radicals $R^1$ stand for groups of the formula (29) or (30) or in which one radical $R^1$ stands for a group of the formula (29) or (30) and the other radicals $R^1$ stand for H.

The proportion of the compound of the formulae (1) to (6) in the mixture of the emitting layer is between 0.1 and 50.0% by weight, preferably between 0.5 and 20.0% by weight, particularly preferably between 1.0 and 10.0% by weight. The proportion of the host material is correspondingly between 50.0 and 99.9% by weight, preferably between 80.0 and 99.5% by weight, particularly preferably between 90.0 and 99.0% by weight.

Suitable host materials for this purpose are materials from various classes of substance. Preferred host materials are selected from the classes of the oligoarylenes (for example 2,2',7,7'-tetraphenylspirobifluorene as described in EP 676461 or dinaphthylanthracene), in particular of the oligoarylenes containing condensed aromatic groups, the oligoarylenevinylenes (for example DPVBi or spiro-DPVBi as described in EP 676461), the polypodal metal complexes (for example as described in WO 04/081017), the hole-conducting compounds (for example as described in WO 04/058911), the electron-conducting compounds, in particular ketones, phosphine oxides, sulfoxides, etc. (for example as described in WO 05/084081 and WO 05/084082), the atropisomers (for example as described in WO 06/048268) or the boronic acid derivatives (for example as described in WO 06/117052). Suitable host materials are furthermore also the compounds according to the invention described above. Apart from the compounds according to the invention, particularly preferred host materials are selected from the classes of the oligoarylenes containing naphthalene, anthracene and/or pyrene or atropisomers of these compounds, the oligoarylenevinylenes, the ketones, the phosphine oxides and the sulfoxides. Apart from the compounds according to the invention, very particularly preferred host materials are selected from the classes of the oligoarylenes containing anthracene and/or pyrene or atropisomers of these compounds, the phosphine oxides and the sulfoxides. For the purposes of this invention, an oligoarylene is intended to be taken to mean a compound in which at least three aryl or arylene groups are bonded to one another.

In yet another embodiment of the invention, the compounds of the formulae (1) to (6) are employed as hole-transport material or hole-injection material. The compounds are then preferably substituted by at least one group $N(Ar)_2$, preferably by at least two groups $N(Ar)_2$. The groups $N(Ar)_2$ are preferably selected from the formulae (29) and (30) described above. This applies, in particular, to the radicals $R^1$ on the structures of the formulae (7a) to (28a). The compound is preferably employed in a hole-transport or hole-injection layer. For the purposes of this invention, a hole-injection layer is a layer which is directly adjacent to the anode. For the purposes of this invention, a hole-transport layer is a layer which is between a hole-injection layer and an emission layer. If the compounds of the formulae (1) to (6) are used as hole-transport or hole-injection material, it may be preferred for them to be doped with electron-acceptor compounds, for example with $F_4$-TCNQ or with compounds as described in EP 1476881 or EP 1596445.

In yet another embodiment of the invention, the compounds of the formulae (1) to (6) are employed as electron-transport material. It is preferred here for one or more substituents $R^1$ to contain at least one unit C═O, P(═O) and/or $SO_2$. It is furthermore preferred here for one or more substituents $R^1$ to contain an electron-deficient heterocycle, such as, for example, imidazole, pyrazole, thiazole, benzimidazole, benzothiazole, triazole, oxadiazole, benzothiadiazole, phenanthroline, etc. These groups are particularly preferably bonded directly to the central unit according to the invention and furthermore particularly preferably also contain one or in the case of the phosphine oxide two further aromatic substituents. This applies, in particular, to the radicals $R^1$ on the structures of the formulae (7a) to (28a). It may furthermore be preferred for the compound to be doped with electron-donor compounds.

Recurring units of the formulae (1) to (6) may also be employed in polymers as polymer backbone, as emitting unit, as hole-transport unit and/or as electron-transport unit. The preferred substitution patterns here correspond to those described above.

Preference is furthermore given to an organic electroluminescent device, characterised in that one or more layers are coated by means of a sublimation process, in which the materials are vapour-deposited in vacuum sublimation units at a pressure below $10^{-5}$ mbar, preferably below $10^{-6}$ mbar, particularly preferably below $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar.

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose. High solubility can be achieved by suitable substitution of the compounds.

The compounds according to the invention have the following surprising advantages over the prior art on use in organic electroluminescent devices:

1. The compounds according to the invention have a lower LUMO (lowest unoccupied molecular orbital) than compounds usually used in accordance with the prior art and are consequently easier to reduce. This results in improved electron injection and thus a reduction in the operating voltage.
2. The compounds according to the invention, in particular those which are substituted by diarylamino substituents, have very good blue colour coordinates and are therefore very suitable as blue emitters.
3. The OLEDs produced using the compounds according to the invention have a good charge balance, which results in low operating voltages.
4. The compounds according to the invention have high thermal stability and can be sublimed without decomposition. In addition, the compounds exhibit a lower evaporation temperature than aromatic compounds in the same molecular weight range which have a symmetrical structure.
5. The OLEDs produced using the compounds according to the invention have a very long lifetime.
6. The OLEDs produced using the compounds according to the invention have very high quantum efficiency.

The present application text is directed to the use of the compounds according to the invention in relation to OLEDs and PLEDs and the corresponding displays. In spite of this restriction of the description, it is possible for the person skilled in the art, without further inventive step, also to employ the compounds according to the invention in other electronic devices, for example in organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photo receptors.

The present invention likewise relates to the use of the compounds according to the invention in the corresponding devices and to these devices themselves.

EXAMPLES

Example 1

1,2-Benzo-3,8-bis(N,N-diphenylamino)-6,6,12,12-tetramethyl-6,12-dihydroindeno[1,2-b]fluorene a) Ethyl 1-(9,9-dimethyl-9H-fluoren-2-yl)naphthalene-2-carboxylate

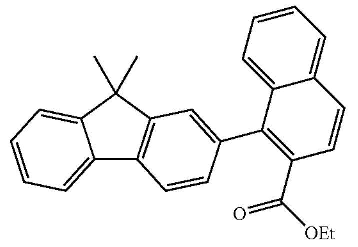

86.3 g (362.55 mmol) of 9,9'-dimethylfluorene-2-boronic acid, 92 g (329.59 mol) of 2-carboxyethylbromonaphthalene and 159.4 g (692 mmol) of tripotassium phosphate monohydrate are suspended in 450 ml of toluene, 230 ml of dioxane and 700 ml of water, 6.0 g (19.8 mmol) of tris-o-tolylphosphine, followed by 740 mg (3.3 mmol) of palladium acetate are added, and the mixture is heated at the boil for 4 h. The organic phase is separated off, filtered through silica gel and evaporated in vacuo. The residue is recrystallised from heptane. Yield: 100.6 g (78%) of a colourless solid.

b) 2-[1-(9,9-Dimethyl-9H-fluoren-2-yl)naphthalen-2-yl]propan-2-ol

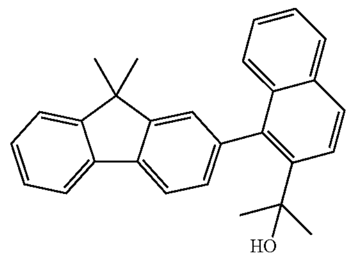

100.6 g of ethyl 1-(9,9-dimethyl-9H-fluoren-2-yl)naphthalene-2-carboxylate (256 mmol) are initially introduced in 1000 ml of dried THF, 510 ml of a 1.5 M methyllithium solution in diethyl ether are added dropwise at −70° C., and the mixture is stirred at this temperature for 2 h. For work-up, 100 ml of ice-water followed by 300 ml of 50% acetic acid are added. The organic phase is separated off, washed twice with water, dried and evaporated in vacuo. The colourless solid which remains is recrystallised twice from heptane/toluene. Yield: 82 g (85%) of colourless crystals.

c) 1,2-Benzo-6,6,12,12-tetramethyl-6,12-dihydroindeno[1,2-b]fluorene

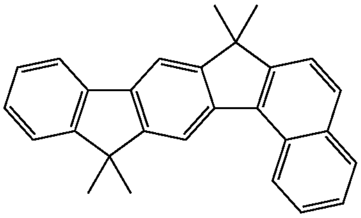

97 g of 2-[1-(9,9-dimethyl-9H-fluoren-2-yl)naphthalen-2-yl]propan-2-ol (256 mmol) are dissolved in 750 ml of dichloromethane, the solution is cooled to 5° C., and a mixture of 75 ml of methanesulfonic acid and 100 g of polyphosphoric acid is added at this temperature. After 2 h at 5° C., 300 ml of ethanol are added dropwise, and the reaction mixture is heated at the boil for 10 min. After cooling to room temperature, the precipitate is filtered off with suction, washed with ethanol and recrystallised from toluene, giving isomerically pure benzindenofluorene as colourless crystals (70 g, 76%).

d) 1,2-Benzo-3,8-dibromo-6,6,12,12-tetramethyl-6,12-dihydroindeno[1,2-b]fluorene

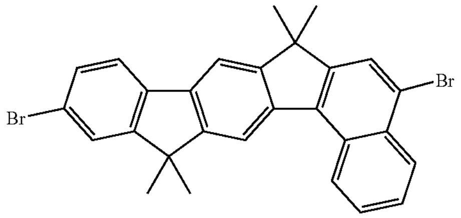

20.9 g (58 mmol) of 1,2-benzo-6,6,12,12-tetramethyl-6,12-dihydroindeno[1,2-b]fluorene are suspended in 600 ml of dichloromethane, the suspension is cooled to 5° C., and 6.5 ml (128 mmol) of bromine in 50 ml of dichloromethane are added dropwise at this temperature. After 6 h, 200 ml of ethanol are added, the mixture is stirred at room temperature for 1 h, and the precipitate is filtered off with suction, washed with ethanol and dried, giving 27 g (90%) of the dibromide having a purity of >99% (RP-HPLC).

e) 1,2-Benzo-3,8-bis(N,N-diphenylamino)-6,6,12,12-tetramethyl-6,12-dihydroindeno[1,2-b]fluorene

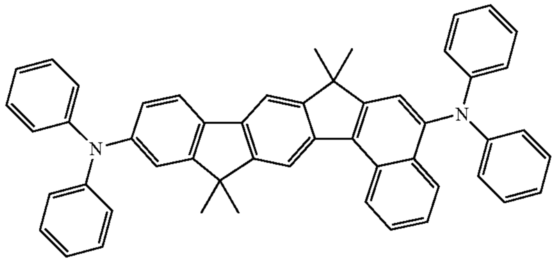

26.4 g (51 mmol) of 1,2-benzo-3,8-dibromo-6,6,12,12-tetramethyl-6,12-dihydroindeno[1,2-b]fluorene and 22.6 g (133 mmol) of diphenylamine are dissolved in 200 ml of dried toluene, the solution is saturated with $N_2$, 1 ml (4 mmol) of tri-tert-butylphosphine, followed by 450 mg (2 mm ol) of palladium acetate and 14.6 g (153 mmol) of sodium tert-butoxide are subsequently added. The mixture is heated at the boil for 3 h, the organic phase is separated off, washed twice with water, filtered and evaporated in a rotary evaporator. Recrystallisation six times from toluene and sublimation twice ($2\times10^{-5}$ mbar/340° C.) gives 12 g (68%) of the diamine in the form of a yellow powder having a purity of >99.9% (RP-HPLC). The compound has excellent thermal stability. No decomposition can be observed on sublimation.

The following compounds are synthesised analogously to the process described above (all purities >99.9%, yields after sublimation twice):

| Example No. | Structure | Yield (%) |
| --- | --- | --- |
| 2 | 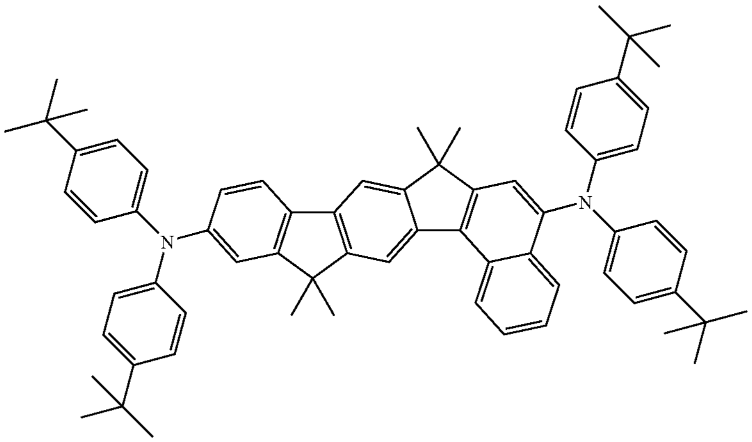 | 69 |

-continued
| Example No. | Structure | Yield (%) |
|---|---|---|
| 3 | 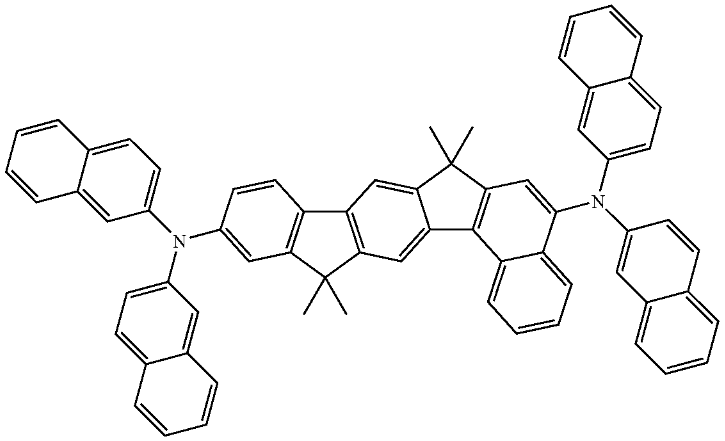 | 54 |
| 4 | 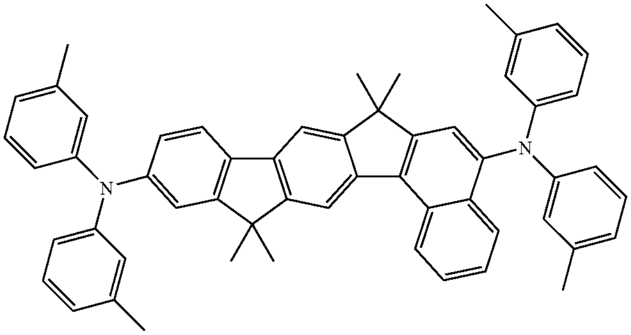 | 77 |
| 5 | 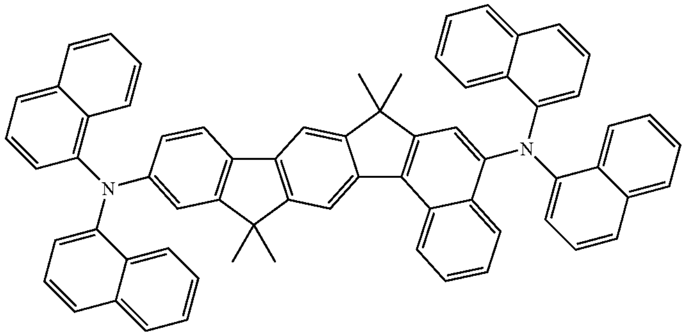 | 79 |
| 6 | 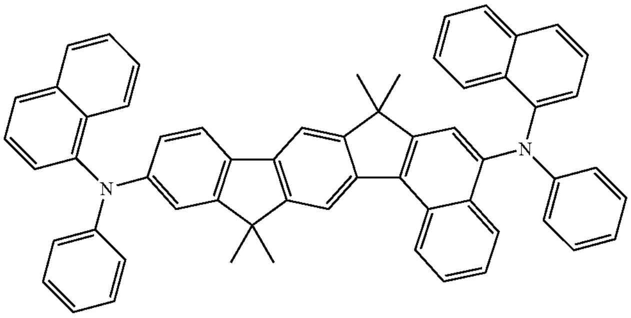 | 84 |

-continued

| Example No. | Structure | Yield (%) |
|---|---|---|
| 7 | 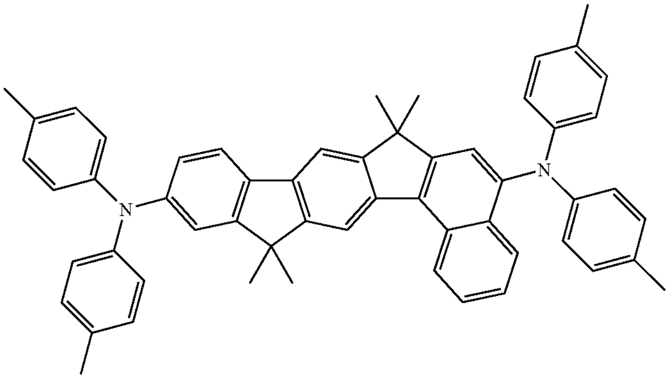 | 82 |

Example 8

1,2-Benzo-3-[9-{10-(2-naphthyl)}anthryl]-6,6,12,12-tetramethyl-6,12-dihydroindeno[1,2-b]fluorene a) 1,2-Benzo-3-bromo-6,6,12,12-tetramethyl-6,12-dihydroindeno[1,2-b]fluorene

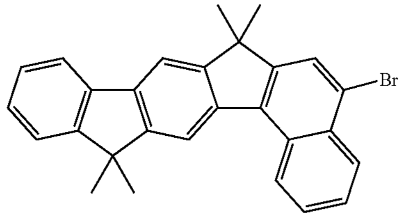

15.5 g (43 mmol) of 1,2-benzo-6,6,12,12-tetramethyl-6,12-dihydroindeno[1,2-b]fluorene are dissolved in 350 ml of THF, 8.4 g (47.3 mmol) of NBS are added, and the mixture is heated at the boil for 4 h. After removal of the solvent in vacuo, the residue is washed by boiling in ethanol/water (1:1), the solid is filtered off with suction, washed with ethanol and dried, leaving 15.4 g (82%) of the monobromide as a colourless powder.

b) 1,2-Benzo-6,6,12,12-tetramethyl-6,12-dihydroindeno[1,2-b]fluorene-3-boronic acid

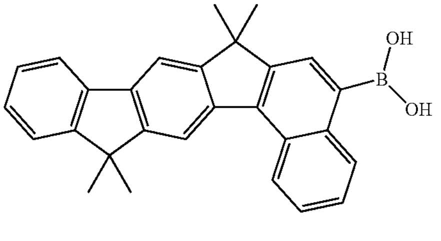

14 g (32 mmol) of 1,2-benzo-3-bromo-6,6,12,12-tetramethyl-6,12-dihydroindeno[1,2-b]fluorene are suspended in 150 ml of dry diethyl ether, 21 ml (42 mmol) of a 2 M solution of n-butyllithium in cyclohexane are added at −70° C., the mixture is stirred at this temperature for 1 h, 8.8 ml (79 mmol) of trim ethyl borate are added dropwise, and the mixture is allowed to come to room temperature. Aqueous work-up, drying of the organic phase and removal of the solvent in vacuo gives 12.5 g (96%) of the boronic acid as a colourless foam, which is reacted without further purification.

c) 1,2-Benzo-3-[9-{10-(2-naphthyl)}anthryl]-6,6,12,12-tetramethyl-6,12-dihydroindeno[1,2-b]fluorene

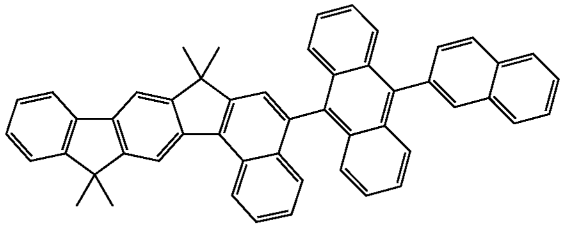

A mixture of 11.3 g (30 mmol) of 9-bromo-10-(2-naphthyl)anthracene, 12.5 g (31 mmol) of 1,2-benzo-6,6,12,12-tetramethyl-6,12-dihydroindeno[1,2-b]fluorene-3-boronic acid and 13.1 g (62 mmol) of tripotassium phosphate trihydrate in 40 ml of toluene, 20 ml of dioxane and 60 ml of water is saturated with $N_2$ for 30 min, 1.1 g (4 mmol) of tris-o-tolylphosphine and 132 mg (1 mmol) of palladium acetate are added, and the mixture is heated at the boil for 4 h. The organic phase is separated off, washed a number of times with water and filtered, and the solvent is removed in vacuo. Recrystallisation six times from dioxane and sublimation twice ($2\times10^{-5}$ mbar/380° C.) gives 12 g (62%) of the target compound in the form of a pale-yellow powder having a purity of >99.9% (RP-HPLC). The compound has excellent thermal stability. No decomposition can be observed on sublimation.

The following compounds are synthesised analogously to the process described above (all purities >99.9%, yields after sublimation twice):

| Example No. | Structure | Yield (%) |
|---|---|---|
| 9 | 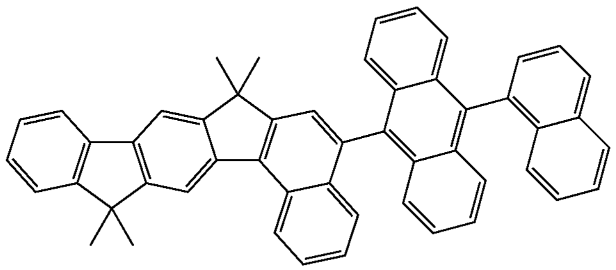 | 58 |
| 10 | 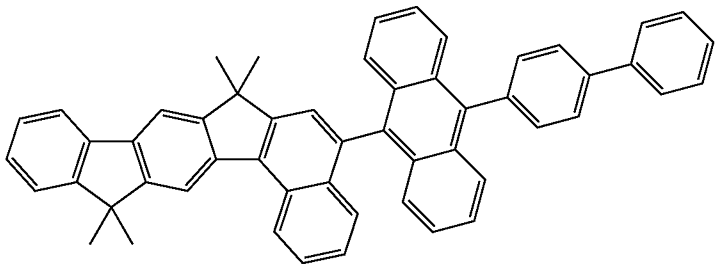 | 62 |
| 11 | 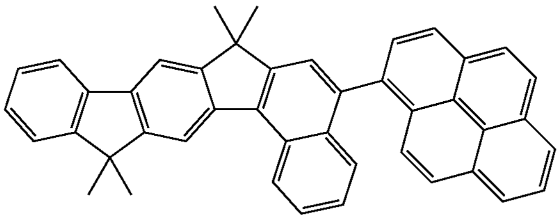 | 71 |
| 12 | 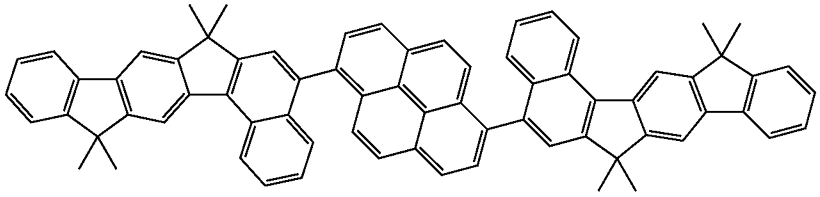 | 66 |

Example 13

1,2-Benzo-3-(N,N-bis-4-tert-butylphenylamino)-6,6,12,12-tetramethyl-6,12-dihydroindeno[1,2-b]fluorene

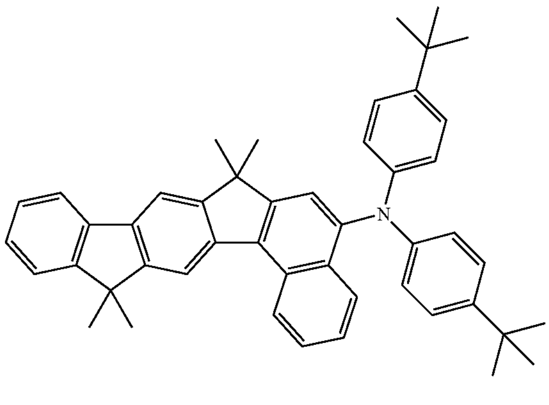

23.1 g (53 mmol) of 1,2-benzo-3-bromo-6,6,12,12-tetramethyl-6,12-dihydroindeno[1,2-b]fluorene and 19.2 g (68 mmol) of di-tert-butylphenylamine are dissolved in 100 ml of dried toluene, the solution is saturated with $N_{21}$ 0.5 ml (2 mmol) of tri-tert-butylphosphine, followed by 240 mg (1 mmol) of palladium acetate and 8.6 g (89 mmol) of sodium tert-butoxide are subsequently added. The mixture is heated at the boil for 3 h, the organic phase is separated off, washed twice with water, filtered and evaporated in a rotary evaporator. Recrystallisation four times from i-PrOH gives 24 g (71%) of the amine in the form of a yellow powder having a purity of >99.9% (RP-HPLC). The compound has excellent thermal stability. No decomposition can be observed on sublimation.

The following compounds are synthesised analogously to the process described above (all purities >99.9%, yields after sublimation twice):

| Example No. | Structure | Yield (%) |
|---|---|---|
| 14 | 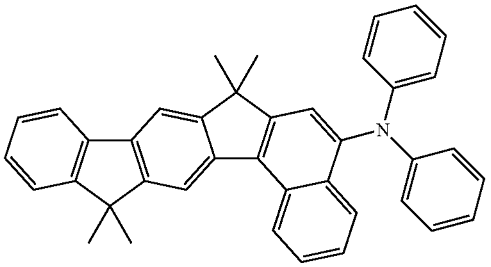 | 82 |
| 15 | 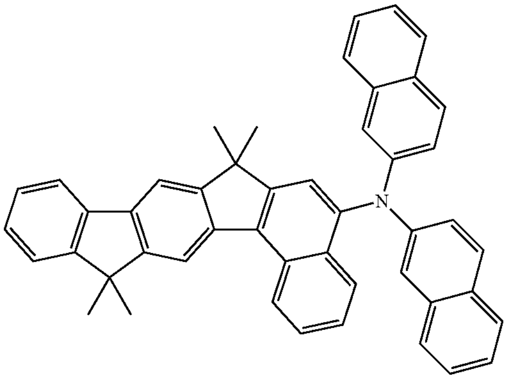 | 74 |
| 16 | 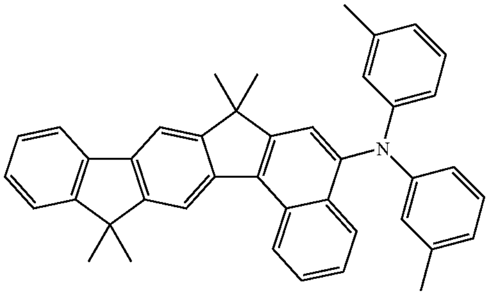 | 78 |

-continued

| Example No. | Structure | Yield (%) |
|---|---|---|
| 17 | 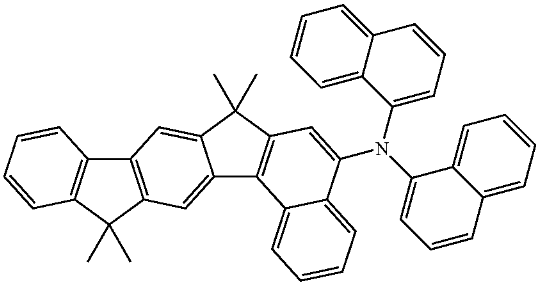 | 66 |
| 18 | 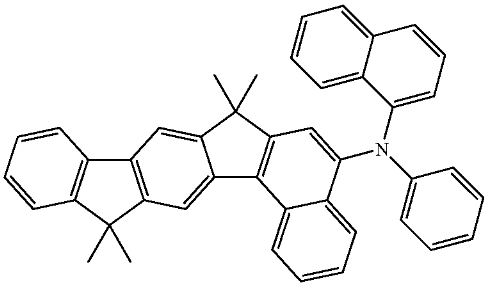 | 63 |
| 19 | 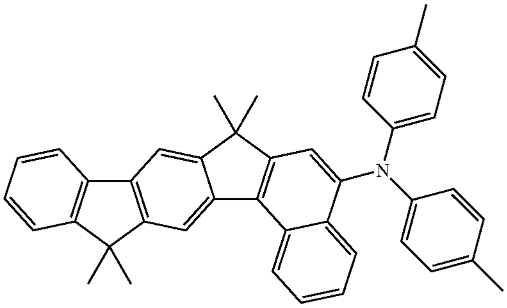 | 74 |

Example 20

3',8-Bis(diphenylamino)-3,4-benzo-6,6,12,12-tetramethyl-6,12-dihydroindeno[1,2-b]fluorene a) 3,4-Benzo-6,6,12,12-tetramethyl-6,12-dihydrindeno[1,2-b]fluorene

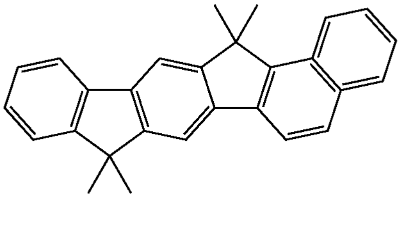

This compound is prepared analogously to the synthesis of 1,2-benzo-6,6,12,12-tetramethyl-6,12-dihydroindeno[1,2-b]fluorene (Example 1c) from 9,9'-dimethylfluorene-2-boronic acid and 1-carboxyethyl-2-bromonaphthalene.

b) 3',8-Dibromo-3,4-benzo-6,6,12,12-tetramethyl-6,12-dihydroindeno[1,2-b]fluorene

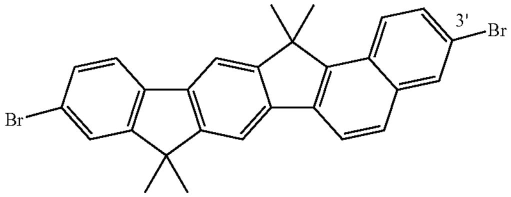

The compound is prepared analogously to the synthesis of 1,2-benzo-3,8-dibromo-6,6,12,12-tetramethyl-6,12-dihydroindeno[1,2-b]fluorene (Example 1d) starting from 3,4-benzo-6,6,12,12-tetramethyl-6,12-dihydroindeno[1,2-b]fluorene.

c) 3',8-Bis(diphenylamino)-3,4-benzo-6,6,12,124-tetramethyl-6,12-dihydroindeno[1,2-b]fluorene

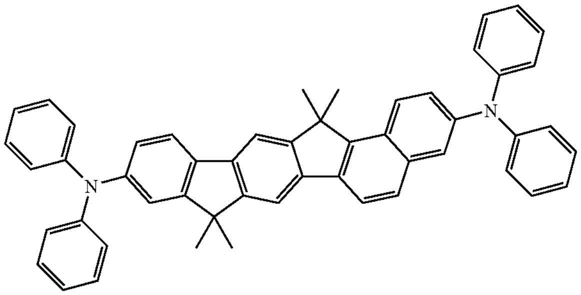

The compound is synthesised analogously to the process described in Example 13. Yield: 77% in a purity of >99.9% after sublimation twice. The compound has excellent thermal stability. No decomposition can be observed on sublimation.

The following compounds are synthesised analogously to Example 20 (all purities >99.9%, yields after sublimation twice):

| Example No. | Structure | Yield (%) |
|---|---|---|
| 21 | 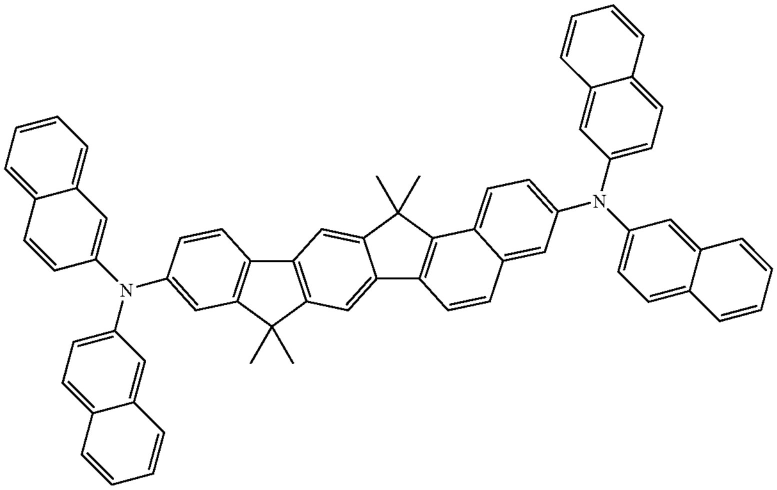 | 75 |
| 22 | 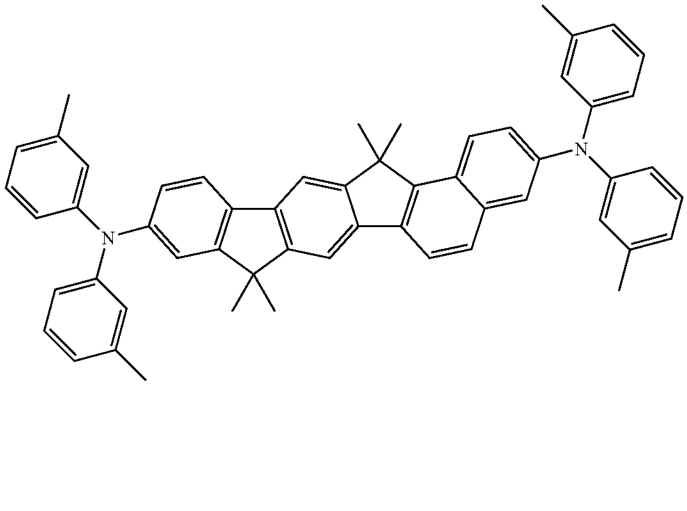 | 73 |

-continued
| Example No. | Structure | Yield (%) |
|---|---|---|
| 23 | 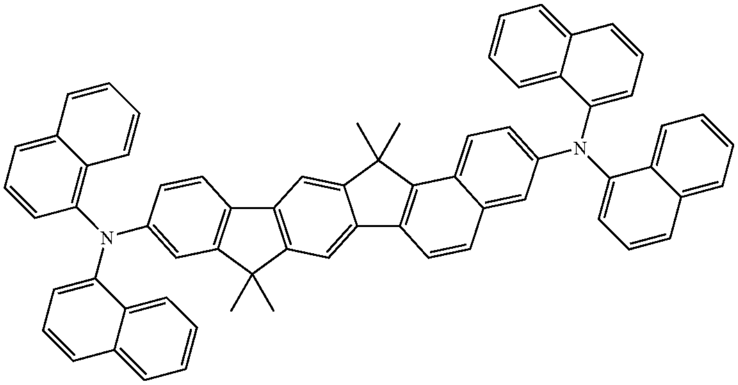 | 54 |
| 24 | 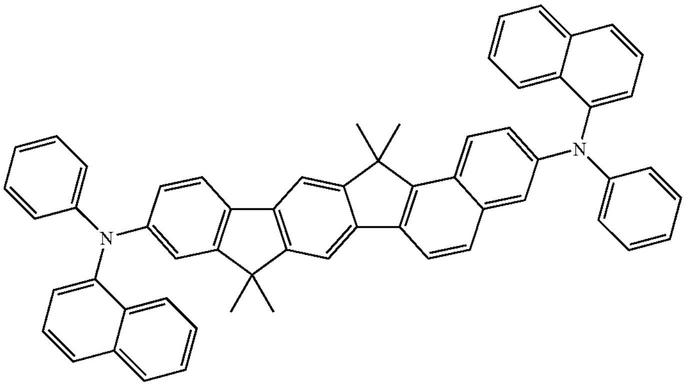 | 44 |
| 25 | 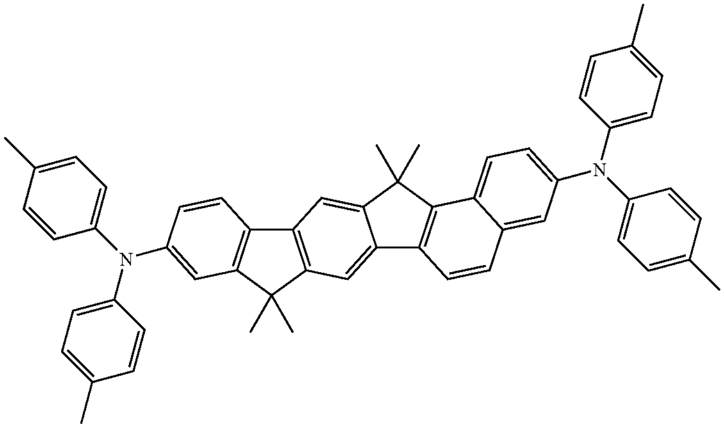 | 55 |

Example 26

2',8-Bis(diphenylamino)-2,3-benzo-6,6,12,12-tetramethyl-6,12-dihydroindeno[1,2-b]fluorene a) 2,3-Benzo-6,6,12,12-tetramethyl-6,12-dihydroindeno[1,2-b]fluorene

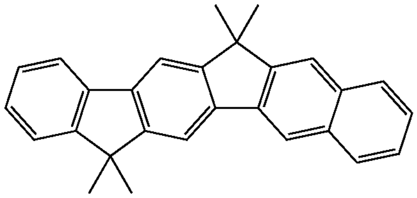

This compound is prepared analogously to the synthesis of 1,2-benzo-6,6,12,12-tetramethyl-6,12-dihydroindeno[1,2-b]fluorene (Example 1c) from 9,9'-dimethylfluorene-2-boronic acid and 3-carboxyethyl-2-bromonaphthalene.

b) 2',8-Dibromo-2,3-benzo-6,6,12,12-tetramethyl-6,12-dihydroindeno[1,2-b]fluorene

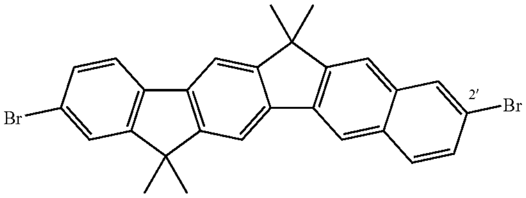

This compound is prepared analogously to the synthesis of 1,2-benzo-3,8-dibromo-6,6,12,12-tetramethyl-6,12-dihydroindeno[1,2-b]fluorene (Example 1d) starting from 2,3-benzo-6,6,12,12-tetramethyl-6,12-dihydroindeno[1,2-b]fluorene.

c) 2',8-Bis(diphenylamino)-2,3-benzo-6,6,12,12-tetramethyl-6,12-dihydroindeno[1,2-b]fluorene

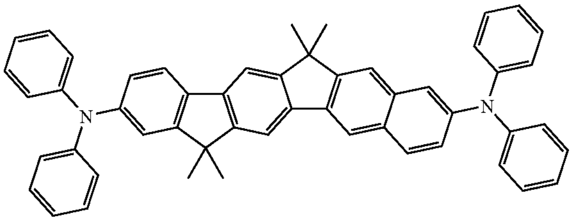

This compound is synthesised analogously to the process described in Example 13. Yield: 74% in a purity of >99.9% after sublimation twice. The compound has excellent thermal stability. No decomposition can be observed on sublimation.

The following compounds are synthesised analogously to the process described in Example 25 (all purities >99.9%, yields after sublimation twice):

| Example No. | Structure | Yield (%) |
|---|---|---|
| 27 | 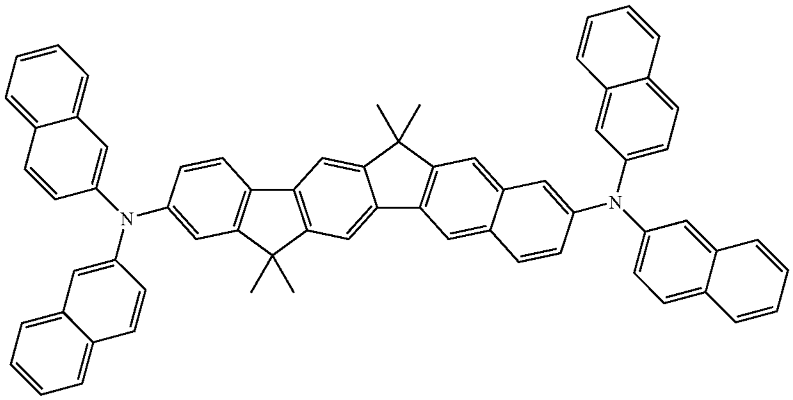 | 68 |

-continued
| Example No. | Structure | Yield (%) |
|---|---|---|
| 28 | 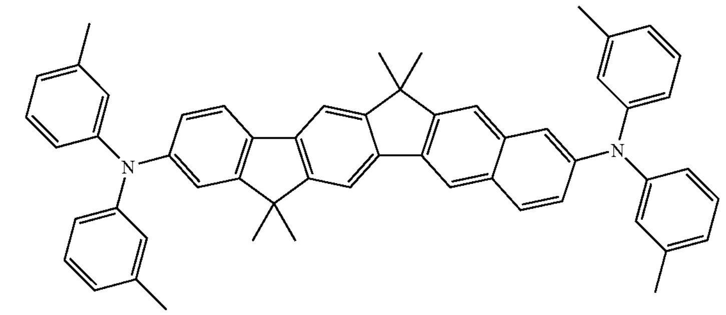 | 54 |
| 29 | 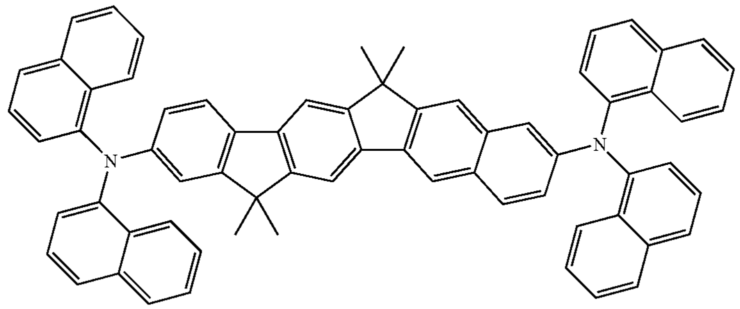 | 57 |
| 30 | 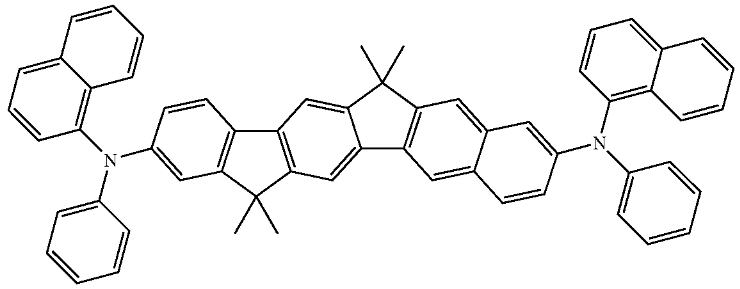 | 79 |
| 31 | 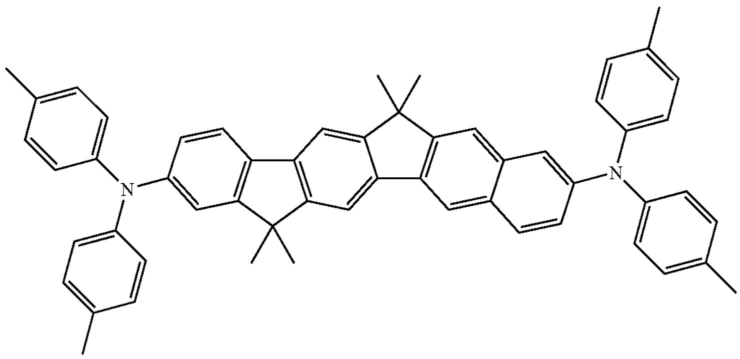 | 81 |

Example 32

1,2-Benzo-3-(N,N-bis-4-tert-butylphenylamino)-6,6-dimethyl-12,12-oxa-6,12-dihydroindeno[1,2-b]fluorene a) Ethyl 1-(dibenzofuran-2-yl)naphthalene-2-carboxylate

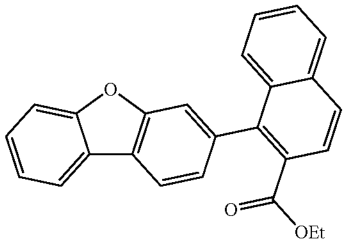

Procedure analogous to Example 1a). Instead of 86.3 g (362 mmol) of 9,9'-dimethylfluorene-2-boronic acid, 42.4 g (200 mmol) of dibenzofuran-2-boronic acid are employed, the molar amount of the other reagents is adapted correspondingly. Yield: 60.8 g (83%) of a colourless solid.

b) 2-[1-(Dibenzofuran-2-yl)naphthalen-2-yl]propan-2-ol

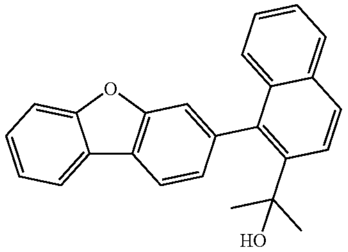

Procedure analogous to Example 1b). Instead of 100.6 g (256 mmol) of ethyl 1-(9,9-dimethyl-9H-fluoren-2-yl)naphthalene-2-carboxylate, 55.0 g (150 mmol) of ethyl 1-(dibenzofuran-2-yl)naphthalene-2-carboxylate are employed, the molar amount of the other reagents is adapted correspondingly. Yield: 41.8 g (79%) of a colourless solid.

c) 1,2-Benzo-6,6-dimethyl-12,12-oxa-6,12-dihydroindeno[1,2-b ]fluorene

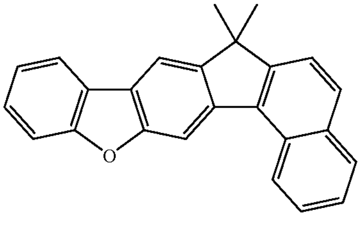

Procedure analogous to Example 1c). Instead of 97 g (256 mmol) of 2-[1-(9,9-dimethyl-9H-fluoren-2-yl)naphthalen-2-yl]propan-2-ol, 39.8 g (113 mmol) of 2-[1-(dibenzofuran-2-yl)naphthalen-2-yl]propan-2-ol are employed, the molar amount of the other reagents is adapted correspondingly. Yield: 29.1 g (77%) of colourless crystals.

d) 1,2-Benzo-3-bromo-6,6-dimethyl-12,12-oxa-6,12-dihydroindeno[1,2-b]fluorene

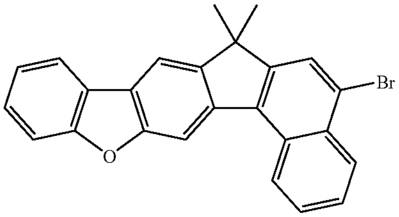

Procedure analogous to Example 8a). Instead of 15.5 g (43 mmol) of 1,2-benzo-6,6,12,12-tetramethyl-6,12-dihydroindeno[1,2-b]fluorene, 20.1 g (60 mmol) of 1,2-benzo-6,6-dimethyl-12,12-oxa-6,12-dihydroindeno[1,2-b]fluorene are employed, the molar amount of the other reagents is adapted correspondingly. The reaction is carried out in DMF at 40° C. After removal of the solvent in vacuo, the residue is washed by boiling in ethanol/water (1:1), the solid is filtered off with suction, washed with ethanol and dried and subsequently recrystallised twice from DMF, leaving 13.9 g (56%) of the monobromide as colourless crystals.

e) 1,2-Benzo-3-(N,N-bis-4 tert-butylphenylamino)-6,6-dimethyl-12,12-oxa-6,12-dihydroindeno[1,2-b] fluorene

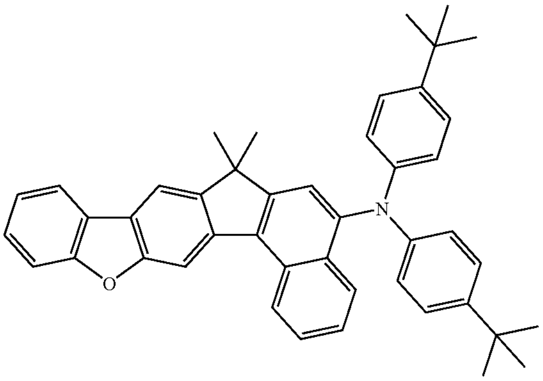

Procedure analogous to Example 13. Instead of 23.1 g (53 mmol) of 1,2-benzo-3-bromo-6,6,12,12-tetramethyl-6,12-dihydroindeno[1,2-b]fluorene, 10.3 g (25 mmol) of 1,2-benzo-3-bromo-6,6-dimethyl-12,12-oxa-6,12-dihydroindeno[1,2-b]fluorene are employed, the molar amount of the other reagents is adapted correspondingly Purification by recrystallisation five times from DMF and sublimation twice (T=315° C., p=5×$10^{-5}$ mbar) gives 9.8 g (64%) of a yellow powder having a purity of >99.8% (RP-HPLC). The compound has excellent thermal stability. No decomposition can be observed on sublimation.

The following compounds are synthesised analogously to the process described above (all purities >99.9%, yields after sublimation twice). Dibenzofuran-3-boronic acid is replaced here by dibenzothiophene-2-boronic acid or N-phenylcarbazole-2-boronic acid.

| Example No. | Structure | Yield, final step (%) |
|---|---|---|
| 33 | 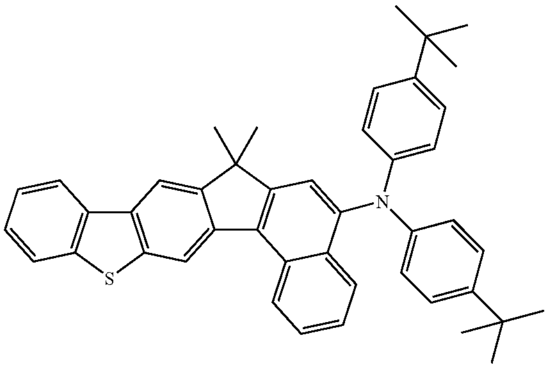 | 78 |
| 34 | 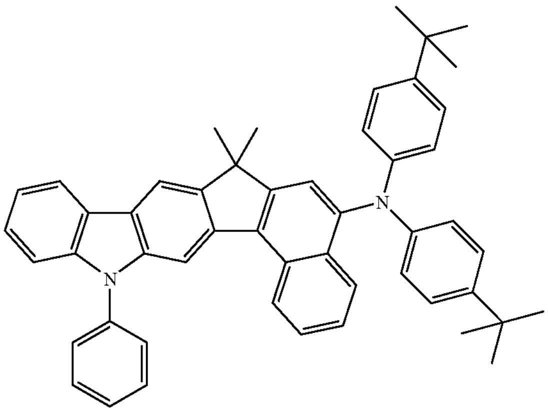 | 51 |

Example 35

1,2-Benzo-3-(1-naphthyl)-6,6,dimethyl-12,12-mesitylboranyl-6,12-dihydroindeno[1,2-b]fluorene a) Ethyl 1-biphenyl-4-ylnaphthalene-2-carboxylate

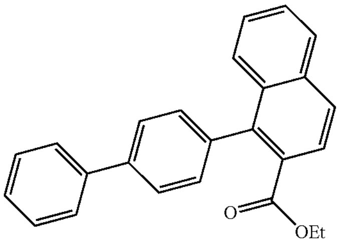

Procedure analogous to Example 1a). Instead of 86.3 g (362 mmol) of 9,9'-dimethylfluorene-2-boronic acid, 39.6 g (200 mmol) of biphenyl-4-boronic acid are employed, the molar amount of the other reagents is adapted correspondingly. Yield: 67.2 g (95%) of a colourless solid.

b) 2-[1-Biphenyl-4-ylnaphthalen-2-yl]propan-2-ol

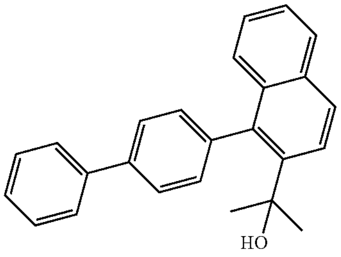

Procedure analogous to Example 1b). Instead of 100.6 g (256 mmol) of ethyl 1-(9,9-dimethyl-9H-fluoren-2-yl)naphthalene-2-carboxylate, 52.9 g (150 mmol) of ethyl 1-biphenyl-4-ylnaphthalene-2-carboxylate are employed, the molar amount of the other reagents is adapted correspondingly. Yield: 36.0 g (71%) of a colourless solid.

c) 7,7-Dimethyl-9-phenyl-7H-benzo[c]fluorene

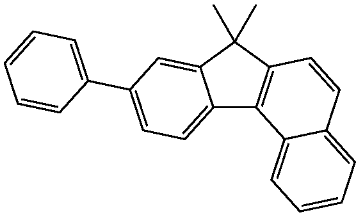

Procedure analogous to Example 1c). Instead of 97 g (256 mmol) of 2-[1-(9,9-dimethyl-9H-fluoren-2-yl)naphthalen-2-yl]propan-2-ol, 35.0 g (103 mmol) of 2-[1-biphenyl-4-yl-naphthalen-2-yl]propan-2-ol are employed, the molar amount of the other reagents is adapted correspondingly. Yield: 26.5 g (80%) of colourless crystals.

d) 1,2-Benzo-6,6-dimethyl-12,12-mestylboranyl-6,12-dihydroindeno[1,2-b]fluorene

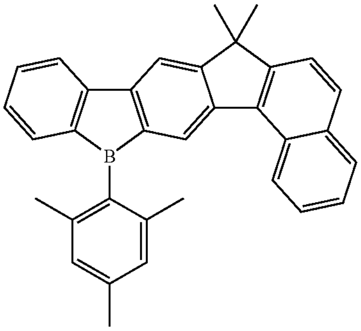

30.0 ml (200 mmol) of N,N,N',N'-tetramethylethylenediamine and then 44.0 ml (110 mmol) of n-butyllithium (2.5 molar in n-hexane) are added with vigorous stirring to a solution of 16.0 g (50 mmol) of 7,7-dimethyl-9-phenyl-7H-benzo[c]fluorene in 300 ml of cyclohexane, and the mixture is stirred at room temperature for 36 h. The reaction mixture is cooled to −78° C., and a solution of 21.8 g (130 mmol) of difluoromesitylborane in 50 ml of toluene is added dropwise. After the reaction mixture has warmed to room temperature, 500 ml of degassed water are added, the organic phase is separated off, dried over magnesium sulfate and evaporated to dryness. The solid is recrystallised three times from toluenein-heptane. Yield: 19.7 g (88%) of a colourless solid.

e) 1,2-Benzo-3-bromo-6,6-dimethyl-12,12-mesitylboranyl-6,12-dihydroindeno[1,2-b]fluorene

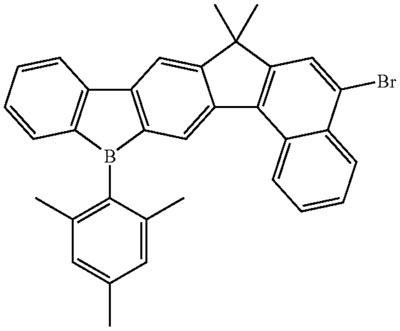

Procedure analogous to Example 32d). Instead of 20.0 g (60 mmol) of 1,2-benzo-6,6-dimethyl-12,12-oxa-6,12-dihydroindeno[1,2-b]fluorene, 11.2 g (25 mmol) of 1,2-benzo-6,6-dimethyl-12,12-mesitylboranyl-6,12-dihydroindeno[1,2-b]fluorene are employed, the molar amount of the other reagents is adapted correspondingly. Yield: 9.8 g (74%) of colourless crystals.

f) 1,2-Benzo-3-(naphth-1-yl)-6,6-dimethyl-12,12-mesitylboranyl-6,12-dihydroindeno[1,2-b]fluorene

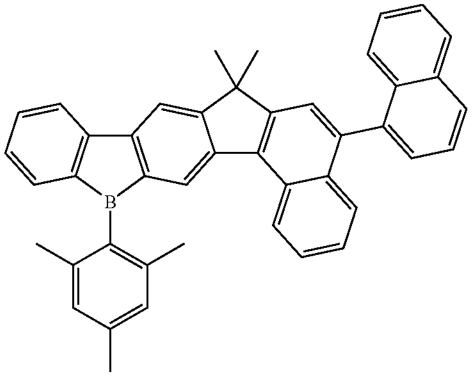

Procedure analogous to Example 8c). Instead of 11.3 g (30 mmol) of 9-bromo(2-naphthyl)anthracene, 5.3 g (10 mmol) of 1,2-benzo-3-bromo-6,6-dimethyl-12,12-mesitylboranyl-6,12-dihydroindeno[1,2-b]fluorene are employed, and instead of 12.5 g (31 mmol) of 1,2-benzo-6,6,12,12-tetramethyl-6,12-dihydroindeno[1,2-b]fluorene-3-boronic acid, 2.1 g (12 mmol) of naphthalene-1-boronic acid are employed, the molar amount of the other reagents is adapted correspondingly based on the bromide. Recrystallisation four times from DMF and subsequent sublimation twice (T=280° C., p=2×$10^{-5}$ mbar) gives 3.1 g (54%) of a colourless powder having a purity of >99.9% (according to RP-HPLC). The compound has excellent thermal stability. No decomposition can be observed on sublimation.

Example 36

Production of OLEDs

OLEDs are produced by a general process as described in WO 04/058911 which is adapted in individual cases to the particular circumstances (for example layer-thickness variation in order to achieve optimum efficiency or colour).

In Examples 37 to 49 below, the results for various OLEDs are presented. Class plates coated with structured ITO (indium tin oxide) form the substrates of the OLEDs. For improved processing, 20 nm of PEDOT (spincoated from water; purchased from H. C. Starck, Goslar, Germany; poly (3,4-ethylenedioxy-2,5-thiophene)) is applied to the substrate. The OLEDs consist of the following layer sequence: substrate/PEDOT/hole-transport layer (HTM1) 60 nm/emission layer (EML) 30 nm/electron-transport layer (ETM) 20 nm and finally a cathode. The materials apart from PEDOT are vapour-deposited thermally in a vacuum chamber. The emission layer here always consists of a matrix material (host) and a dopant, which is admixed with the host by co-evaporation. The cathode is formed by a 1 nm thin LiF layer and a 150 nm Al layer deposited on top. Table 2 shows the chemical structures of the materials used to build up the OLEDs.

These OLEDs are characterised by standard methods; for this purpose, the electroluminescence spectra, the efficiency (measured in cd/A), the power efficiency (measured in lm/W) as a function of the luminance, calculated from current/voltage/luminance characteristics (IUL characteristics), and the lifetime are determined. The lifetime is defined as the time after which the initial luminance of 4000 cd/$m^2$ has dropped to half.

Table 3 shows the results for some OLEDs (Examples 37 to 49). The dopants and host materials according to the invention used are the compounds of Examples 1, 4, 6, 7, 8, 13 and 16. As comparative examples, dopant D1 and host material H1 in accordance with the prior art are used.

TABLE 2

| Chemical structures of the materials used |
|---|
| 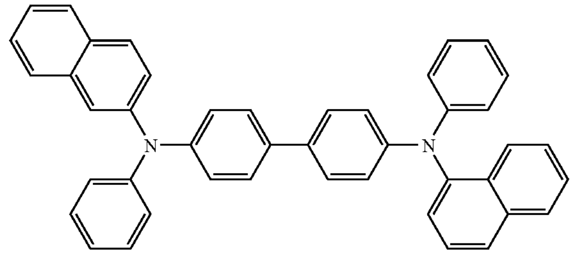 |
| HTM1 |
| 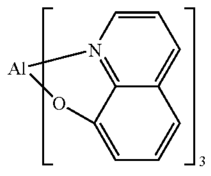 |
| ETM1 |
| 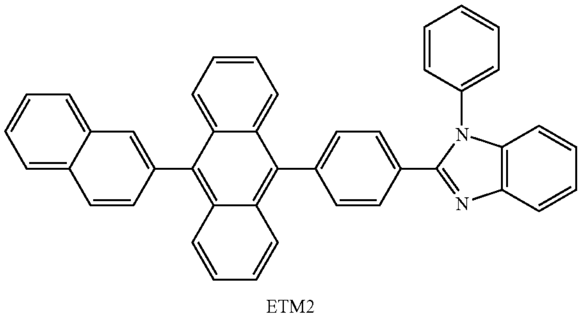 |
| ETM2 |
| 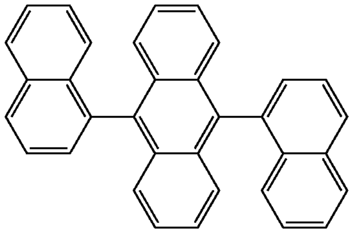 |
| H1 |

TABLE 2-continued

| Chemical structures of the materials used |
|---|
| 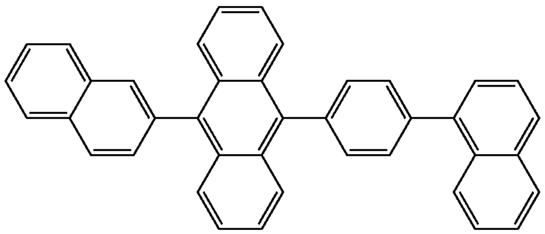 |
| H2 |
| 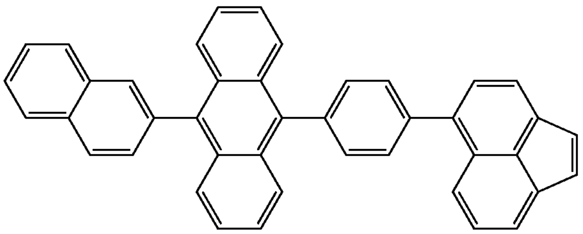 |
| H3 |
| 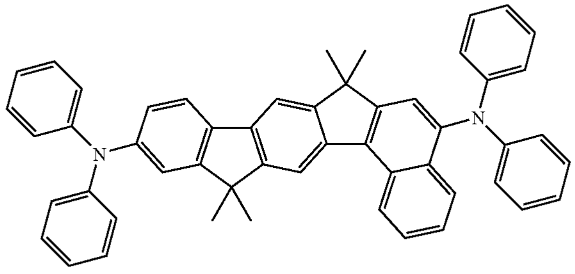 |
| Ex. 1 |
| 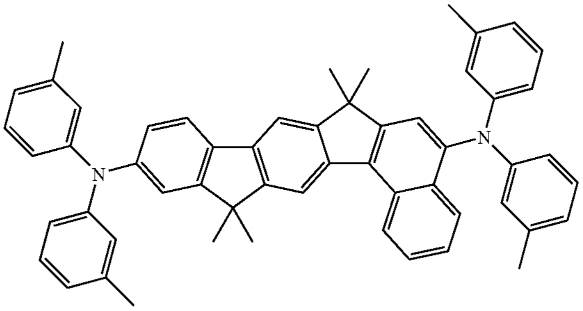 |
| Ex. 4 |
| 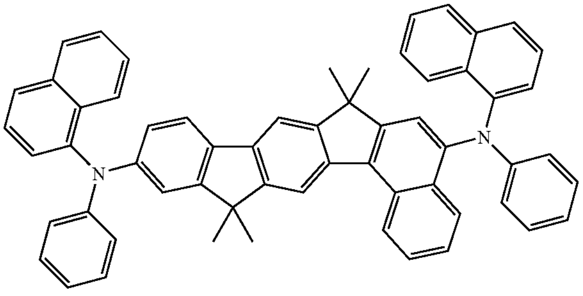 |
| Ex. 6 |

TABLE 2-continued

| Chemical structures of the materials used |
|---|
| 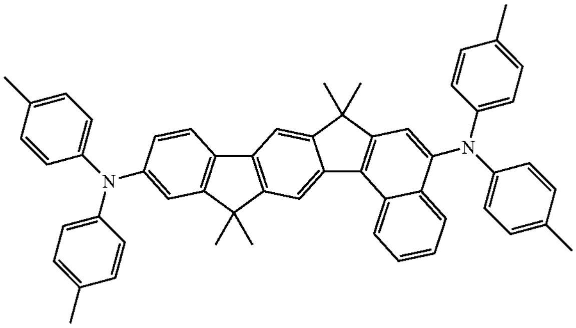 |
| Ex. 7 |
| 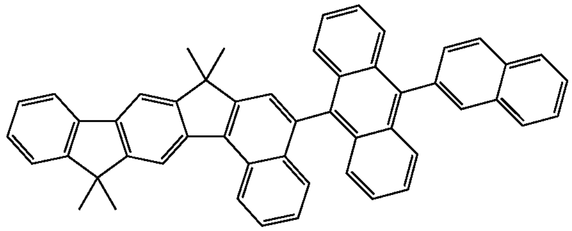 |
| Ex. 8 |
| 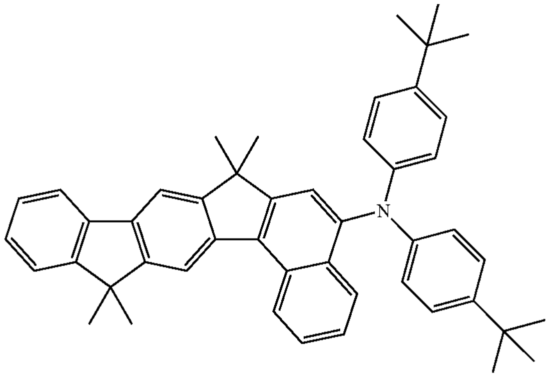 |
| Ex. 13 |
| 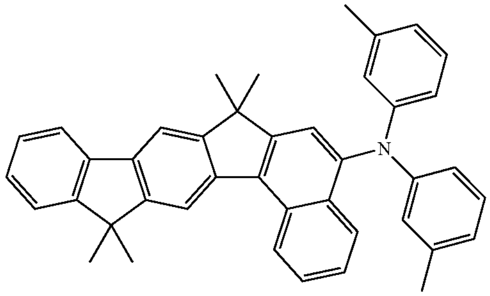 |
| Ex. 16 |
| 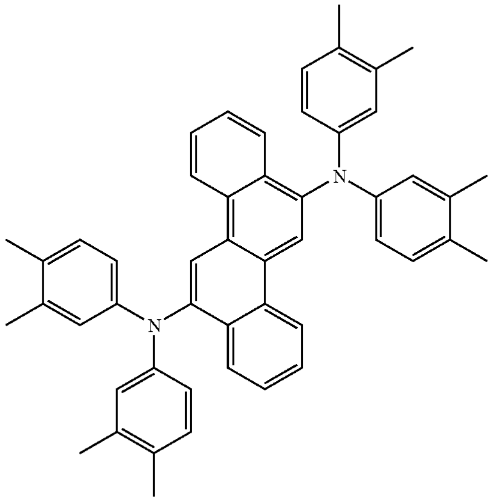 |
| D1 |

As can be seen from the results shown in Table 3, OLEDs according to the invention result in a significantly improved lifetime compared with OLEDs in accordance with the prior art. Furthermore, comparable or higher efficiency compared with the prior art is obtained with darker-blue colour coordinates.

TABLE 3

Results for the OLEDs

| Example | EML | ETM | Max. efficiency (cd/A) | Voltage (V) at 1000 cd/m$^2$ | CIE | Lifetime (h) at 4000 cd/m$^2$ |
|---|---|---|---|---|---|---|
| 37 (comparison) | H1 + 5% D1 | ETM1 | 6.5 | 5.8 | x = 0.14/ y = 0.19 | 450 |
| 38 | H1 + 5% Ex. 1 | ETM1 | 6.8 | 5.8 | x = 0.15/ y = 0.16 | 660 |
| 39 | H2 + 5% Ex. 1 | ETM1 | 6.9 | 5.7 | x = 0.16/ y = 0.17 | 700 |
| 40 | H3 + 5% Ex. 1 | ETM1 | 6.8 | 5.7 | x = 0.16/ y = 0.17 | 770 |
| 41 | H3 + 5% Ex. 1 | ETM2 | 6.7 | 5.3 | x = 0.16/ y = 0.17 | 850 |
| 42 | Ex. 8 + 5% D1 | ETM1 | 6.7 | 5.7 | x = 0.15/ y = 0.17 | 580 |
| 43 | H2 + 5% Ex. 4 | ETM1 | 7.0 | 5.6 | x = 0.16/ y = 0.18 | 930 |
| 44 | H2 + 5% Ex. 4 | ETM2 | 6.9 | 5.2 | x = 0.16/ y = 0.18 | 1050 |

TABLE 3-continued

| Results for the OLEDs | | | | | | |
|---|---|---|---|---|---|---|
| Example | EML | ETM | Max. efficiency (cd/A) | Voltage (V) at 1000 cd/$m^2$ | CIE | Lifetime (h) at 4000 cd/$m^2$ |
| 45 | H2 + 5% Ex. 6 | ETM1 | 5.5 | 5.7 | x = 0.15/ y = 0.13 | 730 |
| 46 | H2 + 5% Ex. 7 | ETM1 | 5.5 | 5.7 | x = 0.17/ y = 0.21 | 1500 |
| 47 | H2 + 5% Ex. 13 | ETM1 | 6.7 | 5.8 | x = 0.14/ y = 0.18 | 690 |
| 48 | H2 + 5% Ex. 16 | ETM1 | 5.2 | 5.9 | x = 0.15/ y = 0.10 | 690 |
| 49 | H2 + 5% Ex. 16 | ETM2 | 5.0 | 5.6 | x = 0.15/ y = 0.10 | 670 |

The invention claimed is:

1. A compound of the formulas (1), (2), (3), (4), (5) or (6)

Formula (1)

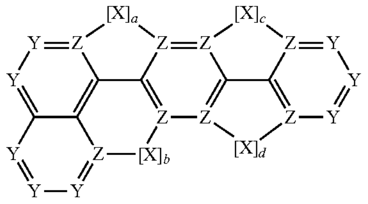

Formula (2)

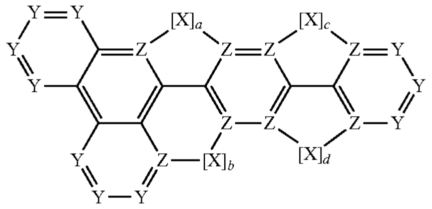

Formula (3)

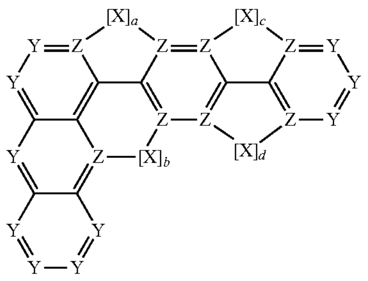

Formula (4)

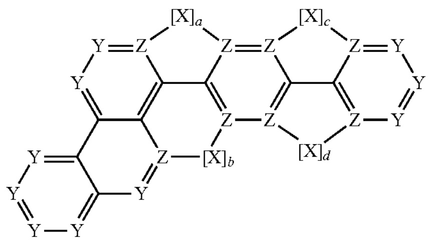

Formula (5)

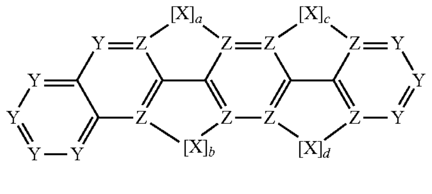

-continued

Formula (6)

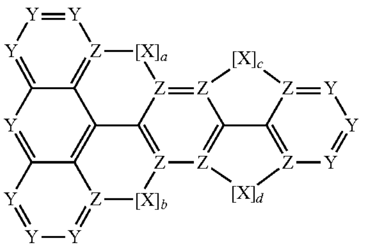

where the following applies to the symbols and indices:

Y is on each occurrence, identically or differently, $CR^1$ or N;

Z is equal to C if a bridge X is bonded to the group Z and is equal to Y if no bridge X is bonded to the group Z;

X is on each occurrence is differently a divalent bridge selected from the group consisting of $B(R^1)$, $C(R^1)_2$, $Si(R^1)_2$, C═O, C═$NR^1$, C═$C(R^1)_2$, O, S, S═O, $SO_2$, $N(R^1)$, $P(R^1)$ and P(═O)$R^1$; or X is on each occurrence is identically a divalent bridge selected from the group consisting of $B(R^1)$, $C(R^1)_2$, $Si(R^1)_2$, C═O, C═$NR^1$, C═$C(R^1)_2$, O, S, S═O, $SO_2$, $P(R^1)$ and P(═O)$R^1$;

$R^1$ is on each occurrence, identically or differently, H, F, Cl, Br, I, CHO, $N(Ar)_2$, C(═O)Ar, P(═O)$Ar_2$, S(═O)Ar, $S(═O)_2Ar$, $CR^2$═$CR^2Ar$, CN, $NO_2$, $Si(R^2)_3$, $B(OR^2)_2$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent $CH_2$ groups is optionally replaced by $R^2C$═$CR^2$, C≡C, $Si(R^2)_2$, $Ge(R^2)_2$, $Sn(R^2)_2$, C═O, C═S, C═Se, C═$NR^2$, P(═O)($R^2$), SO, $SO_2$, $NR^2$, O, S or $CONR^2$ and where one or more H atoms is optionally replaced by F, Cl, Br, I, CN or $NO_2$, or an aromatic or heteroaromatic ring system having 5 to 40 aromatic ring atoms, which may in each case be substituted by one or more radicals $R^2$, or an aryloxy or heteroaryloxy group having 5 to 40 aromatic ring atoms, which is optionally substituted by one or more radicals $R^2$, or a combination of these systems; two or more adjacent substituents $R^1$ here may also form a mono- or polycyclic ring system with one another;

Ar is on each occurrence, identically or differently, an aromatic or heteroaromatic ring system having 5 to 30 aromatic ring atoms, which is optionally substituted by one or more non-aromatic radicals $R^1$; two radicals Ar which are bonded to the same nitrogen or phosphorus atom may also be linked to one another by a single bond or a bridge selected from $B(R^2)$, $C(R^2)_2$, $Si(R^2)_2$, C═O, C═$NR^2$, C═$C(R^2)_2$, O, S, S═O, $SO_2$, $N(R^2)$, $P(R^2)$ and P(═O)$R^2$;

$R^2$ is on each occurrence, identically or differently, H or an aliphatic, aromatic and/or heteroaromatic hydrocarbon radical having 1 to 20 C atoms, in which, in addition, H atoms is optionally replaced by F; two or more adjacent substituents $R^2$ here optionally forms a mono- or polycyclic aliphatic or aromatic ring system with one another;

a, b, c, and d is on each occurrence, identically or differently, 0 or 1, with the proviso that a+b=1 or 2 and c+d=1 or 2, where a=0 or b=0 or c=0 or d=0 in each case means that the corresponding bridge X is not present.

2. The compound according to claim 1, wherein a+b=1 and c+d=1.

3. The compound according to claim 1, wherein the compound is selected from the formulae (7) to (28)

Formula (7)

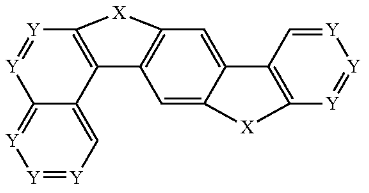

Formula (8)

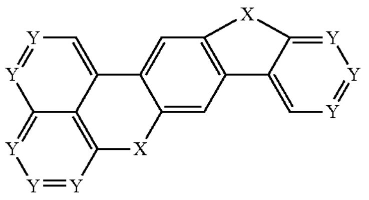

Formula (9)

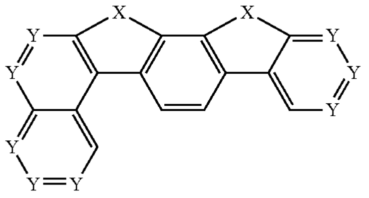

Formula (10)

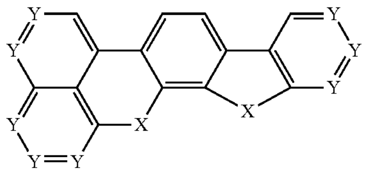

Formula (11)

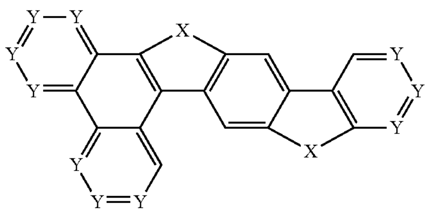

-continued

Formula (12)

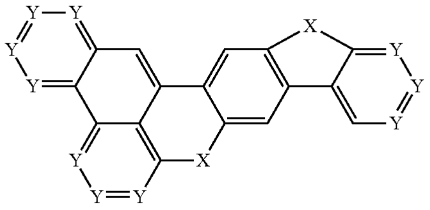

Formula (13)

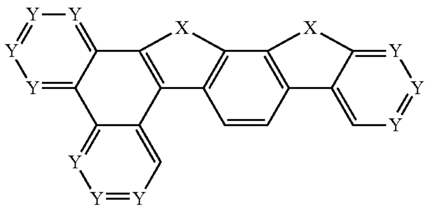

Formula (14)

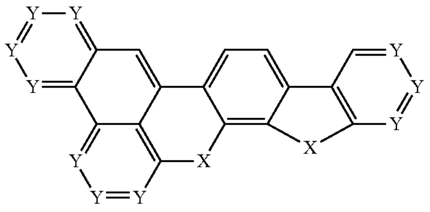

Formula (15)

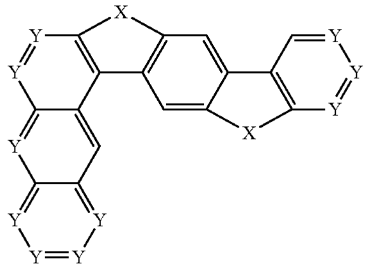

Formula (16)

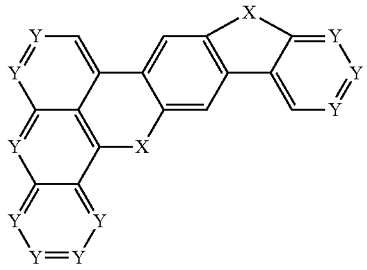

Formula (17)

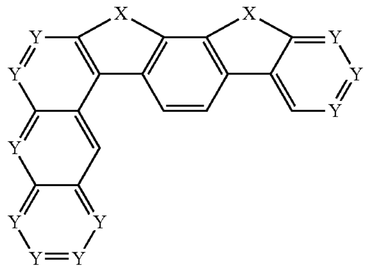

-continued

Formula (18)

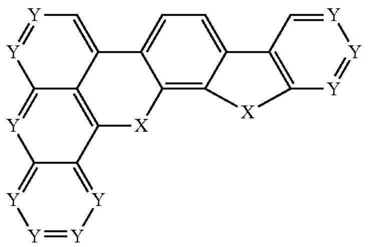

Formula (19)

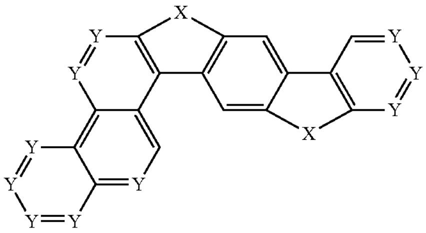

Formula (20)

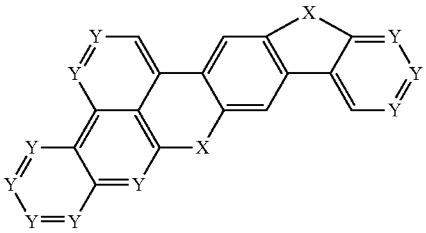

Formula (21)

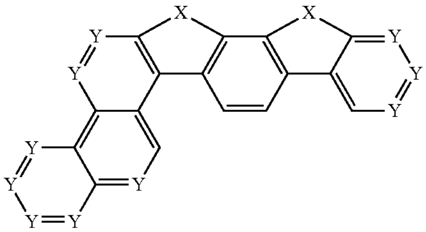

Formula (22)

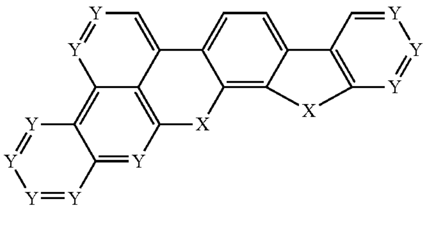

Formula (23)

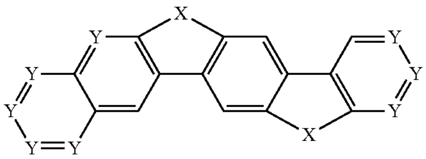

-continued

Formula (24)

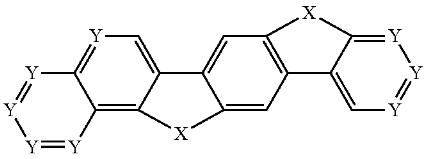

Formula (25)

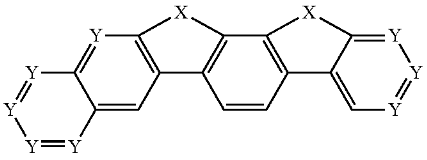

Formula (26)

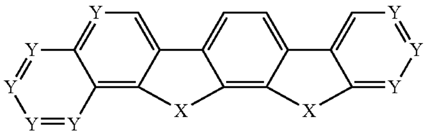

Formula (27)

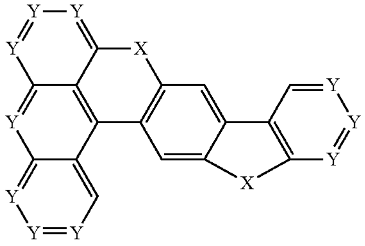

Formula (28)

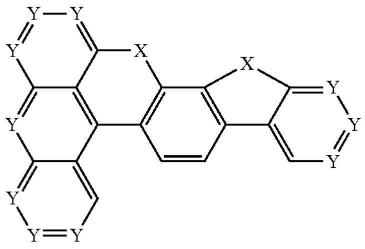

where the symbols X and Y have the same meaning as described in claim 1.

4. The compound according to claim 1, wherein the symbol Y stands for nitrogen a total of 0, 1, 2, 3 or 4 times, where the other symbols Y stand for $CR^1$.

5. The compound according to claim 1, wherein the compound is selected from the formulae (7a) to (28a)

Formula (7a)

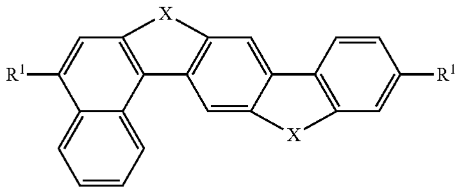

-continued
Formula (8a)
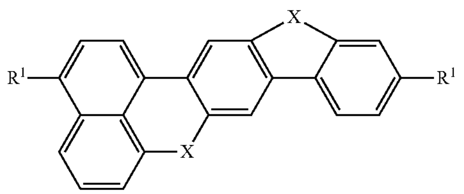
Formula (9a)
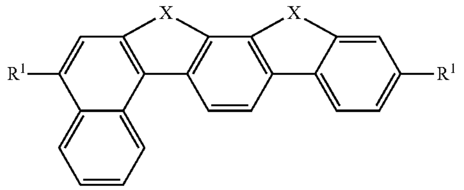
Formula (10a)
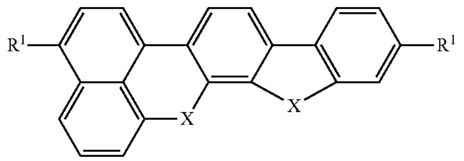
Formula (11a)
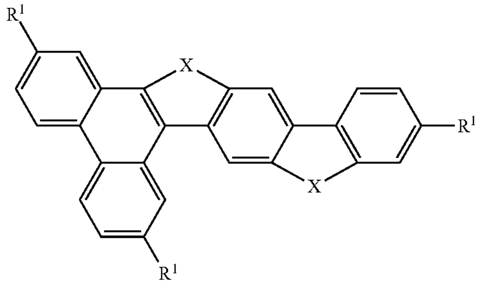
Formula (12a)
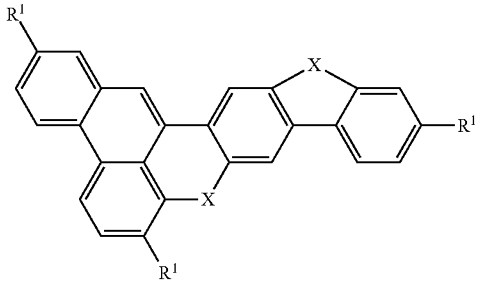
Formula (13a)
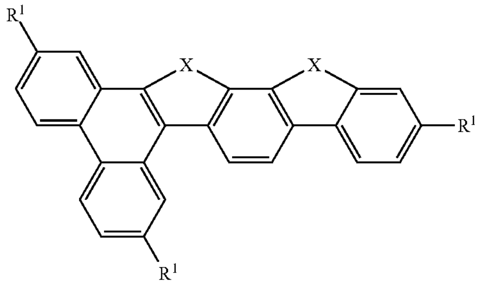
-continued
Formula (14a)
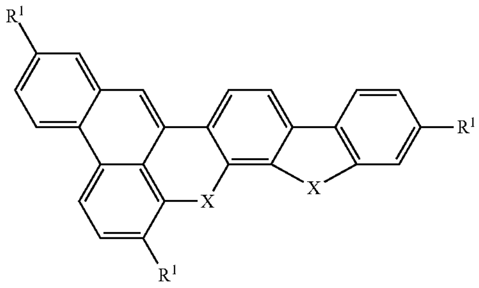
Formula (15a)
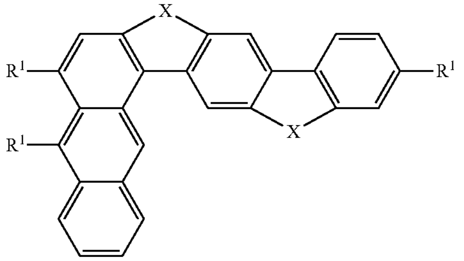
Formula (16a)
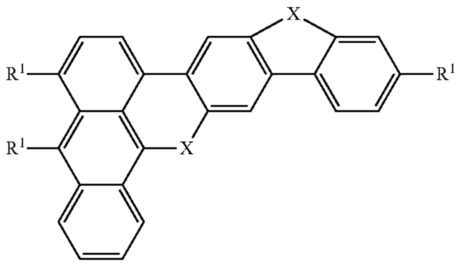
Formula (17a)
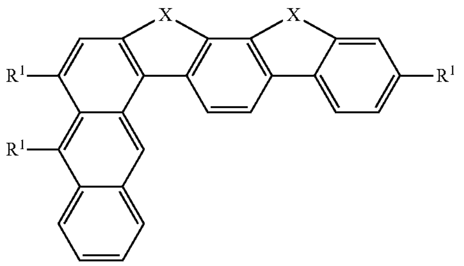
Formula (18a)
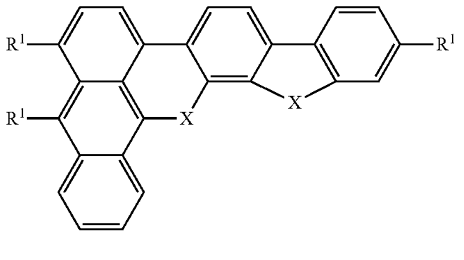

-continued

Formula (19a)

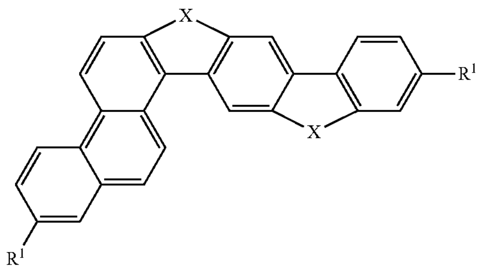

Formula (20a)

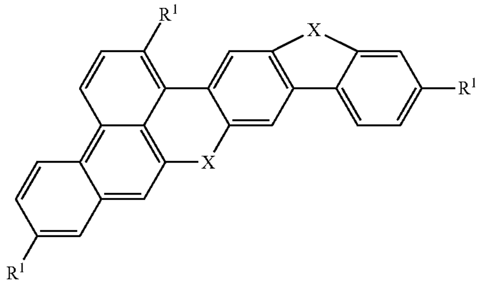

Formula (21a)

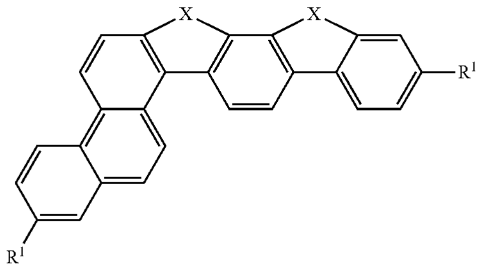

Formula (22a)

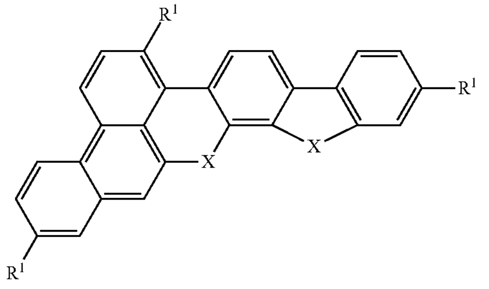

Formula (23a)

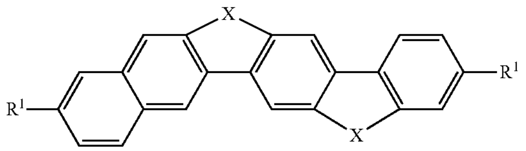

Formula (24a)

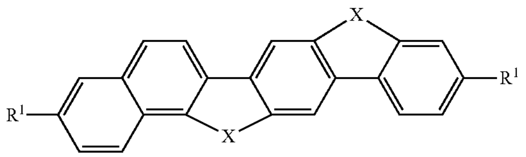

-continued

Formula (25a)

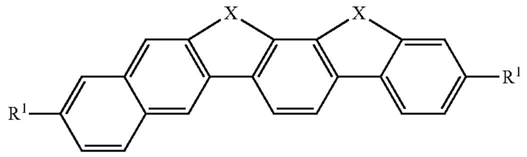

Formula (26a)

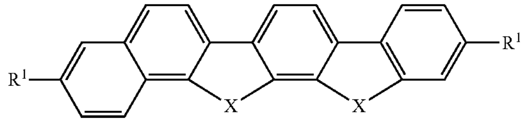

Formula (27a)

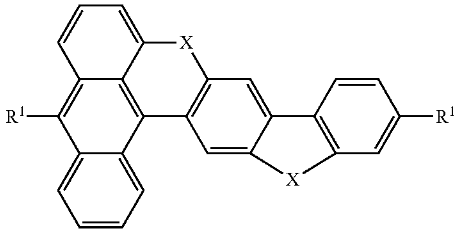

Formula (28a)

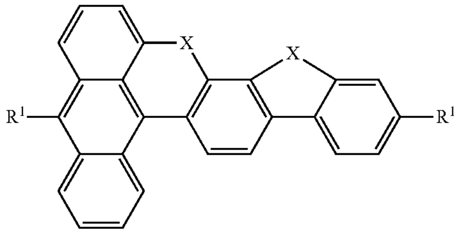

where the symbols X and $R^1$ have the same meaning as described in claim 1.

6. The compound according to claim 1, wherein the symbol $R^1$, which is bonded to the aromatic parent structure of the formulae (1) to (6), stands, identically or differently on each occurrence, for H, F, Br, C(=O)Ar, P(=O)$Ar_2$, $CR^2$=$CR^2$Ar, a straight-chain alkyl group having 1 to 5 C atoms or a branched alkyl group having 3 to 5 C atoms, where one or more non-adjacent $CH_2$ groups is optionally replaced by —$R^2$C=$CR^2$—, —C≡C—or —O— and where one or more H atoms is optionally replaced by F, or a triarylamine group having 18 to 30 C atoms, which is optionally substituted by one or more radicals $R^2$, or an aryl group having 6 to 16 C atoms or heteroaryl group having 2 to 16 C atoms or a spirobifluorene group, each of which is optionally substituted by one or more radicals $R^2$, or a combination of two or three of these systems, and/or in that at least one symbol $R^1$ stands for a group $N(Ar)_2$ of the formula (29) or (30)

Formula (29)

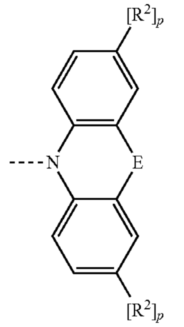

Formula (30)

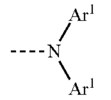

wherein $R^2$ is on each occurrence, identically or differently, H or an aliphatic, aromatic and/or heteroaromatic hydrocarbon radical having 1 to 20 C atoms, in which, in addition, H atoms is optionally replaced by F; two or more adjacent substituents $R^2$ here optionally forms a mono- or polycyclic aliphatic or aromatic ring system with one another;

E stands for a single bond, O, S, $N(R^2)$ or $C(R^2)_2$;

$Ar^1$ is, identically or differently on each occurrence, an aryl or heteroaryl group having 5 to 20 aromatic ring atoms or a triarylamine group having 15 to 30 aromatic ring atoms, each of which is optionally substituted by one or more radicals $R^2$ and;

p is on each occurrence, identically or differently, 0 or 1.

7. The compound as claimed in claim 6, wherein $Ar^1$ is, identically or differently on each occurrence, an aryl or heteroaryl group having 6 to 14 aromatic ring atoms or a triarylamine group having 18 to 30 aromatic ring atoms, each of which is optionally substituted by one or more radicals $R^2$.

8. The compound according to claim 1, wherein the symbol X is on each occurrence is differently a divalent bridge selected from $C(R^1)_2$, C═O, C═$NR^1$, O, S, S═O, $SO_2$, $N(R^1)$, $P(R^1)$ or P(═O)$R^1$ or X is on each occurrence is identically a divalent bridge selected from $C(R^1)_2$, C═O, C═$NR^1$, O, S, S═O, $SO_2$, $P(R^1)$ or P(═O)$R^1$.

9. The compound according to claim 1, wherein radicals $R^1$ which are bonded to the bridges X are identical or different and are H, straight-chain alkyl groups having 1 to 5 C atoms or branched alkyl groups having 3 to 5 C atoms, where one or more non-adjacent $CH_2$ groups is optionally replaced by —$R^2C$═$CR^2$—, —C≡C— or —O— and where one or more H atoms is optionally replaced by F, or aryl groups having 6 to 16 C atoms or heteroaryl groups having 2 to 16 C atoms, each of which is optionally substituted by one or more radicals $R^2$, or a combination of two or three of these systems; two of the radicals $R^1$ which are bonded to the same bridge atom may also form a ring system with one another here; or in that the radicals $R^1$ represent alkyl groups having up to 10 C atoms if the compound of the formulae (1) to (4) is processed as a solution.

10. A polymer, oligomer or dendrimer which comprises one or more compounds according to claim 1, wherein one or more radicals $R^1$ represent bonds to the polymer, oligomer or dendrimer.

11. An electronic device which comprises at least one compound according to claim 1.

12. An electronic device comprising anode, cathode and at least one organic layer comprising at least one compound according to claim 1.

13. The device according to claim 11, wherein the device is selected from organic electroluminescent devices (OLEDs, PLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) and organic photo receptors.

14. The electronic device according to claim 13, wherein the device is an organic electroluminescent device comprising a cathode, an anode, one or more emitting layers and optionally further layers selected from hole-injection layer, hole-transport layer, electron-transport layer, electron-injection layer and/or charge-generation layer.

15. The electronic device according to claim 13, wherein the electronic device is an organic electroluminescent device and one or more substituents $R^1$ are selected from simple or condensed aryl or heteroaryl groups and in that the compound according to formulae (1), (2), (3), (4), (5) and/or (6) is employed as host for a fluorescent dopant and/or in that one or more substituents $R^1$ and/or bridges X contain at least one group C═O, P(═O) and/or $SO_2$ and in that the compound according to formulae (1), (2), (3), (4), (5) and/or (6) is employed as matrix for phosphorescent dopants and/or in that one or more substituents $R^1$ contain at least one vinylaryl unit, at least one vinylarylamine unit and/or at least one arylamino unit and the compounds according to formulae (1), (2), (3), (4), (5) and/or (6) are employed as emitting materials and/or in that one or more substituents $R^1$ stand for a group $N(Ar)_2$ and in that the compound according to formulae (1), (2), (3), (4), (5) and/or (6) may optionally be doped with electron-acceptor compounds and in that it is employed as hole-transport material or hole-injection material, preferably in a hole-transport or hole-injection layer, and/or in that one or more substituents $R^1$ contain at least one unit C═O, P(═O) and/or $SO_2$ and in that the compound according to formulae (1), (2), (3), (4), (5) and/or (6) may optionally be doped with an electron-donor compound and in that it is employed as electron-transport material.

16. The compound according to claim 1, wherein a is 1, b is 0, c is 0, d is 1, Y stand for $CR^1$, Z is C and X is $NR^1$.

17. An electronic device comprising an anode, cathode and at least one organic layer, where a compound according to one of the formulae (1) to (6) and a second compound selected from fluorescent dopants, phosphorescent dopants and host material is present in an emitting layer Formula (1)

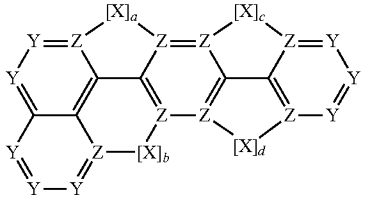

-continued

Formula (2)

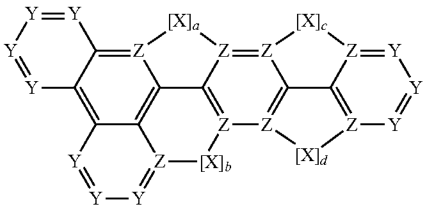

Formula (3)

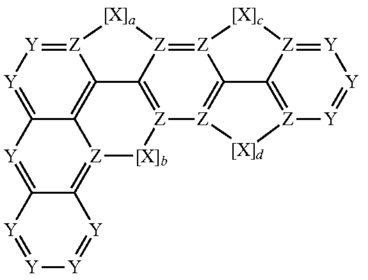

Formula (4)

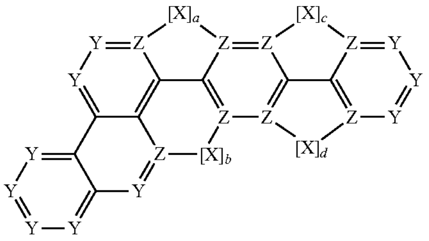

Formula (5)

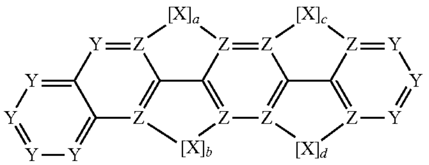

Formula (6)

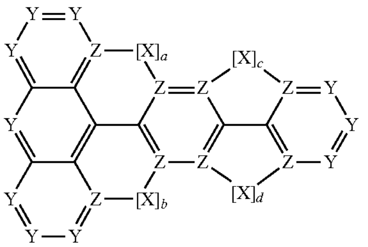

where the following applies to the symbols and indices:

Y is on each occurrence, identically or differently, $CR^1$ or N;

Z is equal to C if a bridge X is bonded to the group Z and is equal to Y if no bridge X is bonded to the group Z;

X is on each occurrence, identically or differently, a divalent bridge selected from the group consisting of $B(R^1)$, $C(R^1)_2$, $Si(R^1)_2$, C=O, $C{=}NR^1$, $C{=}C(R^1)_2$, O, S, S=O, $SO_2$, $N(R^1)$, $P(R^1)$ and $P(=O)R^1$; or $R^1$ is on each occurrence, identically or differently, H, F, Cl, Br, I, CHO, $N(Ar)_2$, C(=O)Ar, $P(=O)Ar_2$, S(=O)Ar, $S(=O)_2Ar$, $CR^2{=}CR^2Ar$, CN, $NO_2$, $Si(R^2)_3$, $B(OR^2)_2$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent $CH_2$ groups is optionally replaced by $R^2C{=}CR^2$, C≡C, $Si(R^2)_2$, $Ge(R^2)_2$, $Sn(R^2)_2$, C=O, C=S, C=Se, $C{=}NR^2$, $P(=O)(R^2)$, SO, $SO_2$, $NR^2$, O, S or $CONR^2$ and where one or more H atoms is optionally replaced by F, Cl, Br, I, CN or $NO_2$, or an aromatic or heteroaromatic ring system having 5 to 40 aromatic ring atoms, which may in each case be substituted by one or more radicals $R^2$, or an aryloxy or heteroaryloxy group having 5 to 40 aromatic ring atoms, which is optionally substituted by one or more radicals $R^2$, or a combination of these systems; two or more adjacent substituents $R^1$ here may also form a mono- or polycyclic ring system with one another;

Ar is on each occurrence, identically or differently, an aromatic or heteroaromatic ring system having 5 to 30 aromatic ring atoms, which is optionally substituted by one or more non-aromatic radicals $R^1$; two radicals Ar which are bonded to the same nitrogen or phosphorus atom may also be linked to one another by a single bond or a bridge selected from $B(R^2)$, $C(R^2)_2$, $Si(R^2)_2$, C=O, $C{=}NR^2$, $C{=}C(R^2)_2$, O, S, S=O, $SO_2$, $N(R^2)$, $P(R^2)$ and $P(=O)R^2$;

$R^2$ is on each occurrence, identically or differently, H or an aliphatic, aromatic and/or heteroaromatic hydrocarbon radical having 1 to 20 C atoms, in which, in addition, H atoms is optionally replaced by F; two or more adjacent substituents $R^2$ here optionally forms a mono- or polycyclic aliphatic or aromatic ring system with one another;

a, b, c, and d is on each occurrence, identically or differently, 0 or 1, with the proviso that a+b=1 or 2 and c+d=1 or 2, where a=0 or b=0 or c=0 or d=0 in each case means that the corresponding bridge X is not present.

* * * * *